US012655159B2

(12) United States Patent
Zheng

(10) Patent No.: US 12,655,159 B2
(45) Date of Patent: Jun. 16, 2026

(54) DEUTERATED IRAK DEGRADERS AND USES THEREOF

(71) Applicant: Kymera Therapeutics, Inc., Watertown, MA (US)

(72) Inventor: Xiaozhang Zheng, Lexington, MA (US)

(73) Assignee: Kymera Therapeutics, Inc., Watertown, MA (US)

( * ) Notice: Subject to any disclaimer, the term of this patent is extended or adjusted under 35 U.S.C. 154(b) by 706 days.

(21) Appl. No.: 18/008,083

(22) PCT Filed: Jun. 3, 2021

(86) PCT No.: PCT/US2021/035745
§ 371 (c)(1),
(2) Date: Dec. 2, 2022

(87) PCT Pub. No.: WO2021/247897
PCT Pub. Date: Dec. 9, 2021

(65) Prior Publication Data

US 2023/0250110 A1 Aug. 10, 2023

Related U.S. Application Data

(60) Provisional application No. 63/033,959, filed on Jun. 3, 2020.

(51) Int. Cl.
*C07D 519/00* (2006.01)

(52) U.S. Cl.
CPC .................................. *C07D 519/00* (2013.01)

(58) Field of Classification Search
CPC .................................................... C07D 519/00
USPC ...................................................... 514/230.5
See application file for complete search history.

(56) References Cited

U.S. PATENT DOCUMENTS

| | | | |
|---|---|---|---|
| 4,650,750 | A | 3/1987 | Giese |
| 4,709,016 | A | 11/1987 | Giese |
| 5,217,866 | A | 6/1993 | Summerton et al. |
| 5,360,811 | A | 11/1994 | Tegeler et al. |
| 5,360,819 | A | 11/1994 | Giese |
| 5,516,931 | A | 5/1996 | Giese et al. |
| 5,602,273 | A | 2/1997 | Giese et al. |
| 5,604,104 | A | 2/1997 | Giese et al. |
| 5,610,020 | A | 3/1997 | Giese et al. |
| 5,650,270 | A | 7/1997 | Giese et al. |
| 5,721,246 | A | 2/1998 | Yoshino et al. |
| 6,306,663 | B1 | 10/2001 | Kenten et al. |
| 6,552,065 | B2 | 4/2003 | Remiszewski et al. |
| 6,559,280 | B2 | 5/2003 | Kenten et al. |
| 6,627,754 | B2 | 9/2003 | Blumenkopf et al. |
| 6,949,537 | B2 | 9/2005 | Garlich et al. |
| 7,041,298 | B2 | 5/2006 | Deshaies et al. |
| 7,071,189 | B2 | 7/2006 | Kawashima et al. |
| 7,074,620 | B2 | 7/2006 | Kenten et al. |
| 7,173,015 | B2 | 2/2007 | Schreiber et al. |
| 7,208,157 | B2 | 4/2007 | Dashaies et al. |
| 7,273,920 | B2 | 9/2007 | Kenten et al. |
| 7,307,077 | B2 | 12/2007 | Kawashima et al. |
| 7,390,799 | B2 | 6/2008 | Bruncko et al. |
| 7,402,325 | B2 | 7/2008 | Addington |
| 7,449,458 | B2 | 11/2008 | Bhamidipati et al. |
| 7,501,496 | B1 | 3/2009 | Endl et al. |
| 7,514,444 | B2 | 4/2009 | Honigberg et al. |
| 7,528,143 | B2 | 5/2009 | Noronha et al. |
| 7,557,210 | B2 | 7/2009 | Singh et al. |
| 7,598,257 | B2 | 10/2009 | Rodgers et al. |
| 7,622,496 | B2 | 11/2009 | Larsen et al. |
| 7,667,039 | B2 | 2/2010 | Garcia-Echeverria et al. |
| 7,713,943 | B2 | 5/2010 | Klippel-Giese et al. |
| 7,781,433 | B2 | 8/2010 | Chuckowree et al. |
| 7,932,260 | B2 | 4/2011 | Fowler et al. |
| 7,989,622 | B2 | 8/2011 | Bajjalieh et al. |
| 8,138,347 | B2 | 3/2012 | Knight et al. |
| 8,185,616 | B2 | 5/2012 | Nagata et al. |
| 8,217,035 | B2 | 7/2012 | Burger et al. |
| 8,338,439 | B2 | 12/2012 | Singh et al. |
| 8,486,941 | B2 | 7/2013 | Burns et al. |
| 8,906,682 | B2 | 12/2014 | June et al. |
| 9,500,653 | B2 | 11/2016 | Crews et al. |
| 9,632,089 | B2 | 4/2017 | Crews et al. |
| 9,694,084 | B2 | 7/2017 | Bradner et al. |
| 9,750,816 | B2 | 9/2017 | Bradner et al. |
| 9,770,512 | B2 | 9/2017 | Bradner et al. |
| 9,821,068 | B2 | 11/2017 | Bradner et al. |
| 9,969,710 | B2 | 5/2018 | Jorand-Lebrun et al. |
| 10,125,114 | B2 | 11/2018 | Bradner et al. |
| 10,336,744 | B2 | 7/2019 | Harling et al. |
| 10,874,743 | B2 | 12/2020 | Mainolfi et al. |

(Continued)

FOREIGN PATENT DOCUMENTS

| | | |
|---|---|---|
| CN | 105085620 B | 5/2018 |
| WO | WO1996007655 A1 | 3/1996 |

(Continued)

OTHER PUBLICATIONS

Michelotti et al., Synthesis 2019, 51, 1319-1328.*
Adams et al., "Big opportunities for small molecules in immuno-oncology," Drug Discov., 2015, 14(9):603-622.
Aruri et al., "Metal-free Cross-Dehydrogenative Coupling of HN-azoles with a-C(sp3)-H Amides via C—H Activation and Its Mechanistic and Application Studies," J Org Chem., 2017, 82(2):1000-1012.
Balasubramanian et al., "Abstract 3646: Novel IRAK-4 inhibitors exhibit highly potent anti-proliferative activity in DLBCL cell lines with activating MYD88 L265P mutation," AACR 106th Annual Meeting 2015; Apr. 18-22, 2015; Philadelphia, PA.
Berge et al., "Pharmaceutical salts," J Pharm Sci., 1977, 66(1):1-19.

(Continued)

*Primary Examiner* — Niloofar Rahmani
(74) *Attorney, Agent, or Firm* — COOLEY LLP; John P. Rearick; Todd K. Macklin

(57) ABSTRACT

The present invention provides deuterium-enriched compounds, compositions thereof, and methods of using the same.

27 Claims, No Drawings

(56) References Cited

U.S. PATENT DOCUMENTS 11,065,231 B2 7/2021 Crew et al.
11,117,889 B1 9/2021 Mainolfi et al.
11,318,205 B1 5/2022 Mainolfi et al.
11,352,350 B2 6/2022 Mainolfi et al.
11,591,332 B2 2/2023 Weiss et al.
11,685,750 B2 * 6/2023 Zheng .................. C07D 519/00 514/230.2
11,707,457 B2 7/2023 Weiss
11,723,980 B2 8/2023 Mainolfi et al.
11,773,103 B2 10/2023 Rong et al.
11,779,578 B2 10/2023 Weiss
11,807,636 B2 11/2023 Mainolfi et al.
12,168,057 B2 12/2024 Mainolfi et al.
12,171,768 B2 12/2024 Gollob et al.
12,187,744 B2 1/2025 Leong et al.
12,258,341 B2 3/2025 Mainolfi et al.
2001/0053782 A1 12/2001 Blumenkopf et al.
2002/0042427 A1 4/2002 Tang et al.
2002/0068063 A1 6/2002 Deshaies et al.
2002/0183360 A1 12/2002 Muller et al.
2004/0029902 A1 2/2004 Singh et al.
2004/0048859 A1 3/2004 Germann et al.
2004/0106569 A1 6/2004 Klippel-Giese et al.
2004/0116421 A1 6/2004 Kawashima et al.
2004/0242631 A1 12/2004 Garlich et al.
2005/0014802 A1 1/2005 Attardo et al.
2005/0075306 A1 4/2005 Schreiber et al.
2006/0211657 A1 9/2006 Singh et al.
2007/0098719 A1 5/2007 Smith et al.
2007/0135461 A1 6/2007 Rodgers et al.
2007/0191405 A1 8/2007 Noronha et al.
2008/0076768 A1 3/2008 Chuckowree et al.
2008/0108636 A1 5/2008 Honigberg et al.
2008/0194579 A1 8/2008 Garcia-Echeverria et al.
2008/0275067 A1 11/2008 Fowler et al.
2009/0055944 A1 2/2009 Korman et al.
2009/0136494 A1 5/2009 Ponath et al.
2009/0233903 A1 9/2009 Rodgers et al.
2010/0087440 A1 4/2010 Bajjalieh et al.
2010/0150892 A1 6/2010 Han
2010/0197671 A1 8/2010 Burns et al.
2010/0197686 A1 8/2010 Xing et al.
2010/0203056 A1 8/2010 Irving et al.
2010/0233183 A1 9/2010 Triebel et al.
2010/0247554 A1 9/2010 Lemke et al.
2010/0249092 A1 9/2010 Singh et al.
2010/0249126 A1 9/2010 Burger et al.
2010/0279316 A1 11/2010 Gorelik et al.
2011/0008331 A1 1/2011 Triebel
2011/0053941 A1 3/2011 Mautino et al.
2011/0136796 A1 6/2011 Mautino et al.
2011/0165156 A1 7/2011 Dimoudis et al.
2011/0196150 A1 8/2011 Man et al.
2011/0223611 A1 9/2011 Salamone et al.
2011/0274683 A1 11/2011 Wong et al.
2012/0015962 A1 1/2012 Arora et al.
2012/0189639 A1 7/2012 Schebye et al.
2012/0277217 A1 11/2012 Mautino et al.
2012/0283238 A1 11/2012 Romero et al.
2012/0329997 A1 12/2012 Fertig et al.
2013/0005949 A1 1/2013 Fertig et al.
2013/0149236 A1 6/2013 Johnson et al.
2013/0190340 A1 7/2013 Hedstrom et al.
2013/0231328 A1 9/2013 Harriman et al.
2013/0274241 A1 10/2013 Jorand-Lebrun et al.
2014/0018343 A1 1/2014 Romero et al.
2014/0018357 A1 1/2014 Harriman et al.
2014/0018361 A1 1/2014 Harriman et al.
2014/0066625 A1 3/2014 Mautino et al.
2014/0079699 A1 3/2014 Wong et al.
2014/0079706 A1 3/2014 Cannarile et al.
2014/0093511 A1 4/2014 Lonberg et al.
2014/0155379 A1 6/2014 Ho et al.
2014/0194404 A1 7/2014 McElroy et al.
2014/0302523 A1 10/2014 Crews et al.
2014/0329799 A1 11/2014 Seganish et al.
2014/0336363 A1 11/2014 Fertig et al.
2014/0341917 A1 11/2014 Nastri et al.
2014/0356322 A1 12/2014 Crews et al.
2015/0011532 A1 1/2015 Paidi et al.
2015/0018344 A1 1/2015 Paidi et al.
2015/0025093 A1 1/2015 Romero et al.
2015/0045347 A1 2/2015 Dodd et al.
2015/0094305 A1 4/2015 Romero et al.
2015/0133451 A1 5/2015 Yoshida et al.
2015/0141396 A1 5/2015 Crosignani et al.
2015/0191464 A1 7/2015 Santella et al.
2015/0225410 A1 8/2015 Castro et al.
2015/0225449 A1 8/2015 Donnell et al.
2015/0274708 A1 10/2015 Seganish et al.
2015/0274738 A1 10/2015 Gray et al.
2015/0284382 A1 10/2015 Bhide et al.
2015/0284405 A1 10/2015 Trzupek et al.
2015/0291562 A1 10/2015 Crew et al.
2015/0299224 A1 10/2015 Seganish et al.
2015/0329498 A1 11/2015 Romero et al.
2015/0374678 A1 12/2015 Chamberlain et al.
2015/0376167 A1 12/2015 Jorand-Lebrun et al.
2015/0376206 A1 12/2015 Jorand-Lebrun et al.
2016/0002265 A1 1/2016 Jenkins et al.
2016/0022642 A1 1/2016 Crews et al.
2016/0045607 A1 2/2016 Crew et al.
2016/0058872 A1 3/2016 Crew et al.
2016/0145252 A1 5/2016 Jorand-Lebrun et al.
2016/0176916 A1 6/2016 Bradner et al.
2016/0214972 A1 7/2016 Jin et al.
2016/0235730 A1 8/2016 Bradner et al.
2016/0235731 A1 8/2016 Bradner et al.
2016/0243247 A1 8/2016 Bradner et al.
2016/0256468 A1 9/2016 Schafer et al.
2016/0272596 A1 9/2016 Chen et al.
2016/0272639 A1 9/2016 Crew et al.
2016/0311833 A1 10/2016 Bothe et al.
2016/0311839 A1 10/2016 Kelley et al.
2016/0326151 A1 11/2016 Gummadi et al.
2016/0340366 A1 11/2016 Gummadi et al.
2017/0001990 A1 1/2017 Chen et al.
2017/0008896 A1 1/2017 Dahmann et al.
2017/0008904 A1 1/2017 Crew et al.
2017/0022189 A1 1/2017 Zhang
2017/0037004 A1 2/2017 Crew et al.
2017/0065719 A1 3/2017 Qian et al.
2017/0121321 A1 5/2017 Crews et al.
2017/0152263 A1 6/2017 Gummadi et al.
2017/0204093 A1 7/2017 Chan et al.
2017/0247388 A1 8/2017 Altman et al.
2017/0281784 A1 10/2017 Wang et al.
2017/0327469 A1 11/2017 Crew et al.
2017/0369476 A1 12/2017 Chen et al.
2018/0009779 A1 1/2018 Bradner et al.
2018/0015087 A1 1/2018 Liu et al.
2018/0051027 A1 2/2018 Lim et al.
2018/0051028 A1 2/2018 Lim et al.
2018/0051029 A1 2/2018 Lim et al.
2018/0051030 A1 2/2018 Lim et al.
2018/0051035 A1 2/2018 Lim et al.
2018/0085465 A1 3/2018 Bradner et al.
2018/0118733 A1 5/2018 Harling et al.
2018/0127432 A1 5/2018 Trzupek et al.
2018/0134684 A1 5/2018 Bradner et al.
2018/0147202 A1 5/2018 Crew et al.
2018/0169097 A1 6/2018 Hammerman et al.
2018/0186799 A1 7/2018 Gardner et al.
2018/0194724 A1 7/2018 Kemp et al.
2018/0201609 A1 7/2018 Gummadi et al.
2018/0208605 A1 7/2018 Gummadi et al.
2018/0228907 A1 8/2018 Crew et al.
2018/0230157 A1 8/2018 Bacon et al.
2018/0298015 A1 10/2018 Bryan et al.
2018/0327419 A1 11/2018 Bradner et al.
2019/0071415 A1 3/2019 Bradner et al.
2019/0076539 A1 3/2019 Phillips et al.
2019/0076540 A1 3/2019 Phillips et al.
2019/0076541 A1 3/2019 Phillips et al.

(56) References Cited

U.S. PATENT DOCUMENTS

| | | | | |
|---|---|---|---|---|
| 2019/0076542 | A1 | 3/2019 | Phillips et al. | |
| 2019/0151295 | A1 | 5/2019 | Crew et al. | |
| 2019/0151457 | A1 | 5/2019 | Bradner et al. | |
| 2019/0192532 | A1 | 6/2019 | Bradner et al. | |
| 2019/0192668 | A1 | 6/2019 | Mainolfi et al. | |
| 2019/0276474 | A1 | 9/2019 | Chan et al. | |
| 2019/0374528 | A1 | 12/2019 | Gray et al. | |
| 2020/0010468 | A1 | 1/2020 | Ji et al. | |
| 2020/0347045 | A1 | 11/2020 | Mainolfi et al. | |
| 2020/0377469 | A1 | 12/2020 | Mainolfi et al. | |
| 2021/0002296 | A1 | 1/2021 | Mainolfi et al. | |
| 2021/0147382 | A1 | 5/2021 | Bellenie et al. | |
| 2021/0228562 | A1 | 7/2021 | Weiss | |
| 2021/0323952 | A1 | 10/2021 | Mainolfi et al. | |
| 2021/0395273 | A1 | 12/2021 | Zheng et al. | |
| 2023/0069104 | A1 | 3/2023 | Mainolfi et al. | |
| 2023/0089916 | A1 | 3/2023 | Mainolfi et al. | |
| 2023/0122219 | A1* | 4/2023 | Weiss .................. | C07D 471/04 514/259.3 |
| 2023/0132715 | A1 | 5/2023 | Ji et al. | |
| 2023/0190940 | A1 | 6/2023 | Zhang et al. | |
| 2023/0219945 | A1 | 7/2023 | Mainolfi et al. | |
| 2023/0234953 | A1 | 7/2023 | Weiss et al. | |
| 2023/0241075 | A1 | 8/2023 | Campbell et al. | |
| 2023/0303526 | A1 | 9/2023 | Mainolfi et al. | |
| 2023/0405012 | A1 | 12/2023 | Rong et al. | |
| 2023/0406866 | A1* | 12/2023 | Zheng .................. | C07D 519/00 |
| 2024/0059674 | A1 | 2/2024 | Mainolfi et al. | |
| 2024/0131016 | A1 | 4/2024 | Weiss | |
| 2024/0252656 | A1 | 8/2024 | Hencken | |
| 2024/0383887 | A1 | 11/2024 | Weiss | |
| 2025/0000985 | A1 | 1/2025 | Mainolfi et al. | |
| 2025/0082645 | A1 | 3/2025 | Gollob et al. | |
| 2025/0084105 | A1 | 3/2025 | Leong et al. | |
| 2025/0121073 | A1 | 4/2025 | Mainolfi et al. | |
| 2025/0163042 | A1 | 5/2025 | Mainolfi et al. | |

FOREIGN PATENT DOCUMENTS

| | | | |
|---|---|---|---|
| WO | WO2001042246 | A2 | 6/2001 |
| WO | WO2002020740 | A2 | 3/2002 |
| WO | WO2002088112 | A1 | 11/2002 |
| WO | WO2003063794 | A2 | 8/2003 |
| WO | WO2004019973 | A1 | 3/2004 |
| WO | WO2004089925 | A1 | 10/2004 |
| WO | WO2004106328 | A1 | 12/2004 |
| WO | WO2005007623 | A2 | 1/2005 |
| WO | WO2005113554 | A2 | 12/2005 |
| WO | WO2006029879 | A2 | 3/2006 |
| WO | WO2006078846 | A1 | 7/2006 |
| WO | WO2006105021 | A2 | 10/2006 |
| WO | WO2006122806 | A2 | 11/2006 |
| WO | WO2007005874 | A2 | 1/2007 |
| WO | WO2007016176 | A2 | 2/2007 |
| WO | WO2007044729 | A2 | 4/2007 |
| WO | WO2007053452 | A1 | 5/2007 |
| WO | WO2007070514 | A1 | 6/2007 |
| WO | WO2007084786 | A1 | 7/2007 |
| WO | WO2007129161 | A2 | 11/2007 |
| WO | WO2008039218 | A2 | 4/2008 |
| WO | WO2008109943 | A1 | 9/2008 |
| WO | WO2008118802 | A1 | 10/2008 |
| WO | WO2008132601 | A1 | 11/2008 |
| WO | WO2009009116 | A2 | 1/2009 |
| WO | WO2009044273 | A2 | 4/2009 |
| WO | WO2009073620 | A2 | 6/2009 |
| WO | WO2009114512 | A1 | 9/2009 |
| WO | WO2009132238 | A2 | 10/2009 |
| WO | WO2010019570 | A2 | 2/2010 |
| WO | WO2010077634 | A1 | 7/2010 |
| WO | WO2011028683 | A1 | 3/2011 |
| WO | WO2011043371 | A1 | 4/2011 |
| WO | WO2011056652 | A1 | 5/2011 |
| WO | WO2011070024 | A1 | 6/2011 |
| WO | WO2011090760 | A1 | 7/2011 |
| WO | WO2011107553 | A1 | 9/2011 |
| WO | WO2011109400 | A2 | 9/2011 |
| WO | WO2011131407 | A1 | 10/2011 |
| WO | WO2011140249 | A2 | 11/2011 |
| WO | WO2012003281 | A2 | 1/2012 |
| WO | WO2012007375 | A1 | 1/2012 |
| WO | WO2012032433 | A1 | 3/2012 |
| WO | WO2012068546 | A1 | 5/2012 |
| WO | WO2012078559 | A2 | 6/2012 |
| WO | WO2012084704 | A1 | 6/2012 |
| WO | WO2012097013 | A1 | 7/2012 |
| WO | WO2012129258 | A1 | 9/2012 |
| WO | WO2012142237 | A1 | 10/2012 |
| WO | WO2012145493 | A1 | 10/2012 |
| WO | WO2013042137 | A1 | 3/2013 |
| WO | WO2013066729 | A1 | 5/2013 |
| WO | WO2013079174 | A1 | 6/2013 |
| WO | WO2013087699 | A1 | 6/2013 |
| WO | WO2013106535 | A1 | 7/2013 |
| WO | WO2013106612 | A1 | 7/2013 |
| WO | WO2013106614 | A1 | 7/2013 |
| WO | WO2013106641 | A1 | 7/2013 |
| WO | WO2013106643 | A2 | 7/2013 |
| WO | WO2013106646 | A2 | 7/2013 |
| WO | WO2013119716 | A1 | 8/2013 |
| WO | WO2013132044 | A1 | 9/2013 |
| WO | WO2013169264 | A1 | 11/2013 |
| WO | WO2014008218 | A1 | 1/2014 |
| WO | WO2014008992 | A1 | 1/2014 |
| WO | WO2014011902 | A1 | 1/2014 |
| WO | WO2014011906 | A2 | 1/2014 |
| WO | WO2014011911 | A2 | 1/2014 |
| WO | WO2014036357 | A1 | 3/2014 |
| WO | WO2014044622 | A1 | 3/2014 |
| WO | WO2014058685 | A1 | 4/2014 |
| WO | WO2014058691 | A1 | 4/2014 |
| WO | WO2014063061 | A1 | 4/2014 |
| WO | WO2014074660 | A1 | 5/2014 |
| WO | WO2014074675 | A1 | 5/2014 |
| WO | WO2014108452 | A1 | 7/2014 |
| WO | WO2014121931 | A1 | 8/2014 |
| WO | WO2014121942 | A1 | 8/2014 |
| WO | WO2014142237 | A1 | 9/2014 |
| WO | WO2014143672 | A1 | 9/2014 |
| WO | WO2015048281 | A1 | 4/2015 |
| WO | WO2015068856 | A1 | 5/2015 |
| WO | WO2015071393 | A1 | 5/2015 |
| WO | WO2015091426 | A1 | 6/2015 |
| WO | WO2015103453 | A1 | 7/2015 |
| WO | WO2015104662 | A1 | 7/2015 |
| WO | WO2015104688 | A1 | 7/2015 |
| WO | WO2015150995 | A1 | 10/2015 |
| WO | WO2015160845 | A2 | 10/2015 |
| WO | WO2015164374 | A1 | 10/2015 |
| WO | WO2015193846 | A1 | 12/2015 |
| WO | WO2016011390 | A1 | 1/2016 |
| WO | WO2016053769 | A1 | 4/2016 |
| WO | WO2016053770 | A1 | 4/2016 |
| WO | WO2016053771 | A1 | 4/2016 |
| WO | WO2016053772 | A1 | 4/2016 |
| WO | WO2016081679 | A1 | 5/2016 |
| WO | WO2016105518 | A1 | 6/2016 |
| WO | WO2016118666 | A1 | 7/2016 |
| WO | WO2016144844 | A1 | 9/2016 |
| WO | WO2016144846 | A1 | 9/2016 |
| WO | WO2016144847 | A1 | 9/2016 |
| WO | WO2016144848 | A1 | 9/2016 |
| WO | WO2016144849 | A1 | 9/2016 |
| WO | WO2016149668 | A1 | 9/2016 |
| WO | WO2016169989 | A1 | 10/2016 |
| WO | WO2016172560 | A1 | 10/2016 |
| WO | WO2016174183 | A1 | 11/2016 |
| WO | WO2016197032 | A1 | 12/2016 |
| WO | WO2016197114 | A1 | 12/2016 |
| WO | WO2016210034 | A1 | 12/2016 |
| WO | WO2017004133 | A1 | 1/2017 |
| WO | WO2017004134 | A1 | 1/2017 |
| WO | WO2017007612 | A1 | 1/2017 |

(56) References Cited

FOREIGN PATENT DOCUMENTS

WO WO2017009798 A1 1/2017
WO WO2017009806 A1 1/2017
WO WO2017011371 A1 1/2017
WO WO2017011590 A1 1/2017
WO WO2017030814 A1 2/2017
WO WO2017033093 A1 3/2017
WO WO2017049068 A1 3/2017
WO WO2017059280 A1 4/2017
WO WO2017079267 A1 5/2017
WO WO2017108723 A2 6/2017
WO WO2017117473 A1 7/2017
WO WO2017117474 A1 7/2017
WO WO2017127430 A1 7/2017
WO WO2017161119 A1 9/2017
WO WO2017176708 A1 10/2017
WO WO2017176957 A1 10/2017
WO WO2017176958 A1 10/2017
WO WO2017197036 A1 11/2017
WO WO2017197046 A1 11/2017
WO WO2017197051 A1 11/2017
WO WO2017197055 A1 11/2017
WO WO2017197056 A1 11/2017
WO WO2017201449 A1 11/2017
WO WO2017205762 A1 11/2017
WO WO2017205766 A1 11/2017
WO WO2017207385 A1 12/2017
WO WO2017211924 A1 12/2017
WO WO2018052058 A1 3/2018
WO WO2018089736 A1 5/2018
WO WO2018098367 A1 5/2018
WO WO2018119441 A1 6/2018
WO WO2018144649 A1 8/2018
WO WO2018209012 A1 11/2018
WO WO2018237026 A1 12/2018
WO WO2019043214 A1 3/2019
WO WO2019060693 A1 3/2019
WO WO2019060742 A1 3/2019
WO WO2019084026 A1 5/2019
WO WO2019084030 A1 5/2019
WO WO2019099868 A2 5/2019
WO WO2019099926 A1 5/2019
WO WO2019133531 A1 7/2019
WO WO2019140380 A1 7/2019
WO WO2019140387 A1 7/2019
WO WO2019160915 A1 8/2019
WO WO2019165229 A1 8/2019
WO WO2019236483 A1 12/2019
WO WO2020010177 A1 1/2020
WO WO2020010210 A1 1/2020
WO WO2020010227 A1 1/2020
WO WO2020018788 A1 1/2020
WO WO2020038415 A1 2/2020
WO WO2020041331 A1 2/2020
WO WO2020113233 A1 6/2020
WO WO2020251969 A1 12/2020
WO WO2020251971 A1 12/2020
WO WO2020251972 A1 12/2020
WO WO2020251974 A1 12/2020
WO WO2020264490 A1 12/2020
WO WO2020264499 A1 12/2020
WO WO2021011631 A1 1/2021
WO WO2021011634 A1 1/2021
WO WO2021011868 A1 1/2021
WO WO2021011871 A1 1/2021
WO WO2021053555 A1 3/2021
WO WO2021119159 A1 6/2021
WO WO2021127190 A1 6/2021
WO WO2021127278 A1 6/2021
WO WO2021127283 A2 6/2021
WO 2021158634 A1 8/2021
WO WO2021247897 A1 12/2021
WO WO2021247899 A1 12/2021
WO WO2021257914 A1 12/2021
WO WO2022174268 A1 8/2022
WO WO2022174269 A1 8/2022
WO WO2022236339 A1 11/2022
WO WO2023076556 A1 5/2023
WO WO2023137439 A1 7/2023
WO WO2024081893 A1 4/2024
WO WO2024129879 A1 6/2024
WO WO2025024305 A2 1/2025
WO WO2025080300 A1 4/2025

OTHER PUBLICATIONS

Berndsen et al., "New insights into ubiquitin E3 ligase mechanism," Nat Struct Mol Biol., 2014, 21(4):301-307.

Blake et al., "Studies with deuterated drugs," J Pharm Sci. 1975;64(3):367-391.

Boichenko et al., "A FRET-Based Assay for the Identification and Characterization of Cereblon Ligands," J Med Chem. 2016, 59(2):770-774.

Buckley et al., "IRAK-4 inhibitors. Part 1: a series of amides," Bioorg Med Chem Lett. 2008, 18(11):3211-3214.

Buckley et al., "IRAK-4 inhibitors. Part II: a structure-based assessment of imidazo[1,2-a]pyridine binding," Bioorg Med Chem Lett., 2008, 18(11):3291-3295.

Buckley et al., "IRAK-4 inhibitors. Part III: A series of imidazo [1,2-a]pyridines," Bioorg Med Chem Lett., 2008, 18(12):3656-3660.

Cameron et al., "Loss of Interleukin Receptor-Associated Kinase 4 Signaling Suppresses Amyloid Pathology and Alters Microglial Phenotype in a Mouse Model of Alzheimer's Disease," J Neurosci., 2012, 32(43):15112-23.

Cario, "Therapeutic Impact of Toll-like Receptors on Inflammatory Bowel Diseases: A Multiple-edged Sword," Inflamm Bowel Dis., 2008, 14(3):411-421.

CAS STN Abstract, RN 1787975-60-3 (Pub. Jun. 24, 2015).

CAS STN Abstract, RN 1795294-81-3 (Pub. Jul. 6, 2015).

CAS STN Abstract, RN 1795451-20-5 (Pub. Jul. 6, 2015).

CAS STN Abstract, RN 1795527-49-9 (Pub. Jul. 6, 2015).

CAS STN Abstract, RN 1871221-08-7 (Pub. Feb. 21, 2016).

CAS STN Abstract, RN 1878956-45-6 (Pub. Mar. 3, 2016).

CAS STN Abstract, RN 1878983-55-1 (Pub. Mar. 3, 2016).

CAS STN Abstract, RN 742039-47-0 (Pub. Sep. 10, 2004).

CAS STN Abstract, RN 779303-42-3 (Pub. Nov. 12, 2004).

Chang et al., "What is the functional role of the thalidomide binding protein cereblon?" Int J Biochem Mol Biol. 2011;2(3):287-94.

Charrier et al., "Desulfonylative Radical Ring Closure onto Aromatics. A Modular Route to Benzazepin-2-ones and 5-Arylpiperidin-2-ones," Org. Lett., 2012, 14(8):2018-2021.

Chaudhary et al., "Recent Advances in the Discovery of Small Molecule Inhibitors of Interleukin-1 Receptor-Associated Kinase 4 (IRAK4) as a Therapeutic Target for Inflammation and Oncology Disorders," J Med Chem., 2015, 58(1):96-110.

Chiang et al., "Immune Complex-Mediated Cell Activation from Systemic Lupus Erythematosus and Rheumatoid Arthritis Patients Elaborate Different Requirements for IRAK1/4 Kinase Activity across human Cell Types," J Immunol., 2011, 186(2):1279-1288.

Chou and Talalay, "Quantitative analysis of dose-effect relationships: the combined effects of multiple drugs or enzyme inhibitors," Adv Enzyme Regul. 1984, 22:27-55.

Cohen, "Targeting protein kinases for the development of anti-inflammatory drugs," Curr Opin Cell Biol., 2009, 21(2):17-24.

Connolly et al., "Complexities of TGF-beta Targeted Cancer Therapy," Int J Biol Sci., 2012, 8(7):964-978.

Contino-Pepin et al., "Preliminary biological evaluations of new thalidomide analogues for multiple sclerosis application," Bioorg Med Chem Lett., 2009, 19(3):878-881.

Crews, "Targeting the Undruggable Proteome: The Small Molecules of My Dreams," Chem Biol., 2010, 17(6):551-555.

Cushing et al., "Interleukin 1/Toll-like receptor-induced autophosphorylation activates interleukin 1 receptor-associated kinase 4 and controls cytokine induction in a cell type-specific manner," J Biol Chem. 2014, 289(15):10865-10875.

Cushing et al., "IRAK4 kinase controls Toll-like receptor induced inflammation through the transcription factor IRF5 in primary human monocytes," J Biol Chem. 2017, 292(45):18689-18698.

(56) References Cited

OTHER PUBLICATIONS

Dalbeth et al., "Hyperuricaemia and gout: state of the art and future perspectives," Ann Rheum Dis. 2014, 73(9):1598-600.
De Nardo et al. "Interleukin-1 receptor-associated kinase 4 (IRAK4) plays a dual role in myddosome formation and Toll-like receptor signaling," J Biol Chem. 2018, 293(39):15195-15207.
Degorce et al., "Optimization of permeability in a series of pyrrolotriazine inhibitors of IRAK4," Bioorg Med Chem., 2018, 26(4):913-924.
Deshaies and Joazeiro, "Ring domain E3 ubiquitin ligases," Annu Rev Biochem., 2009, 78:399-434.
Devi et al., "Medicinal Attributes of Imidazo[1,2-a]pyridine Derivatives: An Update," Curr Top Med Chem, 2016, 16(26):2963-2994.
Dinarello, "IL-1: Discoveries, controversies and future directions," Eur J Immunol. 2010, 40(3):599-606.
Dinarello, "Interleukin 1 and interleukin 18 as mediators of inflammation and the aging process," Am J Clin Nutr., 2006, 83(suppl):447S-455S.
Dinarello, "Interleukin-18 and the Pathogenesis of Inflammatory Diseases," Semin Nephrol., 2007, 27(1):98-114.
Dudhgaonkar et al., "Selective IRAK4 Inhibition Attenuates Disease in Murine Lupus Models and Demonstrates Steroid Sparing Activity," J Immunol., 2017, 198(3):1308-1319.
Dunne et al., "IRAK1 and IRAK4 Promote Phosphorylation, Ubiquitation, and Degradation of MyD88 Adaptor-like (Mal)," J Biol Chem., 2010, 285(24):18276-82.
El-Gamal et al., "Recent Advances of Colony-Stimulating Factor-1 Receptor (CSF-1R) Kinase and Its Inhibitors," J Med Chem., 2018, 61(13):5450-5466.
Fischer et al., "Structure of the DDB1-CRBN E3 ubiquitin ligase in complex with thalidomide," Nature, 2014, 512(7512):49-53.
Fisher et al., "The complexities inherent in attempts to decrease drug clearance by blocking sites of CYP-mediated metabolism," Curr Opin Drug Discov Devel., 2006, 9(1):101-109.
Flannery et al., "The interleukin-1 receptor-associated kinases: Critical regulators of innate immune signaling," Biochem Pharmacol. 2010, 80(12):1981-91.
Foster, "Deuterium isotope effects in the metabolism of drugs and xenobiotics: implications for drug design," Advances in Drug Research, 1985, 14:1-40.
Fukuto et al., "Determination of the mechanism of demethylenation of (methylenedioxy)phenyl compounds by cytochrome P450 using deuterium isotope effects," J Med Chem., 1991, 34(9):2871-2876.
Gearing, "Targeting toll-like receptors for drug development: a summary of commercial approaches," Immunol Cell Biol., 2007;85(6):490-494.
Geyer and Müller-Ladner, "Actual status of antiinterleukin-1 therapies in rheumatic diseases," Curr Opin Rheumatol. 2010;22(3):246-251.
Gottipati et al., "IRAK1: A critical signaling mediator of innate immunity," Cell Signal, 2008, 20(2):269-76.
Hagner et al., "CC-122, a pleiotropic pathway modifier, mimics an interferon response and has antitumor activity in DLBCL," Blood, 2015, 126(6):779-789.
Heightman et al., "Structure-Activity and Structure-Conformation Relationships of Aryl Propionic Acid Inhibitors of the Kelch-like ECH-Associated Protein 1/Nuclear Factor Erythroid 2-Related Factor 2 (KEAP1/NRF2) Protein-Protein Interaction," J. Med. Chem., 2019, 62(9):4683-4702.
Hennessy et al., "Targeting Toll-like receptors: emerging therapeutics?" Nat Rev Drug Discov., 2010, 9(4):293-307.
Hines et al., "MDM2-Recruiting Protac Offers Superior, Synergistic Antiproliferative Activity via Simultaneous Degradation of BRD4 and Stabilization of p53," Cancer Res., 2019, 79(1):251-262.
Hoffman et al., "Efficacy and Safety of Rilonacept (Interleukin-1 Trap) in Patients with Cryopyrin-Associated Periodic Syndromes," Arthritis Rheum., 2008, 58(8):2443-2445.
Iannello et al., "Role of Interleukin-18 in the Development and Pathogenesis of Aids," Aids Rev., 2009, 11(3):115-125.
Iconomou and Saunders, "Systematic approaches to identify E3 ligase substrates," Biochem J. 2016;473(22):4083-4101.
Iriyama et al., "Clinical significance of genetic mutations of CD79B, CARD11, MYD88, and EZH2 genes in diffuse large B-cell lymphoma patients" 53rd ASH Annual Meeting, San Diego, California, Dec. 10-13, 2011.
Ito et al., "Identification of a primary target of thalidomide teratogenicity," Science, 2010, 327(5971):1345-1350.
Kargbo, "Protac Degradation of IRAK4 for the Treatment of Cancer," ACS Med. Chem. Lett., 2019, 10(10):1370-1371.
Kelly et al., "Selective interleukin-1 receptor-associated kinase 4 inhibitors for the treatment of autoimmune disorders and lymphoid malignancy," J Exp Med., 2015, 212(13):2189-2201.
Kester et al., "Optimization of Benzodiazepinones as Selective Inhibitors of the X-Linked Inhibitor of Apoptosis Protein (XIAP) Second Baculovirus IAP Repeat (BIR2) Domain," J Med Chem., 2013, 56(20):7788-7803.
Kim et al., "A critical role for IRAK4 kinase activity in Toll-like receptor-mediated innate immunity," J Exp Med., 2007, 204(5):1025-1036.
Kondo et al., "Renoprotective effects of novel interleukin-1 receptor-associated kinase 4 inhibitor AS2444697 through anti-inflammatory action in 5/6 nephrectomized rats," Naunyn Schmiedebergs Arch Pharmacol., 2014, 387(10):909-919.
Kou et al., "Effects of RuPeng15 Powder (RPP15) on Monosodium Urate Crystal-Induced Gouty Arthritis in Rats," Evid Based Complement Alternat Med., 2015, 2015:527019.
Koziczak-Holbro et al., "IRAK-4 Kinase Activity Is Required for Interleukin-1 (IL-1) Receptor- and Toll-like Receptor 7-mediated Signaling and Gene Expression," J Biol Chem., 2007, 282(18):13552-13560.
Krönke et al., "Lenalidomide causes selective degradation of IKZF1 and IKZF3 in multiple myeloma cells" Science, 2014, 343(6168):301-305.
Ku et al., "Selective predisposition to bacterial infections in IRAK-4-deficient children: IRAK-4-dependent TLRs are otherwise redundant in protective immunity," J Exp Med., 2007, 204(10):2407-2422.
Kubo-Murai et al., "IRAK-4-dependent Degradation of IRAK-1 is a Negative Feedback Signal for TLR-mediated NF-kB Activation," J Biochem., 2008, 143(3):295-302.
Küppers, "IRAK inhibition to shut down TLR signaling in autoimmunity and MyD88-dependent lymphomas," J Exp Med., 2015, 212(13):2184.
Kushner et al., "Pharmacological uses and perspectives of heavy water and deuterated compounds," Can J Physiol Pharmacol., 1999, 77(2):79-88.
Lebakken et al., "A Fluorescence Lifetime Based Binding Assay to Characterize Kinase Inhibitors," J Biomol Screen. 2007, 12(6):828-841.
Lee et al., "Discovery of Clinical Candidate 1-{[2S,3S,4S)-3-ethyl-4-fluoro-5-oxopyrrolidin-2-yl]methoxy}-7-methoxyisoquinoine-6-carboxamide (PF-06650833), a Potent, Selective Inhibitor of Interleukin-1 Receptor Associated Kinase 4 9IRAK4), by Fragment-Based Drug Design," J Med Chem. 2017;60(13):5521-5542.
Li et al., "Genome-wide and functional annotation of human E3 ubiquitin ligases identifies MULAN, a mitochondrial E3 that regulates the organelle's dynamics and signaling, " PLoS One. 2008;3(1):e1487.
Li et al., "IRAK-4: A novel member of the IRAK family with the properties of an IRAK-kinase," Proc Natl Acad Sci USA., 2002, 99(8):5567-5572.
Li et al., "Targeting interleukin-1 receptor-associated kinase for human hepatocellular carcinoma," J Exp Clin Cancer Res., 2016, 35(1):140.
Li, "IRAK4 in TLR/IL-1R signaling: Possible clinical applications," Eur J Immunol., 2008, 38(3):614-618.
Lim et al., "Discovery of 5-Amino-N-(1H-pyrazol-4-yl)pyrazolo[1,5-a]pyrimidine-3-carboxamide Inhibitors of IRAK4," ACS Med Chem Lett. 2015, 6(6):683-688.
Lin et al., "Helical assembly in the MyD88-IRAK4-IRAK2 complex in TLR /IL-1R signalling," Nature, 2010, 465(7300):885-890.

(56) References Cited

OTHER PUBLICATIONS

Lu et al., "Discovery of a Keap1-dependent peptide PROTAC to knockdown Tau by ubiquitination-proteasome degradation pathway," Euro J Med Chem., 2018, 46:251-259.
Lu et al., "Hijacking the E3 Ubiquitin Ligase Cereblon to Efficiently Target BRD4," Chem Biol, 2015, 2(6):755-763.
Lu et al., "The myeloma drug lenalidomide promotes the cereblon-dependent destruction of Ikaros proteins," Science, 2014, 343(6168):305-309.
Lust et al., "Induction of a Chronic Disease State in patients With Smoldering of Indolent Multiple Myeloma by Targeting Interleukin 1ß-Induced Interleukin 6 Production and the Myeloma Proliferative Component," Mayo Clin Proc., 2009, 84(2):114-122.
Martinon et al., "Gout-associated uric acid crystals activate the NALP3 inflammasome," Nature, 2006, 440(7081):237-241.
Maschera et al., "Overexpression of an enzymatically inactive interleukin-1-receptor-associated kinase activates nuclear factor-kB," Biochem J., 1999, 339(Pt2):227-231.
Matyskiela et al., "A Cereblon Modulator (CC-220) with Improved Degradation of Ikaros and Aiolos," J Med Chem., 2018, 61(2):535-542.
McElroy et al., "Discovery and hit-to-lead optimization of 2,6-diaminopyrimidine Inhibitors of interleukin-1 receptor-associated kinase 4," Bioorg Med Chem Lett., 2015, 25(9):1836-1841.
McElroy et al., "Potent and Selective Amidopyrazole Inhibitors of IRAK4 That are Efficacious in a Rodent Model of Inflammation," ACS Med Chem Lett., 2015, 6(6):677-682.
Moynagh, "The Pellino Family: IRAK E3 ligases with emerging roles in innate immune signalling," Trends Immunol., 2009, 30(1):33-42.
Muller et al., "Amino-Substituted Thalidomide Analogs: Potent Inhibitors of TNF-? Production," Bioorg Med Chem Lett, 1999, 9(11):1625-1630.
Ngo et al., "Oncogenically active MYD88 mutations in human lymphoma," Nature, 2011, 470(7332):115-119.
Nunes et al., "Targeting IRAK4 for Degradation with PROTACTSs," ACS Med Chem Lett., 2019, 10(7):1081-1085.
Ohoka et al., "In Vivo Knockdown of Pathogenic Proteins via Specific and Nongenetic Inhibitor of Apoptosis Protein (IAP)-dependent Protein Erasers (SNIPERs)," J Bio Chem., 2017, 292(11):4556-4570.
Ohoka et al., "Development of Small Molecule Chimeras That Recruit AhR E3 Ligase to Target Proteins," ACS Chem. Biol., 2019, 14(12):2822-2832.
Okazaki et al., "A rheostat for immune responses: the unique properties of PD-1 and their advantages for clinical application," Nat. Immunol. 2013, 14(12):1212-1218.
Patra and Choi, "Recent Progress in the Molecular Recognition and Therapeutic Importance of Interleukin-1 Receptor-Associated Kinase 4," Molecules. 2016, 21(11):1529.
PCT International Preliminary Report on Patentability from PCT/US2018/067304, dated Jun. 30, 2020.
PCT International Preliminary Report on Patentability from PCT/US2019/040462, dated Jan. 21, 2021.
PCT International Search Report and Written Opinion from PCT/US2018/052181, dated Feb. 26, 2019.
PCT International Search Report and Written Opinion from PCT/US2018/052242, dated Jan. 30, 2019.
PCT International Search Report and Written Opinion from PCT/US2018/067304, dated Apr. 30, 2019.
PCT International Search Report and Written Opinion from PCT/US2019/013481, dated Mar. 15, 2019.
PCT International Search Report and Written Opinion from PCT/US2019/013491, dated Mar. 18, 2019.
PCT International Search Report and Written Opinion from PCT/US2019/040462, dated Sep. 20, 2019.
PCT International Search Report and Written Opinion from PCT/US2019/040520, dated Nov. 13, 2019.
PCT International Search Report and Written Opinion from PCT/US2019/040545, dated Oct. 21, 2019.
PCT International Search Report and Written Opinion from PCT/US2019/064070, dated Apr. 6, 2020.
PCT International Search Report and Written Opinion from PCT/US2020/026869, dated Jul. 27, 2020.
PCT International Search Report and Written Opinion from PCT/US2020/036913, dated Oct. 26, 2020.
PCT International Search Report and Written Opinion from PCT/US2020/036916, dated Oct. 26, 2020.
PCT International Search Report and Written Opinion from PCT/US2020/036918, dated Oct. 26, 2020.
PCT International Search Report and Written Opinion from PCT/US2020/036921, dated Oct. 26, 2020.
PCT International Search Report and Written Opinion from PCT/US2020/040101, dated Nov. 10, 2020.
PCT International Search Report and Written Opinion from PCT/US2020/040125, dated Nov. 13, 2020.
PCT International Search Report and Written Opinion from PCT/US2020/042105, dated Nov. 20, 2020.
PCT International Search Report and Written Opinion from PCT/US2020/042109, dated Dec. 10, 2020.
PCT International Search Report and Written Opinion from PCT/US2020/042530, dated Oct. 16, 2020.
PCT International Search Report and Written Opinion from PCT/US2020/042534, dated Oct. 26, 2020.
PCT International Search Report and Written Opinion from PCT/US2020/064061, dated Apr. 9, 2021.
PCT International Search Report and Written Opinion from PCT/US2020/065628, dated May 28, 2021.
PCT International Search Report and Written Opinion from PCT/US2020/065752, dated Mar. 25, 2021.
PCT International Search Report and Written Opinion from PCT/US2020/065757, dated May 28, 2021.
PCT International Search Report and Written Opinion from PCT/US2020/066859, dated Apr. 27, 2021.
PCT International Search Report and Written Opinion from PCT/US2021/062640, dated Feb. 25, 2022.
PCT International Search Report and Written Opinion from PCT/US2023/060645, dated Mar. 31, 2023.
PCT International Search Report and Written Opinion from PCT/US2021/035745, dated Sep. 27, 2021.
PCT International Search Report and Written Opinion from PCT/US2021/035747, dated Sep. 27, 2021.
PCT International Search Report and Written Opinion from PCT/US2022/070662, dated Apr. 18, 2022.
PCT International Search Report and Written Opinion from PCT/US2022/070664, dated May 3, 2022.
Picard et al., "Clinical features and outcome of patients with IRAK-4 and MyD88 deficiency," Medicine (Baltimore). 2010, 89(6):403-425.
Picard et al., "Inherited human IRAK-4 deficiency: an update," Immunol Res., 2007, 38(1-3):347-52.
Piya et al., "BRD4 Proteolysis Targeting Chimera (PROTAC) Leads to Sustained Degradation of BRD4 with Broad Activity Against Acute Leukemias and Overcomes Stroma Mediated Resistance by Modulating Surface Expression of CXCR4," Blood, 2016, 126(23): 675-676.
Powers et al., "Discovery and initial SAR of inhibitors of interleukin-1 receptor-associated kinase-4," Bioorg Med Chem Lett., 2006;16(11):2842-2845.
Priyadarshini et al., "Copper catalyzed oxidative cross-coupling of aromatic amines with 2-pyrrolidinone: a facile synthesis of N-aryl-r-amino-r-lactams," Tetrahedron. 2014, 70(36):6068-6074.
Pubmed Compound Summary for CID 101524675, "(2R)-3-Fluoro-2-(2-methylpropyl)-3-phenyl-1,3-azasilinan-6-one," U.S. National Library of Medicine, created Dec. 18, 2015, https://pubchem.ncbi.nlm.nih.gov/compound/101524675. Date Accessed: Sep. 5, 2019 (5 pages).
Pubmed Compound Summary for CID 102164987, "3-[(4S)-2,5-Dioxo-4-phenylimidazolidine-1-yl]-2,6-piperidinedione," U.S. National Library of Medicine, created Dec. 24, 2015, https://pubchem.ncbi.nlm.nih.gov/compound/102164987. Date Accessed: Feb. 25, 2020 (7 pages).

(56) References Cited

OTHER PUBLICATIONS

Pubmed Compound Summary for CID 110491408, 3-(5-Amino-2-oxo-3H-benzimidazol-1-yl)piperidine-2,6-dione, U.S. Library of Medicine, created Jan. 18, 2016, https://pubchem.ncbi.nlm.nih.gov/compound/110491408. Date Accessed: Feb. 25, 2020 (7 pages).
Pubmed Compound Summary for CID 110491555, 3-(6-Amino-2-oxo-3H-benzimidazol-1-yl)piperidine-2,6-dione, U.S. Library of Medicine, created Jan. 18, 2016, https://pubchem.ncbi.nlm.nih.gov/compound/110491555. Date Accessed: Feb. 25, 2020 (7 pages).
Pubmed Compound Summary for CID 115370667, "5-(2-Oxoimidazolidin-1-yl)piperidin-2-one." U.S. National Library of Medicine, created Oct. 22, 2012, https://pubchem.ncbi.nlm.nih.gov/compound/115370667. Date Feb. 25, 2020 (10 pages).
Pubmed Compound Summary for CID 138728787, "3-(6-Ethylpyrido[2,3-b]indol-9-yl)piperidine-2,6-dione," U.S. National Library of Medicine, created Jul. 20, 2019, https://pubchem.ncbi.nlm.nih.gov/compound/138728787. Sep. 5, 2019 (6 pages).
Pubmed Compound Summary for CID 17607528, "4-(Carbazol-9-ylmethyl)-1,3-oxazolidin-2-one," U.S. National Library of Medicine, Nov. 13, 2007, https://pubchem.ncbi.nlm.nih.gov/compound/17607528. Date Accessed: Feb. 25, 2020 (6 pages).
Pubmed Compound Summary for CID 5426, "Thalidomide," created Mar. 25, 2005.
Pubmed Compound Summary for CID 63661260, "5-[2-(1-Chloroethyl)benzimidazol-1-yl]piperidin-2-one," U.S. National Library of Medicine, created Oct. 22, 2012, https://pubchem.ncbi.nlm.nih.gov/compound/63661260. Date Accessed: Sep. 4, 2019 (6 pages).
Pubmed Compound Summary for CID 63661460, "6-Oxo-1-(6-oxopiperidin-3-yl)piperidine-3-carboxylic acid," U.S. National Library of Medicine, created Oct. 22, 2012, https://pubchem.ncbi.nlm.nih.gov/compound/63661460. Date Accessed: Feb. 25, 2020 (7 pages).
Pubmed Compound Summary for CID 65967733, "3-(2,5-Dioxo-3-phenylpyrrolidin-1-yl)piperidine-2,6-dione," U.S. National Library of Medicine, created Dec. 24, 2015, https://pubchem.ncbi.nlm.nih.gov/compound/65967733. Date Accessed: Feb. 25, 2020 (7 pages).
Pubmed Compound Summary for CID 65968760, "1-(2,6-Dioxopiperidin-3-yl)benzimidazole-5-carboxylic acid," U.S. National Library of Medicine, created Oct. 24, 2012, https://pubchem.ncbi.nlm.nih.gov/compound/65968760. Date Accessed: Sep. 4, 2019 (6 pages).
Pubmed Compound Summary for CID 67258040, "[1-(9H-Fluoren-9-yl)-1-(6-oxopiperidin-3-yl)ethyl] hydrogen carbonate," U.S. National Library of Medicine, Nov. 30, 2012, https://pubchem.ncbi.nlm.nih.gov/compound/67258040. Date Accessed: Feb. 25, 2020 (9 pages).
Pubmed Compound Summary for CID 83543479, "5(Aminomethyl)-5-(1H-indol-3-yl)piperidin-2-one," U.S. National Library of Medicine, created Oct. 20, 2014, https://pubchem.ncbi.nlm.nih.gov/compound/83543479. Date Accessed: Feb. 25, 2020 (6 pages).
Pubmed Compound Summary for CID 84036945, 1-Piperidin-3-yl-3H-indol-2-one, U.S. Library of Medicine, created Oct. 20, 2014, https://pubchem.ncbi.nlm.nih.gov/compound/84036945. Date Accessed: Feb. 25, 2020 (7 pages).
Pubmed Compound Summary for CID 86793742, 3-[(6-chloro-1H-1,3-benzodiazol-2-yl)sulfanyl]piperidine-2,6-dione, created Feb. 7, 2015, https://pubchem.ncbi.nlm.nih.gov/compound/86793742. Date Accessed: Jan. 10, 2022.
Pubmed Compound Summary for CID 91648396, 3-[(4-Fluorophenyl)sulfanyl]piperidine-2,6-dione, created Mar. 20, 2015, https://pubchem.ncbi.nlm.nih.gov/compound/91648396#section=Structures. Date Accessed: Jan. 10, 2022.
Pubmed Compound Summary for CID 99784232, (3S)-3-(4-fluorophenyl)sulfanylpiperidine-2,6-dione, created Dec. 11, 2015, https://pubchem.ncbi.nlm.nih.gov/compound/99784232. Date Accessed: Jan. 10, 2022.
Raina et al., "Chemical Inducers of Targeted Protein Degradation," J Biol Chem. 2010, 285(15):11057-110560.
Ramirez et al., "Defining causative factors contributing in the activation of hedgehog signaling in diffuse large B-cell lymphoma," Leuk. Res. 2012;36(10):1267-1273.
Rokosz et al., "Kinase inhibitors as drugs for chronic inflammatory and immunological diseases: progress and challenges," Expert Opin Ther Targets. 2008; 12(7):883-903.
Ronnebaum et al., "Synthesis of 1, 2, 3-triazole 'click' analogues of thalidomide," Tetrahedron. 2016;72(40): 6136-6141.
Ross et al., "Bispecific T cell engager (BITE®) antibody constructs can mediate bystander tumor cell killing," PLoS ONE. 2017; 12(8): e0183390.
Rostovtsev et al., "A Stepwise Huisgen Cycloaddition Process: Copper(I)-Catalyzed Regioselective "Ligation" of Azides and Terminal Alkynes," Angew Chem Int Ed Engl. 2002, 41(14):2596-2599.
Rusnac et al., "Recognition of the Diglycine C-End Degron by CRL2 KLHDC2 Ubiquitin Ligase," Mol. Cell. 2018, 72(5):813-822.e4.
Schnnekloth et al., "Chemical Approaches to Controlling Intracellular Protein Degradation," Chembiochem, 2005, 6(1):40-46.
Scott et al., "Discovery and Optimization of Pyrrolopyrimidine Inhibitors of Interleukin-1 Receptor Associated Kinase 4 (IRAK4) for the Treatment of Mutant MYD88L265P Diffuse Large B-Cell Lymphoma," J Med Chem. 2017, 60(24):10071-10091.
Seganish et al., "Discovery and Structure Enabled Synthesis of 2,6-diaminopyrimidine-4-one IRAK4 Inhibitors," ACS Med Chem Lett. 2015, 6(8):942-947.
Seganish et al., "Initial optimization and series evolution of diaminopyrimidine inhibitors of interleukin-1 receptor associated kinase 4," Bioorg Med Chem Lett. 2015, 25(16):3203-3207.
Seitz et al., "Sulfenylation and Halogenation of Di-and Trianions Derived from Substituted Glutarimides," Synthetic Communications, 1977, 7(6):367-374.
Sen et al., "Transcriptional signaling by double-stranded RNA: role of TLR3," Cytokine Growth Factor Rev., 2005, 16(1):1-14.
Shanmugasundaram et al., "A modular PROTAC design for target destruction using a degradation signal based on a single amino acid," J Biol Chem. 2019, 294(41):15172-15175.
Smith et al., "Identification of quinazoline based inhibitors of IRAK4 for the treatment of inflammation," Bioorg Med Chem Lett., 2017, 27(12):2721-2726.
So et al., "A pilot study of IL-1 inhibition by anakinra in acute gout," Arthritis Res Ther., 2007, 9(2):R28.
Song et al., "The kinase activities of interleukin-e receptor associated kinase (IRAK)-1 and 4 are redundant in the control of inflammatory cytokine expression in human cells," Mol Immunol. 2009, 46(7):1458-66.
Spradin et al., "Harnessing the Anti-Cancer Natural Product Nimbolide for Targeted Protein Degradation," Nature Chemical Biology, 2019, 15(7):747-755. (31 pages.).
Spratt et al., "RBR E3 ubiquitin ligases: new structures, new insights, new question," Biochem J., 2014, 458(3):421-437.
Stewart et al., "Efforts toward elucidating Thalidomide's molecular target: an expedient synthesis of the first Thalidomide biotin analogue," Organic & Biomolecular Chemistry, 2010, 8(18): 4059-4062.
Sun et al., "Carbohydrate and protein immobilization onto solid surfaces by sequential Diels-Alder and azide-alkyne cycloadditions," Bioconjug Chem., 2006, 17(1):52-57.
Suzuki et al., "IRAK-4 as the central TIR signaling mediator in innate immunity," Trends Immunol. 2002, 23(10):503-506.
Suzuki et al., "Severe impairment of interleukin-1 and Toll-like receptor signalling in mice lacking IRAK-4," Nature, 2002, 416(6882):750-756.
Swantek et al., "IL-1 Receptor-Associated Kinase Modulates Host Responsiveness to Endotoxin," Journal of Immunology, 2000, 164(8):4301-4316.
Terkeltaub et al., "The interleukin 1 inhibitor rilonacept in treatment of chronic gouty arthritis: results of a placebo-controlled, monosequence crossover, non-randomised, single-blind pilot study," Ann Rheum Dis. 2009, 68(10):1613-1617.
Terkeltaub, "Update on gout: new therapeutic strategies and options," Nat Rev Rheumatol. 2010, 6(1):30-38.
Tong et al., "Targeted Protein Degradation via a Covalent Reversible Degrader Based on Bardoxolone", ChemRxiv. First Posted Online: Apr. 2, 2020, 23 pages.

(56) References Cited

OTHER PUBLICATIONS

Toogood, "Small molecule immuno-oncology therapeutic agents," Bioorg. Med. Chem. Lett., 2018, 28(3):319-329.
Torres et al., "Hyperalgesia, synovitis and multiple biomarkers of inflammation are suppressed by interleukin 1 inhibition in a novel animal model of gouty arthritis," Ann Rheum Dis., 2009, 68(10):1602-1608.
Toure and Crews, "Small-Molecule PROTACS: New Approaches to Protein Degradation," Angew Chem Int Ed Engl., 2016, 55(6):1966-1973.
Treon et al., "Whole genome sequencing reveals a widely expressed mutation (MYD88 L265P) with oncogenic activity in Waldenström's Macroglobulinemia" 53rd ASH Annual Meeting, San Diego, California, Dec. 10-13, 2011 [abstract].
Trøseid et al., "The role of interleukin-18 in the metabolic syndrome," Cardiovasc Diabetol., 2010, 9:11.
Tumey et al., "Identification and optimization of indolo[2,3-c]quinoline inhibitors of IRAK4," Bioorg Med Chem Lett., 2014, 24(9):2066-2072.
Uehara et al., "Selective degradation of splicing factor CAPER? by anticancer sulfonamides," Nat Chem Biol., 2017, 13(6):675-680.
Varfolomeev et al., "IAP antagonists induce autoubiquitination of c-IAPs, NF-kappaB activation, and TNFalpha-dependent apoptosis," Cell, 2007, 131(4):669-681.
Vollmer et al., "The mechanism of activation of IRAK1 and IRAK4 by interleukin-1 and Toll-like receptor agonists," Biochem J., 2017, 474(12):2027-2038.
Wang et al., "Crystal Structure of IRAK-4 Kinase in Complex with Inhibitors: Serine/Threonine Kinase with Tyrosine as a Gatekeeper," Structure, 2006, 14(12):1835-1844.
Wang et al., "Discovery of potent, selective, and orally bioavailable inhibitors of interleukin-1 receptor-associated kinase 4," Bioorg Med Chem Lett, 2015, 25(23):5546-5550.
Wang et al., "IRAK-4 Inhibitors for Inflammation," Curr Top Med Chem., 2009, 9(8):724-37.
Wang et al., "Roles of F-box proteins in cancer," Nat Rev Cancer., 2014, 14(4):233-47.
Ward et al., "Covalent Ligand Screening Uncovers a RNF4 E3 Ligase Recruiter for Targeted Protein Degradation Applications," ACS Chem. Biol., 2019, 14(11):2430-2440 (24 pages).
Weaver, "Epidemiology of gout," Cleve Clin J Med., 2008, 75(Suppl 5):S9-12.
Winter et al., "Selective Target Protein Degradation via Phthalimide Conjugation," Science., 2015, 348(6241):1376-1381.
Xia and Chen, "Iron-catalyzed N-alkylation of azoles via cleavage of an sp3 C—H bond adjacent to a nitrogen atom," J Org Chem., 2012, 77(20):9366-9373.
Xu et al., "A somatic variant in MYD88 (L256P) revealed by whole genome sequencing differentiates lymphoplasmacytic lymphoma from marginal zone lymphomas" 53rd ASH Annual Meeting, San Diego, California, Dec. 10-13, 2011.
Yang et al., "Disruption of MYD88 pathway signaling leads to loss of constitutive IRAK1, NK-kB and JAK/STAT signaling and induces apoptosis of cells expressing the MYD88 L265P mutation in Waldenström's Macroglobulinemia" 53rd ASH Annual Meeting, San Diego, California, Dec. 10-13, 2011.
Yang et al., "Exploiting synthetic lethality for the therapy of ABC diffuse large B cell lymphoma," Cancer Cell, 2012, 21(6):723-737.
Zhang et al., "Constitutive IRAK4 Activation Underlies Poor Prognosis and Chemoresistance in Pancreatic Ductal Adenocarcinoma," Clin Cancer Res., 2017, 23(7):1748-1759.
Zhang et al., "Electrophilic PROTACs that degrade nuclear proteins by engaging DCAF16," Nature Chemical Biology, 2019, 15(7):737-746. (31 pages).
Zhou et al., "Targets of curcumin," Curr Drug Targets., 2011, 12(3):332-347.
Zinc 170596280, Date Added Aug. 8, 2015, https://zinc.docking.org/substances/ZINC000170596280/. Date Accessed: Jan. 10, 2022.
Zou et al., "PD-L1 (B7-H1) and PD-1 pathway blockage for cancer therapy: Mechanisms, response biomarkers, and combinations," Sci Transl. Med. 2016;8(328):328rv4.
PCT International Preliminary Report on Patentability from PCT/US2021/035745, dated Dec. 15, 2022, 6 pages.
PCT International Search Report received from PCT/US2023/061673, dated Jul. 25, 2023, 4 pages.
PCT International Search Report and Written Opinion from PCT/US2022/048163, dated Mar. 10, 2021, 11 pages.
PCT International Preliminary Report on Patentability from PCT/US2021/035747, dated Dec. 15, 2022, 6 pages.
Stieger et al., "Recrystallization of Active Pharmaceutical Ingredients", Crystallization—Science and Technology, 2012, pp. 183-201.
Ackerman et al., "Extended Data Fig. 1: Identification of KT-474 (SAR444656) as a potent and selective degrader of IRAK4. From: IRAK4 degrader in hidradenitis suppurativa and atopic dermatitis: a phase 1 trial", Nature Medicine, Retrieved from URL:https://www.nature.com/articles/s41591-023-02635-7/figures/5, 2023, pp. 1-3.
Ackerman et al., "IRAK4 degrader in hidradenitis suppurativa and atopic dermatitis: a phase 1 trial", Nature Medicine, Retrieved from: URL:https://www.nature.com/articles/s41591-023-02635-7.pdf>, 2023, 29:3127-3136.
Anonymous, "Kymera Therapeutics to Present Interim Results from a Non-Interventional Study Characterizing IRAK4 Expression and Demonstrating Proof of Mechanism of an IRAK4 Degrader in Patients with Hidradenitis Suppurativa", Kymera, Retrieved from: URL:https://www.globenewswire.com/news-release/2020/10/09/2106256/0/en/Kymera-Therapeutics-to-Present-Interim-Results-from-a-Non-Interventional-Study-Characterizing-IRAK4-Expression-and-Demonstrating-Proof-of-Mechanism-of-an-IRAK4-Degrader-in-Patients.html, Oct. 9, 2020, pp. 1-7.
Anonymous, "Targeted protein degradation: treating inflammatory diseases in a new way", Kymera, STAT—Reporting from the frontiers of health and medicine, Retrieved from: https://www.statnews.com/sponsor/2020/01/29/targeted-protein-degradation-treating-inflammatory-disease-in-a-new-way/, Jan. 29, 2020, pp. 1-53.
Campbell et al., "A First-in-Class Selective and Potent IRAK4 Degrader Demonstrates Robust in Vitro and in Vivo Inhibition of TLR/IL-1R Activation and Inflammation", ACR, Oral poster presentation Kymera Therapeutics, Nov. 11, 2019, 14 pages.
Campbell et al., "Abstract No. 1768: A First-in-class Selective and Potent IRAK4 Degrader Demonstrates Robust in Vitro and in Vivo Inhibition of TLR/IL-1R Activation and Inflammation", ACR/ARP Annual Meeting, Nov. 11, 2019, 2 pages.
Carabaza et al., "Targeting IRAK4 disrupts inflammatory pathways and delays tumor development in chronic lymphocytic leukemia", Blood, 2018, 132(Supplement 1):2650, 3 pages.
CAS Registry No. 2432994-31-3, KT474, Iuphar (Pub. 2024), 2 pages.
Ishida et al., "E3 Ligase Ligands for PROTACs: How They Were Found and How to Discover New Ones", SLAS Discovery, 2021, 26(4):484-502.
Lai et al., "Induced protein degradation: an emerging drug discovery paradigm", Nature Reviews, Drug Discovery, Feb. 2016, 16(2):101-114.
Mullard, "IRAK4 degrader to take on innate immunity", Nature Biotechnology, Nov. 2020, 38(11):1221-1233.
PRNewswire, "Kymera Therapeutics to Present Preclinical Data on its First-in-Class Selective and Potent Oral IRAK4 Degraders in Cutaneous Inflammation", Retrieved from: https://www.prnewswire.com/news-releases/kymera-therapeutics-to-present-preclinical-data-on-its-first-in-class-selective-and-potent-oral-irak4-degraders-in-cutaneous-inflammation-300998974.html, Feb. 5, 2020, pp. 1-3.
Slavin et al., "Abstract 588: Identification of highly potent and selective Interleukin-1 receptor associated kinase 4 (IRAK4) degraders for the treatment of hidradenitis suppurativa", Journal of Investigative Dermatology, 2020, 140(7):S80.
Slavin et al., "Identification of highly potent and selective Interlukin-1 receptor associated kinase 4 (IRAK4) degraders for the treatment of

(56) References Cited

OTHER PUBLICATIONS hidradenitis suppurativa", Kymera, retrieved from https://www.kymeratx.com/wp-content/uploads/2020/07/EHSF_Kymera_2020_Final.pdf, Feb. 2020, 1 page.
Steinebach et al., "A MedChem toolbox for cereblon-directed PROTACs", MedChemComm, 2019, 10(6):1037-1041.
International Preliminary Report on Patentability received for PCT Application No. PCT/US2019/064070, mailed on Jun. 10, 2021, 7 pages.
International Preliminary Report on Patentability received for PCT Application No. PCT/US2020/040101, mailed on Jan. 6, 2022, 8 pages.
International Preliminary Report on Patentability received for PCT Application No. PCT/US2020/040125, mailed on Jan. 6, 2022, 8 pages.
International Preliminary Report on Patentability received for PCT Application No. PCT/US2020/042530, mailed on Jan. 27, 2022, 6 pages.
International Preliminary Report on Patentability received for PCT Application No. PCT/US2020/064061, mailed on Jun. 23, 2022, 13 pages.
International Preliminary Report on Patentability received for PCT Application No. PCT/US2020/065628, mailed on Jun. 30, 2022, 9 pages.
International Preliminary Report on Patentability received for PCT Application No. PCT/US2020/065752, mailed on Jun. 30, 2022, 7 pages.
International Preliminary Report on Patentability received for PCT Application No. PCT/US2020/065757 mailed on Jun. 30, 2022, 9 pages.
International Preliminary Report on Patentability received for PCT Application No. PCT/US2021/016377, mailed on Aug. 18, 2022, 8 pages.
International Preliminary Report on Patentability received for PCT Application No. PCT/US2021/037952, mailed on Dec. 29, 2022, 9 pages.
International Preliminary Report on Patentability received for PCT Application No. PCT/US2022/048163, mailed on May 10, 2024, 8 pages.
International Preliminary Report on Patentability received for PCT Application No. PCT/US2022/070662, mailed on Aug. 24, 2023, 6 pages.
International Preliminary Report on Patentability received for PCT Application No. PCT/US2022/070664, mailed on Aug. 24, 2023, 7 pages.
International Preliminary Report on Patentability received for PCT Application No. PCT/US2022/072194, mailed on Nov. 16, 2023, 7 pages.
International Search Report and Written Opinion received for PCT Application No. PCT/US2021/016377, mailed on Jun. 15, 2021, 11 pages.
International Search Report and Written Opinion received for PCT Application No. PCT/US2021/037952, mailed on Sep. 29, 2021, 11 pages.
International Search Report and Written Opinion received for PCT Application No. PCT/US2022/072194, mailed on Sep. 6, 2022, 10 pages.
International Search Report and Written Opinion received for PCT Application No. PCT/US2023/076862, mailed on Feb. 27, 2024, 12 pages.
International Search Report and Written Opinion received for PCT Application No. PCT/US2023/083863, mailed on Apr. 2, 2024, 10 pages.
International Search Report and Written Opinion received for PCT Application No. PCT/US2024/038827, mailed on Apr. 2, 2025, 11 pages.
U.S. Appl. No. 19/027,791 of Mainolfi et al., filed on Jan. 17, 2025.
U.S. Appl. No. 19/138,326 of Gollob et al., filed on Jun. 12, 2025.
U.S. Appl. No. 19/178,057 of Weiss et al., filed on Apr. 14, 2025.

* cited by examiner

DEUTERATED IRAK DEGRADERS AND USES THEREOF

CROSS-REFERENCE TO RELATED APPLICATIONS

This application is a national stage filing under U.S.C. § 371 of PCT International Application PCT/US2021/035745, filed Jun. 3, 2021, which claims the benefit of U.S. Provisional Application No. 63/033,959, filed Jun. 3, 2020, the entirety of each of which is hereby incorporated by reference.

TECHNICAL FIELD OF THE INVENTION

The present invention provides deuterium-enriched compounds and methods useful for the modulation of one or more interleukin-1 receptor-associated kinases ("IRAK") via ubiquitination and/or degradation by compounds according to the present invention. The invention also provides pharmaceutically acceptable compositions comprising the deuterium-enriched compounds of the present invention and methods of using said compositions in the treatment of various disorders.

BACKGROUND OF THE INVENTION

Ubiquitin-Proteasome Pathway (UPP) is a critical pathway that regulates key regulator proteins and degrades misfolded or abnormal proteins. UPP is central to multiple cellular processes, and if defective or imbalanced, it leads to pathogenesis of a variety of diseases. The covalent attachment of ubiquitin to specific protein substrates is achieved through the action of E3 ubiquitin ligases.

There are over 600 E3 ubiquitin ligases which facilitate the ubiquitination of different proteins in vivo, which can be divided into four families: HECT-domain E3s, U-box E3s, monomeric RING E3s and multi-subunit E3s. See generally Li et al. (PLOS One, 2008, 3, 1487) titled "Genome-wide and functional annotation of human E3 ubiquitin ligases identifies MULAN, a mitochondrial E3 that regulates the organelle's dynamics and signaling."; Berndsen et al. (Nat. Struct. Mol. Biol., 2014, 21, 301-307) titled "New insights into ubiquitin E3 ligase mechanism"; Deshaies et al. (Ann. Rev. Biochem., 2009, 78, 399-434) titled "RING domain E3 ubiquitin ligases."; Spratt et al. (Biochem. 2014, 458, 421-437) titled "RBR E3 ubiquitin ligases: new structures, new insights, new questions."; and Wang et al. (Nat. Rev. Cancer., 2014, 14, 233-347) titled "Roles of F-box proteins in cancer."

UPP plays a key role in the degradation of short-lived and regulatory proteins important in a variety of basic cellular processes, including regulation of the cell cycle, modulation of cell surface receptors and ion channels, and antigen presentation. The pathway has been implicated in several forms of malignancy, in the pathogenesis of several genetic diseases (including cystic fibrosis, Angelman's syndrome, and Liddle syndrome), in immune surveillance/viral pathogenesis, and in the pathology of muscle wasting. Many diseases are associated with an abnormal UPP and negatively affect cell cycle and division, the cellular response to stress and to extracellular modulators, morphogenesis of neuronal networks, modulation of cell surface receptors, ion channels, the secretory pathway, DNA repair and biogenesis of organelles.

Aberrations in the process have recently been implicated in the pathogenesis of several diseases, both inherited and acquired. These diseases fall into two major groups: (a) those that result from loss of function with the resultant stabilization of certain proteins, and (b) those that result from gain of function, i.e. abnormal or accelerated degradation of the protein target.

The UPP is used to induce selective protein degradation, including use of fusion proteins to artificially ubiquitinate target proteins and synthetic small-molecule probes to induce proteasome-dependent degradation. Bifunctional compounds composed of a target protein-binding ligand and an E3 ubiquitin ligase ligand, induced proteasome-mediated degradation of selected proteins via their recruitment to E3 ubiquitin ligase and subsequent ubiquitination. These drug-like molecules offer the possibility of temporal control over protein expression. Such compounds are capable of inducing the inactivation of a protein of interest upon addition to cells or administration to an animal or human, and could be useful as biochemical reagents and lead to a new paradigm for the treatment of diseases by removing pathogenic or oncogenic proteins (Crews C, Chemistry & Biology, 2010, 17(6):551-555; Schnnekloth J S Jr., Chembiochem, 2005, 6(1):40-46).

An ongoing need exists in the art for effective treatments for disease, especially autoinflammatory and autoimmune diseases with high unmet medical need. However, non-specific effects, and the inability to target and modulate certain classes of proteins altogether, such as transcription factors, remain as obstacles to the development of effective anti-cancer agents. As such, small molecule therapeutic agents that leverage E3 ligase mediated protein degradation to target disease-associated proteins such as interleukin-1 receptor-associated kinases ("IRAK") hold promise as therapeutic agents. Accordingly, there remains a need to find compounds that are IRAK degraders useful as therapeutic agents.

Many potential drugs suffer from poor absorption, distribution, metabolism and/or excretion (ADME) properties that prevent their wider use or limit their use in certain indications. A potentially attractive strategy for improving a drug's metabolic properties is deuterium enrichment. Replacing one or more hydrogen atoms with deuterium atoms may result in an improved metabolic profile and reduce unwanted degradation of the compound. Deuterium is a safe, stable, non-radioactive isotope of hydrogen. Compared to hydrogen, deuterium forms a stronger bond with carbon. In some cases, the increased bond strength imparted by deuterium can positively impact the ADME properties of a drug, creating the potential for improved drug efficacy, safety, and/or tolerability. At the same time, because the size and shape of deuterium are essentially identical to those of hydrogen, replacement of hydrogen by deuterium would not be expected to affect the biochemical potency and selectivity of the drug as compared to the original chemical entity that contains only hydrogen.

Over recent decades, the effects of deuterium substitution on the rate of metabolism have been reported for a very small percentage of approved drugs (see, e.g., Blake, M. I. et al., J Pharm Sci, 1975, 64:367-91; Foster, A. B., Adv Drug Res, 1985, 14:1-40 ("Foster"); Kushner, D. J. et al., Can J Physiol Pharmacol, 1999, 79-88; Fisher, M. B. et al., Curr Opin Drug Discov Devel, 2006, 9:101-09 ("Fisher")). The results have been variable and unpredictable. For some compounds, deuteration caused decreased metabolic clearance in vivo. For others, there was no change in metabolism. Still others demonstrated increased metabolic clearance. The variability in deuterium effects has also led experts to question or dismiss deuterium modification as a viable drug design strategy for inhibiting adverse metabolism (see Foster at p. 35 and Fisher at p. 101).

The effects of deuterium modification on a drug's metabolic properties are not predictable even when deuterium atoms are incorporated at known sites of metabolism. Only by actually preparing and testing a deuterated drug can one determine if and how the rate of metabolism will differ from that of its non-deuterated counterpart. See, for example, Fukuto et al. (J. Med. Chem., 1991, 34, 2871-76). Many drugs have multiple sites where metabolism is possible. The site(s) where deuterium substitution is required and the extent of deuteration necessary to see an effect on metabolism, if any, will be different for each drug.

The present invention addresses the need for improved IRAK degraders and provides additional advantages.

SUMMARY OF THE INVENTION

The present application provides novel bifunctional compounds, which function to recruit IRAK kinases to E3 ubiquitin ligase for degradation, and methods of preparation and uses thereof. In particular, the present disclosure provides deuterium-enriched bifunctional compounds, which find utility as modulators of targeted ubiquitination of IRAK kinases, which are then degraded and/or otherwise inhibited by the bifunctional compounds as described herein.

It has now been found that deuterium-enriched IRAK degraders, such as the deuterium-enriched analogs, pharmaceutically acceptable salts thereof, and pharmaceutically acceptable compositions thereof, are effective for use in treating IRAK-mediated diseases, disorders, and conditions, such as those described herein. In one aspect, the present invention provides a compound of formula I:

or a pharmaceutically acceptable salt thereof, wherein:

each of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{28}$, $R^{29}$, $R^{30}$, $R^{31}$, $R^{32}$, $R^{33}$, $R^{34}$, $R^{35}$, $R^{36}$, $R^{37}$, $R^{38}$, $R^{39}$, $R^{40}$, $R^{41}$, $R^{42}$, $R^{43}$, $R^{44}$, $R^{45}$, $R^{46}$, $R^{47}$, $R^{48}$, and $R^{49}$ is as defined herein.

Compounds of the present invention, and pharmaceutically acceptable compositions thereof, are useful for treating a variety of diseases, disorders or conditions, associated with regulation of signaling pathways implicating IRAK kinases. Such diseases, disorders, or conditions include those described herein.

Compounds provided by this invention are also useful for the study of IRAK enzymes in biological and pathological phenomena; the study of intracellular signal transduction pathways occurring in bodily tissues; and the comparative evaluation of new IRAK inhibitors or IRAK degraders or other regulators of kinases, signaling pathways, and cytokine levels in vitro or in vivo.

DETAILED DESCRIPTION OF THE INVENTION

1. General Description of Certain Aspects of the Invention

The present invention provides compounds, compositions, and methods for treatment, prevention, and/or reduction of a risk of diseases, disorders, or conditions such as those mediated by IRAK or a mutant thereof. In some embodiments, such compounds include those of the formulae described herein, or a pharmaceutically acceptable salt thereof, wherein each variable is as defined herein and described in embodiments. In some embodiments, a provided compound degrades and/or inhibits IRAK4.

In one aspect, the present invention provides a compound of formula I:

I

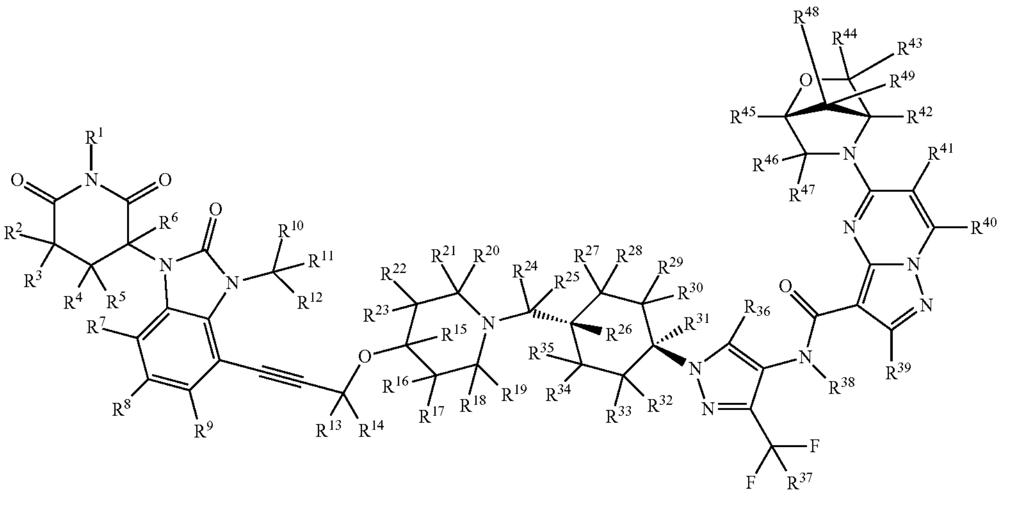

I

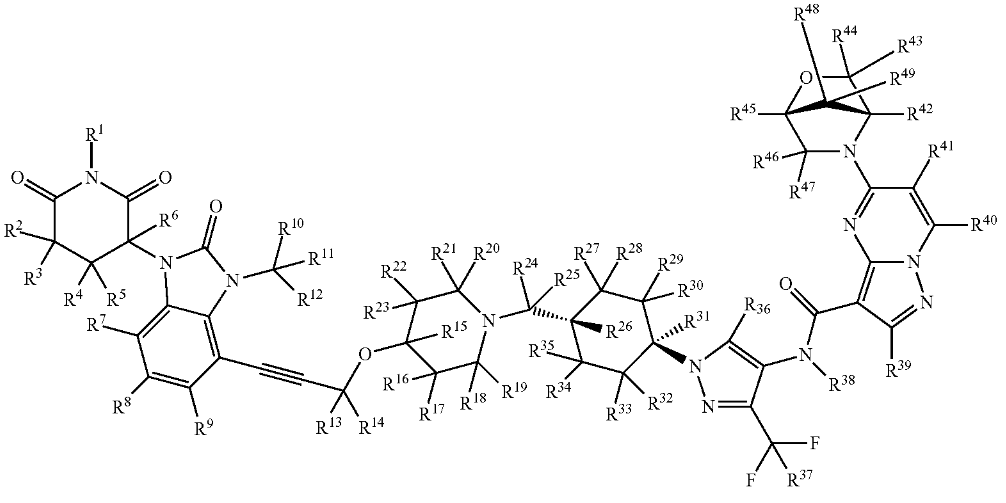

or a pharmaceutically acceptable salt thereof, wherein:

each of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{28}$, $R^{29}$, $R^{30}$, $R^{31}$, $R^{32}$, $R^{33}$, $R^{34}$, $R^{35}$, $R^{36}$, $R^{37}$, $R^{38}$, $R^{39}$, $R^{40}$, $R^{41}$, $R^{42}$, $R^{43}$, $R^{44}$, $R^{45}$, $R^{46}$, $R^{47}$, $R^{48}$, and $R^{49}$ is independently H or D, provided that at least one of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{28}$, $R^{29}$, $R^{30}$, $R^{31}$, $R^{32}$, $R^{33}$, $R^{34}$, $R^{35}$, $R^{36}$, $R^{37}$, $R^{38}$, $R^{39}$, $R^{40}$, $R^{41}$, $R^{42}$, $R^{43}$, $R^{44}$, $R^{45}$, $R^{46}$, $R^{47}$, $R^{48}$, and $R^{49}$ is D.

2. Definitions

The term "compound" refers to a quantity of molecules that is sufficient to be weighed, tested for its structural identity, and to have a demonstrable use (e.g., a quantity that can be shown to be active in an assay, an in vitro test, or in vivo test, or a quantity that can be administered to a patient and provide a therapeutic benefit).

Deuterium (D or $^2H$) is a stable, non-radioactive isotope of hydrogen and has an atomic weight of 2.0144. Hydrogen naturally occurs as a mixture of the isotopes $^1H$ (hydrogen or protium), D (2H or deuterium), and T (3H or tritium). The natural abundance of deuterium is 0.015%. One of ordinary skill in the art recognizes that in all chemical compounds with a H atom, the H atom actually represents a mixture of Hand D, with about 0.0150% being D. Thus, compounds with a level of deuterium that has been enriched to be greater than its natural abundance of 0.015% should be considered unnatural and, as a result, novel, over their non-enriched counterparts.

All percentages given for the amount of deuterium present are mole percentages.

It can be quite difficult in the laboratory to achieve 100% deuteration at any one site of a lab scale amount of compound (e.g., milligram or greater). When 100% deuteration is recited or a deuterium atom is specifically shown in a structure, it is assumed that a small percentage of hydrogen may still be present. Deuterium-enrichment can be achieved by either exchanging protons with deuterium or by synthesizing the molecule with enriched starting materials.

Unless indicated otherwise, when a D is specifically recited at a position or is shown in a formula, this D represents a mixture of hydrogen and deuterium where the amount (incorporation, abundance or enrichment) of deuterium is about 50% or greater. In some embodiments, the amount (incorporation, abundance or enrichment) of deuterium is about 100% (i.e., the % incorporation of deuterium ranges from greater than 90% up to 100%). In certain embodiments, the incorporation of deuterium in D is from 95% to 100%, or from 97% to 100%. As used herein in the context of deuterium enrichment, the term "about" means±2%. In compounds provided by the present invention, any atom not designated as deuterium is present at its natural isotopic abundance, unless indicated otherwise.

The term "patient" refers to organisms to be treated by the methods of the present invention. Such organisms preferably include, but are not limited to, mammals (e.g., murines, simians, equines, bovines, porcines, canines, felines, and the like). In some embodiments, the patient is a human.

As used herein, the term "effective amount" refers to the amount of a compound sufficient to effect beneficial or desired results. An effective amount can be administered in one or more administrations, applications or dosages and is not intended to be limited to a particular formulation or administration route. As used herein, the term "treating" includes any effect, e.g., lessening, reducing, modulating, ameliorating or eliminating, that results in the improvement of the condition, disease, disorder, and the like, or ameliorating a symptom thereof.

"Therapeutically effective amount" includes an amount of a compound of the invention that is effective when administered alone or in combination to treat the desired condition or disorder. "Therapeutically effective amount" includes an amount of a combination of compounds claimed that is effective to treat the desired condition or disorder. The combination of compounds can be additive and is preferably a synergistic combination. Synergy, as described, for example, by Chou and Talalay, Adv. Enzyme Regul. 1984, 22:27-55, occurs when the effect of the compounds when administered in combination is greater than the additive effect of the compounds when administered alone as a single agent. In general, a synergistic effect is most clearly demonstrated at sub-optimal concentrations of the compounds. Synergy can be in terms of lower incidence of adverse side effects and/or toxicity, increased efficacy, or some other beneficial effect of the combination compared with the individual components.

The invention provides deuterium-enriched compounds and pharmaceutically acceptable salts thereof, pharmaceutical compositions thereof, and methods of treating a disease, disorder, or condition using a deuterium-enriched compound or pharmaceutically acceptable salt thereof described herein. The deuterium-enriched compounds described herein contain deuterium enrichment at one or more positions. Deuterium enrichment at a chiral center of the compound may reduce the rate at which the two enantiomers of the compound may interconvert. Further, the deuterium-enriched compounds may be provided in enantiomerically pure form. These features are contemplated to provide therapeutic agents with improved properties.

Compounds of this invention include those described generally above, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, 75$^{th}$ Ed. Additionally, general principles of organic chemistry are described in *Organic Chemistry*, Thomas Sorrell, University Science Books, Sausalito: 1999, and *March's Advanced Organic Chemistry,* 5$^{th}$ Ed., Ed.: Smith, M. B. and March, J., John Wiley & Sons, New York: 2001, the entire contents of which are hereby incorporated by reference.

As used herein, the term "provided compound" refers to any genus, subgenus, and/or species set forth herein.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in J. Pharmaceutical Sciences, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, pivalate, propionate, stearate, succinate, sulfate, tartrate, thiocyanate, p-toluenesulfonate, undecanoate, valerate salts, and the like.

Salts derived from appropriate bases include alkali metal, alkaline earth metal, ammonium and $N^+(C_{1-4}alkyl)_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

Unless otherwise stated, structures depicted herein are also meant to include all isomeric (e.g., enantiomeric, diastereomeric, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention.

As used herein, the term "inhibitor" is defined as a compound that binds to and/or inhibits an IRAK kinase with measurable affinity. In certain embodiments, an inhibitor has an $IC_{50}$ and/or binding constant of less than about 50 μM, less than about 1 μM, less than about 500 nM, less than about 100 nM, less than about 10 nM, or less than about 1 nM.

As used herein, the term "degrader" is defined as a heterobifunctional compound that binds to and/or inhibits both an IRAK kinase and an E3 ligase with measurable affinity resulting in the ubiqitination and subsequent degradation of the IRAK kinase. In certain embodiments, a degrader has an $DC_{50}$ of less than about 50 μM, less than about 1 μM, less than about 500 nM, less than about 100 nM, less than about 10 nM, or less than about 1 nM.

The terms "measurable affinity" and "measurably inhibit," as used herein, means a measurable change in an IRAK protein kinase activity between a sample comprising a compound of the present invention, or composition thereof, and an IRAK protein kinase, and an equivalent sample comprising an IRAK protein kinase, in the absence of said compound, or composition thereof.

3. Description of Exemplary Compounds

Complete deuteration, or 100% deuteration, at any one site can be difficult to achieve in the laboratory. When a deuterium atom is indicated at a given site on any compound described herein, it is understood that a small percentage of hydrogen may still be present. Such compounds are said to be enriched with deuterium. Typically, deuterium-enriched compounds are prepared via chemical synthesis utilizing appropriately enriched starting materials or by exchange of H atoms for D atoms using deuterium-containing reagents. As used herein, the terms "deuterium-enriched" or "deuterium enrichment" refer to a compound, or a particular site of said compound, which comprises deuterium in an amount that is greater than its natural isotopic abundance (0.015%). Accordingly, in some embodiments, the present invention provides compounds comprising deuterium at a given site, wherein the percentage or level of deuterium incorporation is greater than its natural isotopic abundance.

According to one aspect, the present invention provides a compound of formula I:

I

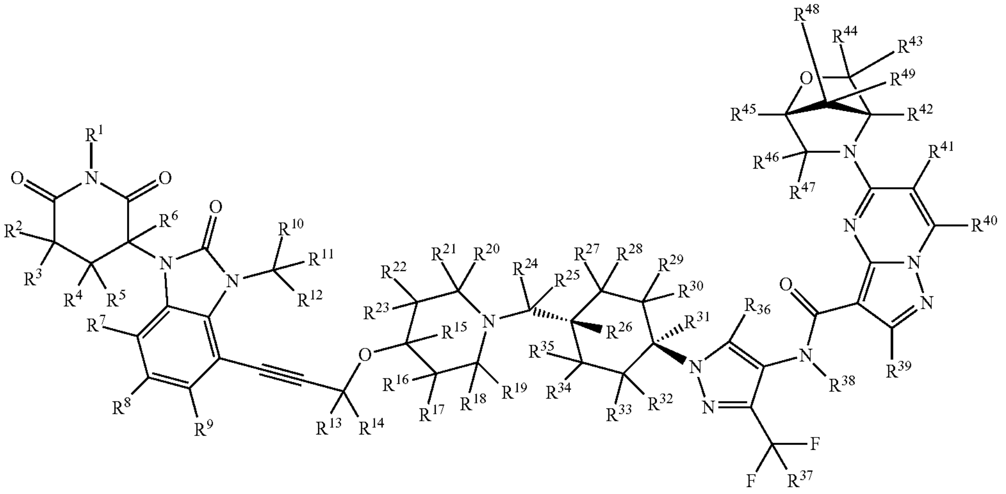

or a pharmaceutically acceptable salt thereof, wherein:

each of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{28}$, $R^{29}$, $R^{30}$, $R^{31}$, $R^{32}$, $R^{33}$, $R^{34}$, $R^{35}$, $R^{36}$, $R^{37}$, $R^{38}$, $R^{39}$, $R^{40}$, $R^{41}$, $R^{42}$, $R^{43}$, $R^{44}$, $R^{45}$, $R^{46}$, $R^{47}$, $R^{48}$, and $R^{49}$ is independently H or D, provided that at least one of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{28}$, $R^{29}$, $R^{30}$, $R^{31}$, $R^{32}$, $R^{33}$, $R^{34}$, $R^{35}$, $R^{36}$, $R^{37}$, $R^{38}$, $R^{39}$, $R^{40}$, $R^{41}$, $R^{42}$, $R^{43}$, $R^{44}$, $R^{45}$, $R^{46}$, $R^{47}$, $R^{48}$, and $R^{49}$ is D.

In some embodiments, at least one of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{28}$, $R^{29}$, $R^{30}$, $R^{31}$, $R^{32}$, $R^{33}$, $R^{34}$, $R^{35}$, $R^{36}$, $R^{37}$, $R^{38}$, $R^{39}$, $R^{40}$, $R^{41}$, $R^{42}$, $R^{43}$, $R^{44}$, $R^{45}$, $R^{46}$, $R^{47}$, $R^{48}$, and $R^{49}$ is D.

In some embodiments, the present invention provides a compound of Formula I-a, I-b, I-c, I-d, I-e, I-f, I-g, I-h, I-i, I-j, or I-k:

I-a

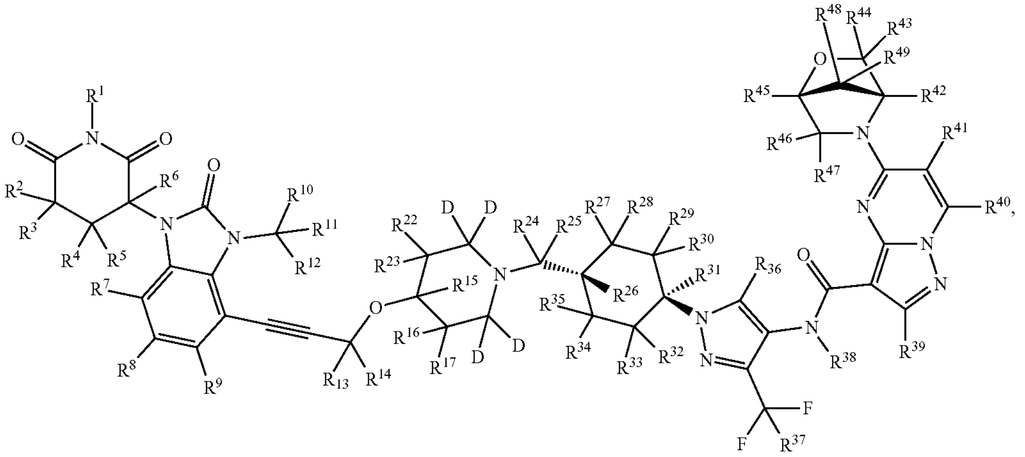

-continued
I-b
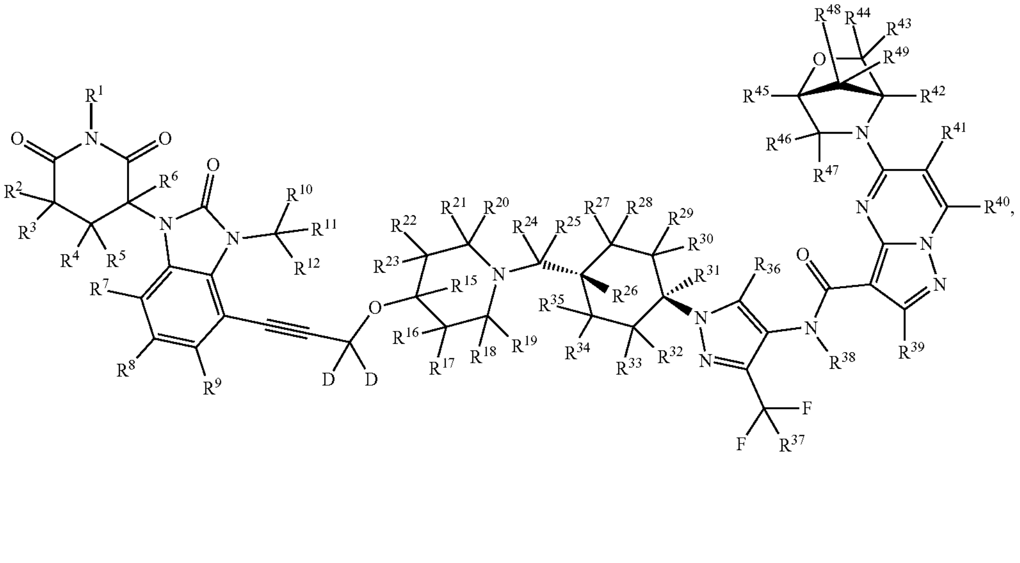
I-c
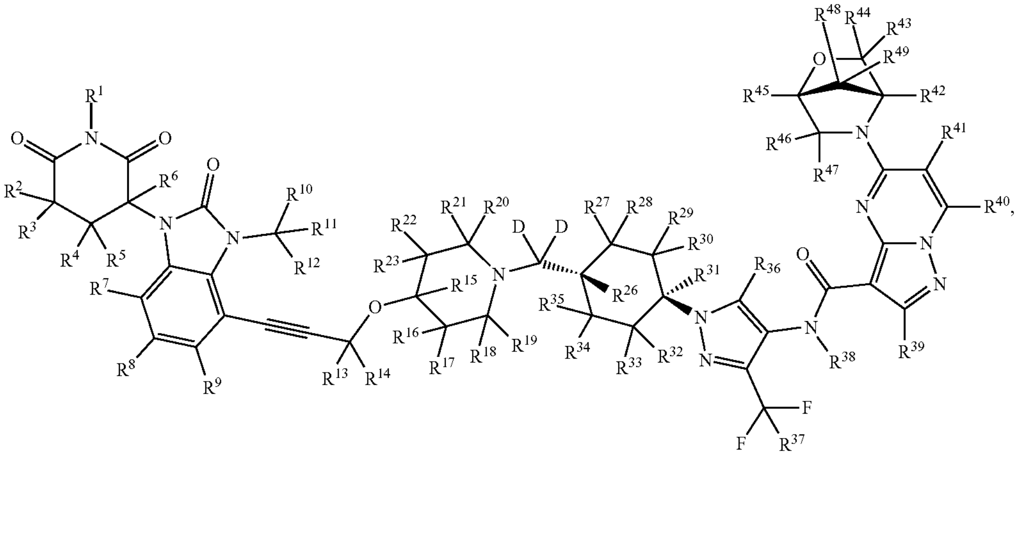
I-d
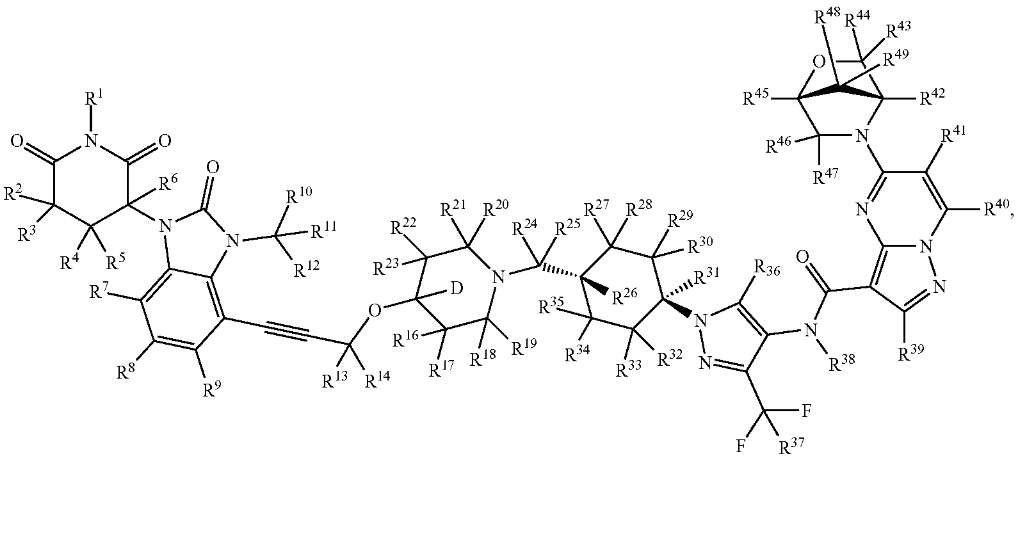

-continued
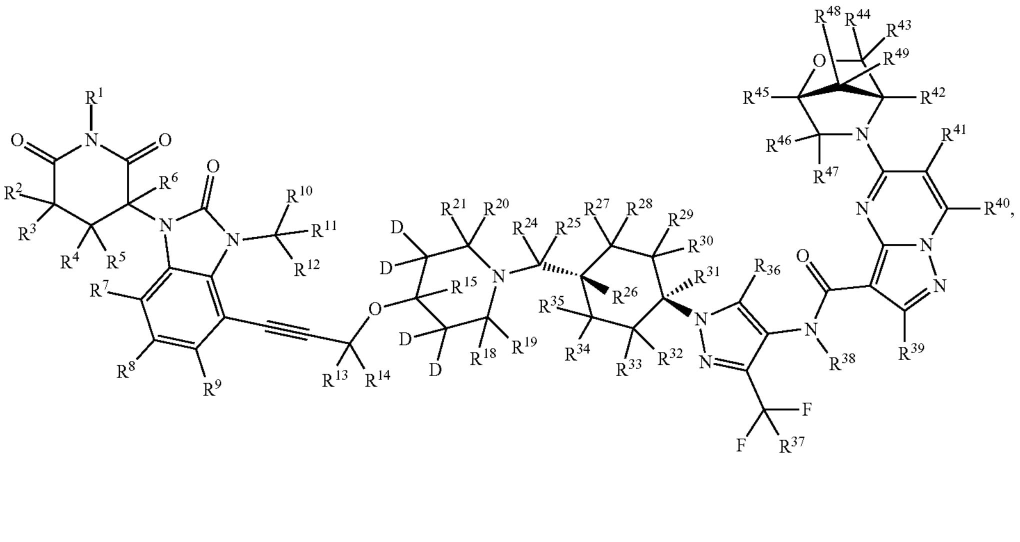
I-e
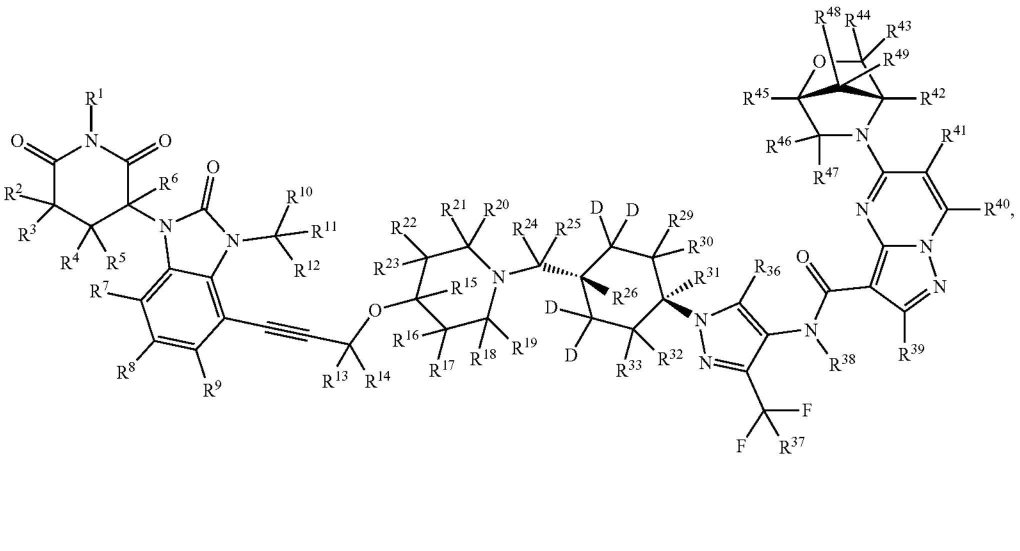
I-f
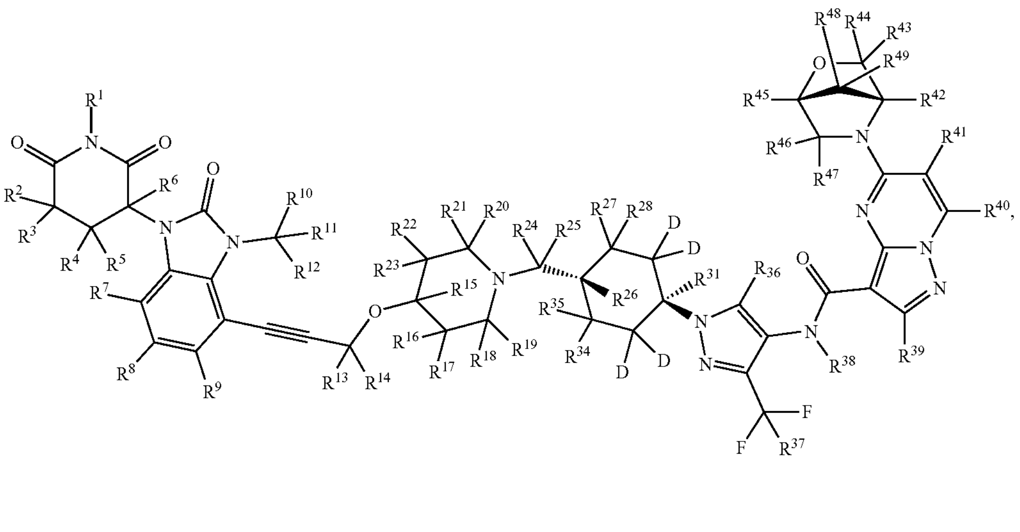
I-g

-continued
I-h
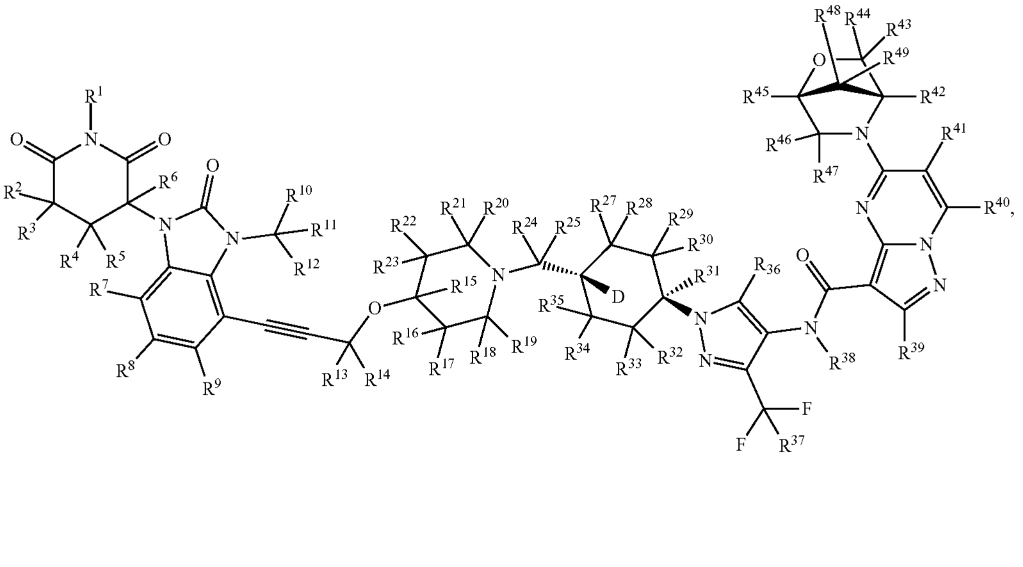
I-i
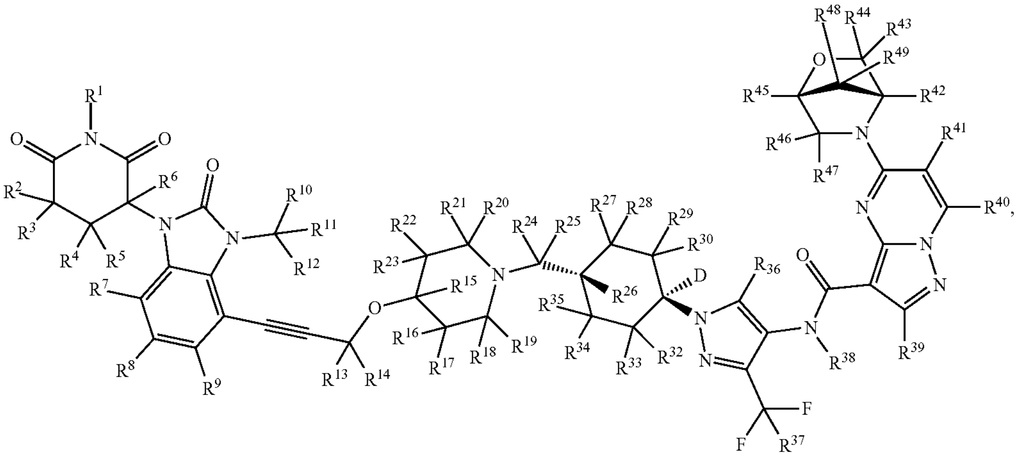
I-j
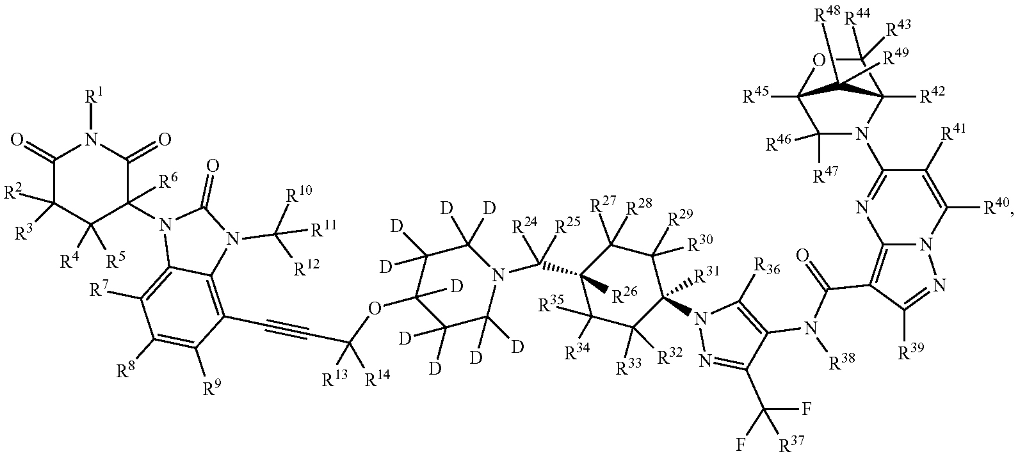

-continued

I-k

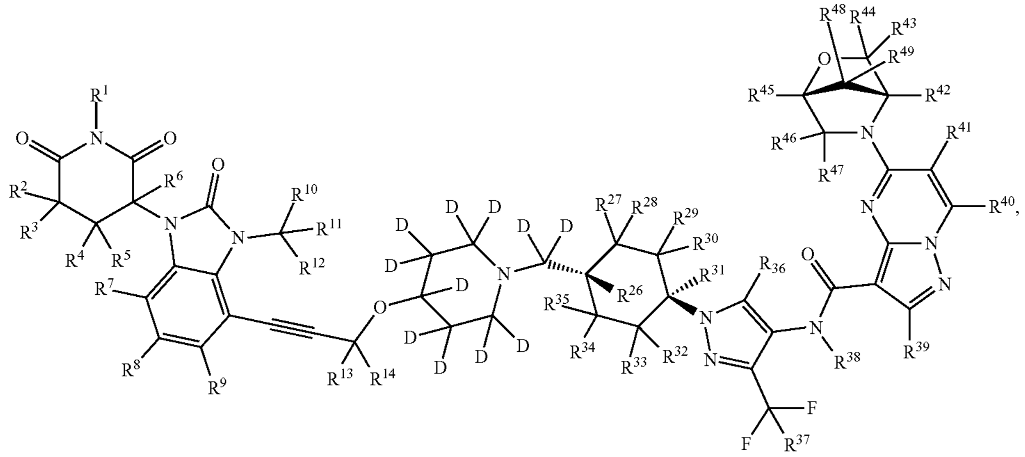

or a pharmaceutically acceptable salt thereof, wherein each variable is as defined herein, either singly or in combination.

The following embodiments are applicable to each of the preceding formulae.

As defined above and described herein, $R^1$ is H or D.

In some embodiments, $R^1$ is H. In some embodiments, $R^1$ is H and at least one of $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{28}$, $R^{29}$, $R^{30}$, $R^{31}$, $R^{32}$, $R^{33}$, $R^{34}$, $R^{35}$, $R^{36}$, $R^{37}$, $R^{38}$, $R^{39}$, $R^{40}$, $R^{41}$, $R^{42}$, $R^{43}$, $R^{44}$, $R^{45}$, $R^{46}$, $R^{47}$, $R^{48}$, and $R^{49}$ is D. In some embodiments, $R^1$ is D.

As defined above and described herein, $R^2$ is H or D.

In some embodiments, $R^2$ is H. In some embodiments, $R^2$ is H and at least one of $R^1$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{28}$, $R^{29}$, $R^{30}$, $R^{31}$, $R^{32}$, $R^{33}$, $R^{34}$, $R^{35}$, $R^{36}$, $R^{37}$, $R^{38}$, $R^{39}$, $R^{40}$, $R^{41}$, $R^{42}$, $R^{43}$, $R^{44}$, $R^{45}$, $R^{46}$, $R^{47}$, $R^{48}$, and $R^{49}$ is D. In some embodiments, $R^2$ is D.

As defined above and described herein, $R^3$ is H or D.

In some embodiments, $R^3$ is H. In some embodiments, $R^3$ is H and at least one of $R^1$, $R^2$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{28}$, $R^{29}$, $R^{30}$, $R^{31}$, $R^{32}$, $R^{33}$, $R^{34}$, $R^{35}$, $R^{36}$, $R^{37}$, $R^{38}$, $R^{39}$, $R^{40}$, $R^{41}$, $R^{42}$, $R^{43}$, $R^{44}$, $R^{45}$, $R^{46}$, $R^{47}$, $R^{48}$, and $R^{49}$ is D. In some embodiments, $R^3$ is D.

As defined above and described herein, $R^4$ is H or D.

In some embodiments, $R^4$ is H. In some embodiments, $R^4$ is H and at least one of $R^1$, $R^2$, $R^3$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{28}$, $R^{29}$, $R^{30}$, $R^{31}$, $R^{32}$, $R^{33}$, $R^{34}$, $R^{35}$, $R^{36}$, $R^{37}$, $R^{38}$, $R^{39}$, $R^{40}$, $R^{41}$, $R^{42}$, $R^{43}$, $R^{44}$, $R^{45}$, $R^{46}$, $R^{47}$, $R^{48}$, and $R^{49}$ is D. In some embodiments, $R^4$ is D.

As defined above and described herein, R is H or D.

In some embodiments, R is H. In some embodiments, R is H and at least one of $R^1$, $R^2$, $R^3$, $R^4$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{28}$, $R^{29}$, $R^{30}$, $R^{31}$, $R^{32}$, $R^{33}$, $R^{34}$, $R^{35}$, $R^{36}$, $R^{37}$, $R^{38}$, $R^{39}$, $R^{40}$, $R^{41}$, $R^{42}$, $R^{43}$, $R^{44}$, $R^{45}$, $R^{46}$, $R^{47}$, $R^{48}$, and $R^{49}$ is D. In some embodiments, $R^5$ is D.

As defined above and described herein, $R^6$ is H or D.

In some embodiments, $R^6$ is H. In some embodiments, $R^6$ is H and at least one of $R^1$, $R^2$, $R^3$, $R^4$, $R^5$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{28}$, $R^{29}$, $R^{30}$, $R^{31}$, $R^{32}$, $R^{33}$, $R^{34}$, $R^{35}$, $R^{36}$, $R^{37}$, $R^{38}$, $R^{39}$, $R^{40}$, $R^{41}$, $R^{42}$, $R^{43}$, $R^{44}$, $R^{45}$, $R^{46}$, $R^{47}$, $R^{48}$, and $R^{49}$ is D. In some embodiments, $R^6$ is D.

As defined above and described herein, $R^7$ is H or D.

In some embodiments, $R^7$ is H. In some embodiments, $R^7$ is H and at least one of $R^1$, $R^2$, $R^3$, $R^4$, $R^5$, $R^6$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{28}$, $R^{29}$, $R^{30}$, $R^{31}$, $R^{32}$, $R^{33}$, $R^{34}$, $R^{35}$, $R^{36}$, $R^{37}$, $R^{38}$, $R^{39}$, $R^{40}$, $R^{41}$, $R^{42}$, $R^{43}$, $R^{44}$, $R^{45}$, $R^{46}$, $R^{47}$, $R^{48}$, and $R^{49}$ is D. In some embodiments, $R^7$ is D.

As defined above and described herein, $R^8$ is H or D.

In some embodiments, $R^8$ is H. In some embodiments, $R^8$ is H and at least one of $R^1$, $R^2$, $R^3$, $R^4$, $R^5$, $R^6$, $R^7$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{28}$, $R^{29}$, $R^{30}$, $R^{31}$, $R^{32}$, $R^{33}$, $R^{34}$, $R^{35}$, $R^{36}$, $R^{37}$, $R^{38}$, $R^{39}$, $R^{40}$, $R^{41}$, $R^{42}$, $R^{43}$, $R^{44}$, $R^{45}$, $R^{46}$, $R^{47}$, $R^{48}$, and $R^{49}$ is D. In some embodiments, $R^8$ is D.

As defined above and described herein, $R^9$ is H or D.

In some embodiments, $R^9$ is H. In some embodiments, $R^9$ is H and at least one of $R^1$, $R^2$, $R^3$, $R^4$, $R^5$, $R^6$, $R^7$, $R^8$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{28}$, $R^{29}$, $R^{30}$, $R^{31}$, $R^{32}$, $R^{33}$, $R^{34}$, $R^{35}$, $R^{36}$, $R^{37}$, $R^{38}$, $R^{39}$, $R^{40}$, $R^{41}$, $R^{42}$, $R^{43}$, $R^{44}$, $R^{45}$, $R^{46}$, $R^{47}$, $R^{48}$, and $R^{49}$ is D. In some embodiments, $R^9$ is D.

As defined above and described herein, $R^{10}$ is H or D.

In some embodiments, $R^{10}$ is H. In some embodiments, $R^{10}$ is H and at least one of $R^1$, $R^2$, $R^3$, $R^4$, $R^5$, $R^6$, $R^7$, $R^8$, $R^9$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{28}$, $R^{29}$, $R^{30}$, $R^{31}$, $R^{32}$, $R^{33}$, $R^{34}$, $R^{35}$, $R^{36}$, $R^{37}$, $R^{38}$, $R^{39}$, $R^{40}$, $R^{41}$, $R^{42}$, $R^{43}$, $R^{44}$, $R^{45}$, $R^{46}$, $R^{47}$, $R^{48}$, and $R^{49}$ is D. In some embodiments, $R^{10}$ is D.

As defined above and described herein, $R^{11}$ is H or D.

In some embodiments, $R^{11}$ is H. In some embodiments, $R^{11}$ is H and at least one of $R^1$, $R^2$, $R^3$, $R^4$, $R^5$, $R^6$, $R^7$, $R^8$, $R^9$, $R^{10}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{28}$, $R^{29}$, $R^{30}$, $R^{31}$, $R^{32}$, $R^{33}$, $R^{34}$, $R^{35}$, $R^{36}$, $R^{37}$, $R^{38}$, $R^{39}$, $R^{40}$, $R^{41}$, $R^{42}$, $R^{43}$, $R^{44}$, $R^{45}$, $R^{46}$, $R^{47}$, $R^{48}$, and $R^{49}$ is D. In some embodiments, $R^{11}$ is D.

As defined above and described herein, $R^{12}$ is H or D.

In some embodiments, $R^{12}$ is H. In some embodiments, $R^{12}$ is H and at least one of $R^1$, $R^2$, $R^3$, $R^4$, $R^5$, $R^6$, $R^7$, $R^8$, $R^9$, $R^{10}$, $R^{11}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{28}$, $R^{29}$, $R^{30}$, $R^{31}$, $R^{32}$, $R^{33}$, $R^{34}$, $R^{35}$, $R^{36}$, $R^{37}$, $R^{38}$, $R^{39}$, $R^{40}$, $R^{41}$, $R^{42}$, $R^{43}$, $R^{44}$, $R^{45}$, $R^{46}$, $R^{47}$, $R^{48}$, and $R^{49}$ is D. In some embodiments, $R^{12}$ is D.

As defined above and described herein, $R^{13}$ is H or D.

In some embodiments, $R^{13}$ is H. In some embodiments, $R^{13}$ is H and at least one of $R^1$, $R^2$, $R^3$, $R^4$, $R^5$, $R^6$, $R^7$, $R^8$, $R^9$, $R^{10}$, $R^{11}$, $R^{12}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{28}$, $R^{29}$, $R^{30}$, $R^{31}$, $R^{32}$, $R^{33}$, $R^{34}$, $R^{35}$, $R^{36}$, $R^{37}$, $R^{38}$, $R^{39}$, $R^{40}$, $R^{41}$, $R^{42}$, $R^{43}$, $R^{44}$, $R^{45}$, $R^{46}$, $R^{47}$, $R^{48}$, and $R^{49}$ is D. In some embodiments, $R^{13}$ is D.

As defined above and described herein, $R^{14}$ is H or D.

In some embodiments, $R^{14}$ is H. In some embodiments, $R^{14}$ is H and at least one of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{28}$, $R^{29}$, $R^{30}$, $R^{31}$, $R^{32}$, $R^{33}$, $R^{34}$, $R^{35}$, $R^{36}$, $R^{37}$, $R^{38}$, $R^{39}$, $R^{40}$, $R^{41}$, $R^{42}$, $R^{43}$, $R^{44}$, $R^{45}$, $R^{46}$, $R^{47}$, $R^{48}$, and $R^{49}$ is D. In some embodiments, $R^{14}$ is D.

As defined above and described herein, $R^{15}$ is H or D.

In some embodiments, $R^{15}$ is H. In some embodiments, $R^{15}$ is H and at least one of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{28}$, $R^{29}$, $R^{30}$, $R^{31}$, $R^{32}$, $R^{33}$, $R^{34}$, $R^{35}$, $R^{36}$, $R^{37}$, $R^{38}$, $R^{39}$, $R^{40}$, $R^{41}$, $R^{42}$, $R^{43}$, $R^{44}$, $R^{45}$, $R^{46}$, $R^{47}$, $R^{48}$, and $R^{49}$ is D. In some embodiments, $R^{15}$ is D.

As defined above and described herein, $R^{16}$ is H or D.

In some embodiments, $R^{16}$ is H. In some embodiments, $R^{16}$ is H and at least one of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{28}$, $R^{29}$, $R^{30}$, $R^{31}$, $R^{32}$, $R^{33}$, $R^{34}$, $R^{35}$, $R^{36}$, $R^{37}$, $R^{38}$, $R^{39}$, $R^{40}$, $R^{41}$, $R^{42}$, $R^{43}$, $R^{44}$, $R^{45}$, $R^{46}$, $R^{47}$, $R^{48}$, and $R^{49}$ is D. In some embodiments, $R^{16}$ is D.

As defined above and described herein, $R^{17}$ is H or D.

In some embodiments, $R^{17}$ is H. In some embodiments, $R^{17}$ is H and at least one of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{18}$, $R^{19}$, $R^{20}$, $R^{21}$, $R^{22}$, $R^{23}$, $R^{24}$, $R^{25}$, $R^{26}$, $R^{27}$, $R^{28}$, $R^{29}$, $R^{30}$, $R^{31}$, $R^{32}$, $R^{33}$, $R^{34}$, $R^{35}$, $R^{36}$, $R^{37}$, $R^{38}$, $R^{39}$, $R^{40}$, $R^{41}$, $R^{42}$, $R^{43}$, $R^{44}$, $R^{45}$, $R^{46}$, $R^{47}$, $R^{48}$, and $R^{49}$ is D. In some embodiments, $R^{17}$ is D.

As defined above and described herein, $R^{18}$ is H or D.

In some embodiments, $R^{18}$ is H. In some embodiments, $R^8$ is H and at least one of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{19}$, $R^{20}$, $R^{21}$, $R^{22}$, $R^{23}$, $R^{24}$, $R^{25}$, $R^{26}$, $R^{27}$, $R^{28}$, $R^{29}$, $R^{30}$, $R^{31}$, $R^{32}$, $R^{33}$, $R^{34}$, $R^{35}$, $R^{36}$, $R^{37}$, $R^{38}$, $R^{39}$, $R^{40}$, $R^{41}$, $R^{42}$, $R^{43}$, $R^{44}$, $R^{45}$, $R^{46}$, $R^{47}$, $R^{48}$, and $R^{49}$ is D. In some embodiments, $R^{18}$ is D.

As defined above and described herein, $R^{19}$ is H or D.

In some embodiments, $R^{19}$ is H. In some embodiments, $R^{19}$ is H and at least one of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{20}$, $R^{21}$, $R^{22}$, $R^{23}$, $R^{24}$, $R^{25}$, $R^{26}$, $R^{27}$, $R^{28}$, $R^{29}$, $R^{30}$, $R^{31}$, $R^{32}$, $R^{33}$, $R^{34}$, $R^{35}$, $R^{36}$, $R^{37}$, $R^{38}$, $R^{39}$, $R^{40}$, $R^{41}$, $R^{42}$, $R^{43}$, $R^{44}$, $R^{45}$, $R^{46}$, $R^{47}$, $R^{48}$, and $R^{49}$ is D. In some embodiments, $R^{19}$ is D.

As defined above and described herein, $R^{20}$ is H or D.

In some embodiments, $R^{20}$ is H. In some embodiments, $R^{20}$ is H and at least one of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{21}$, $R^{22}$, $R^{23}$, $R^{24}$, $R^{25}$, $R^{26}$, $R^{27}$, $R^{28}$, $R^{29}$, $R^{30}$, $R^{31}$, $R^{32}$, $R^{33}$, $R^{34}$, $R^{35}$, $R^{36}$, $R^{37}$, $R^{38}$, $R^{39}$, $R^{40}$, $R^{41}$, $R^{42}$, $R^{43}$, $R^{44}$, $R^{45}$, $R^{46}$, $R^{47}$, $R^{48}$, and $R^{49}$ is D. In some embodiments, $R^{20}$ is D.

As defined above and described herein, $R^{21}$ is H or D.

In some embodiments, $R^{21}$ is H. In some embodiments, $R^{21}$ is H and at least one of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{22}$, $R^{23}$, $R^{24}$, $R^{25}$, $R^{26}$, $R^{27}$, $R^{28}$, $R^{29}$, $R^{30}$, $R^{31}$, $R^{32}$, $R^{33}$, $R^{34}$, $R^{35}$, $R^{36}$, $R^{37}$, $R^{38}$, $R^{39}$, $R^{40}$, $R^{41}$, $R^{42}$, $R^{43}$, $R^{44}$, $R^{45}$, $R^{46}$, $R^{47}$, $R^{48}$, and $R^{49}$ is D. In some embodiments, $R^{21}$ is D.

As defined above and described herein, $R^{22}$ is H or D.

In some embodiments, $R^{22}$ is H. In some embodiments, $R^{22}$ is H and at least one of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{23}$, $R^{24}$, $R^{25}$, $R^{26}$, $R^{27}$, $R^{28}$, $R^{29}$, $R^{30}$, $R^{31}$, $R^{32}$, $R^{33}$, $R^{34}$, $R^{35}$, $R^{36}$, $R^{37}$, $R^{38}$, $R^{39}$, $R^{40}$, $R^{41}$, $R^{42}$, $R^{43}$, $R^{44}$, $R^{45}$, $R^{46}$, $R^{47}$, $R^{48}$, and $R^{49}$ is D. In some embodiments, $R^{22}$ is D.

As defined above and described herein, $R^{23}$ is H or D.

In some embodiments, $R^{23}$ is H. In some embodiments, $R^{23}$ is H and at least one of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{24}$, $R^{25}$, $R^{26}$, $R^{27}$, $R^{28}$, $R^{29}$, $R^{30}$, $R^{31}$, $R^{32}$, $R^{33}$, $R^{34}$, $R^{35}$, $R^{36}$, $R^{37}$, $R^{38}$, $R^{39}$, $R^{40}$, $R^{41}$, $R^{42}$, $R^{43}$, $R^{44}$, $R^{45}$, $R^{46}$, $R^{47}$, $R^{48}$, and $R^{49}$ is D. In some embodiments, $R^{23}$ is D.

As defined above and described herein, $R^{24}$ is H or D.

In some embodiments, $R^{24}$ is H. In some embodiments, $R^{24}$ is H and at least one of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{25}$, $R^{26}$, $R^{27}$, $R^{28}$, $R^{29}$, $R^{30}$, $R^{31}$, $R^{32}$, $R^{33}$, $R^{34}$, $R^{35}$, $R^{36}$, $R^{37}$, $R^{38}$, $R^{39}$, $R^{40}$, $R^{41}$, $R^{42}$, $R^{43}$, $R^{44}$, $R^{45}$, $R^{46}$, $R^{47}$, $R^{48}$, and $R^{49}$ is D. In some embodiments, $R^{24}$ is D.

As defined above and described herein, $R^{25}$ is H or D.

In some embodiments, $R^{25}$ is H. In some embodiments, $R^{25}$ is H and at least one of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{26}$, $R^{27}$, $R^{28}$, $R^{29}$, $R^{30}$, $R^{31}$, $R^{32}$, $R^{33}$, $R^{34}$, $R^{35}$, $R^{36}$, $R^{37}$, $R^{38}$, $R^{39}$, $R^{40}$, $R^{41}$, $R^{42}$, $R^{43}$, $R^{44}$, $R^{45}$, $R^{46}$, $R^{47}$, $R^{48}$, and $R^{49}$ is D. In some embodiments, $R^{25}$ is D.

As defined above and described herein, $R^{26}$ is H or D.

In some embodiments, $R^{26}$ is H. In some embodiments, $R^{26}$ is H and at least one of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{27}$, $R^{28}$, $R^{29}$, $R^{30}$, $R^{31}$, $R^{32}$, $R^{33}$, $R^{34}$, $R^{35}$, $R^{36}$, $R^{37}$, $R^{38}$, $R^{39}$, $R^{40}$, $R^{41}$, $R^{42}$, $R^{43}$, $R^{44}$, $R^{45}$, $R^{46}$, $R^{47}$, $R^{48}$, and $R^{49}$ is D. In some embodiments, $R^{26}$ is D.

As defined above and described herein, $R^{27}$ is H or D.

In some embodiments, $R^{27}$ is H. In some embodiments, $R^{27}$ is H and at least one of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{28}$, $R^{29}$, $R^{30}$, $R^{31}$, $R^{32}$, $R^{33}$, $R^{34}$, $R^{35}$, $R^{36}$, $R^{37}$, $R^{38}$, $R^{39}$, $R^{40}$, $R^{41}$, $R^{42}$, $R^{43}$, $R^{44}$, $R^{45}$, $R^{46}$, $R^{47}$, $R^{48}$, and $R^{49}$ is D. In some embodiments, $R^{27}$ is D.

As defined above and described herein, $R^{28}$ is H or D.

In some embodiments, $R^{28}$ is H. In some embodiments, $R^{28}$ is H and at least one of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{29}$, $R^{30}$, $R^{31}$, $R^{32}$, $R^{33}$, $R^{34}$, $R^{35}$, $R^{36}$, $R^{37}$, $R^{38}$, $R^{39}$, $R^{40}$, $R^{41}$, $R^{42}$, $R^{43}$, $R^{44}$, $R^{45}$, $R^{46}$, $R^{47}$, $R^{48}$, and $R^{49}$ is D. In some embodiments, $R^{28}$ is D.

As defined above and described herein, $R^{29}$ is H or D.

In some embodiments, $R^{29}$ is H. In some embodiments, $R^{29}$ is H and at least one of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{28}$, $R^{30}$, $R^{31}$, $R^{32}$, $R^{33}$, $R^{34}$, $R^{35}$, $R^{36}$, $R^{37}$, $R^{38}$, $R^{39}$, $R^{40}$, $R^{41}$, $R^{42}$, $R^{43}$, $R^{44}$, $R^{45}$, $R^{46}$, $R^{47}$, $R^{48}$, and $R^{49}$ is D. In some embodiments, $R^{29}$ is D.

As defined above and described herein, $R^{30}$ is H or D.

In some embodiments, $R^{30}$ is H. In some embodiments, $R^{30}$ is H and at least one of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{28}$, $R^{29}$, $R^{31}$, $R^{32}$, $R^{33}$, $R^{34}$, $R^{35}$, $R^{36}$, $R^{37}$, $R^{38}$, $R^{39}$, $R^{40}$, $R^{41}$, $R^{42}$, $R^{43}$, $R^{44}$, $R^{45}$, $R^{46}$, $R^{47}$, $R^{48}$, and $R^{49}$ is D. In some embodiments, $R^{30}$ is D.

As defined above and described herein, $R^{31}$ is H or D.

In some embodiments, $R^{31}$ is H. In some embodiments, $R^{31}$ is H and at least one of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{28}$, $R^{29}$, $R^{30}$, $R^{32}$, $R^{33}$, $R^{34}$, $R^{35}$, $R^{36}$, $R^{37}$, $R^{38}$, $R^{39}$, $R^{40}$, $R^{41}$, $R^{42}$, $R^{43}$, $R^{44}$, $R^{45}$, $R^{46}$, $R^{47}$, $R^{48}$, and $R^{49}$ is D. In some embodiments, $R^{31}$ is D.

As defined above and described herein, $R^{32}$ is H or D.

In some embodiments, $R^{32}$ is H. In some embodiments, $R^{32}$ is H and at least one of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{28}$, $R^{29}$, $R^{30}$, $R^{31}$, $R^{33}$, $R^{34}$, $R^{35}$, $R^{36}$, $R^{37}$, $R^{38}$, $R^{39}$, $R^{40}$, $R^{41}$, $R^{42}$, $R^{43}$, $R^{44}$, $R^{45}$, $R^{46}$, $R^{47}$, $R^{48}$, and $R^{49}$ is D. In some embodiments, $R^{32}$ is D.

As defined above and described herein, $R^{33}$ is H or D.

In some embodiments, $R^{33}$ is H. In some embodiments, $R^{33}$ is H and at least one of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{28}$, $R^{29}$, $R^{30}$, $R^{31}$, $R^{32}$, $R^{34}$, $R^{35}$, $R^{36}$, $R^{37}$, $R^{38}$, $R^{39}$, $R^{40}$, $R^{41}$, $R^{42}$, $R^{43}$, $R^{44}$, $R^{45}$, $R^{46}$, $R^{47}$, $R^{48}$, and $R^{49}$ is D. In some embodiments, $R^{33}$ is D.

As defined above and described herein, $R^{34}$ is H or D.

In some embodiments, $R^{34}$ is H. In some embodiments, $R^{34}$ is H and at least one of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{28}$, $R^{29}$, $R^{30}$, $R^{31}$, $R^{32}$, $R^{33}$, $R^{35}$, $R^{36}$, $R^{37}$, $R^{38}$, $R^{39}$, $R^{40}$, $R^{41}$, $R^{42}$, $R^{43}$, $R^{44}$, $R^{45}$, $R^{46}$, $R^{47}$, $R^{48}$, and $R^{49}$ is D. In some embodiments, $R^{34}$ is D.

As defined above and described herein, $R^{35}$ is H or D.

In some embodiments, $R^{35}$ is H. In some embodiments, $R^{35}$ is H and at least one of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{28}$, $R^{29}$, $R^{30}$, $R^{31}$, $R^{32}$, $R^{33}$, $R^{34}$, $R^{36}$, $R^{37}$, $R^{38}$, $R^{39}$, $R^{40}$, $R^{41}$, $R^{42}$, $R^{43}$, $R^{44}$, $R^{45}$, $R^{46}$, $R^{47}$, $R^{48}$, and $R^{49}$ is D. In some embodiments, $R^{35}$ is D.

As defined above and described herein, $R^{36}$ is H or D.

In some embodiments, $R^{36}$ is H. In some embodiments, $R^{36}$ is H and at least one of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{28}$, $R^{29}$, $R^{30}$, $R^{31}$, $R^{32}$, $R^{33}$, $R^{34}$, $R^{35}$, $R^{37}$, $R^{38}$, $R^{39}$, $R^{40}$, $R^{41}$, $R^{42}$, $R^{43}$, $R^{44}$, $R^{45}$, $R^{46}$, $R^{47}$, $R^{48}$, and $R^{49}$ is D. In some embodiments, $R^{36}$ is D.

As defined above and described herein, $R^{37}$ is H or D.

In some embodiments, $R^{37}$ is H. In some embodiments, $R^{37}$ is H and at least one of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{28}$, $R^{29}$, $R^{30}$, $R^{31}$, $R^{32}$, $R^{33}$, $R^{34}$, $R^{35}$, $R^{36}$, $R^{38}$, $R^{39}$, $R^{40}$, $R^{41}$, $R^{42}$, $R^{43}$, $R^{44}$, $R^{45}$, $R^{46}$, $R^{47}$, $R^{48}$, and $R^{49}$ is D. In some embodiments, $R^{37}$ is D.

As defined above and described herein, $R^{38}$ is H or D.

In some embodiments, $R^{38}$ is H. In some embodiments, $R^{38}$ is H and at least one of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{28}$, $R^{29}$, $R^{30}$, $R^{31}$, $R^{32}$, $R^{33}$, $R^{34}$, $R^{35}$, $R^{36}$, $R^{37}$, $R^{39}$, $R^{40}$, $R^{41}$, $R^{42}$, $R^{43}$, $R^{44}$, $R^{45}$, $R^{46}$, $R^{47}$, $R^{48}$, and $R^{49}$ is D. In some embodiments, $R^{38}$ is D.

As defined above and described herein, $R^{39}$ is H or D.

In some embodiments, $R^{39}$ is H. In some embodiments, $R^{39}$ is H and at least one of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{28}$, $R^{29}$, $R^{30}$, $R^{31}$, $R^{32}$, $R^{33}$, $R^{34}$, $R^{35}$, $R^{36}$, $R^{37}$, $R^{38}$, $R^{40}$, $R^{41}$, $R^{42}$, $R^{43}$, $R^{44}$, $R^{45}$, $R^{46}$, $R^{47}$, $R^{48}$, and $R^{49}$ is D. In some embodiments, $R^{39}$ is D.

As defined above and described herein, $R^{40}$ is H or D.

In some embodiments, $R^{40}$ is H. In some embodiments, $R^{40}$ is H and at least one of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{28}$, $R^{29}$, $R^{30}$, $R^{31}$, $R^{32}$, $R^{33}$, $R^{34}$, $R^{35}$, $R^{36}$, $R^{37}$, $R^{38}$, $R^{39}$, $R^{41}$, $R^{42}$, $R^{43}$, $R^{44}$, $R^{45}$, $R^{46}$, $R^{47}$, $R^{48}$, and $R^{49}$ is D. In some embodiments, $R^{40}$ is D.

As defined above and described herein, $R^{41}$ is H or D.

In some embodiments, $R^{41}$ is H. In some embodiments, $R^{41}$ is H and at least one of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{28}$, $R^{29}$, $R^{30}$, $R^{31}$, $R^{32}$, $R^{33}$, $R^{34}$, $R^{35}$, $R^{36}$, $R^{37}$, $R^{38}$, $R^{39}$, $R^{40}$, $R^{42}$, $R^{43}$, $R^{44}$, $R^{45}$, $R^{46}$, $R^{47}$, $R^{48}$, and $R^{49}$ is D. In some embodiments, $R^{41}$ is D.

As defined above and described herein, $R^{42}$ is H or D.

In some embodiments, $R^{42}$ is H. In some embodiments, $R^{42}$ is H and at least one of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{28}$, $R^{29}$, $R^{30}$, $R^{31}$, $R^{32}$, $R^{33}$, $R^{34}$, $R^{35}$, $R^{36}$, $R^{37}$, $R^{38}$, $R^{39}$, $R^{40}$, $R^{41}$, $R^{43}$, $R^{44}$, $R^{45}$, $R^{46}$, $R^{47}$, $R^{48}$, and $R^{49}$ is D. In some embodiments, $R^{42}$ is D.

As defined above and described herein, $R^{43}$ is H or D.

In some embodiments, $R^{43}$ is H. In some embodiments, $R^{43}$ is H and at least one of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{28}$, $R^{29}$, $R^{30}$, $R^{31}$, $R^{32}$, $R^{33}$, $R^{34}$, $R^{35}$, $R^{36}$, $R^{37}$, $R^{38}$, $R^{39}$, $R^{40}$, $R^{41}$, $R^{42}$, $R^{44}$, $R^{45}$, $R^{46}$, $R^{47}$, $R^{48}$, and $R^{49}$ is D. In some embodiments, $R^{43}$ is D.

As defined above and described herein, $R^{44}$ is H or D.

In some embodiments, $R^{44}$ is H. In some embodiments, $R^{44}$ is H and at least one of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{28}$, $R^{29}$, $R^{30}$, $R^{31}$, $R^{32}$, $R^{33}$, $R^{34}$, $R^{35}$, $R^{36}$, $R^{37}$, $R^{38}$, $R^{39}$, $R^{40}$, $R^{41}$, $R^{42}$, $R^{43}$, $R^{45}$, $R^{46}$, $R^{47}$, $R^{48}$, and $R^{49}$ is D. In some embodiments, $R^{44}$ is D.

As defined above and described herein, $R^{45}$ is H or D.

In some embodiments, $R^{45}$ is H. In some embodiments, $R^{45}$ is H and at least one of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{28}$, $R^{29}$, $R^{30}$, $R^{31}$, $R^{32}$, $R^{33}$, $R^{34}$, $R^{35}$, $R^{36}$, $R^{37}$, $R^{38}$, $R^{39}$, $R^{40}$, $R^{41}$, $R^{42}$, $R^{43}$, $R^{44}$, $R^{46}$, $R^{47}$, $R^{48}$, and $R^{49}$ is D. In some embodiments, $R^{45}$ is D.

As defined above and described herein, $R^{46}$ is H or D.

In some embodiments, $R^{46}$ is H. In some embodiments, $R^{46}$ is H and at least one of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{28}$, $R^{29}$, $R^{30}$, $R^{31}$, $R^{32}$, $R^{33}$, $R^{34}$, $R^{35}$, $R^{36}$, $R^{37}$, $R^{38}$, $R^{39}$, $R^{40}$, $R^{41}$, $R^{42}$, $R^{43}$, $R^{44}$, $R^{45}$, $R^{47}$, $R^{48}$, and $R^{49}$ is D. In some embodiments, $R^{46}$ is D.

As defined above and described herein, $R^{47}$ is H or D.

In some embodiments, $R^{47}$ is H. In some embodiments, $R^{47}$ is H and at least one of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{28}$, $R^{29}$, $R^{30}$, $R^{31}$, $R^{32}$, $R^{33}$, $R^{34}$, $R^{35}$, $R^{36}$, $R^{37}$, $R^{38}$, $R^{39}$, $R^{40}$, $R^{41}$, $R^{42}$, $R^{43}$, $R^{44}$, $R^{45}$, $R^{46}$, $R^{48}$, and $R^{49}$ is D. In some embodiments, $R^{47}$ is D.

As defined above and described herein, $R^{48}$ is H or D.

In some embodiments, $R^{48}$ is H. In some embodiments, $R^{48}$ is H and at least one of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{28}$, $R^{29}$, $R^{30}$, $R^{31}$, $R^{32}$, $R^{33}$, $R^{34}$, $R^{35}$, $R^{36}$, $R^{37}$, $R^{38}$, $R^{39}$, $R^{40}$, $R^{41}$, $R^{42}$, $R^{43}$, $R^{44}$, $R^{45}$, $R^{46}$, $R^{47}$, and $R^{49}$ is D. In some embodiments, $R^{48}$ is D.

As defined above and described herein, $R^{49}$ is H or D.

In some embodiments, $R^{49}$ is H. In some embodiments, $R^{49}$ is H and at least one of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{28}$, $R^{29}$, $R^{30}$, $R^{31}$, $R^{32}$, $R^{33}$, $R^{34}$, $R^{35}$, $R^{36}$, $R^{37}$, $R^{38}$, $R^{39}$, $R^{40}$, $R^{41}$, $R^{42}$, $R^{43}$, $R^{44}$, $R^{45}$, $R^{46}$, $R^{47}$, and $R^{48}$ is D. In some embodiments, $R^{49}$ is D.

In some embodiments, at least one of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{28}$, $R^{29}$, $R^{30}$, $R^{31}$, $R^{32}$, $R^{33}$, $R^{34}$, $R^{35}$, $R^{36}$, $R^{37}$, $R^{38}$, $R^{39}$, $R^{40}$, $R^{41}$, $R^{42}$, $R^{43}$, $R^{44}$, $R^{45}$, $R^{46}$, $R^{47}$, $R^{48}$, and $R^{49}$ has a % deuterium incorporation of 50% or greater.

In some embodiments, at least one of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{28}$, $R^{29}$, $R^{30}$, $R^{31}$, $R^{32}$, $R^{33}$, $R^{34}$, $R^{35}$, $R^{36}$, $R^{37}$, $R^{38}$, $R^{39}$, $R^{40}$, $R^{41}$, $R^{42}$, $R^{43}$, $R^{44}$, $R^{45}$, $R^{46}$, $R^{47}$, $R^{48}$, and $R^{49}$ has a % deuterium incorporation of 60% or greater.

In some embodiments, at least one of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{28}$, $R^{29}$, $R^{30}$, $R^{31}$, $R^{32}$, $R^{33}$, $R^{34}$, $R^{35}$, $R^{36}$, $R^{37}$, $R^{38}$, $R^{39}$, $R^{40}$, $R^{41}$, $R^{42}$, $R^{43}$, $R^{44}$, $R^{45}$, $R^{46}$, $R^{47}$, $R^{48}$, and $R^{49}$ has a % deuterium incorporation of 70% or greater.

In some embodiments, at least one of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{28}$, $R^{29}$, $R^{30}$, $R^{31}$, $R^{32}$, $R^{33}$, $R^{34}$, $R^{35}$, $R^{36}$, $R^{37}$, $R^{38}$, $R^{39}$, $R^{40}$, $R^{41}$, $R^{42}$, $R^{43}$, $R^{44}$, $R^{45}$, $R^{46}$, $R^{47}$, $R^{48}$, and $R^{49}$ has a % deuterium incorporation of 80% or greater.

In some embodiments, at least one of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{28}$, $R^{29}$, $R^{30}$, $R^{31}$, $R^{32}$, $R^{33}$, $R^{34}$, $R^{35}$, $R^{36}$, $R^{37}$, $R^{38}$, $R^{39}$, $R^{40}$, $R^{41}$, $R^{42}$, $R^{43}$, $R^{44}$, $R^{45}$, $R^{46}$, $R^{47}$, $R^{48}$, and $R^{49}$ has a % deuterium incorporation of 90% or greater.

In some embodiments, at least one of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{28}$, $R^{29}$, $R^{30}$, $R^{31}$, $R^{32}$, $R^{33}$, $R^{34}$, $R^{35}$, $R^{36}$, $R^{37}$, $R^{38}$, $R^{39}$, $R^{40}$, $R^{41}$, $R^{42}$, $R^{43}$, $R^{44}$, $R^{45}$, $R^{46}$, $R^{47}$, $R^{48}$, and $R^{49}$ has a % deuterium incorporation of 95% or greater.

In some embodiments, the present invention provides a compound of any one of formulae I, I-a, I-b, I-c, I-d, I-e, I-f, I-g, I-h, I-i, I-j, or I-k, or a pharmaceutically acceptable salt thereof, wherein each of $R^1$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{28}$, $R^{29}$, $R^{30}$, $R^{31}$, $R^{32}$, $R^{33}$, $R^{34}$, and $R^{35}$ is as defined above and described herein, and wherein each of $R^1$, $R^2$, $R^3$, $R^4$, $R^5$, $R^6$, $R^7$, $R^8$, $R^9$, $R^{10}$, $R^{11}$, $R^{12}$, $R^{36}$, $R^{37}$, $R^{38}$, $R^{39}$, $R^{40}$, $R^{41}$, $R^{42}$, $R^{43}$, $R^{44}$, $R^{45}$, $R^{46}$, $R^{47}$, $R^{48}$, and $R^{49}$ is as defined in an entry set forth in Table 1a, below.

TABLE 1a

Exemplary Deuterium-Enriched Compounds

| Entry | $R^1$ | $R^2$ | $R^3$ | $R^4$ | $R^5$ | $R^6$ | $R^7$ | $R^8$ | $R^9$ | $R^{10}$ | $R^{11}$ | $R^{12}$ | $R^{36}$ | $R^{37}$ | $R^{38}$ | $R^{39}$ |
|---|---|---|---|---|---|---|---|---|---|---|---|---|---|---|---|---|
| i | D | H | H | H | H | H | H | H | H | H | H | H | H | H | H | H |
| ii | H | D | H | H | H | H | H | H | H | H | H | H | H | H | H | H |
| iii | H | H | D | H | H | H | H | H | H | H | H | H | H | H | H | H |
| iv | H | H | H | D | H | H | H | H | H | H | H | H | H | H | H | H |
| v | H | H | H | H | D | H | H | H | H | H | H | H | H | H | H | H |
| vi | H | H | H | H | H | D | H | H | H | H | H | H | H | H | H | H |
| vii | H | H | H | H | H | H | D | H | H | H | H | H | H | H | H | H |
| viii | H | H | H | H | H | H | H | D | H | H | H | H | H | H | H | H |
| ix | H | H | H | H | H | H | H | H | D | H | H | H | H | H | H | H |
| x | H | H | H | H | H | H | H | H | H | D | H | H | H | H | H | H |
| xi | H | H | H | H | H | H | H | H | H | H | D | H | H | H | H | H |
| xii | H | H | H | H | H | H | H | H | H | H | H | D | H | H | H | H |
| xiii | H | H | H | H | H | H | H | H | H | H | H | H | D | H | H | H |
| xiv | H | H | H | H | H | H | H | H | H | H | H | H | H | D | H | H |
| xv | H | H | H | H | H | H | H | H | H | H | H | H | H | H | D | H |
| xvi | H | H | H | H | H | H | H | H | H | H | H | H | H | H | H | D |
| xvii | H | H | H | H | H | H | H | H | H | H | H | H | H | H | H | H |
| xviii | H | H | H | H | H | H | H | H | H | H | H | H | H | H | H | H |
| xix | H | H | H | H | H | H | H | H | H | H | H | H | H | H | H | H |
| xx | H | H | H | H | H | H | H | H | H | H | H | H | H | H | H | H |
| xxi | H | H | H | H | H | H | H | H | H | H | H | H | H | H | H | H |
| xxii | H | H | H | H | H | H | H | H | H | H | H | H | H | H | H | H |
| xxiii | H | H | H | H | H | H | H | H | H | H | H | H | H | H | H | H |
| xxiv | H | H | H | H | H | H | H | H | H | H | H | H | H | H | H | H |
| xxv | H | H | H | H | H | H | H | H | H | H | H | H | H | H | H | H |
| xxvi | H | H | H | H | H | H | H | H | H | H | H | H | H | H | H | H |
| xxvii | H | H | H | H | H | D | H | H | H | H | H | H | H | H | H | H |
| xxviii | H | H | H | H | H | H | D | D | D | H | H | H | H | H | H | H |
| xxix | H | H | H | H | H | H | H | H | H | D | D | D | H | H | H | H |
| xxx | H | H | H | H | H | H | H | H | H | H | H | H | D | H | H | H |
| xxxi | H | H | H | H | H | H | H | H | H | H | H | H | H | H | H | D |
| xxxii | H | H | H | H | H | H | H | H | H | H | H | H | H | H | H | H |

| Entry | $R^{40}$ | $R^{41}$ | $R^{42}$ | $R^{43}$ | $R^{44}$ | $R^{45}$ | $R^{46}$ | $R^{47}$ | $R^{48}$ | $R^{49}$ |
|---|---|---|---|---|---|---|---|---|---|---|
| i | H | H | H | H | H | H | H | H | H | H |
| ii | H | H | H | H | H | H | H | H | H | H |
| iii | H | H | H | H | H | H | H | H | H | H |
| iv | H | H | H | H | H | H | H | H | H | H |
| v | H | H | H | H | H | H | H | H | H | H |
| vi | H | H | H | H | H | H | H | H | H | H |
| vii | H | H | H | H | H | H | H | H | H | H |
| viii | H | H | H | H | H | H | H | H | H | H |
| ix | H | H | H | H | H | H | H | H | H | H |
| x | H | H | H | H | H | H | H | H | H | H |
| xi | H | H | H | H | H | H | H | H | H | H |
| xii | H | H | H | H | H | H | H | H | H | H |
| xiii | H | H | H | H | H | H | H | H | H | H |
| xiv | H | H | H | H | H | H | H | H | H | H |
| xv | H | H | H | H | H | H | H | H | H | H |
| xvi | H | H | H | H | H | H | H | H | H | H |
| xvii | D | H | H | H | H | H | H | H | H | H |

TABLE 1a-continued

| Exemplary Deuterium-Enriched Compounds | | | | | | | | | | |
|---|---|---|---|---|---|---|---|---|---|---|
| xviii | H | D | H | H | H | H | H | H | H | H |
| xix | H | H | D | H | H | H | H | H | H | H |
| xx | H | H | H | D | H | H | H | H | H | H |
| xxi | H | H | H | H | D | H | H | H | H | H |
| xxii | H | H | H | H | H | D | H | H | H | H |
| xxiii | H | H | H | H | H | H | D | H | H | H |
| xxiv | H | H | H | H | H | H | H | D | H | H |
| xxv | H | H | H | H | H | H | H | H | D | H |
| xxvi | H | H | H | H | H | H | H | H | H | D |
| xxvii | H | H | H | H | H | H | H | H | H | H |
| xxviii | H | H | H | H | H | H | H | H | H | H |
| xxix | H | H | H | H | H | H | H | H | H | H |
| xxx | H | H | H | H | H | H | H | H | H | H |
| xxxi | H | H | H | H | H | H | H | H | H | H |
| xxxii | D | D | H | H | H | H | H | H | H | H |

In some embodiments, the present invention provides a compound of any one of Formulae I, I-a, I-b, I-c, I-d, I-e, I-f, I-g, I-h, I-i, I-j, or I-k, or a pharmaceutically acceptable salt thereof, wherein each of $R^6$, $R^7$, $R^8$, $R^9$, $R^{10}$, $R^{11}$, $R^{12}$, $R^{36}$, $R^{39}$, $R^{40}$ and $R^{41}$ is as defined in an entry set forth below:

TABLE 1b

| Exemplary Deuterium-Enriched Compounds. | | | | | | | | | | | |
|---|---|---|---|---|---|---|---|---|---|---|---|
| Entry | $R^6$ | $R^7$ | $R^8$ | $R^9$ | $R^{10}$ | $R^{11}$ | $R^{12}$ | $R^{36}$ | $R^{39}$ | $R^{40}$ | $R^{41}$ |
| i | D | D | D | D | H | H | H | H | H | H | H |
| ii | D | H | H | H | D | D | D | H | H | H | H |
| iii | D | H | H | H | H | H | H | D | H | H | H |
| iv | D | H | H | H | H | H | H | H | D | H | H |
| v | D | H | H | H | H | H | H | H | H | D | D |
| vi | H | D | D | D | D | D | D | H | H | H | H |
| vii | H | D | D | D | H | H | H | D | H | H | H |
| viii | H | D | D | D | H | H | H | H | D | H | H |
| ix | H | D | D | D | H | H | H | H | H | D | D |
| x | H | H | H | H | D | D | D | D | H | H | H |
| xi | H | H | H | H | D | D | D | H | D | H | H |
| xii | H | H | H | H | D | D | D | H | H | D | D |
| xiii | H | H | H | H | H | H | H | D | D | H | H |
| xiv | H | H | H | H | H | H | H | D | H | D | D |
| xv | H | H | H | H | H | H | H | H | D | D | D |
| xvi | H | H | H | H | D | D | H | H | H | H | H |
| xvii | H | H | H | H | H | D | D | H | H | H | H |
| xviii | H | H | H | H | D | H | D | H | H | H | H |
| xix | H | H | H | H | D | D | H | D | H | H | H |
| xx | H | H | H | H | H | D | D | D | H | H | H |
| xxi | H | H | H | H | D | H | D | D | H | H | H |
| xxii | H | H | H | H | D | D | H | H | D | H | H |
| xxiii | H | H | H | H | H | D | D | H | D | H | H |
| xxiv | H | H | H | H | D | H | D | H | D | H | H |
| xxv | H | H | H | H | D | D | H | H | H | D | H |
| xxvi | H | H | H | H | H | D | D | H | H | D | H |
| xxvii | H | H | H | H | D | H | D | H | H | D | H |
| xxviii | H | H | H | H | D | D | H | H | H | H | D |
| xxix | H | H | H | H | H | D | D | H | H | H | D |
| xxx | H | H | H | H | D | H | D | H | H | H | D |
| xxxi | H | H | H | H | D | D | H | H | H | D | D |
| xxxii | H | H | H | H | H | D | D | H | H | D | D |
| xxxiii | H | H | H | H | D | H | D | H | H | D | D |

In some embodiments, the present invention provides a deuterium-enriched compound or pharmaceutically acceptable salt thereof of formulae I-a, I-b, I-c, I-d, I-e, I-f, I-g, I-h, I-i, I-j, or I-k, wherein a variable indicated as D has a deuterium % incorporation (% abundance) of about 30% or greater. In some embodiments, the % deuterium incorporation is about 50% or greater; or about 70%, 75%, 80%, 85%, 90%, 91%, 92%, 93%, 94%, 95%, 96%, 97%, 98%, 99%, or about 99.50% or greater.

In some embodiments, present invention provides a compound of formula I selected from these depicted in Table 2, below.

TABLE 2
| Exemplary Deuterium-Enriched Compounds | |
|---|---|
| I-# | Structure |
| I-1 | 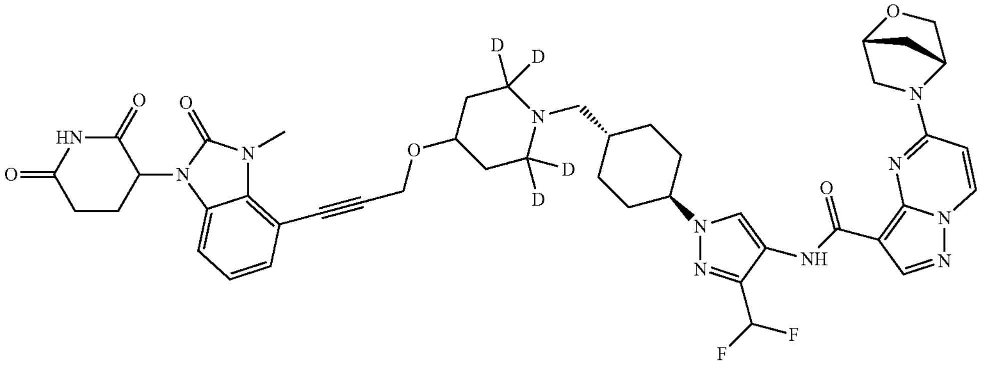 [SMILES: [2H]C1([2H])CC(OCC#Cc2cccc3c2n(C)c(=O)n3C2CCC(=O)NC2=O)CC([2H])([2H])N1C[C@H]1CC[C@H](n2cc(NC(=O)c3cnn4ccc(N5C[C@H]6C[C@@H]5CO6)nc34)c(C(F)F)n2)CC1] |
| I-2 | 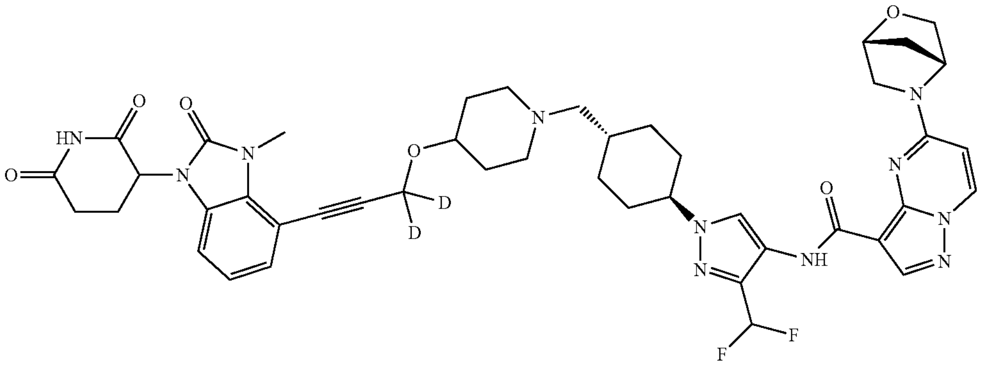 [SMILES: [2H]C([2H])(C#Cc1cccc2c1n(C)c(=O)n2C1CCC(=O)NC1=O)OC1CCN(C[C@H]2CC[C@H](n3cc(NC(=O)c4cnn5ccc(N6C[C@H]7C[C@@H]6CO7)nc45)c(C(F)F)n3)CC2)CC1] |
| I-3 | 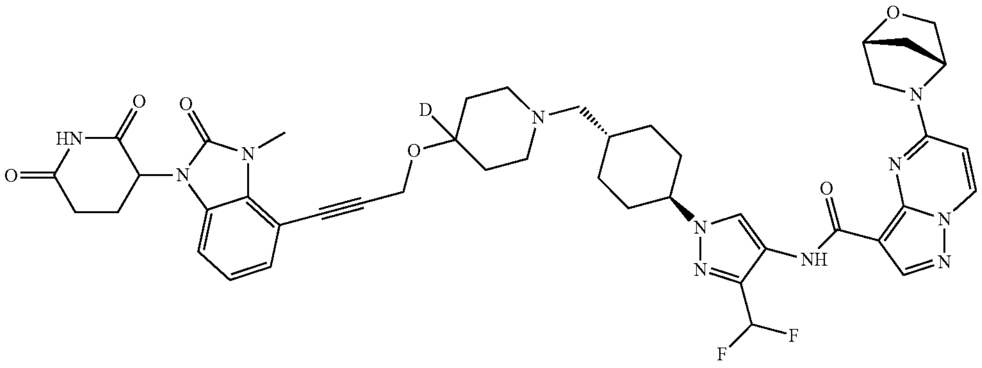 [SMILES: [2H]C1(OCC#Cc2cccc3c2n(C)c(=O)n3C2CCC(=O)NC2=O)CCN(C[C@H]2CC[C@H](n3cc(NC(=O)c4cnn5ccc(N6C[C@H]7C[C@@H]6CO7)nc45)c(C(F)F)n3)CC2)CC1] |
| I-4 | 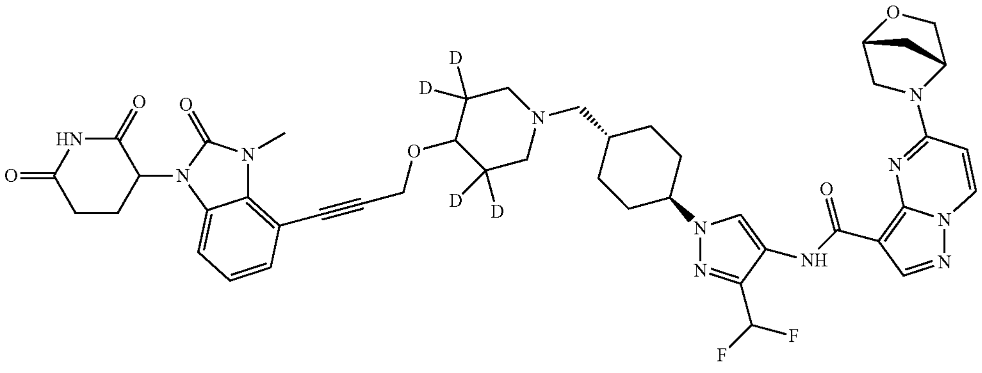 [SMILES: [2H]C1([2H])CN(C[C@H]2CC[C@H](n3cc(NC(=O)c4cnn5ccc(N6C[C@H]7C[C@@H]6CO7)nc45)c(C(F)F)n3)CC2)CC([2H])([2H])C1OCC#Cc1cccc2c1n(C)c(=O)n2C1CCC(=O)NC1=O] |

TABLE 2-continued
| Exemplary Deuterium-Enriched Compounds | |
|---|---|
| I-# | Structure |
| I-5 | 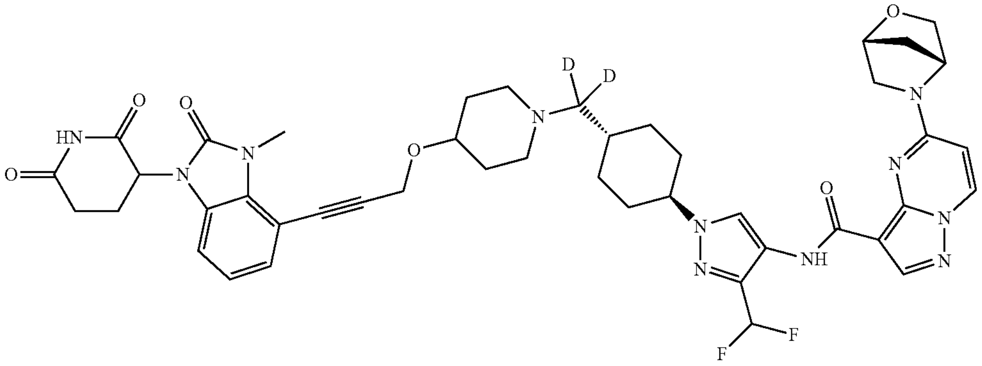 [SMILES: [2H]C([2H])([C@H]1CC[C@H](n2cc(NC(=O)c3cnn4ccc(N5C[C@H]6C[C@@H]5CO6)nc34)c(C(F)F)n2)CC1)N1CCC(OCC#Cc2cccc3c2n(C)c(=O)n3C2CCC(=O)NC2=O)CC1] |
| I-6 | 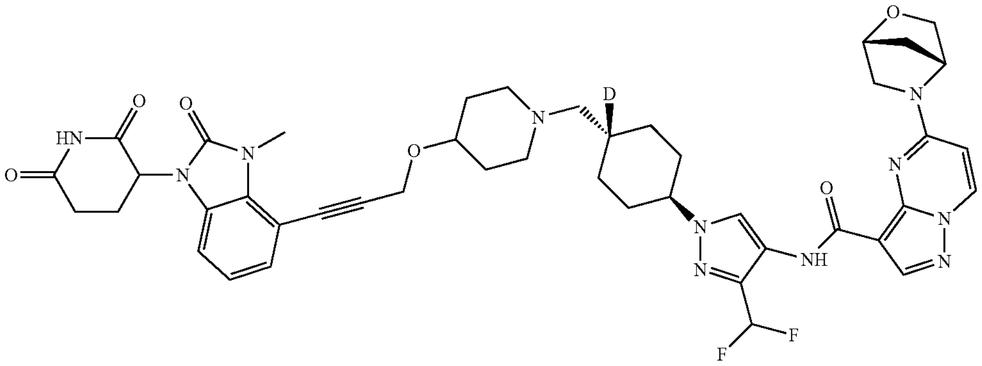 [SMILES: [2H][C@]1(CN2CCC(OCC#Cc3cccc4c3n(C)c(=O)n4C3CCC(=O)NC3=O)CC2)CC[C@H](n2cc(NC(=O)c3cnn4ccc(N5C[C@H]6C[C@@H]5CO6)nc34)c(C(F)F)n2)CC1] |
| I-7 | 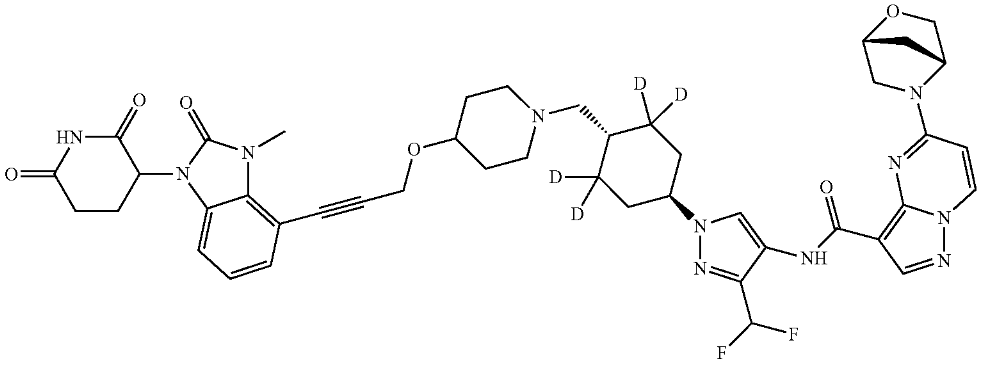 [SMILES: [2H]C1([2H])C[C@H](n2cc(NC(=O)c3cnn4ccc(N5C[C@H]6C[C@@H]5CO6)nc34)c(C(F)F)n2)CC([2H])([2H])[C@H]1CN1CCC(OCC#Cc2cccc3c2n(C)c(=O)n3C2CCC(=O)NC2=O)CC1] |
| I-8 | 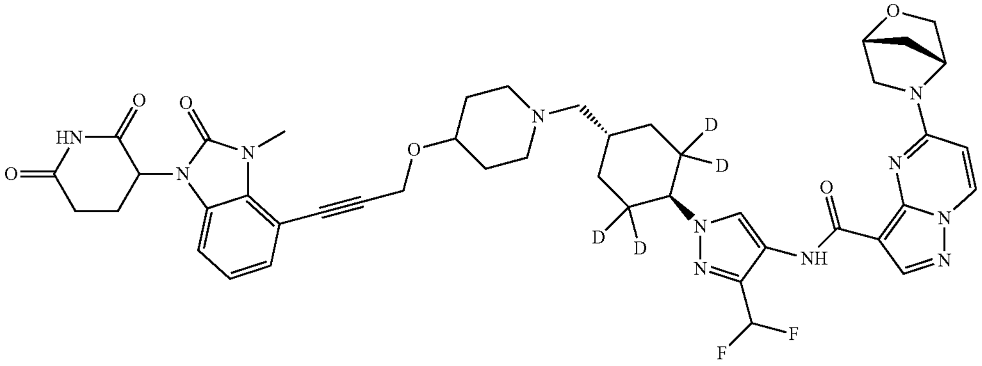 [SMILES: [2H]C1([2H])C[C@H](CN2CCC(OCC#Cc3cccc4c3n(C)c(=O)n4C3CCC(=O)NC3=O)CC2)CC([2H])([2H])[C@H]1n1cc(NC(=O)c2cnn3ccc(N4C[C@H]5C[C@@H]4CO5)nc23)c(C(F)F)n1] |

TABLE 2-continued

| Exemplary Deuterium-Enriched Compounds | |
|---|---|
| I-# | Structure |
| I-9 | 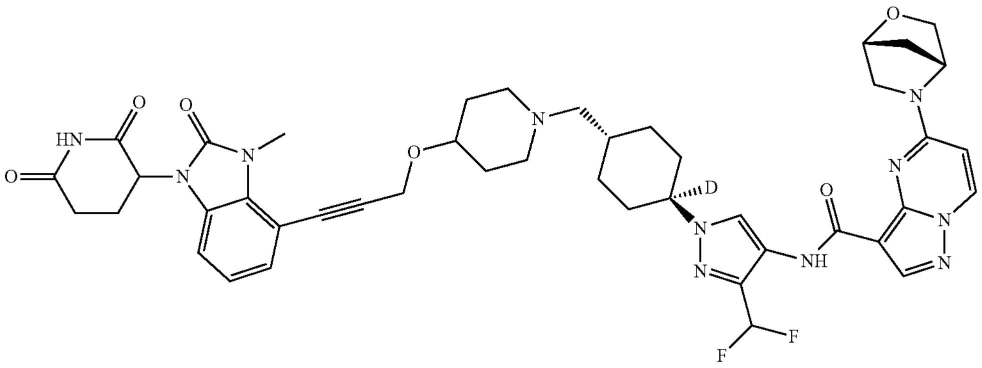 [SMILES: [2H][C@]1(n2cc(NC(=O)c3cnn4ccc(N5C[C@H]6C[C@@H]5CO6)nc34)c(C(F)F)n2)CC[C@H](CN2CCC(OCC#Cc3cccc4c3n(C)c(=O)n4C3CCC(=O)NC3=O)CC2)CC1] |
| I-10 | 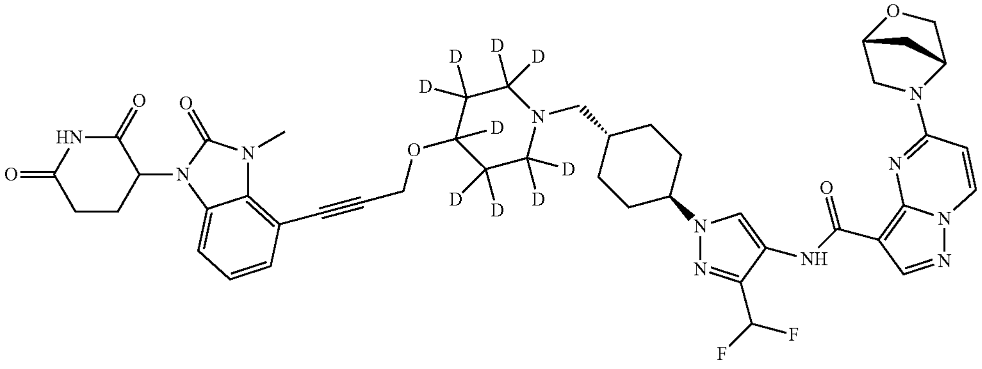 |
| I-11 | 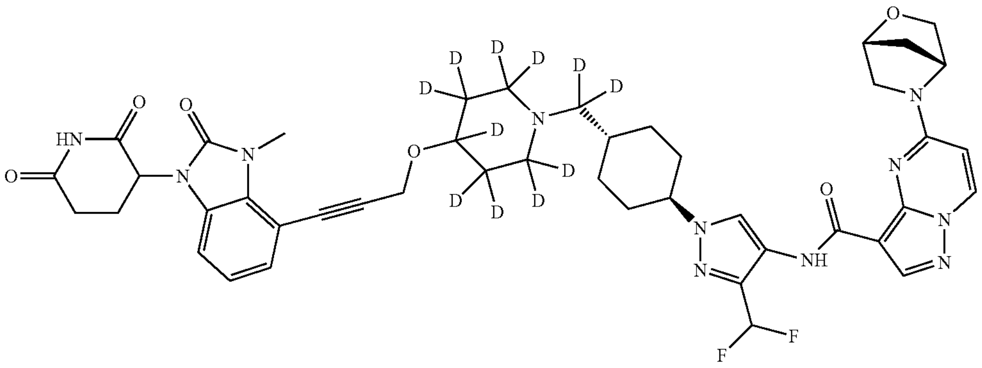 |

In some embodiments, the present invention provides a compound depicted in Table 2, above, or a pharmaceutically acceptable salt thereof.

In some embodiments, the present invention provides any compound described herein comprising one, two, three, four, five, six, seven, eight, nine, ten, eleven, twelve, thirteen, or more deuterium atoms (i.e., one or more variables in a Formula depicted herein having deuterium enrichment).

In some embodiments, each position comprising deuterium has a % deuterium incorporation in an amount of at least 5%. In some embodiments, each position comprising deuterium has a % deuterium incorporation in an amount of at least 30%. In some embodiments, each position comprising deuterium has a % deuterium incorporation in an amount of at least about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 99%, or at least about 99.5%.

In some embodiments, each position comprising deuterium has a % deuterium incorporation in an amount of about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%. In some embodiments, one, two, three, four, five, six, seven, eight, nine, ten, or more positions of deuterium enrichment each independently has a % deuterium incorporation in an amount of about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 99% or about 99.5%. In some embodiments, every position of deuterium enrichment has a % deuterium incorporation in an amount of about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 99%, or about 100%. As used herein in the context of deuterium enrichment, the term "about" means±2%.

In some embodiments, each position comprising deuterium has a % deuterium incorporation in an amount of about 5% to 99%, 10% to 95%, 15% to 90%, 20% to 85%, 25% to 80%, 30% to 80%, 35% to 75%, 40% to 70%, 30% to 99%, 30% to 95%, 30% to 90%, 50% to 75%, 50% to 99%, 50% to 95%, 50% to 90%, 60% to 99%, 60% to 95%, 60% to 90%, 70% to 99%, 70% to 95%, 70% to 90%, 80% to 99%, 80% to 95%, 80% to 90%, 90% to 99%, or 90% to 95%.

Deuterium-enriched compounds of the above formulae may be further characterized according to the extent of deuterium enrichment (% incorporation or % abundance) at the any one of the chiral positions defined by variables $R^6$, $R^{42}$, and $R^{45}$ and/or the stereochemical purity of the compound at the position defined by variables $R^6$, $R^{42}$, and $R^{45}$. For example, in certain embodiments, the % incorporation of deuterium in $R^6$, $R^{42}$, or $R^{45}$ is at least 60%. In certain other embodiments, the % incorporation of deuterium in $R^6$, $R^{42}$, or $R^{45}$ is at least 75%. In yet other embodiments, the % incorporation of deuterium in $R^6$, $R^{42}$, or $R^{45}$ is at least 90%. In yet other embodiments, the % incorporation of deuterium in $R^6$, $R^{42}$, or $R^{45}$ is at least 95%. In yet other embodiments, the % incorporation of deuterium in $R^6$, $R^{42}$, or $R^{45}$ is from about 80% to about 99%, about 85% to about 99%, or about 90% to about 99%. In yet other embodiments, the % incorporation of deuterium in $R^6$, $R^{42}$, or $R^{45}$ is selected from: (a) at least 40%, (b) at least 50%, (c) at least 60%, (d) at least 70%, (e) at least 75%, (f) at least 80%, (g) at least 90%, (h) at least 95%, (i) at least 97%, and (j) about 100%. Additional examples of the % incorporation of deuterium in $R^6$, $R^{42}$, or $R^{45}$ include about 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, and 99 to about 100%.

In certain embodiments, the compound has a stereochemical purity of at least 85% enantiomeric excess at the carbon atom bearing variable $R^6$, $R^{42}$, or $R^{45}$. In certain other embodiments, the compound has a stereochemical purity of at least 90% enantiomeric excess at the carbon atom bearing variable $R^6$, $R^{42}$, or $R^{45}$. In certain other embodiments, the compound has a stereochemical purity of at least 95% enantiomeric excess at the carbon atom bearing variable $R^6$, $R^{42}$, or $R^{45}$. In certain other embodiments, the compound has a stereochemical purity of at least 98% enantiomeric excess at the carbon atom bearing variable $R^6$, $R^{42}$, or $R^{45}$. In certain other embodiments, the compound has a stereochemical purity of at least 99% enantiomeric excess at the carbon atom bearing variable $R^6$, $R^{42}$, or $R^{45}$. In other embodiments, the deuterium-enriched compound has a stereochemical purity of at least 80%, 85%, 90%, 95%, or 98% enantiomeric excess at a chiral carbon atom bearing variable $R^6$, $R^{42}$, or $R^{45}$, and yet additional examples of stereochemical purity include an enantiomeric excess of at least 71, 72, 73, 74, 75, 76, 77, 78, 79, 80, 81, 82, 83, 84, 85, 86, 87, 88, 89, 90, 91, 92, 93, 94, 95, 96, 97, 98, or 99% at the chiral carbon atom bearing variable $R^6$, $R^{42}$, or $R^{45}$.

In some embodiments, a provided compound is selected from the following:

(1)

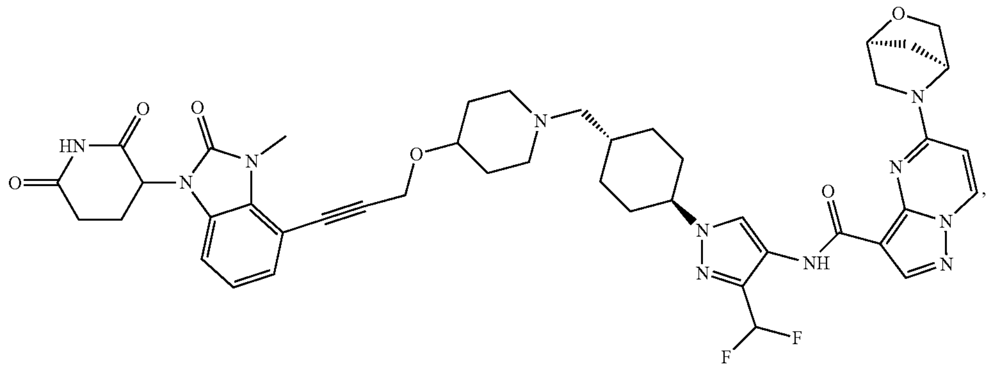

, (2)

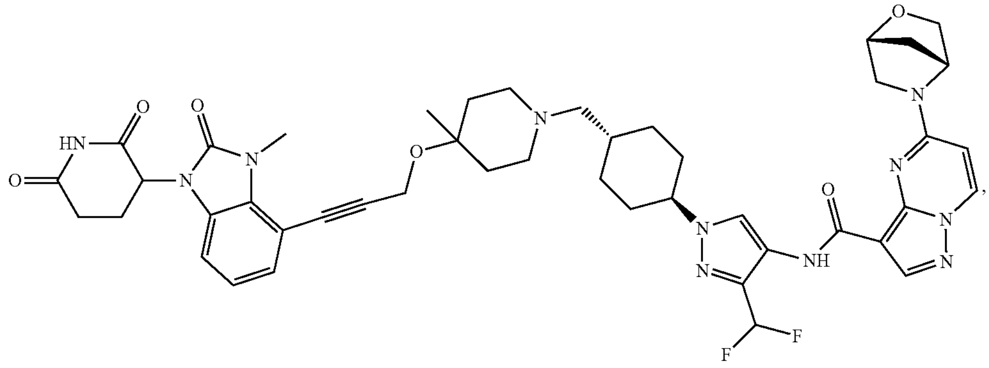

,

-continued (3)

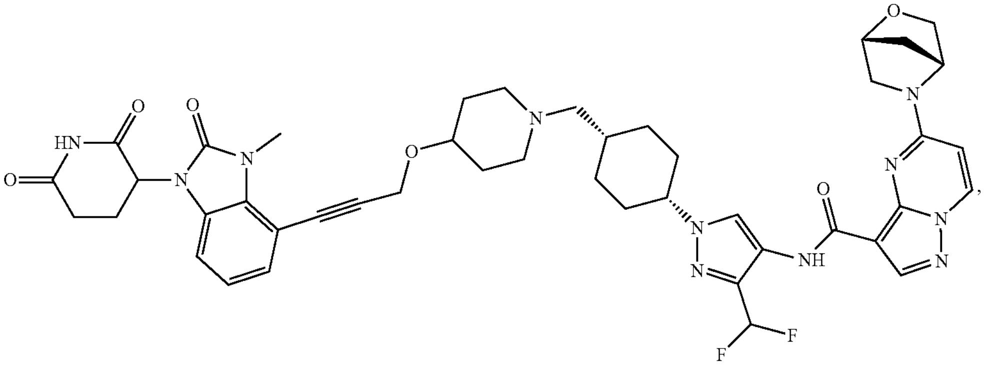

(4)

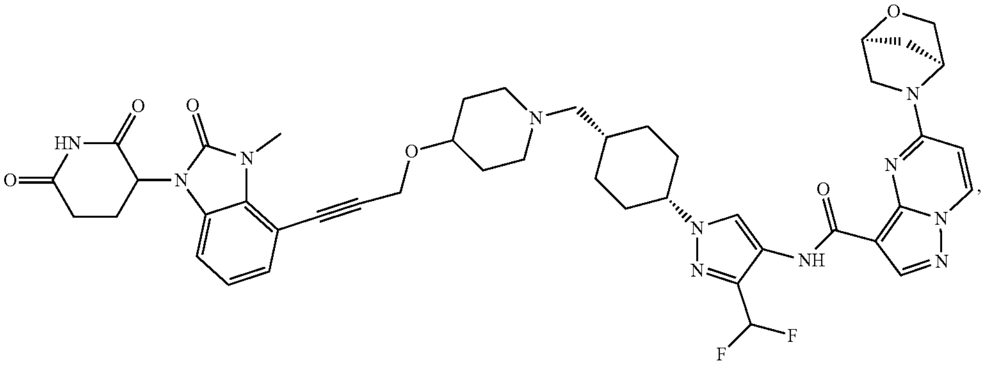

or a pharmaceutically acceptable salt thereof.

4. General Methods of Providing the Present Compounds

The compounds of this invention may be prepared or isolated in general by synthetic and/or semi-synthetic methods known to those skilled in the art for analogous compounds and by methods described in detail in the Examples, herein.

In the Scheme below, where a particular protecting group, leaving group, or transformation condition is depicted, one of ordinary skill in the art will appreciate that other protecting groups, leaving groups, and transformation conditions are also suitable and are contemplated. Such groups and transformations are described in detail in *March's Advanced Organic Chemistry: Reactions, Mechanisms, and Structure*, M. B. Smith and J. March, $5^{th}$ Edition, John Wiley & Sons, 2001, *Comprehensive Organic Transformations*, R. C. Larock, $2^{nd}$ a Edition, John Wiley & Sons, 1999, and *Protecting Groups in Organic Synthesis*, T. W. Greene and P. G. M. Wuts, $3^{rd}$ edition, John Wiley & Sons, 1999, the entirety of each of which is hereby incorporated herein by reference.

In some embodiments, compounds of the present invention are generally prepared according to Scheme 1 set forth below:

Scheme 1: Synthesis of Compounds of The Invention

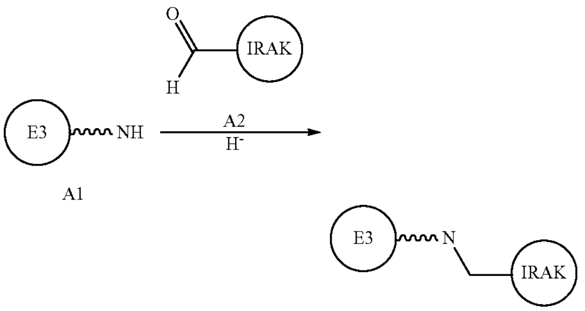

As depicted in Scheme 1, in one embodiment, reductive alkylation of the IRAK binder comprising aldehyde A-2 by the E3 ligase comprising amine A-1 is effected in the presence of a mild hydride source (e.g., sodium cyanoborohydride or sodium triacetoxyborohydride) to form a provided compound. The squiggly bond, , represents the portion of the linker between the E3 ligase and the terminal amino group of A-11.

5. Uses, Formulation and Administration

Pharmaceutically Acceptable Compositions

According to another embodiment, the invention provides a composition comprising a compound of this invention or a pharmaceutically acceptable derivative thereof and a pharmaceutically acceptable carrier, adjuvant, or vehicle. The amount of compound in compositions of this invention is such that is effective to measurably degrade and/or inhibit an IRAK protein kinase, or a mutant thereof, in a biological sample or in a patient. In certain embodiments, the amount of compound in compositions of this invention is such that is effective to measurably degrade and/or inhibit an IRAK protein kinase, or a mutant thereof, in a biological sample or in a patient. In certain embodiments, a composition of this invention is formulated for administration to a patient in need of such composition. In some embodiments, a composition of this invention is formulated for oral administration to a patient.

In some embodiments, the patient is an animal, preferably a mammal, and most preferably a human.

The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants or vehicles that may be used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

A "pharmaceutically acceptable derivative" means any non-toxic salt, ester, salt of an ester or other derivative of a compound of this invention that, upon administration to a recipient, is capable of providing, either directly or indirectly, a compound of this invention or an inhibitorily or degratorily active metabolite or residue thereof.

As used herein, the term "inhibitorily active metabolite or residue thereof" means that a metabolite or residue thereof is also an inhibitor of an IRAK protein kinase, or a mutant thereof.

As used herein, the term "degratorily active metabolite or residue thereof" means that a metabolite or residue thereof is also a degrader of an IRAK protein kinase, or a mutant thereof.

Compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

Pharmaceutically acceptable compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, pharmaceutically acceptable compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

Pharmaceutically acceptable compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, provided pharmaceutically acceptable compositions may be formulated in a suitable ointment containing the active component suspended or dissolved in one or more carriers. Carriers for topical administration of compounds of this invention include, but are not limited to, mineral oil, liquid petrolatum, white petrolatum, propylene glycol, polyoxyethylene, polyoxypropylene compound, emulsifying wax and water. Alternatively, provided pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, provided pharmaceutically acceptable compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutically acceptable compositions may be formulated in an ointment such as petrolatum.

Pharmaceutically acceptable compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Most preferably, pharmaceutically acceptable compositions of this invention are formulated for oral administration. Such formulations may be administered with or without food. In some embodiments, pharmaceutically acceptable compositions of this invention are administered without food. In other embodiments, pharmaceutically acceptable compositions of this invention are administered with food.

The amount of compounds of the present invention that may be combined with the carrier materials to produce a composition in a single dosage form will vary depending upon the host treated, the particular mode of administration. Preferably, provided compositions should be formulated so that a dosage of between 0.01-100 mg/kg body weight/day of the compound can be administered to a patient receiving these compositions.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of a compound of the present invention in the composition will also depend upon the particular compound in the composition.

Uses of Compounds and Pharmaceutically Acceptable Compositions

Compounds and compositions described herein are generally useful for the degradation and/or inhibition of kinase activity of one or more enzymes.

Examples of kinases that are degraded and/or inhibited by the compounds and compositions described herein and against which the methods described herein are useful include those of the interleukin-1 receptor-associated kinase (IRAK) family of kinases, the members of which include IRAK-1, IRAK-2, and IRAK-4, or a mutant thereof. Li et al., "IRAK-4: A novel member of the IRAK family with the properties of an IRAK-kinase," *PNAS* 2002, 99(8), 5567-5572, Flannery et al., "The interleukin-1 receptor-associated kinases: Critical regulators of innate immune signaling" Biochem Pharm 2010, 80(12), 1981-1991 incorporated by reference in its entirety.

The activity of a compound utilized in this invention as a degrader and/or inhibitor of IRAK-1, IRAK-2, and/or IRAK-4, or a mutant thereof, may be assayed in vitro, in vivo or in a cell line. In vitro assays include assays that determine inhibition of either the phosphorylation activity and/or the subsequent functional consequences, or ATPase activity of activated IRAK-1, IRAK-2, and/or IRAK-4, or a mutant thereof. Alternate in vitro assays quantitate the ability of the inhibitor to bind to IRAK-1, IRAK-2 and/or IRAK-4. Inhibitor binding may be measured by radiolabeling the inhibitor prior to binding, isolating the inhibitor/IRAK-1, inhibitor/IRAK-2, or inhibitor/IRAK-4 complex and determining the amount of radiolabel bound. Alternatively, inhibitor binding may be determined by running a competition experiment where new inhibitors are incubated with IRAK-1, IRAK-2, and/or IRAK-4 bound to known radioligands. Representative in vitro and in vivo assays useful in assaying an IRAK-4 inhibitor include those described and disclosed in, e.g., Kim et al., "A critical role for IRAK4 kinase activity in Toll-like receptor-mediated innate immunity," *J. Exp. Med.* 2007 204(5), 1025-1036; Lebakken et al., "A Fluorescence Lifetime Based Binding Assay to Characterize Kinase Inhibitors," *J. Biomol. Screen.* 2007, 12(6), 828-841; Maschera et al., "Overexpression of an enzymatically inactive interleukin-1-receptor-associated kinase activates nuclear factor-KB," *Biochem. J.* 1999, 339, 227-231; Song et al., "The kinase activities of interleukin-e receptor associated kinase (IRAK)-1 and 4 are redundant in the control of inflammatory cytokine expression in human cells," *Mol. Immunol.* 2009, 46, 1458-1466, the entirety of each of which is herein incorporated by reference. Detailed conditions for assaying a compound utilized in this invention as a degrader and/or inhibitor of IRAK-1, IRAK-2, and/or IRAK-4, or a mutant thereof, are set forth in the Examples below.

The best characterized member of the IRAK family is the serine/threonine kinase IRAK-4. IRAK-4 is implicated in signaling innate immune responses from Toll-like receptors (TLRs) and Toll/IL-1 receptors (TIRs).

Innate immunity detects pathogens through the recognition of pathogen-associated molecular patterns by TLRs, when then links to the adaptive immune response. TLRs recognize conserved structures of both microbes and endogenous molecules. TLRs which recognize bacterial and fungal components are located on the cell surface, whereas TLRs which recognize viral or microbial nucleic acids are localized to intracellular membranes such as endosomes and phagosomes. Cell surface TLRs can be targeted by small molecules and antibodies, whereas intracellular TLRs require targeting with oligonucleotides.

TLRs mediate the innate immune response by upregulating the expression of inflammatory genes in multiple target cells. See, e.g., Sen et al., "Transcriptional signaling by double-stranded RNA: role of TLR3," *Cytokine & Growth Factor Rev.* 2005, 16, 1-14, incorporated by reference in its entirety. While TLR-mediated inflammatory response is critical for innate immunity and host defense against infections, uncontrolled inflammation is detrimental to the host leading to sepsis and chronic inflammatory diseases, such as chronic arthritis, atherosclerosis, multiple sclerosis, cancers, autoimmune disorders such as rheumatoid arthritis, lupus, asthma, psoriasis, and inflammatory bowel diseases.

Upon binding of a ligand, most TLRs recruit the adaptor molecule MyD88 through the TIR domain, mediating the MyD88-dependent pathway. MyD88 then recruits IRAK-4, which engages with the nuclear factor-κB (NF-κB), mitogen-activated protein (MAP) kinase and interferon-regulatory factor cascades and leads to the induction of pro-inflammatory cytokines. The activation of NF-κB results in the induction of inflammatory cytokines and chemokines, such as TNF-α, IL-1α, IL-6 and IL-8. The kinase activity of IRAK-4 has been shown to play a critical role in the TLR-mediated immune and inflammatory responses. IRAK4 is a key mediator of the innate immune response orchestrated by interleukin-1 receptor (IL-1R), interleukin-18 receptor (IL-18R), IL-33 receptor (IL-33R), and Toll-like receptors (TLRs). Inactivation of IRAK-1 and/or IRAK-4 activity has been shown to result in diminished production of cytokines and chemokines in response to stimulation of IL-1 and TLR ligands. See, e.g., Picard et al., "Clinical features and outcome of patients with IRAK-4 and MyD88 deficiency," *Medicine* (*Baltimore*), 2010, 89(6), 043-25; Li, "IRAK4 in TLR/IL-1R signaling: Possible clinical applications," *Eur. J. Immunology* 2008, 38:614-618; Cohen et al., "Targeting protein kinases for the development of anti-inflammatory drugs," *Curr. Opin. Cell Bio.* 2009, 21:317-324; Flannery et al., "The interleukin-1 receptor-associated kinases: Critical regulators of innate immune signalling," *Biochem. Pharm.* 2010, 80(12), 1981-1991; Gottipati et al., "IRAK1: A critical signaling mediator of innate immunity," Cellular Signaling 2008, 20, 269-276; Kim et al., "A critical role for IRAK4 kinase activity in Toll-like receptor-mediated innate immunity," *J Exp. Med.* 2007 204(5), 1025-1036; Koziczak-Holbro et al., "IRAK-4 Kinase Activity Is Required for Interleukin-1 (IL-1) Receptor- and Toll-like Receptor 7-mediated Signaling and Gene Expression," *J. Biol. Chem.* 2007, 282(18), 13552-13560; Kubo-Murai et al., "IRAK-4-dependent Degradation of IRAK-1 is a Negative Feedback Signal for TLR-mediated NF-κB Activation," *J Biochem.* 2008, 143, 295-302; Maschera et al., "Overexpression of an enzymatically inactive interleukin-1-receptor-associated kinase activates nuclear factor-κB," *Biochem. J.* 1999, 339, 227-231; Lin et al., "Helical assembly in the MyD88-IRAK4-IRAK2 complex in TLR/IL-1R signalling," *Nature* 2010, 465(17), 885-891; Suzuki et al., "IRAK-4 as the central TIR signaling mediator in innate immunity," *TRENDS in Immunol.* 2002, 23(10), 503-506; Suzuki et al., "Severe impairment of interleukin-1 and Toll-like receptor signalling in mice lacking IRAK-4," *Nature* 2002, 416, 750-754; Swantek et al., "IL-1 Receptor-Associated Kinase Modulates Host Responsiveness to Endotoxin," *J. Immunol.* 2000, 164, 4301-4306; Hennessy, E., et al., "Targeting Toll-like receptors: emerging therapeutics?" *Nature Reviews*, vol. 9, pp: 293-307 (2010); Dinarello, C. "Interleukin-18 and the Pathogenesis of Inflammatory Diseases," *Seminars in Nephrology*, vol. 27, no. 1, pp: 98-114 (2007), the entirety of each of which is herein incorporated by reference. In fact, knockdown mice that express a catalytically inactive mutant IRAK-4 protein are completely resistant to septic shock and show impaired IL-1 activity. Moreover, these mice are resistant to joint and bone inflammation/destruction in an arthritis model, suggesting that IRAK-4 may be targeted to treat chronic inflammation. Further, while IRAK-4 appears to be vital for childhood immunity against some pyogenic bacteria, it has been shown to play a redundant role in protective immunity to most infections in adults, as demonstrated by one study in which patients older than 14 lacking IRAK-4 activity exhibited no invasive infections. Cohen et al., "Targeting protein kinases for the development of anti-inflammatory drugs," *Curr. Opin. Cell Bio.* 2009, 21:317-324; Ku et al., "Selective predisposition to bacterial infections in IRAK-4-deficient children: IRAK-4-dependent TLRs are otherwise redundant in protective immunity," *J Exp. Med.* 2007, 204(10), 2407-2422; Picard et al., "Inherited human IRAK-4 deficiency: an update," *Immunol. Res.* 2007, 38, 347-352; Song et al., "The kinase activities of interleukin-e receptor associated kinase (IRAK)-1 and 4 are redundant in the control of inflammatory cytokine expression in human cells," *Mol. Immunol.* 2009, 46, 1458-1466; Rokosz, L. et al., "Kinase inhibitors as drugs for chronic inflammatory and immunological diseases: progress and challenges," *Expert Opinions on Therapeutic Targets,* 12(7), pp: 883-903 (2008); Gearing, A. "Targeting toll-like receptors for drug development: a summary of commercial approaches," *Immunology and Cell Biology,* 85, pp: 490-494 (2007); Dinarello, C. "IL-1: Discoveries, controversies and future directions," *European Journal of Immunology,* 40, pp: 595-653 (2010), the entirety of each of which is herein incorporated by reference. Because TLR activation triggers IRAK-4 kinase activity, IRAK-4 inhibition presents an attractive target for treating the underlying causes of inflammation in countless diseases.

Representative IRAK-4 inhibitors include those described and disclosed in e.g., Buckley et al., *Bioorg. Med. Chem. Lett.* 2008, 18, 3211-3214; Buckley et al., *Bioorg. Med. Chem. Lett.* 2008, 18, 3291-3295; Buckley et al., *Bioorg. Med. Chem. Lett.* 2008, 18, 3656-3660; Powers et al., "Discovery and initial SAR of inhibitors of interleukin-1 receptor-associated kinase-4," *Bioorg. Med. Chem. Lett.* 2006, 16, 2842-2845; Wang et al., "IRAK-4 Inhibitors for Inflammation," *Curr. Topics in Med. Chem.* 2009, 9, 724-737, the entirety of each of which is herein incorporated by reference.

As used herein, the terms "treatment," "treat," and "treating" refer to reversing, alleviating, delaying the onset of, or inhibiting the progress of a disease or disorder, or one or more symptoms thereof, as described herein. In some embodiments, treatment may be administered after one or more symptoms have developed. In other embodiments, treatment may be administered in the absence of symptoms. For example, treatment may be administered to a susceptible individual prior to the onset of symptoms (e.g., in light of a history of symptoms and/or in light of genetic or other susceptibility factors). Treatment may also be continued after symptoms have resolved, for example to prevent or delay their recurrence.

Provided compounds are degraders and/or inhibitors of one of more of IRAK-1, IRAK-2, and/or IRAK-4 and are therefore useful for treating one or more disorders associated with activity of one or more of IRAK-1, IRAK-2, and/or IRAK-4. Thus, in certain embodiments, the present invention provides a method for treating a IRAK-1-mediated, a IRAK-2-mediated, and/or a IRAK-4-mediated disorder comprising the step of administering to a patient in need thereof a compound of the present invention, or pharmaceutically acceptable composition thereof.

As used herein, the terms "IRAK-1-mediated", "IRAK-2-mediated", and/or "IRAK-4-mediated" disorders, diseases, and/or conditions as used herein means any disease or other deleterious condition in which one or more of IRAK-1, IRAK-2, and/or IRAK-4, or a mutant thereof, are known to play a role. Accordingly, another embodiment of the present invention relates to treating or lessening the severity of one or more diseases in which one or more of IRAK-1, IRAK-2, and/or IRAK-4, or a mutant thereof, are known to play a role.

In some embodiments, the present invention provides a method for treating one or more disorders, diseases, and/or conditions wherein the disorder, disease, or condition is a cancer, a neurodegenerative disorder, a viral disease, an autoimmune disease, an inflammatory disorder, a hereditary disorder, a hormone-related disease, a metabolic disorder, conditions associated with organ transplantation, immunodeficiency disorders, a destructive bone disorder, a proliferative disorder, an infectious disease, a condition associated with cell death, thrombin-induced platelet aggregation, liver disease, pathologic immune conditions involving T cell activation, a cardiovascular disorder, or a CNS disorder.

Diseases and conditions treatable according to the methods of this invention include, but are not limited to, cancer (see, e.g., Ngo, V. et al., "Oncogenically active MYD88 mutations in human lymphoma," *Nature*, vol. 000, pp: 1-7 (2010); Lust, J. et al., "Induction of a Chronic Disease State in patients With Smoldering of Indolent Multiple Myeloma by Targeting Interleukin 1ß-Induced Interleukin 6 Production and the Myeloma Proliferative Component," *Mayo*

*Clinic Proceedings,* 84(2), pp: 114-122 (2009)), diabetes, cardiovascular disease, viral disease, autoimmune diseases such as lupus (see, e.g., Dinarello, C. "Interleukin-18 and the Pathogenesis of Inflammatory Diseases," *Seminars in Nephrology*, vol. 27, no. 1, pp: 98-114 (2007); Cohen et al., "Targeting protein kinases for the development of anti-inflammatory drugs," *Curr. Opin. Cell Bio.* 2009, 21:317-324) and rheumatoid arthritis (see, e.g., Geyer, M. et al., "Actual status of antiinterleukin-1 therapies in rheumatic diseases," Current Opinion in Rheumatology, 22, pp: 246-251 (2010)), autoinflammatory syndromes (see, e.g., Hoffman, H. et al., "Efficacy and Safety of Rilonacept (Interleukin-1 Trap) in Patients with Cryopyrin-Associated Periodic Syndromes," *Arthritis & Rheumatism*, vol. 58, no. 8, pp: 2443-2452 (2008)), atherosclerosis, psoriasis, allergic disorders, inflammatory bowel disease (see, e.g., Cario, E. "Therapeutic Impact of Toll-like Receptors on Inflammatory Bowel Diseases: A Multiple-edged Sword," *Inflamm. Bowel Dis.,* 14, pp: 411-421 (2008)), inflammation (see, e.g., Dinarello, C. "Interleukin 1 and interleukin 18 as mediators of inflammation and the aging process," The American *Journal of Clinical Nutrition,* 83, pp: 447S-455S (2006)), acute and chronic gout and gouty arthritis (see, e.g., Terkeltaub, R. "Update on gout: new therapeutic strategies and options," *Nature*, vol. 6, pp: 30-38 (2010); Weaver, A. "Epidemiology of gout," *Cleveland Clinic Journal of Medicine*, vol. 75, suppl. 5, pp: S9-S12 (2008); Dalbeth, N. et al., "Hyperuricaemia and gout: state of the art and future perspectives," *Annals of Rheumatic Diseases,* 69, pp: 1738-1743 (2010); Martinon, F. et al., "Gout-associated uric acid crystals activate the NALP3 inflammasome," *Nature*, vol. 440, pp: 237-241 (2006); So, A. et al., "A pilot study of IL-1 inhibition by anakinra in acute gout," *Arthritis Research & Therapy*, vol. 9, no. 2, pp: 1-6 (2007); Terkeltaub, R. et al., "The interleukin 1 inhibitor rilonacept in treatment of chronic gouty arthritis: results of a placebo-controlled, monosequence crossover, non-randomised, single-blind pilot study," *Annals of Rheumatic Diseases,* 68, pp: 1613-1617 (2009); Torres, R. et al., "Hyperalgesia, synovitis and multiple biomarkers of inflammation are suppressed by interleukin 1 inhibition in a novel animal model of gouty arthritis," *Annals of Rheumatic Diseases,* 68, pp: 1602-1608 (2009)), neurological disorders, metabolic syndrome (see, e.g., Troseid, M. "The role of interleukin-18 in the metabolic syndrome," *Cardiovascular Diabetology,* 9:11, pp: 1-8 (2010)), immunodeficiency disorders such as AIDS and HIV (see, e.g., Iannello, A. et al., "Role of Interleukin-18 in the Development and Pathogenesis of AIDS," *AIDS Reviews,* 11, pp: 115-125 (2009)), destructive bone disorders (see, e.g., Hennessy, E., et al., "Targeting Toll-like receptors: emerging therapeutics?" *Nature Reviews*, vol. 9, pp: 293-307 (2010)), osteoarthritis, proliferative disorders, Waldenström's Macroglobulinemia (see, e.g., Treon, et al., "Whole genome sequencing reveals a widely expressed mutation (MYD88 L265P) with oncogenic activity in Waldenström's Macroglobulinemia" 53$^{rd}$ ASH Annual Meeting; Xu, et al., "A somatic variant in MYD88 (L256P) revealed by whole genome sequencing differentiates lymphoplasmacytic lymphoma from marginal zone lymphomas" 53$^{rd}$ ASH Annual Meeting; Yang et al., "Disruption of MYD88 pathway signaling leads to loss of constitutive IRAK1, NK-kB and JAK/STAT signaling and induces apoptosis of cells expressing the MYD88 L265P mutation in Waldenström's Macroglobulinemia" 53$^{rd}$ ASH Annual Meeting; Iriyama et al., "Clinical significance of genetic mutations of CD79B, CARD11, MYD88, and EZH2 genes in diffuse large B-cell lymphoma patients" 53$^{rd}$ ASH Annual Meeting; infectious diseases, conditions associated with cell death, pathologic immune conditions involving T cell activation, and CNS disorders in a patient. In one embodiment, a human patient is treated with a compound of the current invention and a pharmaceutically acceptable carrier, adjuvant, or vehicle, wherein said compound is present in an amount to measurably degrade and/or inhibit IRAK-1 only, IRAK-2-only, IRAK-4-only and/or IRAK1 and IRAK4 kinase activity.

Compounds of the current invention are useful in the treatment of a proliferative disease selected from a benign or malignant tumor, solid tumor, carcinoma of the brain, kidney, liver, adrenal gland, bladder, breast, stomach, gastric tumors, ovaries, colon, rectum, prostate, pancreas, lung, vagina, cervix, testis, genitourinary tract, esophagus, larynx, skin, bone or thyroid, sarcoma, glioblastomas, neuroblastomas, multiple myeloma, gastrointestinal cancer, especially colon carcinoma or colorectal adenoma, a tumor of the neck and head, an epidermal hyperproliferation, psoriasis, prostate hyperplasia, a neoplasia, a neoplasia of epithelial character, adenoma, adenocarcinoma, keratoacanthoma, epidermoid carcinoma, large cell carcinoma, non-small-cell lung carcinoma, lymphomas, Hodgkins and Non-Hodgkins, a mammary carcinoma, follicular carcinoma, undifferentiated carcinoma, papillary carcinoma, seminoma, melanoma, an IL-1 driven disorder, an MyD88 driven disorder, Smoldering of indolent multiple myeloma, or hematological malignancies (including leukemia, diffuse large B-cell lymphoma (DLBCL), ABC DLBCL, chronic lymphocytic leukemia (CLL), chronic lymphocytic lymphoma, primary effusion lymphoma, Burkitt lymphoma/leukemia, acute lymphocytic leukemia, B-cell prolymphocytic leukemia, lymphoplasmacytic lymphoma, Waldenström's macroglobulinemia (WM), splenic marginal zone lymphoma, multiple myeloma, plasmacytoma, intravascular large B-cell lymphoma, AML, MDS).

In some embodiments the proliferative disease which can be treated according to the methods of this invention is an MyD88 driven disorder. In some embodiments, the MyD88 driven disorder which can be treated according to the methods of this invention is selected from ABC DLBCL, primary CNS lymphomas, primary extranodal lymphomas, Waldenström's macroglobulinemia, Hodgkin's lymphoma, primary cutaneous T-cell lymphoma and chronic lymphocytic leukemia.

In some embodiments the proliferative disease which can be treated according to the methods of this invention is an IL-1 driven disorder. In some embodiments the IL-1 driven disorder is Smoldering of indolent multiple myeloma.

Compounds according to the invention are useful in the treatment of inflammatory or obstructive airways diseases, resulting, for example, in reduction of tissue damage, airways inflammation, bronchial hyperreactivity, remodeling or disease progression. Inflammatory or obstructive airways diseases to which the present invention is applicable include asthma of whatever type or genesis including both intrinsic (non-allergic) asthma and extrinsic (allergic) asthma, mild asthma, moderate asthma, severe asthma, bronchitic asthma, exercise-induced asthma, occupational asthma and asthma induced following bacterial infection. Treatment of asthma is also to be understood as embracing treatment of subjects, e.g. of less than 4 or 5 years of age, exhibiting wheezing symptoms and diagnosed or diagnosable as "wheezy infants", an established patient category of major medical concern and now often identified as incipient or early-phase asthmatics.

Compounds according to the invention are useful in the treatment of heteroimmune diseases. Examples of such heteroimmune diseases include, but are not limited to, graft versus host disease, transplantation, transfusion, anaphylaxis, allergies (e.g., allergies to plant pollens, latex, drugs, foods, insect poisons, animal hair, animal dander, dust mites, or cockroach calyx), type I hypersensitivity, allergic conjunctivitis, allergic rhinitis, and atopic dermatitis.

Prophylactic efficacy in the treatment of asthma will be evidenced by reduced frequency or severity of symptomatic attack, e.g. of acute asthmatic or bronchoconstrictor attack, improvement in lung function or improved airways hyperreactivity. It may further be evidenced by reduced requirement for other, symptomatic therapy, such as therapy for or intended to restrict or abort symptomatic attack when it occurs, for example antiinflammatory or bronchodilatory. Prophylactic benefit in asthma may in particular be apparent in subjects prone to "morning dipping". "Morning dipping" is a recognized asthmatic syndrome, common to a substantial percentage of asthmatics and characterized by asthma attack, e.g. between the hours of about 4 to 6 am, i.e. at a time normally substantially distant form any previously administered symptomatic asthma therapy.

Compounds of the current invention can be used for other inflammatory or obstructive airways diseases and conditions to which the present invention is applicable and include acute lung injury (ALI), adult/acute respiratory distress syndrome (ARDS), chronic obstructive pulmonary, airways or lung disease (COPD, COAD or COLD), including chronic bronchitis or dyspnea associated therewith, emphysema, as well as exacerbation of airways hyperreactivity consequent to other drug therapy, in particular other inhaled drug therapy. The invention is also applicable to the treatment of bronchitis of whatever type or genesis including, but not limited to, acute, arachidic, catarrhal, croupus, chronic or phthinoid bronchitis. Further inflammatory or obstructive airways diseases to which the present invention is applicable include pneumoconiosis (an inflammatory, commonly occupational, disease of the lungs, frequently accompanied by airways obstruction, whether chronic or acute, and occasioned by repeated inhalation of dusts) of whatever type or genesis, including, for example, aluminosis, anthracosis, asbestosis, chalicosis, ptilosis, siderosis, silicosis, tabacosis and byssinosis.

With regard to their anti-inflammatory activity, in particular in relation to inhibition of eosinophil activation, compounds of the invention are also useful in the treatment of eosinophil related disorders, e.g. eosinophilia, in particular eosinophil related disorders of the airways (e.g. involving morbid eosinophilic infiltration of pulmonary tissues) including hypereosinophilia as it effects the airways and/or lungs as well as, for example, eosinophil-related disorders of the airways consequential or concomitant to Loffler's syndrome, eosinophilic pneumonia, parasitic (in particular metazoan) infestation (including tropical eosinophilia), bronchopulmonary aspergillosis, polyarteritis nodosa (including Churg-Strauss syndrome), eosinophilic granuloma, eosinophilic asthma, eosinophilic COPD, and eosinophil-related disorders affecting the airways occasioned by drug-reaction.

Compounds of the invention are also useful in the treatment of inflammatory or allergic conditions of the skin, for example psoriasis, generalized pustular psoriasis (GPP), psoriasis vulgaris, contact dermatitis, atopic dermatitis, alopecia areata, erythema multiforma, dermatitis herpetiformis, scleroderma, vitiligo, hypersensitivity angiitis, urticaria, bullous pemphigoid, lupus erythematosus, systemic lupus erythematosus, pemphigus vulgaris, pemphigus foliaceus, paraneoplastic pemphigus, epidermolysis bullosa acquisita, acne vulgaris, hidradenitis suppurativa, Sweet Syndrome, pyoderma gangrenosum, and other inflammatory or allergic conditions of the skin.

Compounds of the invention may also be used for the treatment of other diseases or conditions, such as diseases or conditions having an inflammatory component, for example, treatment of diseases and conditions of the eye such as ocular allergy, conjunctivitis, keratoconjunctivitis sicca, and vernal conjunctivitis, diseases affecting the nose including allergic rhinitis, and inflammatory disease in which autoimmune reactions are implicated or having an autoimmune component or etiology, including autoimmune hematological disorders (e.g. hemolytic anemia, aplastic anemia, pure red cell anemia and idiopathic thrombocytopenia), systemic lupus erythematosus, rheumatoid arthritis, polychondritis, scleroderma, Wegener granulamatosis, dermatomyositis, chronic active hepatitis, myasthenia gravis, Steven-Johnson syndrome, idiopathic sprue, autoimmune inflammatory bowel disease (e.g. ulcerative colitis and Crohn's disease), irritable bowel syndrome, celiac disease, periodontitis, hyaline membrane disease, kidney disease, glomerular disease, alcoholic liver disease, multiple sclerosis, endocrine opthalmopathy, Grave's disease, sarcoidosis, alveolitis, chronic hypersensitivity pneumonitis, multiple sclerosis, primary biliary cirrhosis, uveitis (anterior and posterior), Sjogren's syndrome, keratoconjunctivitis sicca and vernal keratoconjunctivitis, interstitial lung fibrosis, psoriatic arthritis, systemic juvenile idiopathic arthritis, cryopyrin-associated periodic syndrome, nephritis, vasculitis, diverticulitis, interstitial cystitis, glomerulonephritis (with and without nephrotic syndrome, e.g. including idiopathic nephrotic syndrome or minal change nephropathy), chronic granulomatous disease, endometriosis, leptospiriosis renal disease, glaucoma, retinal disease, ageing, headache, pain, complex regional pain syndrome, cardiac hypertrophy, musclewasting, catabolic disorders, obesity, fetal growth retardation, hyperchlolesterolemia, heart disease, chronic heart failure, mesothelioma, anhidrotic ecodermal dysplasia, Behcet's disease, incontinentia pigmenti, Paget's disease, pancreatitis, hereditary periodic fever syndrome, asthma (allergic and non-allergic, mild, moderate, severe, bronchitic, and exercise-induced), acute lung injury, acute respiratory distress syndrome, eosinophilia, hypersensitivities, anaphylaxis, nasal sinusitis, ocular allergy, silica induced diseases, COPD (reduction of damage, airways inflammation, bronchial hyperreactivity, remodeling or disease progression), pulmonary disease, cystic fibrosis, acid-induced lung injury, pulmonary hypertension, polyneuropathy, cataracts, muscle inflammation in conjunction with systemic sclerosis, inclusion body myositis, myasthenia gravis, thyroiditis, Addison's disease, lichen planus, Type 1 diabetes, or Type 2 diabetes, appendicitis, atopic dermatitis, asthma, allergy, blepharitis, bronchiolitis, bronchitis, bursitis, cervicitis, cholangitis, cholecystitis, chronic graft rejection, colitis, conjunctivitis, Crohn's disease, cystitis, dacryoadenitis, dermatitis, dermatomyositis, encephalitis, endocarditis, endometritis, enteritis, enterocolitis, epicondylitis, epididymitis, fasciitis, fibrositis, gastritis, gastroenteritis, Henoch-Schonlein purpura, hepatitis, hidradenitis suppurativa, immunoglobulin A nephropathy, interstitial lung disease, laryngitis, mastitis, meningitis, myelitis myocarditis, myositis, nephritis, oophoritis, orchitis, osteitis, otitis, pancreatitis, parotitis, pericarditis, peritonitis, pharyngitis, pleuritis, phlebitis, pneumonitis, pneumonia, polymyositis, proctitis, prostatitis, pyelonephritis, rhinitis, salpingitis, sinusitis, stomatitis, synovitis, tendonitis, tonsillitis, ulcerative colitis, uveitis, vaginitis, vasculitis, or vulvitis.

In some embodiments the inflammatory disease which can be treated according to the methods of this invention is an disease of the skin. In some embodiments, the inflammatory disease of the skin is selected from contact dermatitis, atopic dermatitis, alopecia areata, erythema multiforma, dermatitis herpetiformis, scleroderma, vitiligo, hypersensitivity angiitis, urticaria, bullous pemphigoid, pemphigus vulgaris, pemphigus foliaceus, paraneoplastic pemphigus, epidermolysis bullosa acquisita, hidradenitis suppurativa, and other inflammatory or allergic conditions of the skin.

In some embodiments the inflammatory disease which can be treated according to the methods of this invention is selected from acute and chronic gout, chronic gouty arthritis, psoriasis, psoriatic arthritis, rheumatoid arthritis, Juvenile rheumatoid arthritis, Systemic juvenile idiopathic arthritis (SJIA), Cryopyrin Associated Periodic Syndrome (CAPS), Adult Onset Still's disease, macrophage activation syndrome (MAS), primary and secondary hemophagocytic lymphohistiocytosis (HLH), Familial Mediterranean Fever, NLRP12 autoinflammatory syndrome, and osteoarthritis.

In some embodiments the inflammatory disease which can be treated according to the methods of this invention is a TH17 mediated disease. In some embodiments the TH17 mediated disease is selected from Systemic lupus erythematosus, Multiple sclerosis, psoriasis vulgaris, hidradenitis suppurativa, and inflammatory bowel disease (including Crohn's disease or ulcerative colitis).

In some embodiments the inflammatory disease which can be treated according to the methods of this invention is selected from Sjogren's syndrome, allergic disorders, osteoarthritis, conditions of the eye such as ocular allergy, conjunctivitis, keratoconjunctivitis sicca and vernal conjunctivitis, and diseases affecting the nose such as allergic rhinitis or chronic rhinosinusitis with nasal polyps (CRSwNP).

In some embodiments, the present invention provides a method of treating a TLR/IL-1R-driven autoinflammatory and autoimmune diseases with high unmet medical need, such as hidradenitis suppurativa, atopic dermatitis and rheumatoid arthritis. As such, in some embodiments, the present invention provides a method of treating hidradenitis suppurativa in a patient in need thereof, comprising administrating a compound of the present invention, or a pharmaceutically acceptable salt thereof. In some embodiments, the present invention provides a method of treating atopic dermatitis in a patient in need thereof, comprising administrating a compound of the present invention, or a pharmaceutically acceptable salt thereof. In some embodiments, the present invention provides a method of treating rheumatoid arthritis in a patient in need thereof, comprising administrating a compound of the present invention, or a pharmaceutically acceptable salt thereof.

Cardiovascular diseases which can be treated according to the methods of this invention include, but are not limited to, restenosis, cardiomegaly, atherosclerosis, myocardial infarction, ischemic stroke, congestive heart failure, angina pectoris, reocclusion after angioplasty, restenosis after angioplasty, reocclusion after aortocoronary bypass, restenosis after aortocoronary bypass, stroke, transitory ischemia, a peripheral arterial occlusive disorder, pulmonary embolism, and deep venous thrombosis.

In some embodiments, the neurodegenerative disease which can be treated according to the methods of this invention include, but are not limited to, Alzheimer's disease, Parkinson's disease, amyotrophic lateral sclerosis, Huntington's disease, cerebral ischemia, and neurodegenerative disease caused by traumatic injury, glutamate neurotoxicity, hypoxia, epilepsy, treatment of diabetes, metabolic syndrome, obesity, organ transplantation and graft versus host disease.

The loss of IRAK4 function results in decreased Δβ levels in an in vivo murine model of Alzheimer's disease and was associated with diminished microgliosis and astrogliosis in aged mice. Analysis of microglia isolated from the adult mouse brain revealed an altered pattern of gene expression associated with changes in microglial phenotype that were associated with expression of IRF transcription factors that govern microglial phenotype. Further, loss of IRAK4 function also promoted amyloid clearance mechanisms, including elevated expression of insulin-degrading enzyme. Finally, blocking IRAK function restored olfactory behavior (Cameron et al. "Loss of Interleukin Receptor-Associated Kinase 4 Signaling Suppresses Amyloid Pathology and Alters Microglial Phenotype in a Mouse Model of Alzheimer's Disease" Journal of Neuroscience (2012) 32(43), 15112-15123).

In some embodiments the invention provides a method of treating, preventing or lessening the severity of Alzheimer's disease comprising administering to a patient in need thereof a provided compound or a pharmaceutically acceptable salt or composition thereof.

In some embodiments the invention provides a method of treating a disease condition commonly occurring in connection with transplantation. In some embodiments, the disease or condition commonly occurring in connection with transplantation is selected from organ transplantation, organ transplant rejection, and graft versus host disease.

In some embodiments the invention provides a method of treating a metabolic disease. In some embodiments the metabolic disease is selected from Type 1 diabetes, Type 2 diabetes, metabolic syndrome, and obesity.

In some embodiments the invention provides a method of treating a viral disease. In some embodiments, the viral infection is HIV infection.

Furthermore, the invention provides the use of a compound according to the definitions herein, or a pharmaceutically acceptable salt, or a hydrate or solvate thereof for the preparation of a medicament for the treatment of a proliferative disease, an inflammatory disease, an obstructive respiratory disease, a cardiovascular disease, a metabolic disease, a neurological disease, a neurodegenerative disease, a viral disease, or a disorder commonly occurring in connection with transplantation.

Combination Therapies

Depending upon the particular condition, or disease, to be treated, additional therapeutic agents, which are normally administered to treat that condition, may be administered in combination with compounds and compositions of this invention. As used herein, additional therapeutic agents that are normally administered to treat a particular disease, or condition, are known as "appropriate for the disease, or condition, being treated."

In certain embodiments, a provided combination, or composition thereof, is administered in combination with another therapeutic agent.

In some embodiments, the present invention provides a method of treating a disclosed disease or condition comprising administering to a patient in need thereof an effective amount of a compound disclosed herein or a pharmaceutically acceptable salt thereof and co-administering simultaneously or sequentially an effective amount of one or more additional therapeutic agents, such as those described herein. In some embodiments, the method includes co-administering one additional therapeutic agent. In some embodiments, the method includes co-administering two additional therapeutic agents. In some embodiments, the combination of the disclosed compound and the additional therapeutic agent or agents acts synergistically.

Examples of agents the combinations of this invention may also be combined with include, without limitation: treatments for Alzheimer's Disease such as Aricept® and Excelon®; treatments for HIV such as ritonavir; treatments for Parkinson's Disease such as L-DOPA/carbidopa, entacapone, ropinrole, pramipexole, bromocriptine, pergolide, trihexephendyl, and amantadine; agents for treating Multiple Sclerosis (MS) such as beta interferon (e.g., Avonex® and Rebif©), Copaxone®, and mitoxantrone; treatments for asthma such as albuterol and Singulair®; agents for treating schizophrenia such as zyprexa, risperdal, seroquel, and haloperidol; anti-inflammatory agents such as corticosteroids, TNF blockers, IL-1 RA, azathioprine, cyclophosphamide, and sulfasalazine; immunomodulatory and immunosuppressive agents such as cyclosporin, tacrolimus, rapamycin, mycophenolate mofetil, interferons, corticosteroids, cyclophophamide, azathioprine, and sulfasalazine; neurotrophic factors such as acetylcholinesterase inhibitors, MAO inhibitors, interferons, anti-convulsants, ion channel blockers, riluzole, and anti-Parkinsonian agents; agents for treating cardiovascular disease such as beta-blockers, ACE inhibitors, diuretics, nitrates, calcium channel blockers, and statins; agents for treating liver disease such as corticosteroids, cholestyramine, interferons, and anti-viral agents; agents for treating blood disorders such as corticosteroids, anti-leukemic agents, and growth factors; agents that prolong or improve pharmacokinetics such as cytochrome P450 inhibitors (i.e., inhibitors of metabolic breakdown) and CYP3A4 inhibitors (e.g., ketokenozole and ritonavir), and agents for treating immunodeficiency disorders such as gamma globulin.

In certain embodiments, combination therapies of the present invention, or a pharmaceutically acceptable composition thereof, are administered in combination with a monoclonal antibody or an siRNA therapeutic.

Those additional agents may be administered separately from a provided combination therapy, as part of a multiple dosage regimen. Alternatively, those agents may be part of a single dosage form, mixed together with a compound of this invention in a single composition. If administered as part of a multiple dosage regime, the two active agents may be submitted simultaneously, sequentially or within a period of time from one another normally within five hours from one another.

As used herein, the term "combination," "combined," and related terms refers to the simultaneous or sequential administration of therapeutic agents in accordance with this invention. For example, a combination of the present invention may be administered with another therapeutic agent simultaneously or sequentially in separate unit dosage forms or together in a single unit dosage form.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

One or more other therapeutic agent may be administered separately from a compound or composition of the invention, as part of a multiple dosage regimen. Alternatively, one or more other therapeutic agents may be part of a single dosage form, mixed together with a compound of this invention in a single composition. If administered as a multiple dosage regime, one or more other therapeutic agent and a compound or composition of the invention may be administered simultaneously, sequentially or within a period of time from one another, for example within 1, 2, 3, 4, 5, 6, 7, 8, 9, 10, 11, 12, 13, 14, 15, 16, 17, 18, 18, 20, 21, 22, 23, or 24 hours from one another. In some embodiments, one or more other therapeutic agent and a compound or composition of the invention are administered as a multiple dosage regimen within greater than 24 hours apart.

In one embodiment, the present invention provides a composition comprising a provided compound or a pharmaceutically acceptable salt thereof and one or more additional therapeutic agents. The therapeutic agent may be administered together with a provided compound or a pharmaceutically acceptable salt thereof, or may be administered prior to or following administration of a provided compound or a pharmaceutically acceptable salt thereof. Suitable therapeutic agents are described in further detail below. In certain embodiments, a provided compound or a pharmaceutically acceptable salt thereof may be administered up to 5 minutes, 10 minutes, 15 minutes, 30 minutes, 1 hour, 2 hours, 3 hours, 4 hours, 5, hours, 6 hours, 7 hours, 8 hours, 9 hours, 10 hours, 11 hours, 12 hours, 13 hours, 14 hours, 15 hours, 16 hours, 17 hours, or 18 hours before the therapeutic agent. In other embodiments, a provided compound or a pharmaceutically acceptable salt thereof may be administered up to 5 minutes, 10 minutes, 15 minutes, 30 minutes, 1 hour, 2 hours, 3 hours, 4 hours, 5, hours, 6 hours, 7 hours, 8 hours, 9 hours, 10 hours, 11 hours, 12 hours, 13 hours, 14 hours, 15 hours, 16 hours, 17 hours, or 18 hours following the therapeutic agent.

In another embodiment, the present invention provides a method of treating an inflammatory disease, disorder or condition by administering to a patient in need thereof a provided compound or a pharmaceutically acceptable salt thereof and one or more additional therapeutic agents. Such additional therapeutic agents may be small molecules or recombinant biologic agents and include, for example, acetaminophen, non-steroidal anti-inflammatory drugs (NSAIDS) such as aspirin, ibuprofen, naproxen, etodolac (Lodine®) and celecoxib, colchicine (Colcrys®), corticosteroids such as prednisone, prednisolone, methylprednisolone, hydrocortisone, and the like, probenecid, allopurinol, febuxostat (Uloric®), sulfasalazine (Azulfidine®), antimalarials such as hydroxychloroquine (Plaquenil®) and chloroquine (Aralen®), methotrexate (Rheumatrex®), gold salts such as gold thioglucose (Solganal®), gold thiomalate (Myochrysine®) and auranofin (Ridaura®), D-penicillamine (Depen® or Cuprimine®), azathioprine (Imuran®), cyclophosphamide (Cytoxan®), chlorambucil (Leukeran®), cyclosporine (Sandimmune®), leflunomide (Arava®) and "anti-TNF" agents such as etanercept (Enbrel®), infliximab (Remicade®), golimumab (Simponi®), certolizumab pegol (Cimzia®) and adalimumab (Humira®), "anti-IL-1" agents such as anakinra (Kineret®) and rilonacept (Arcalyst®), canakinumab (Ilaris®), anti-Jak inhibitors such as tofacitinib, antibodies such as rituximab (Rituxan®), "anti-T-cell" agents such as abatacept (Orencia®), "anti-IL-6" agents such as tocilizumab (Actemra®), diclofenac, cortisone, hyaluronic acid (Synvisc® or Hyalgan®), monoclonal antibodies such as tanezumab, anticoagulants such as heparin (Calcinparine® or Liquaemin®) and warfarin (Coumadin®), antidiarrheals such as diphenoxylate (Lomotil®) and loperamide (Imodium®), bile acid binding agents such as cholestyramine, alosetron (Lotronex®), lubiprostone (Amitiza®), laxatives such as Milk of Magnesia, polyethylene glycol (MiraLax®), Dulcolax®, Correctol® and Senokot®, anticholinergics or antispasmodics such as dicyclomine (Bentyl®), Singulair®, beta-2 agonists such as albuterol (Ventolin® HFA, Proventil® HFA), levalbuterol (Xopenex®), metaproterenol (Alupent®), pirbuterol acetate (Maxair®), terbutaline sulfate (Brethaire®), salmeterol xinafoate (Serevent®) and formoterol (Foradil®), anticholinergic agents such as ipratropium bromide (Atrovent®) and tiotropium (Spiriva®), inhaled corticosteroids such as beclomethasone dipropionate (Beclovent®, Qvar®, and Vanceril®), triamcinolone acetonide (Azmacort®), mometasone (Asthmanex®), budesonide (Pulmocort®), and flunisolide (Aerobid®), Afviar®, Symbicort®, Dulera®, cromolyn sodium (Intal®), methylxanthines such as theophylline (Theo-Dur®, Theolair®, Slo-bid®, Uniphyl®, Theo-24®) and aminophylline, IgE antibodies such as omalizumab (Xolair®), nucleoside reverse transcriptase inhibitors such as zidovudine (Retrovir®), abacavir (Ziagen®), abacavir/lamivudine (Epzicom®), abacavir/lamivudine/zidovudine (Trizivir®), didanosine (Videx®), emtricitabine (Emtriva®), lamivudine (Epivir®), lamivudine/zidovudine (Combivir®), stavudine (Zerit®), and zalcitabine (Hivid®), non-nucleoside reverse transcriptase inhibitors such as delavirdine (Rescriptor®), efavirenz (Sustiva®), nevairapine (Viramune®) and etravirine (Intelence®), nucleotide reverse transcriptase inhibitors such as tenofovir (Viread®), protease inhibitors such as amprenavir (Agenerase®), atazanavir (Reyataz®), darunavir (Prezista®), fosamprenavir (Lexiva®), indinavir (Crixivan®), lopinavir and ritonavir (Kaletra®), nelfinavir (Viracept®), ritonavir (Norvir®), saquinavir (Fortovase® or Invirase®), and tipranavir (Aptivus®), entry inhibitors such as enfuvirtide (Fuzeon®) and maraviroc (Selzentry®), integrase inhibitors such as raltegravir (Isentress®), doxorubicin (Hydrodaunorubicin®), vincristine (Oncovin®), bortezomib (Velcade®), and dexamethasone (Decadron®) in combination with lenalidomide (Revlimid®), or any combination(s) thereof.

In another embodiment, the present invention provides a method of treating gout comprising administering to a patient in need thereof a provided compound or a pharmaceutically acceptable salt thereof and one or more additional therapeutic agents selected from non-steroidal anti-inflammatory drugs (NSAIDS) such as aspirin, ibuprofen, naproxen, etodolac (Lodine®) and celecoxib, colchicine (Colcrys®), corticosteroids such as prednisone, prednisolone, methylprednisolone, hydrocortisone, and the like, probenecid, allopurinol and febuxostat (Uloric®).

In another embodiment, the present invention provides a method of treating rheumatoid arthritis comprising administering to a patient in need thereof a provided compound or a pharmaceutically acceptable salt thereof and one or more additional therapeutic agents selected from non-steroidal anti-inflammatory drugs (NSAIDS) such as aspirin, ibuprofen, naproxen, etodolac (Lodine®) and celecoxib, corticosteroids such as prednisone, prednisolone, methylprednisolone, hydrocortisone, and the like, sulfasalazine (Azulfidine®), antimalarials such as hydroxychloroquine (Plaquenil®) and chloroquine (Aralen®), methotrexate (Rheumatrex®), gold salts such as gold thioglucose (Solganal®), gold thiomalate (Myochrysine®) and auranofin (Ridaura®), D-penicillamine (Depen® or Cuprimine®), azathioprine (Imuran®), cyclophosphamide (Cytoxan®), chlorambucil (Leukeran®), cyclosporine (Sandimmune®), leflunomide (Arava®) and "anti-TNF" agents such as etanercept (Enbrel®), infliximab (Remicade®), golimumab (Simponi®), certolizumab pegol (Cimzia®) and adalimumab (Humira®), "anti-IL-1" agents such as anakinra (Kineret®) and rilonacept (Arcalyst®), antibodies such as rituximab (Rituxan®), "anti-T-cell" agents such as abatacept (Orencia®) and "anti-IL-6" agents such as tocilizumab (Actemra®).

In some embodiments, the present invention provides a method of treating osteoarthritis comprising administering to a patient in need thereof a provided compound or a pharmaceutically acceptable salt thereof and one or more additional therapeutic agents selected from acetaminophen, non-steroidal anti-inflammatory drugs (NSAIDS) such as aspirin, ibuprofen, naproxen, etodolac (Lodine®) and celecoxib, diclofenac, cortisone, hyaluronic acid (Synvisc® or Hyalgan®) and monoclonal antibodies such as tanezumab.

In some embodiments, the present invention provides a method of treating lupus comprising administering to a patient in need thereof a provided compound or a pharmaceutically acceptable salt thereof and one or more additional therapeutic agents selected from acetaminophen, non-steroidal anti-inflammatory drugs (NSAIDS) such as aspirin, ibuprofen, naproxen, etodolac (Lodine®) and celecoxib, corticosteroids such as prednisone, prednisolone, methylprednisolone, hydrocortisone, and the like, antimalarials such as hydroxychloroquine (Plaquenil®) and chloroquine (Aralen®), cyclophosphamide (Cytoxan®), methotrexate (Rheumatrex®), azathioprine (Imuran®) and anticoagulants such as heparin (Calcinparine® or Liquaemin®) and warfarin (Coumadin®).

In some embodiments, the present invention provides a method of treating inflammatory bowel disease comprising administering to a patient in need thereof a provided compound or a pharmaceutically acceptable salt thereof and one or more additional therapeutic agents selected from mesalamine (Asacol®) sulfasalazine (Azulfidine®), antidiarrheals such as diphenoxylate (Lomotil®) and loperamide (Imodium®), bile acid binding agents such as cholestyramine, alosetron (Lotronex®), lubiprostone (Amitiza®), laxatives such as Milk of Magnesia, polyethylene glycol (MiraLax®), Dulcolax®, Correctol® and Senokot® and anticholinergics or antispasmodics such as dicyclomine (Bentyl®), anti-TNF therapies, steroids, and antibiotics such as Flagyl or ciprofloxacin.

In some embodiments, the present invention provides a method of treating asthma comprising administering to a patient in need thereof a provided compound or a pharmaceutically acceptable salt thereof and one or more additional therapeutic agents selected from anti-IL-33 antibodies such as REGN3500 (SAR440340) or CNTO 7160, Singulair®, beta-2 agonists such as albuterol (Ventolin® HFA, Proventil® HFA), levalbuterol (Xopenex®), metaproterenol (Alupent®), pirbuterol acetate (Maxair®), terbutaline sulfate (Brethaire®), salmeterol xinafoate (Serevent®) and formoterol (Foradil®), anticholinergic agents such as ipratropium bromide (Atrovent®) and tiotropium (Spiriva®), inhaled corticosteroids such as prednisone, prednisolone, beclomethasone dipropionate (Beclovent®, Qvar®, and Vanceril®), triamcinolone acetonide (Azmacort®), mometasone (Asthmanex®), budesonide (Pulmocort®), flunisolide (Aerobid®), Afviar®, Symbicort®, and Dulera®, cromolyn sodium (Intal®), methylxanthines such as theophylline (Theo-Dur®, Theolair®, Slo-bid®, Uniphyl®, Theo-24®) and aminophylline, and IgE antibodies such as omalizumab (Xolair®).

In some embodiments, the present invention provides a method of treating COPD comprising administering to a patient in need thereof a provided compound or a pharmaceutically acceptable salt thereof and one or more additional therapeutic agents selected from beta-2 agonists such as albuterol (Ventolin® HFA, Proventil® HFA), levalbuterol (Xopenex®), metaproterenol (Alupent®), pirbuterol acetate (Maxair®), terbutaline sulfate (Brethaire®), salmeterol xinafoate (Serevent®) and formoterol (Foradil®), anticholinergic agents such as ipratropium bromide (Atrovent®) and tiotropium (Spiriva®), methylxanthines such as theophylline (Theo-Dur®, Theolair®, Slo-bid®, Uniphyl®, Theo-24®) and aminophylline, inhaled corticosteroids such as prednisone, prednisolone, beclomethasone dipropionate (Beclovent®, Qvar®, and Vanceril®), triamcinolone acetonide (Azmacort®), mometasone (Asthmanex®), budesonide (Pulmocort®), flunisolide (Aerobid®), Afviar®, Symbicort®, and Dulera®, In some embodiments, the present invention provides a method of treating eosinophilic COPD comprising administering to a patient in need thereof a provided compound or a pharmaceutically acceptable salt thereof and one or more additional therapeutic agents selected from an anti-IL-33 antibody such as REGN3500 (SAR440340) or CNTO 7160. In some embodiments, the present invention provides a method of treating eosinophilic asthma comprising administering to a patient in need thereof a provided compound or a pharmaceutically acceptable salt thereof and one or more additional therapeutic agents selected from an anti-IL-33 antibody such as REGN3500 (SAR440340) or CNTO 7160.

In some embodiments, the present invention provides a method of treating HIV comprising administering to a patient in need thereof a provided compound or a pharmaceutically acceptable salt thereof and one or more additional therapeutic agents selected from nucleoside reverse transcriptase inhibitors such as zidovudine (Retrovir®), abacavir (Ziagen®), abacavir/lamivudine (Epzicom®), abacavir/lamivudine/zidovudine (Trizivir®), didanosine (Videx®), emtricitabine (Emtriva®), lamivudine (Epivir®), lamivudine/zidovudine (Combivir®), stavudine (Zerit®), and zalcitabine (Hivid®), non-nucleoside reverse transcriptase inhibitors such as delavirdine (Rescriptor®), efavirenz (Sustiva®), nevairapine (Viramune®) and etravirine (Intelence®), nucleotide reverse transcriptase inhibitors such as tenofovir (Viread®), protease inhibitors such as amprenavir (Agenerase®), atazanavir (Reyataz®), darunavir (Prezista®), fosamprenavir (Lexiva®), indinavir (Crixivan®), lopinavir and ritonavir (Kaletra®), nelfinavir (Viracept®), ritonavir (Norvir®), saquinavir (Fortovase® or Invirase®), and tipranavir (Aptivus®), entry inhibitors such as enfuvirtide (Fuzeon®) and maraviroc (Selzentry®), integrase inhibitors such as raltegravir (Isentress®), and combinations thereof.

In another embodiment, the present invention provides a method of treating a hematological malignancy comprising administering to a patient in need thereof a provided compound or a pharmaceutically acceptable salt thereof and one or more additional therapeutic agents selected from rituximab (Rituxan®), cyclophosphamide (Cytoxan®), doxorubicin (Hydrodaunorubicin®), vincristine (Oncovin®), prednisone, a hedgehog signaling inhibitor, a BTK inhibitor, a JAK/pan-JAK inhibitor, a TYK2 inhibitor, a PI3K inhibitor, a SYK inhibitor, and combinations thereof.

In another embodiment, the present invention provides a method of treating a solid tumor comprising administering to a patient in need thereof a provided compound or a pharmaceutically acceptable salt thereof and one or more additional therapeutic agents selected from rituximab (Rituxan®), cyclophosphamide (Cytoxan®), doxorubicin (Hydrodaunorubicin®), vincristine (Oncovin®), prednisone, a hedgehog signaling inhibitor, a BTK inhibitor, a JAK/pan-JAK inhibitor, a TYK2 inhibitor, a PI3K inhibitor, a SYK inhibitor, and combinations thereof.

In another embodiment, the present invention provides a method of treating a hematological malignancy comprising administering to a patient in need thereof a provided compound or a pharmaceutically acceptable salt thereof and a Hedgehog (Hh) signaling pathway inhibitor. In some embodiments, the hematological malignancy is DLBCL (Ramirez et al "Defining causative factors contributing in the activation of hedgehog signaling in diffuse large B-cell lymphoma" Leuk. Res. (2012), published online July 17, and incorporated herein by reference in its entirety).

In another embodiment, the present invention provides a method of treating diffuse large B-cell lymphoma (DLBCL) comprising administering to a patient in need thereof a provided compound or a pharmaceutically acceptable salt thereof and one or more additional therapeutic agents selected from rituximab (Rituxan®), cyclophosphamide (Cytoxan®), doxorubicin (Hydrodaunorubicin®), vincristine (Oncovin®), prednisone, a hedgehog signaling inhibitor, and combinations thereof.

In some embodiments, the present invention provides a method of treating DLBCL comprising administering to a patient in need thereof a provided compound or a pharmaceutically acceptable salt thereof and a CHOP (cyclophosphamide, Hydrodaunorubicin®, Oncovin®, and prednisone or prednisolone) or R-CHOP (rituximab, cyclophosphamide, Hydrodaunorubicin®, Oncovin®, and prednisone or prednisolone) chemotherapy regimen.

In some embodiments, the present invention provides a method of treating DLBCL comprising administering to a patient in need thereof a provided compound or a pharmaceutically acceptable salt thereof and a rituximab/bendamustine chemotherapy regimen.

In some embodiments, the present invention provides a method of treating DLBCL comprising administering to a patient in need thereof a provided compound or a pharmaceutically acceptable salt thereof and a BTK inhibitor (e.g., ibrutinib).

In some embodiments, the present invention provides a method of treating DLBCL comprising administering to a patient in need thereof a provided compound or a pharmaceutically acceptable salt thereof and an anti-CD20 antibody (e.g., rituximab).

In some embodiments, the present invention provides a method of treating DLBCL comprising administering to a patient in need thereof a provided compound or a pharmaceutically acceptable salt thereof and an anti-CD79B ADC (e.g., polatuzumab).

In some embodiments, the present invention provides a method of treating DLBCL comprising administering to a patient in need thereof a provided compound or a pharmaceutically acceptable salt thereof and a BCL2 inhibitor (e.g., venetoclax).

In some embodiments, the present invention provides a method of treating DLBCL comprising administering to a patient in need thereof a provided compound or a pharmaceutically acceptable salt thereof and lenalidomide or pomalidomide In some embodiments, the present invention provides a method of treating DLBCL comprising administering to a patient in need thereof a provided compound or a pharmaceutically acceptable salt thereof and a PI3K inhibitor (e.g., umbralisib).

In some embodiments, the present invention provides a method of treating a T-cell disease or deficiency describing herein comprising administering to a patient in need thereof a provided compound or a pharmaceutically acceptable salt thereof and a PI3K inhibitor (e.g., umbralisib).

In some embodiments, the present invention provides a method of treating DLBCL comprising administering to a patient in need thereof a provided compound or a pharmaceutically acceptable salt thereof and a protesome inhibitor (e.g., bortezomib)

In some embodiments, the present invention provides a method of treating a T-cell disease or deficiency describing herein comprising administering to a patient in need thereof a provided compound or a pharmaceutically acceptable salt thereof and a protesome inhibitor (e.g., bortezomib).

In another embodiment, the present invention provides a method of treating multiple myeloma comprising administering to a patient in need thereof a provided compound or a pharmaceutically acceptable salt thereof and one or more additional therapeutic agents selected from bortezomib (Velcade®), and dexamethasone (Decadron®), a hedgehog signaling inhibitor, a BTK inhibitor, a JAK/pan-JAK inhibitor, a TYK2 inhibitor, a PI3K inhibitor, a SYK inhibitor in combination with lenalidomide (Revlimid®).

In another embodiment, the present invention provides a method of treating Waldenström's macroglobulinemia comprising administering to a patient in need thereof a provided compound or a pharmaceutically acceptable salt thereof and one or more additional therapeutic agents selected from chlorambucil (Leukeran®), cyclophosphamide (Cytoxan®, Neosar®), fludarabine (Fludara®), cladribine (Leustatin®), rituximab (Rituxan®), a hedgehog signaling inhibitor, a BTK inhibitor, a JAK/pan-JAK inhibitor, a TYK2 inhibitor, a PI3K inhibitor, and a SYK inhibitor.

In some embodiments, one or more other therapeutic agent is an antagonist of the hedgehog pathway. Approved hedgehog pathway inhibitors which may be used in the present invention include sonidegib (Odomzo®, Sun Pharmaceuticals); and vismodegib (Erivedge®, Genentech), both for treatment of basal cell carcinoma.

In some embodiments, one or more other therapeutic agent is a Poly ADP ribose polymerase (PARP) inhibitor. In some embodiments, a PARP inhibitor is selected from olaparib (Lynparza®, AstraZeneca); rucaparib (Rubraca®, Clovis Oncology); niraparib (Zejula®, Tesaro); talazoparib (MDV3800/BMN 673/LT00673, Medivation/Pfizer/Biomarin); veliparib (ABT-888, AbbVie); and BGB-290 (BeiGene, Inc.).

In some embodiments, one or more other therapeutic agent is a histone deacetylase (HDAC) inhibitor. In some embodiments, an HDAC inhibitor is selected from vorinostat (Zolinza®, Merck); romidepsin (Istodax®, Celgene); panobinostat (Farydak®, Novartis); belinostat (Beleodaq®, Spectrum Pharmaceuticals); entinostat (SNDX-275, Syndax Pharmaceuticals) (NCT00866333); and chidamide (Epidaza®, HBI-8000, Chipscreen Biosciences, China).

In some embodiments, one or more other therapeutic agent is a CDK inhibitor, such as a CDK4/CDK6 inhibitor. In some embodiments, a CDK 4/6 inhibitor is selected from palbociclib (Ibrance®, Pfizer); ribociclib (Kisqali®, Novartis); abemaciclib (Ly2835219, Eli Lilly); and trilaciclib (G1T28, G1 Therapeutics).

In some embodiments, one or more other therapeutic agent is a folic acid inhibitor. Approved folic acid inhibitors useful in the present invention include pemetrexed (Alimta®, Eli Lilly).

In some embodiments, one or more other therapeutic agent is a CC chemokine receptor 4 (CCR4) inhibitor. CCR4 inhibitors being studied that may be useful in the present invention include mogamulizumab (Poteligeo®, Kyowa Hakko Kirin, Japan).

In some embodiments, one or more other therapeutic agent is an isocitrate dehydrogenase (IDH) inhibitor. IDH inhibitors being studied which may be used in the present invention include AG120 (Celgene; NCT02677922); AG221 (Celgene, NCT02677922; NCT02577406); BAY1436032 (Bayer, NCT02746081); IDH305 (Novartis, NCT02987010).

In some embodiments, one or more other therapeutic agent is an arginase inhibitor. Arginase inhibitors being studied which may be used in the present invention include AEB1102 (pegylated recombinant arginase, Aeglea Biotherapeutics), which is being studied in Phase 1 clinical trials for acute myeloid leukemia and myelodysplastic syndrome (NCT02732184) and solid tumors (NCT02561234); and CB-1158 (Calithera Biosciences).

In some embodiments, one or more other therapeutic agent is a glutaminase inhibitor. Glutaminase inhibitors being studied which may be used in the present invention include CB-839 (Calithera Biosciences).

In some embodiments, one or more other therapeutic agent is an antibody that binds to tumor antigens, that is, proteins expressed on the cell surface of tumor cells. Approved antibodies that bind to tumor antigens which may be used in the present invention include rituximab (Rituxan®, Genentech/BiogenIdec); ofatumumab (anti-CD20, Arzerra®, GlaxoSmithKline); obinutuzumab (anti-CD20, Gazyva®, Genentech), ibritumomab (anti-CD20 and Yttrium-90, Zevalin®, Spectrum Pharmaceuticals); daratumumab (anti-CD38, Darzalex®, Janssen Biotech), dinutuximab (anti-glycolipid GD2, Unituxin®, United Therapeutics); trastuzumab (anti-HER2, Herceptin®, Genentech); ado-trastuzumab emtansine (anti-HER2, fused to emtansine, Kadcyla®, Genentech); and pertuzumab (anti-HER2, Perjeta®, Genentech); and brentuximab vedotin (anti-CD30-drug conjugate, Adcetris®, Seattle Genetics).

In some embodiments, one or more other therapeutic agent is a topoisomerase inhibitor. Approved topoisomerase inhibitors useful in the present invention include irinotecan (Onivyde®, Merrimack Pharmaceuticals); topotecan (Hycamtin®, GlaxoSmithKline). Topoisomerase inhibitors being studied which may be used in the present invention include pixantrone (Pixuvri®, CTI Biopharma).

In some embodiments, one or more other therapeutic agent is an inhibitor of anti-apoptotic proteins, such as BCL-2. Approved anti-apoptotics which may be used in the present invention include venetoclax (Venclexta®, AbbVie/Genentech); and blinatumomab (Blincyto®, Amgen). Other therapeutic agents targeting apoptotic proteins which have undergone clinical testing and may be used in the present invention include navitoclax (ABT-263, Abbott), a BCL-2 inhibitor (NCT02079740).

In some embodiments, one or more other therapeutic agent is an androgen receptor inhibitor. Approved androgen receptor inhibitors useful in the present invention include enzalutamide (Xtandi®, Astellas/Medivation); approved inhibitors of androgen synthesis include abiraterone (Zytiga®, Centocor/Ortho); approved antagonist of gonadotropin-releasing hormone (GnRH) receptor (degaralix, Firmagon®, Ferring Pharmaceuticals).

In some embodiments, one or more other therapeutic agent is a selective estrogen receptor modulator (SERM), which interferes with the synthesis or activity of estrogens.

Approved SERMs useful in the present invention include raloxifene (Evista®, Eli Lilly).

In some embodiments, one or more other therapeutic agent is an inhibitor of bone resorption. An approved therapeutic which inhibits bone resorption is Denosumab (Xgeva®, Amgen), an antibody that binds to RANKL, prevents binding to its receptor RANK, found on the surface of osteoclasts, their precursors, and osteoclast-like giant cells, which mediates bone pathology in solid tumors with osseous metastases. Other approved therapeutics that inhibit bone resorption include bisphosphonates, such as zoledronic acid (Zometa®, Novartis).

In some embodiments, one or more other therapeutic agent is an inhibitor of interaction between the two primary p53 suppressor proteins, MDMX and MDM2. Inhibitors of p53 suppression proteins being studied which may be used in the present invention include ALRN-6924 (Aileron), a stapled peptide that equipotently binds to and disrupts the interaction of MDMX and MDM2 with p53. ALRN-6924 is currently being evaluated in clinical trials for the treatment of AML, advanced myelodysplastic syndrome (MDS) and peripheral T-cell lymphoma (PTCL) (NCT02909972; NCT02264613).

In some embodiments, one or more other therapeutic agent is an inhibitor of transforming growth factor-beta (TGF-beta or TGFß). Inhibitors of TGF-beta proteins being studied which may be used in the present invention include NIS793 (Novartis), an anti-TGF-beta antibody being tested in the clinic for treatment of various cancers, including breast, lung, hepatocellular, colorectal, pancreatic, prostate and renal cancer (NCT 02947165). In some embodiments, the inhibitor of TGF-beta proteins is fresolimumab (GC1008; Sanofi-Genzyme), which is being studied for melanoma (NCT00923169); renal cell carcinoma (NCT00356460); and non-small cell lung cancer (NCT02581787). Additionally, in some embodiments, the additional therapeutic agent is a TGF-beta trap, such as described in Connolly et al. (2012) Int'l J. Biological Sciences 8:964-978. One therapeutic compound currently in clinical trials for treatment of solid tumors is M7824 (Merck KgaA—formerly MSB0011459X), which is a bispecific, anti-PD-L1/TGFß trap compound (NCT02699515); and (NCT02517398). M7824 is comprised of a fully human IgG1 antibody against PD-L1 fused to the extracellular domain of human TGF-beta receptor II, which functions as a TGFß "trap."

In some embodiments, one or more other therapeutic agent is selected from glembatumumab vedotin-monomethyl auristatin E (MMAE) (Celldex), an anti-glycoprotein NMB (gpNMB) antibody (CR011) linked to the cytotoxic MMAE. gpNMB is a protein overexpressed by multiple tumor types associated with cancer cells' ability to metastasize.

In some embodiments, one or more other therapeutic agent is an antiproliferative compound. Such antiproliferative compounds include, but are not limited to aromatase inhibitors; antiestrogens; topoisomerase I inhibitors; topoisomerase II inhibitors; microtubule active compounds; alkylating compounds; histone deacetylase inhibitors; compounds which induce cell differentiation processes; cyclooxygenase inhibitors; MMP inhibitors; mTOR inhibitors; antineoplastic antimetabolites; platin compounds; compounds targeting/decreasing a protein or lipid kinase activity and further anti-angiogenic compounds; compounds which target, decrease or inhibit the activity of a protein or lipid phosphatase; gonadorelin agonists; anti-androgens; methionine aminopeptidase inhibitors; matrix metalloproteinase inhibitors; bisphosphonates; biological response modifiers; antiproliferative antibodies; heparanase inhibitors; inhibitors of Ras oncogenic isoforms; telomerase inhibitors; proteasome inhibitors; compounds used in the treatment of hematologic malignancies; compounds which target, decrease or inhibit the activity of Flt-3; Hsp90 inhibitors such as 17-AAG (17-allylaminogeldanamycin, NSC330507), 17-DMAG (17-dimethylaminoethylamino-17-demethoxy-geldanamycin, NSC707545), IPI-504, CNF1010, CNF2024, CNF1010 from Conforma Therapeutics; temozolomide (Temodal®); kinesin spindle protein inhibitors, such as SB715992 or SB743921 from GlaxoSmithKline, or pentamidine/chlorpromazine from CombinatoRx; MEK inhibitors such as ARRY142886 from Array BioPharma, AZd$_6$244 from AstraZeneca, PD181461 from Pfizer and leucovorin.

In some embodiments, the present invention provides a method of treating Alzheimer's disease comprising administering to a patient in need thereof a provided compound or a pharmaceutically acceptable salt thereof and one or more additional therapeutic agents selected from donepezil (Aricept®), rivastigmine (Excelon®), galantamine (Razadyne®), tacrine (Cognex®), and memantine (Namenda®).

In some embodiments, one or more other therapeutic agent is a taxane compound, which causes disruption of microtubules, which are essential for cell division. In some embodiments, a taxane compound is selected from paclitaxel (Taxol®, Bristol-Myers Squibb), docetaxel (Taxotere®, Sanofi-Aventis; Docefrez®, Sun Pharmaceutical), albumin-bound paclitaxel (Abraxane®; Abraxis/Celgene), cabazitaxel (Jevtana®, Sanofi-Aventis), and SID530 (SK Chemicals, Co.) (NCT00931008).

In some embodiments, one or more other therapeutic agent is a nucleoside inhibitor, or a therapeutic agent that interferes with normal DNA synthesis, protein synthesis, cell replication, or will otherwise inhibit rapidly proliferating cells.

In some embodiments, a nucleoside inhibitor is selected from trabectedin (guanidine alkylating agent, Yondelis®, Janssen Oncology), mechlorethamine (alkylating agent, Valchlor®, Aktelion Pharmaceuticals); vincristine (Oncovin®, Eli Lilly; Vincasar®, Teva Pharmaceuticals; Marqibo®, Talon Therapeutics); temozolomide (prodrug to alkylating agent 5-(3-methyltriazen-1-yl)-imidazole-4-carboxamide (MTIC) Temodar®, Merck); cytarabine injection (ara-C, antimetabolic cytidine analog, Pfizer); lomustine (alkylating agent, CeeNU®, Bristol-Myers Squibb; Gleostine®, NextSource Biotechnology); azacitidine (pyrimidine nucleoside analog of cytidine, Vidaza®, Celgene); omacetaxine mepesuccinate (cephalotaxine ester) (protein synthesis inhibitor, Synribo®; Teva Pharmaceuticals); asparaginase *Erwinia chrysanthemi* (enzyme for depletion of asparagine, Elspar®, Lundbeck; Erwinaze®, EUSA Pharma); eribulin mesylate (microtubule inhibitor, tubulin-based antimitotic, Halaven®, Eisai); cabazitaxel (microtubule inhibitor, tubulin-based antimitotic, Jevtana®, Sanofi-Aventis); capacetrine (thymidylate synthase inhibitor, Xeloda®, Genentech); bendamustine (bifunctional mechlorethamine derivative, believed to form interstrand DNA cross-links, Treanda®, Cephalon/Teva); ixabepilone (semi-synthetic analog of epothilone B, microtubule inhibitor, tubulin-based antimitotic, Ixempra®, Bristol-Myers Squibb); nelarabine (prodrug of deoxyguanosine analog, nucleoside metabolic inhibitor, Arranon®, Novartis); clorafabine (prodrug of ribonucleotide reductase inhibitor, competitive inhibitor of deoxycytidine, Clolar®, Sanofi-Aventis); and trifluridine and tipiracil (thymidine-based nucleoside analog and thymidine phosphorylase inhibitor, Lonsurf®, Taiho Oncology).

In some embodiments, one or more other therapeutic agent is a kinase inhibitor or VEGF-R antagonist. Approved VEGF inhibitors and kinase inhibitors useful in the present invention include: bevacizumab (Avastin®, Genentech/Roche) an anti-VEGF monoclonal antibody; ramucirumab (Cyramza®, Eli Lilly), an anti-VEGFR-2 antibody and ziv-aflibercept, also known as VEGF Trap (Zaltrap®; Regeneron/Sanofi). VEGFR inhibitors, such as regorafenib (Stivarga®, Bayer); vandetanib (Caprelsa®, AstraZeneca); axitinib (Inlyta®, Pfizer); and lenvatinib (Lenvima®, Eisai); Raf inhibitors, such as sorafenib (Nexavar®, Bayer AG and Onyx); dabrafenib (Tafinlar®, Novartis); and vemurafenib (Zelboraf®, Genentech/Roche); MEK inhibitors, such as cobimetanib (Cotellic®, Exelexis/Genentech/Roche); trametinib (Mekinist®, Novartis); Bcr-Abl tyrosine kinase inhibitors, such as imatinib (Gleevec®, Novartis); nilotinib (Tasigna®, Novartis); dasatinib (Sprycel®, BristolMyersSquibb); bosutinib (Bosulif®, Pfizer); and ponatinib (Inclusig®, Ariad Pharmaceuticals); Her2 and EGFR inhibitors, such as gefitinib (Iressa®, AstraZeneca); erlotinib (Tarceeva®, Genentech/Roche/Astellas); lapatinib (Tykerb®, Novartis); afatinib (Gilotrif®, Boehringer Ingelheim); osimertinib (targeting activated EGFR, Tagrisso®, AstraZeneca); and brigatinib (Alunbrig®, Ariad Pharmaceuticals); c-Met and VEGFR2 inhibitors, such as cabozanitib (Cometriq®, Exelexis); and multikinase inhibitors, such as sunitinib (Sutent®, Pfizer); pazopanib (Votrient®, Novartis); ALK inhibitors, such as crizotinib (Xalkori®, Pfizer); ceritinib (Zykadia®, Novartis); and alectinib (Alecenza®, Genentech/Roche); Bruton's tyrosine kinase inhibitors, such as ibrutinib (Imbruvica®, Pharmacyclics/Janssen); and Flt3 receptor inhibitors, such as midostaurin (Rydapt®, Novartis).

Other kinase inhibitors and VEGF-R antagonists that are in development and may be used in the present invention include tivozanib (Aveo Pharmaecuticals); vatalanib (Bayer/Novartis); lucitanib (Clovis Oncology); dovitinib (TK1258, Novartis); Chiauanib (Chipscreen Biosciences); CEP-11981 (Cephalon); linifanib (Abbott Laboratories); neratinib (HKI-272, Puma Biotechnology); radotinib (Supect®, IY5511, Il-Yang Pharmaceuticals, S. Korea); ruxolitinib (Jakafi®, Incyte Corporation); PTC299 (PTC Therapeutics); CP-547,632 (Pfizer); foretinib (Exelexis, GlaxoSmithKline); quizartinib (Daiichi Sankyo) and motesanib (Amgen/Takeda).

In another embodiment, the present invention provides a method of treating organ transplant rejection or graft vs. host disease comprising administering to a patient in need thereof a provided compound or a pharmaceutically acceptable salt thereof and one or more additional therapeutic agents selected from a steroid, cyclosporin, FK506, rapamycin, a hedgehog signaling inhibitor, a BTK inhibitor, a JAK/pan-JAK inhibitor, a TYK2 inhibitor, a PI3K inhibitor, and a SYK inhibitor.

In another embodiment, the present invention provides a method of treating or lessening the severity of a disease comprising administering to a patient in need thereof a provided compound or a pharmaceutically acceptable salt thereof and a BTK inhibitor, wherein the disease is selected from inflammatory bowel disease, arthritis, systemic lupus erythematosus (SLE), vasculitis, idiopathic thrombocytopenic purpura (ITP), rheumatoid arthritis, psoriatic arthritis, osteoarthritis, Still's disease, juvenile arthritis, diabetes, myasthenia gravis, Hashimoto's thyroiditis, Ord's thyroiditis, Graves' disease, autoimmune thyroiditis, Sjogren's syndrome, multiple sclerosis, systemic sclerosis, Lyme neuroborreliosis, Guillain-Barre syndrome, acute disseminated encephalomyelitis, Addison's disease, opsoclonus-myoclonus syndrome, ankylosing spondylosis, antiphospholipid antibody syndrome, aplastic anemia, autoimmune hepatitis, autoimmune gastritis, pernicious anemia, celiac disease, Goodpasture's syndrome, idiopathic thrombocytopenic purpura, optic neuritis, scleroderma, primary biliary cirrhosis, Reiter's syndrome, Takayasu's arteritis, temporal arteritis, warm autoimmune hemolytic anemia, Wegener's granulomatosis, psoriasis, alopecia universalis, Behcet's disease, chronic fatigue, dysautonomia, membranous glomerulonephropathy, endometriosis, interstitial cystitis, pemphigus vulgaris, bullous pemphigoid, neuromyotonia, scleroderma, vulvodynia, a hyperproliferative disease, rejection of transplanted organs or tissues, Acquired Immunodeficiency Syndrome (AIDS, also known as HIV), type 1 diabetes, graft versus host disease, transplantation, transfusion, anaphylaxis, allergies (e.g., allergies to plant pollens, latex, drugs, foods, insect poisons, animal hair, animal dander, dust mites, or cockroach calyx), type I hypersensitivity, allergic conjunctivitis, allergic rhinitis, and atopic dermatitis, asthma, appendicitis, atopic dermatitis, asthma, allergy, blepharitis, bronchiolitis, bronchitis, bursitis, cervicitis, cholangitis, cholecystitis, chronic graft rejection, colitis, conjunctivitis, Crohn's disease, cystitis, dacryoadenitis, dermatitis, dermatomyositis, encephalitis, endocarditis, endometritis, enteritis, enterocolitis, epicondylitis, epididymitis, fasciitis, fibrositis, gastritis, gastroenteritis, Henoch-Schonlein purpura, hepatitis, hidradenitis suppurativa, immunoglobulin A nephropathy, interstitial lung disease, laryngitis, mastitis, meningitis, myelitis myocarditis, myositis, nephritis, oophoritis, orchitis, osteitis, otitis, pancreatitis, parotitis, pericarditis, peritonitis, pharyngitis, pleuritis, phlebitis, pneumonitis, pneumonia, polymyositis, proctitis, prostatitis, pyelonephritis, rhinitis, salpingitis, sinusitis, stomatitis, synovitis, tendonitis, tonsillitis, ulcerative colitis, uveitis, vaginitis, vasculitis, or vulvitis, B-cell proliferative disorder, e.g., diffuse large B cell lymphoma, follicular lymphoma, chronic lymphocytic lymphoma, chronic lymphocytic leukemia, acute lymphocytic leukemia, B-cell prolymphocytic leukemia, lymphoplasmacytic lymphoma/Waldenstrom macroglobulinemia, splenic marginal zone lymphoma, multiple myeloma (also known as plasma cell myeloma), non-Hodgkin's lymphoma, Hodgkin's lymphoma, plasmacytoma, extranodal marginal zone B cell lymphoma, nodal marginal zone B cell lymphoma, mantle cell lymphoma, mediastinal (thymic) large B cell lymphoma, intravascular large B cell lymphoma, primary effusion lymphoma, Burkitt lymphoma/leukemia, or lymphomatoid granulomatosis, breast cancer, prostate cancer, or cancer of the mast cells (e.g., mastocytoma, mast cell leukemia, mast cell sarcoma, systemic mastocytosis), bone cancer, colorectal cancer, pancreatic cancer, diseases of the bone and joints including, without limitation, rheumatoid arthritis, seronegative spondyloarthropathies (including ankylosing spondylitis, psoriatic arthritis and Reiter's disease), Behcet's disease, Sjogren's syndrome, systemic sclerosis, osteoporosis, bone cancer, bone metastasis, athromboembolic disorder, (e.g., myocardial infarct, angina pectoris, reocclusion after angioplasty, restenosis after angioplasty, reocclusion after aortocoronary bypass, restenosis after aortocoronary bypass, stroke, transitory ischemia, a peripheral arterial occlusive disorder, pulmonary embolism, deep venous thrombosis), inflammatory pelvic disease, urethritis, skin sunburn, sinusitis, pneumonitis, encephalitis, meningitis, myocarditis, nephritis, osteomyelitis, myositis, hepatitis, gastritis, enteritis, dermatitis, gingivitis, appendicitis, pancreatitis, cholocystitus, agammaglobulinemia, psoriasis, allergy, Crohn's disease, irritable bowel syndrome, ulcerative colitis, Sjogren's disease, tissue graft rejection, hyperacute rejection of transplanted organs, asthma, allergic rhinitis, chronic obstructive pulmonary disease (COPD), autoimmune polyglandular disease (also known as autoimmune polyglandular syndrome), autoimmune alopecia, pernicious anemia, glomerulonephritis, dermatomyositis, multiple sclerosis, scleroderma, vasculitis, autoimmune hemolytic and thrombocytopenic states, Goodpasture's syndrome, atherosclerosis, Addison's disease, Parkinson's disease, Alzheimer's disease, diabetes, septic shock, systemic lupus erythematosus (SLE), rheumatoid arthritis, psoriatic arthritis, juvenile arthritis, osteoarthritis, chronic idiopathic thrombocytopenic purpura, Waldenstrom macroglobulinemia, myasthenia gravis, Hashimoto's thyroiditis, atopic dermatitis, degenerative joint disease, vitiligo, autoimmune hypopituitarism, Guillain-Barre syndrome, Behcet's disease, scleraderma, mycosis fungoides, acute inflammatory responses (such as acute respiratory distress syndrome and ischemia/reperfusion injury), and Graves' disease.

In another embodiment, the present invention provides a method of treating or lessening the severity of a disease comprising administering to a patient in need thereof a provided compound or a pharmaceutically acceptable salt thereof and a PI3K inhibitor, wherein the disease is selected from a cancer, a neurodegenerative disorder, an angiogenic disorder, a viral disease, an autoimmune disease, an inflammatory disorder, a hormone-related disease, conditions associated with organ transplantation, immunodeficiency disorders, a destructive bone disorder, a proliferative disorder, an infectious disease, a condition associated with cell death, thrombin-induced platelet aggregation, chronic myelogenous leukemia (CML), chronic lymphocytic leukemia (CLL), liver disease, pathologic immune conditions involving T cell activation, a cardiovascular disorder, and a CNS disorder.

In another embodiment, the present invention provides a method of treating or lessening the severity of a disease comprising administering to a patient in need thereof a provided compound or a pharmaceutically acceptable salt thereof and a PI3K inhibitor, wherein the disease is selected from benign or malignant tumor, carcinoma or solid tumor of the brain, kidney (e.g., renal cell carcinoma (RCC)), liver, adrenal gland, bladder, breast, stomach, gastric tumors, ovaries, colon, rectum, prostate, pancreas, lung, vagina, endometrium, cervix, testis, genitourinary tract, esophagus, larynx, skin, bone or thyroid, sarcoma, glioblastomas, neuroblastomas, multiple myeloma or gastrointestinal cancer, especially colon carcinoma or colorectal adenoma or a tumor of the neck and head, an epidermal hyperproliferation, psoriasis, prostate hyperplasia, a neoplasia, a neoplasia of epithelial character, adenoma, adenocarcinoma, keratoacanthoma, epidermoid carcinoma, large cell carcinoma, non-small-cell lung carcinoma, lymphomas, (including, for example, non-Hodgkin's Lymphoma (NHL) and Hodgkin's lymphoma (also termed Hodgkin's or Hodgkin's disease)), a mammary carcinoma, follicular carcinoma, undifferentiated carcinoma, papillary carcinoma, seminoma, melanoma, or a leukemia, diseases include Cowden syndrome, Lhermitte-Dudos disease and Bannayan-Zonana syndrome, or diseases in which the PI3K/PKB pathway is aberrantly activated, asthma of whatever type or genesis including both intrinsic (non-allergic) asthma and extrinsic (allergic) asthma, mild asthma, moderate asthma, severe asthma, bronchitic asthma, exercise-induced asthma, occupational asthma and asthma induced following bacterial infection, acute lung injury (ALI), adult/acute respiratory distress syndrome (ARDS), chronic obstructive pulmonary, airways or lung disease (COPD, COAD or COLD), including chronic bronchitis or dyspnea associated therewith, emphysema, as well as exacerbation of airways hyperreactivity consequent to other drug therapy, in particular other inhaled drug therapy, bronchitis of whatever type or genesis including, but not limited to, acute, arachidic, catarrhal, croupus, chronic or phthinoid bronchitis, pneumoconiosis (an inflammatory, commonly occupational, disease of the lungs, frequently accompanied by airways obstruction, whether chronic or acute, and occasioned by repeated inhalation of dusts) of whatever type or genesis, including, for example, aluminosis, anthracosis, asbestosis, chalicosis, ptilosis, siderosis, silicosis, tabacosis and byssinosis, Loffler's syndrome, eosinophilic, pneumonia, parasitic (in particular metazoan) infestation (including tropical eosinophilia), bronchopulmonary aspergillosis, polyarteritis nodosa (including Churg-Strauss syndrome), eosinophilic granuloma and eosinophil-related disorders affecting the airways occasioned by drug-reaction, psoriasis, contact dermatitis, atopic dermatitis, alopecia areata, erythema multiforma, dermatitis herpetiformis, scleroderma, vitiligo, hypersensitivity angiitis, urticaria, bullous pemphigoid, lupus erythematosus, pemphisus, epidermolysis bullosa acquisita, conjunctivitis, keratoconjunctivitis sicca, and vernal conjunctivitis, diseases affecting the nose including allergic rhinitis, and inflammatory disease in which autoimmune reactions are implicated or having an autoimmune component or etiology, including autoimmune hematological disorders (e.g. hemolytic anemia, aplastic anemia, pure red cell anemia and idiopathic thrombocytopenia), systemic lupus erythematosus, rheumatoid arthritis, polychondritis, sclerodoma, Wegener granulamatosis, dermatomyositis, chronic active hepatitis, myasthenia gravis, Steven-Johnson syndrome, idiopathic sprue, autoimmune inflammatory bowel disease (e.g. ulcerative colitis and Crohn's disease), endocrine opthalmopathy, Grave's disease, sarcoidosis, alveolitis, chronic hypersensitivity pneumonitis, multiple sclerosis, primary biliary cirrhosis, uveitis (anterior and posterior), keratoconjunctivitis sicca and vernal keratoconjunctivitis, interstitial lung fibrosis, psoriatic arthritis and glomerulonephritis (with and without nephrotic syndrome, e.g. including idiopathic nephrotic syndrome or minal change nephropathy, restenosis, cardiomegaly, atherosclerosis, myocardial infarction, ischemic stroke and congestive heart failure, Alzheimer's disease, Parkinson's disease, amyotrophic lateral sclerosis, Huntington's disease, and cerebral ischemia, and neurodegenerative disease caused by traumatic injury, glutamate neurotoxicity and hypoxia.

In some embodiments, one or more other therapeutic agent is a phosphatidylinositol 3 kinase (PI3K) inhibitor. In some embodiments, a PI3K inhibitor is selected from idelalisib (Zydelig®, Gilead), alpelisib (BYL719, Novartis), taselisib (GDC-0032, Genentech/Roche); pictilisib (GDC-0941, Genentech/Roche); copanlisib (BAY806946, Bayer); duvelisib (formerly IPI-145, Infinity Pharmaceuticals); PQR309 (Piqur Therapeutics, Switzerland); and TGR1202 (formerly RP5230, TG Therapeutics).

In some embodiments, the present invention provides a method of treating AML comprising administering to a patient in need thereof a provided compound or a pharmaceutically acceptable salt thereof and one or more additional therapeutic agents selected from: FLT3 inhibitors; targeted agents such as IDH inhibitors, anti-CD33 ADCs (e.g. Mylotarg), BCL2 inhibitors, and Hedgehog inhibitors; and chemotherapy such as AraC, daunarubicin, etoposide, methotrexate, fludarabine, mitozantrone, azacytidine, and corticosteroids.

In some embodiments, the present invention provides a method of treating MDS comprising administering to a patient in need thereof a provided compound or a pharmaceutically acceptable salt thereof and one or more additional therapeutic agents selected from azacytidine, decitabine and revlimid.

In some embodiments, the present invention provides a method of treating inflammatory skin conditions such as hidradenitis suppurativa, comprising administering to a patient in need thereof a provided compound or a pharmaceutically acceptable salt thereof and one or more additional therapeutic agents selected from anti-TNF drugs.

In some embodiments, the present invention provides a method of treating inflammatory skin conditions such as atopic dermatitis, comprising administering to a patient in need thereof a provided compound or a pharmaceutically acceptable salt thereof and one or more additional therapeutic agents selected from IL-4/IL-13-targeted agents such as dupilumab.

In some embodiments, the present invention provides a method of treating inflammatory skin conditions such as psoriasis, comprising administering to a patient in need thereof a provided compound or a pharmaceutically acceptable salt thereof and one or more additional therapeutic agents selected from anti-IL-17 and anti-IL-23 antibodies.

The compounds and compositions, according to the method of the present invention, may be administered using any amount and any route of administration effective for treating or lessening the severity of a cancer, an autoimmune disorder, a proliferative disorder, an inflammatory disorder, a neurodegenerative or neurological disorder, schizophrenia, a bone-related disorder, liver disease, or a cardiac disorder. The exact amount required will vary from subject to subject, depending on the species, age, and general condition of the subject, the severity of the infection, the particular agent, its mode of administration, and the like. Compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts. In some embodiments, the patient is an animal, preferably a mammal, and most preferably a human.

Pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, the compounds of the invention may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polyethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

According to one embodiment, the invention relates to a method of inhibiting protein kinase activity or degrading a protein kinase in a biological sample comprising the step of contacting said biological sample with a compound of this invention, or a composition comprising said compound.

According to another embodiment, the invention relates to a method of inhibiting or degrading IRAK-1, IRAK-2, and/or IRAK-4, or a mutant thereof, activity in a biological sample comprising the step of contacting said biological sample with a compound of this invention, or a composition comprising said compound.

The term "biological sample", as used herein, includes, without limitation, cell cultures or extracts thereof, biopsied material obtained from a mammal or extracts thereof, and blood, saliva, urine, feces, semen, tears, or other body fluids or extracts thereof.

Inhibition and/or degradation of a protein kinase, or a protein kinase selected from IRAK-1, IRAK-2, and/or IRAK-4, or a mutant thereof, activity in a biological sample is useful for a variety of purposes that are known to one of skill in the art. Examples of such purposes include, but are not limited to, blood transfusion, organ-transplantation, biological specimen storage, and biological assays.

Another embodiment of the present invention relates to a method of degrading a protein kinase and/or inhibiting protein kinase activity in a patient comprising the step of administering to said patient a compound of the present invention, or a composition comprising said compound.

According to another embodiment, the invention relates to a method of degrading and/or inhibiting one or more of IRAK-1, IRAK-2, and/or IRAK-4, or a mutant thereof, activity in a patient comprising the step of administering to said patient a compound of the present invention, or a composition comprising said compound. In other embodiments, the present invention provides a method for treating a disorder mediated by one or more of IRAK-1, IRAK-2, and/or IRAK-4, or a mutant thereof, in a patient in need thereof, comprising the step of administering to said patient a compound according to the present invention or pharmaceutically acceptable composition thereof. Such disorders are described in detail herein.

Depending upon the particular condition, or disease, to be treated, additional therapeutic agents that are normally administered to treat that condition, may also be present in the compositions of this invention. As used herein, additional therapeutic agents that are normally administered to treat a particular disease, or condition, are known as "appropriate for the disease, or condition, being treated."

A compound of the current invention may also be used to advantage in combination with other antiproliferative compounds. Such antiproliferative compounds include, but are not limited to aromatase inhibitors; antiestrogens; topoisomerase I inhibitors; topoisomerase II inhibitors; microtubule active compounds; alkylating compounds; histone deacetylase inhibitors; compounds which induce cell differentiation processes; cyclooxygenase inhibitors; MMP inhibitors; mTOR inhibitors; antineoplastic antimetabolites; platin compounds; compounds targeting/decreasing a protein or lipid kinase activity and further anti-angiogenic compounds; compounds which target, decrease or inhibit the activity of a protein or lipid phosphatase; gonadorelin agonists; anti-androgens; methionine aminopeptidase inhibitors; matrix metalloproteinase inhibitors; bisphosphonates; biological response modifiers; antiproliferative antibodies; heparanase inhibitors; inhibitors of Ras oncogenic isoforms; telomerase inhibitors; proteasome inhibitors; compounds used in the treatment of hematologic malignancies; compounds which target, decrease or inhibit the activity of Flt-3; Hsp90 inhibitors such as 17-AAG (17-allylaminogeldanamycin, NSC330507), 17-DMAG (17-dimethylaminoethylamino-17-demethoxy-geldanamycin, NSC707545), IPI-504, CNF1010, CNF2024, CNF1010 from Conforma Therapeutics; temozolomide (Temodal®); kinesin spindle protein inhibitors, such as SB715992 or SB743921 from GlaxoSmithKline, or pentamidine/chlorpromazine from CombinatoRx; MEK inhibitors such as ARRY142886 from Array BioPharma, AZD6244 from AstraZeneca, PD181461 from Pfizer and leucovorin.

The term "aromatase inhibitor" as used herein relates to a compound which inhibits estrogen production, for instance, the conversion of the substrates androstenedione and testosterone to estrone and estradiol, respectively. The term includes, but is not limited to steroids, especially atamestane, exemestane and formestane and, in particular, non-steroids, especially aminoglutethimide, roglethimide, pyridoglutethimide, trilostane, testolactone, ketokonazole, vorozole, fadrozole, anastrozole and letrozole. Exemestane is marketed under the trade name Aromasin™. Formestane is marketed under the trade name Lentaron™. Fadrozole is marketed under the trade name Afema™. Anastrozole is marketed under the trade name Arimidex™. Letrozole is marketed under the trade names Femara™ or Femar™. Aminoglutethimide is marketed under the trade name Orimeten™. A combination of the invention comprising a chemotherapeutic agent which is an aromatase inhibitor is particularly useful for the treatment of hormone receptor positive tumors, such as breast tumors.

In some embodiments, one or more other therapeutic agent is an mTOR inhibitor, which inhibits cell proliferation, angiogenesis and glucose uptake. In some embodiments, an mTOR inhibitor is everolimus (Afinitor®, Novartis); temsirolimus (Torisel®, Pfizer); and sirolimus (Rapamune®, Pfizer).

In some embodiments, one or more other therapeutic agent is an aromatase inhibitor. In some embodiments, an aromatase inhibitor is selected from exemestane (Aromasin®, Pfizer); anastazole (Arimidex®, AstraZeneca) and letrozole (Femara®, Novartis).

The term "antiestrogen" as used herein relates to a compound which antagonizes the effect of estrogens at the estrogen receptor level. The term includes, but is not limited to tamoxifen, fulvestrant, raloxifene and raloxifene hydrochloride. Tamoxifen is marketed under the trade name Nolvadex™ Raloxifene hydrochloride is marketed under the trade name Evista™. Fulvestrant can be administered under the trade name Faslodex™. A combination of the invention comprising a chemotherapeutic agent which is an antiestrogen is particularly useful for the treatment of estrogen receptor positive tumors, such as breast tumors.

The term "anti-androgen" as used herein relates to any substance which is capable of inhibiting the biological effects of androgenic hormones and includes, but is not limited to, bicalutamide (Casodex™) The term "gonadorelin agonist" as used herein includes, but is not limited to abarelix, goserelin and goserelin acetate. Goserelin can be administered under the trade name Zoladex™.

The term "topoisomerase I inhibitor" as used herein includes, but is not limited to topotecan, gimatecan, irinotecan, camptothecian and its analogues, 9-nitrocamptothecin and the macromolecular camptothecin conjugate PNU-166148. Irinotecan can be administered, e.g. in the form as it is marketed, e.g. under the trademark Camptosar™. Topotecan is marketed under the trade name Hycamptin™.

The term "topoisomerase II inhibitor" as used herein includes, but is not limited to the anthracyclines such as doxorubicin (including liposomal formulation, such as Caelyx™), daunorubicin, epirubicin, idarubicin and nemorubicin, the anthraquinones mitoxantrone and losoxantrone, and the podophillotoxines etoposide and teniposide. Etoposide is marketed under the trade name Etopophos™ Teniposide is marketed under the trade name VM 26-Bristol Doxorubicin is marketed under the trade name Acriblastin™ or Adriamycin™. Epirubicin is marketed under the trade name Farmorubicin™. Idarubicin is marketed. under the trade name Zavedos™. Mitoxantrone is marketed under the trade name Novantron.

The term "microtubule active agent" relates to microtubule stabilizing, microtubule destabilizing compounds and microtublin polymerization inhibitors including, but not limited to taxanes, such as paclitaxel and docetaxel; vinca alkaloids, such as vinblastine or vinblastine sulfate, vincristine or vincristine sulfate, and vinorelbine; discodermolides; cochicine and epothilones and derivatives thereof. Paclitaxel is marketed under the trade name Taxol™. Docetaxel is marketed under the trade name Taxotere™. Vinblastine sulfate is marketed under the trade name Vinblastin R.P™. Vincristine sulfate is marketed under the trade name Farmistin™.

The term "alkylating agent" as used herein includes, but is not limited to, cyclophosphamide, ifosfamide, melphalan or nitrosourea (BCNU or Gliadel). Cyclophosphamide is marketed under the trade name Cyclostin™. Ifosfamide is marketed under the trade name Holoxan™.

The term "histone deacetylase inhibitors" or "HDAC inhibitors" relates to compounds which inhibit the histone deacetylase and which possess antiproliferative activity. This includes, but is not limited to, suberoylanilide hydroxamic acid (SAHA).

The term "antineoplastic antimetabolite" includes, but is not limited to, 5-fluorouracil or 5-FU, capecitabine, gemcitabine, DNA demethylating compounds, such as 5-azacytidine and decitabine, methotrexate and edatrexate, and folic acid antagonists such as pemetrexed. Capecitabine is marketed under the trade name Xeloda™. Gemcitabine is marketed under the trade name Gemzar™.

The term "platin compound" as used herein includes, but is not limited to, carboplatin, cis-platin, cisplatinum and oxaliplatin. Carboplatin can be administered, e.g., in the form as it is marketed, e.g. under the trademark Carboplat™. Oxaliplatin can be administered, e.g., in the form as it is marketed, e.g. under the trademark Eloxatin™.

The term "Bcl-2 inhibitor" as used herein includes, but is not limited to compounds having inhibitory activity against B-cell lymphoma 2 protein (Bcl-2), including but not limited to ABT-199, ABT-731, ABT-737, apogossypol, Ascenta's pan-Bcl-2 inhibitors, curcumin (and analogs thereof), dual Bcl-2/Bcl-xL inhibitors (Infinity Pharmaceuticals/Novartis Pharmaceuticals), Genasense (G3139), HA14-1 (and analogs thereof; see WO 2008/118802, US 2010/0197686), navitoclax (and analogs thereof, see U.S. Pat. No. 7,390,799), NH-1 (Shenayng Pharmaceutical University), obatoclax (and analogs thereof, see WO 2004/106328, US 2005/0014802), S-001 (Gloria Pharmaceuticals), TW series compounds (Univ. of Michigan), and venetoclax. In some embodiments the Bcl-2 inhibitor is a small molecule therapeutic. In some embodiments the Bcl-2 inhibitor is a peptidomimetic.

The term "compounds targeting/decreasing a protein or lipid kinase activity; or a protein or lipid phosphatase activity; or further anti-angiogenic compounds" as used herein includes, but is not limited to, protein tyrosine kinase and/or serine and/or threonine kinase inhibitors or lipid kinase inhibitors, such as a) compounds targeting, decreasing or inhibiting the activity of the platelet-derived growth factor-receptors (PDGFR), such as compounds which target, decrease or inhibit the activity of PDGFR, especially compounds which inhibit the PDGF receptor, such as an N-phenyl-2-pyrimidine-amine derivative, such as imatinib, SU101, SU6668 and GFB-111; b) compounds targeting, decreasing or inhibiting the activity of the fibroblast growth factor-receptors (FGFR); c) compounds targeting, decreasing or inhibiting the activity of the insulin-like growth factor receptor I (IGF-IR), such as compounds which target, decrease or inhibit the activity of IGF-IR, especially compounds which inhibit the kinase activity of IGF-I receptor, or antibodies that target the extracellular domain of IGF-I receptor or its growth factors; d) compounds targeting, decreasing or inhibiting the activity of the Trk receptor tyrosine kinase family, or ephrin B4 inhibitors; e) compounds targeting, decreasing or inhibiting the activity of the AxI receptor tyrosine kinase family; f) compounds targeting, decreasing or inhibiting the activity of the Ret receptor tyrosine kinase; g) compounds targeting, decreasing or inhibiting the activity of the Kit/SCFR receptor tyrosine kinase, such as imatinib; h) compounds targeting, decreasing or inhibiting the activity of the C-kit receptor tyrosine kinases, which are part of the PDGFR family, such as compounds which target, decrease or inhibit the activity of the c-Kit receptor tyrosine kinase family, especially compounds which inhibit the c-Kit receptor, such as imatinib; i) compounds targeting, decreasing or inhibiting the activity of members of the c-Abl family, their gene-fusion products (e.g. BCR-Abl kinase) and mutants, such as compounds which target decrease or inhibit the activity of c-Abl family members and their gene fusion products, such as an N-phenyl-2-pyrimidine-amine derivative, such as imatinib or nilotinib (AMN107); PD180970; AG957; NSC 680410; PD173955 from ParkeDavis; or dasatinib (BMS-354825); j) compounds targeting, decreasing or inhibiting the activity of members of the protein kinase C (PKC) and Raf family of serine/threonine kinases, members of the MEK, SRC, JAK/pan-JAK, FAK, PDK1, PKB/Akt, Ras/MAPK, PI3K, SYK, TYK2, BTK and TEC family, and/or members of the cyclin-dependent kinase family (CDK) including staurosporine derivatives, such as midostaurin; examples of further compounds include UCN-01, safingol, BAY 43-9006, Bryostatin 1, Perifosine; llmofosine; RO 318220 and RO 320432; GO 6976; lsis 3521; LY333531/LY379196; isochinoline compounds; FTIs; PD184352 or QAN697 (a PI3K inhibitor) or AT7519 (CDK inhibitor); k) compounds targeting, decreasing or inhibiting the activity of protein-tyrosine kinase inhibitors, such as compounds which target, decrease or inhibit the activity of protein-tyrosine kinase inhibitors include imatinib mesylate (Gleevec™) or tyrphostin such as Tyrphostin A23/RG-50810; AG 99; Tyrphostin AG 213; Tyrphostin AG 1748; Tyrphostin AG 490; Tyrphostin B44; Tyrphostin B44 (+) enantiomer; Tyrphostin AG 555; AG 494; Tyrphostin AG 556, AG957 and adaphostin (4-{[(2,5-dihydroxyphenyl)methyl]amino}-benzoic acid adamantyl ester; NSC 680410, adaphostin); 1) compounds targeting, decreasing or inhibiting the activity of the epidermal growth factor family of receptor tyrosine kinases ($EGFR_1$ ErbB2, ErbB3, ErbB4 as homo- or heterodimers) and their mutants, such as compounds which target, decrease or inhibit the activity of the epidermal growth factor receptor family are especially compounds, proteins or antibodies which inhibit members of the EGF receptor tyrosine kinase family, such as EGF receptor, ErbB2, ErbB3 and ErbB4 or bind to EGF or EGF related ligands, CP 358774, ZD 1839, ZM 105180; trastuzumab (Herceptin™), cetuximab (Erbitux™), Iressa, Tarceva, OSI-774, Cl-1033, EKB-569, GW-2016, ELI, E2.4, E2.5, E6.2, E6.4, E2.11, E6.3 or E7.6.3, and 7H-pyrrolo-[2,3-d]pyrimidine derivatives; m) compounds targeting, decreasing or inhibiting the activity of the c-Met receptor, such as compounds which target, decrease or inhibit the activity of c-Met, especially compounds which inhibit the kinase activity of c-Met receptor, or antibodies that target the extracellular domain of c-Met or bind to HGF, n) compounds targeting, decreasing or inhibiting the kinase activity of one or more JAK family members (JAK1/JAK2/JAK3/TYK2 and/or pan-JAK), including but not limited to PRT-062070, SB-1578, baricitinib, pacritinib, momelotinib, VX-509, AZD-1480, TG-101348, tofacitinib, and ruxolitinib; o) compounds targeting, decreasing or inhibiting the kinase activity of PI3 kinase (PI3K) including but not limited to ATU-027, SF-1126, DS-7423, PBI-05204, GSK-2126458, ZSTK-474, buparlisib, pictrelisib, PF-4691502, BYL-719, dactolisib, XL-147, XL-765, and idelalisib; and; and q) compounds targeting, decreasing or inhibiting the signaling effects of hedgehog protein (Hh) or smoothened receptor (SMO) pathways, including but not limited to cyclopamine, vismodegib, itraconazole, erismodegib, and IPI-926 (saridegib).

Compounds which target, decrease or inhibit the activity of a protein or lipid phosphatase are e.g. inhibitors of phosphatase 1, phosphatase 2A, or CDC25, such as okadaic acid or a derivative thereof.

In some embodiments, one or more other therapeutic agent is a growth factor antagonist, such as an antagonist of platelet-derived growth factor (PDGF), or epidermal growth factor (EGF) or its receptor (EGFR). Approved PDGF antagonists which may be used in the present invention include olaratumab (Lartruvo®; Eli Lilly). Approved EGFR antagonists which may be used in the present invention include cetuximab (Erbitux®, Eli Lilly); necitumumab (Portrazza®, Eli Lilly), panitumumab (Vectibix®, Amgen); and osimertinib (targeting activated EGFR, Tagrisso®, AstraZeneca).

The term "PI3K inhibitor" as used herein includes, but is not limited to compounds having inhibitory activity against one or more enzymes in the phosphatidylinositol-3-kinase family, including, but not limited to PI3Kα, PI3Kγ, PI3Kδ, PI3Kβ, PI3K-C2α, PI3K-C2β, PI3K-C2γ, Vps34, p110-α, p110-β, p110-γ, p110-δ, p85-α, p85-β, p55-γ, p150, p101, and p87. Examples of PI3K inhibitors useful in this invention include but are not limited to ATU-027, SF-1126, DS-7423, PBI-05204, GSK-2126458, ZSTK-474, buparlisib, pictrelisib, PF-4691502, BYL-719, dactolisib, XL-147, XL-765, and idelalisib.

The term "BTK inhibitor" as used herein includes, but is not limited to compounds having inhibitory activity against Bruton's Tyrosine Kinase (BTK), including, but not limited to AVL-292 and ibrutinib.

The term "SYK inhibitor" as used herein includes, but is not limited to compounds having inhibitory activity against spleen tyrosine kinase (SYK), including but not limited to PRT-062070, R-343, R-333, Excellair, PRT-062607, and fostamatinib Further examples of BTK inhibitory compounds, and conditions treatable by such compounds in combination with compounds of this invention can be found in WO 2008/039218, US 2008/0108636 and WO 2011/090760, US 2010/0249092, the entirety of each of which is herein incorporated by reference.

Further examples of SYK inhibitory compounds, and conditions treatable by such compounds in combination with compounds of this invention can be found in WO 2003/063794, US 2004/0029902, WO 2005/007623, US 2005/0075306, and WO 2006/078846, US 2006/0211657, the entirety of each of which is herein incorporated by reference.

Further examples of PI3K inhibitory compounds, and conditions treatable by such compounds in combination with compounds of this invention can be found in WO 2004/019973, US 2004/0106569, WO 2004/089925, US 2004/0242631, U.S. Pat. No. 8,138,347, WO 2002/088112, US 2004/0116421, WO 2007/084786, US 2010/0249126, WO 2007/129161, US 2008/0076768, WO 2006/122806, US 2008/0194579, WO 2005/113554, US 2008/0275067, and WO 2007/044729, US 2010/0087440, the entirety of each of which is herein incorporated by reference.

Further examples of JAK inhibitory compounds, and conditions treatable by such compounds in combination with compounds of this invention can be found in WO 2009/114512, US 2009/0233903, WO 2008/109943, US 2010/0197671, WO 2007/053452, US 2007/0191405, WO 2001/0142246, US 2001/0053782, and WO 2007/070514, US 2007/0135461, the entirety of each of which is herein incorporated by reference.

Further anti-angiogenic compounds include compounds having another mechanism for their activity, e.g. unrelated to protein or lipid kinase inhibition e.g. thalidomide (Thalomid™) and TNP-470.

Examples of proteasome inhibitors useful for use in combination with compounds of the invention include, but are not limited to bortezomib, disulfiram, epigallocatechin-3-gallate (EGCG), salinosporamide A, carfilzomib, ONX-0912, CEP-18770, and MLN9708.

Compounds which target, decrease or inhibit the activity of a protein or lipid phosphatase are e.g. inhibitors of phosphatase 1, phosphatase 2A, or CDC25, such as okadaic acid or a derivative thereof.

Compounds which induce cell differentiation processes include, but are not limited to, retinoic acid, α- γ- or δ-tocopherol or α- γ- or δ-tocotrienol.

The term cyclooxygenase inhibitor as used herein includes, but is not limited to, Cox-2 inhibitors, 5-alkyl substituted 2-arylaminophenylacetic acid and derivatives, such as celecoxib (Celebrex™), rofecoxib (Vioxx™), etoricoxib, valdecoxib or a 5-alkyl-2-arylaminophenylacetic acid, such as 5-methyl-2-(2'-chloro-6'-fluoroanilino)phenyl acetic acid, lumiracoxib.

The term "bisphosphonates" as used herein includes, but is not limited to, etridonic, clodronic, tiludronic, pamidronic, alendronic, ibandronic, risedronic and zoledronic acid. Etridonic acid is marketed under the trade name Didronel™. Clodronic acid is marketed under the trade name Bonefos™. Tiludronic acid is marketed under the trade name Skelid™. Pamidronic acid is marketed under the trade name Aredia™. Alendronic acid is marketed under the trade name Fosamax™. Ibandronic acid is marketed under the trade name Bondranat™. Risedronic acid is marketed under the trade name Actonel™. Zoledronic acid is marketed under the trade name Zometa™. The term "mTOR inhibitors" relates to compounds which inhibit the mammalian target of rapamycin (mTOR) and which possess antiproliferative activity such as sirolimus (Rapamune®), everolimus (Certican™), CCI-779 and ABT578.

The term "heparanase inhibitor" as used herein refers to compounds which target, decrease or inhibit heparin sulfate degradation. The term includes, but is not limited to, PI-88. The term "biological response modifier" as used herein refers to a lymphokine or interferons.

The term "inhibitor of Ras oncogenic isoforms", such as H-Ras, K-Ras, or N-Ras, as used herein refers to compounds which target, decrease or inhibit the oncogenic activity of Ras; for example, a "farnesyl transferase inhibitor" such as L-744832, DK8G557 or R115777 (Zarnestra™). The term "telomerase inhibitor" as used herein refers to compounds which target, decrease or inhibit the activity of telomerase. Compounds which target, decrease or inhibit the activity of telomerase are especially compounds which inhibit the telomerase receptor, such as telomestatin.

The term "methionine aminopeptidase inhibitor" as used herein refers to compounds which target, decrease or inhibit the activity of methionine aminopeptidase. Compounds which target, decrease or inhibit the activity of methionine aminopeptidase include, but are not limited to, bengamide or a derivative thereof.

The term "proteasome inhibitor" as used herein refers to compounds which target, decrease or inhibit the activity of the proteasome. Compounds which target, decrease or inhibit the activity of the proteasome include, but are not limited to, Bortezomib (Velcade™); carfilzomib (Kyprolis®, Amgen); and ixazomib (Ninlaro®, Takeda), and MLN 341.

The term "matrix metalloproteinase inhibitor" or ("MMP" inhibitor) as used herein includes, but is not limited to, collagen peptidomimetic and nonpeptidomimetic inhibitors, tetracycline derivatives, e.g. hydroxamate peptidomimetic inhibitor batimastat and its orally bioavailable analogue marimastat (BB-2516), prinomastat (AG3340), metastat (NSC 683551) BMS-279251, BAY 12-9566, TAA211, MMI270B or AAJ996.

The term "compounds used in the treatment of hematologic malignancies" as used herein includes, but is not limited to, FMS-like tyrosine kinase inhibitors, which are compounds targeting, decreasing or inhibiting the activity of FMS-like tyrosine kinase receptors (Flt-3R); interferon, 1-f3-D-arabinofuransylcytosine (ara-c) and bisulfan; and ALK inhibitors, which are compounds which target, decrease or inhibit anaplastic lymphoma kinase.

Compounds which target, decrease or inhibit the activity of FMS-like tyrosine kinase receptors (Flt-3R) are especially compounds, proteins or antibodies which inhibit members of the Flt-3R receptor kinase family, such as PKC412, midostaurin, a staurosporine derivative, SU11248 and MLN518.

The term "HSP90 inhibitors" as used herein includes, but is not limited to, compounds targeting, decreasing or inhibiting the intrinsic ATPase activity of HSP90; degrading, targeting, decreasing or inhibiting the HSP90 client proteins via the ubiquitin proteosome pathway. Compounds targeting, decreasing or inhibiting the intrinsic ATPase activity of HSP90 are especially compounds, proteins or antibodies which inhibit the ATPase activity of HSP90, such as 17-allylamino,17-demethoxygeldanamycin (17AAG), a geldanamycin derivative; other geldanamycin related compounds; radicicol and HDAC inhibitors.

The term "antiproliferative antibodies" as used herein includes, but is not limited to, trastuzumab (Herceptin™), Trastuzumab-DM1, erbitux, bevacizumab (Avastin™), rituximab (Rituxan©), PR064553 (anti-CD40) and 2C4 Antibody. By antibodies is meant intact monoclonal antibodies, polyclonal antibodies, multispecific antibodies formed from at least 2 intact antibodies, and antibodies fragments so long as they exhibit the desired biological activity.

For the treatment of acute myeloid leukemia (AML), compounds of the current invention can be used in combination with standard leukemia therapies, especially in combination with therapies used for the treatment of AML. In particular, compounds of the current invention can be administered in combination with, for example, farnesyl transferase inhibitors and/or other drugs useful for the treatment of AML, such as Daunorubicin, Adriamycin, Ara-C, VP-16, Teniposide, Mitoxantrone, Idarubicin, Carboplatinum and PKC412.

Other anti-leukemic compounds include, for example, Ara-C, a pyrimidine analog, which is the 2'-alpha-hydroxy ribose (arabinoside) derivative of deoxycytidine. Also included is the purine analog of hypoxanthine, 6-mercaptopurine (6-MP) and fludarabine phosphate. Compounds which target, decrease or inhibit activity of histone deacetylase (HDAC) inhibitors such as sodium butyrate and suberoylanilide hydroxamic acid (SAHA) inhibit the activity of the enzymes known as histone deacetylases. Specific HDAC inhibitors include MS275, SAHA, FK228 (formerly FR901228), Trichostatin A and compounds disclosed in U.S. Pat. No. 6,552,065 including, but not limited to, N-hydroxy-3-[4-[[[2-(2-methyl-1H-indol-3-yl)-ethyl]-amino]methyl] phenyl]-2E-2-propenamide, or a pharmaceutically acceptable salt thereof and N-hydroxy-3-[4-[(2-hydroxyethyl){2-(1H-indol-3-yl)ethyl]-amino]methyl]phenyl]-2E-2-propenamide, or a pharmaceutically acceptable salt thereof, especially the lactate salt. Somatostatin receptor antagonists as used herein refer to compounds which target, treat or inhibit the somatostatin receptor such as octreotide, and SOM230. Tumor cell damaging approaches refer to approaches such as ionizing radiation. The term "ionizing radiation" referred to above and hereinafter means ionizing radiation that occurs as either electromagnetic rays (such as X-rays and gamma rays) or particles (such as alpha and beta particles). Ionizing radiation is provided in, but not limited to, radiation therapy and is known in the art. See Hellman, Principles of Radiation Therapy, Cancer, in Principles and Practice of Oncology, Devita et al., Eds., $4^{th}$ Edition, Vol. 1, pp. 248-275 (1993).

Also included are EDG binders and ribonucleotide reductase inhibitors. The term "EDG binders" as used herein refers to a class of immunosuppressants that modulates lymphocyte recirculation, such as FTY720. The term "ribonucleotide reductase inhibitors" refers to pyrimidine or purine nucleoside analogs including, but not limited to, fludarabine and/or cytosine arabinoside (ara-C), 6-thioguanine, 5-fluorouracil, cladribine, 6-mercaptopurine (especially in combination with ara-C against ALL) and/or pentostatin. Ribonucleotide reductase inhibitors are especially hydroxyurea or 2-hydroxy-1H-isoindole-1,3-dione derivatives.

Also included are in particular those compounds, proteins or monoclonal antibodies of VEGF such as 1-(4-chloroanilino)-4-(4-pyridylmethyl)phthalazine or a pharmaceutically acceptable salt thereof, 1-(4-chloroanilino)-4-(4-pyridylmethyl)phthalazine succinate; Angiostatin™; Endostatin™; anthranilic acid amides; ZD4190; ZD6474; SU5416; SU6668; bevacizumab; or anti-VEGF antibodies or anti-VEGF receptor antibodies, such as rhuMAb and RHUFab, VEGF aptamer such as Macugon; FLT-4 inhibitors, FLT-3 inhibitors, VEGFR-2 IgG1 antibody, Angiozyme (RPI 4610) and Bevacizumab (Avastin™).

Photodynamic therapy as used herein refers to therapy which uses certain chemicals known as photosensitizing compounds to treat or prevent cancers. Examples of photodynamic therapy include treatment with compounds, such as Visudyne™ and porfimer sodium.

Angiostatic steroids as used herein refers to compounds which block or inhibit angiogenesis, such as, e.g., anecortave, triamcinolone, hydrocortisone, 11-α-epihydrocotisol, cortexolone, 17α-hydroxyprogesterone, corticosterone, desoxycorticosterone, testosterone, estrone and dexamethasone.

Implants containing corticosteroids refers to compounds, such as fluocinolone and dexamethasone.

Other chemotherapeutic compounds include, but are not limited to, plant alkaloids, hormonal compounds and antagonists; biological response modifiers, preferably lymphokines or interferons; antisense oligonucleotides or oligonucleotide derivatives; shRNA or siRNA; or miscellaneous compounds or compounds with other or unknown mechanism of action.

The compounds of the invention are also useful as co-therapeutic compounds for use in combination with other drug substances such as anti-inflammatory, bronchodilatory or antihistamine drug substances, particularly in the treatment of obstructive or inflammatory airways diseases such as those mentioned hereinbefore, for example as potentiators of therapeutic activity of such drugs or as a means of reducing required dosaging or potential side effects of such drugs. A compound of the invention may be mixed with the other drug substance in a fixed pharmaceutical composition or it may be administered separately, before, simultaneously with or after the other drug substance. Accordingly the invention includes a combination of a compound of the invention as hereinbefore described with an anti-inflammatory, bronchodilatory, antihistamine or anti-tussive drug substance, said compound of the invention and said drug substance being in the same or different pharmaceutical composition.

Suitable anti-inflammatory drugs include steroids, in particular glucocorticosteroids such as budesonide, beclamethasone dipropionate, fluticasone propionate, ciclesonide or mometasone furoate; non-steroidal glucocorticoid receptor agonists; LTB4 antagonists such LY293111, CGS025019C, CP-195543, SC-53228, BIIL 284, ONO 4057, SB 209247; LTD4 antagonists such as montelukast and zafirlukast; PDE4 inhibitors such cilomilast (Ariflo® GlaxoSmithKline), Roflumilast (Byk Gulden), V-11294A (Napp), BAY19-8004 (Bayer), SCH-351591 (Schering-Plough), Arofylline (Almirall Prodesfarma), PD189659/PD168787 (Parke-Davis), AWD-12-281 (Asta Medica), CDC-801 (Celgene), SeICID™ CC-10004 (Celgene), VM554/UM565 (Vernalis), T-440 (Tanabe), KW-4490 (Kyowa Hakko Kogyo); A2a agonists; A2b antagonists; and beta-2 adrenoceptor agonists such as albuterol (salbutamol), metaproterenol, terbutaline, salmeterol fenoterol, procaterol, and especially, formoterol and pharmaceutically acceptable salts thereof. Suitable bronchodilatory drugs include anticholinergic or antimuscarinic compounds, in particular ipratropium bromide, oxitropium bromide, tiotropium salts and CHF 4226 (Chiesi), and glycopyrrolate.

Suitable antihistamine drug substances include cetirizine hydrochloride, acetaminophen, clemastine fumarate, promethazine, loratidine, desloratidine, diphenhydramine and fexofenadine hydrochloride, activastine, astemizole, azelastine, ebastine, epinastine, mizolastine and tefenadine.

Other useful combinations of compounds of the invention with anti-inflammatory drugs are those with antagonists of chemokine receptors, e.g. CCR-1, CCR-2, CCR-3, CCR-4, CCR-5, CCR-6, CCR-7, CCR-8, CCR-9 and CCR10, CXCR1, CXCR2, CXCR3, CXCR4, CXCR5, particularly CCR-5 antagonists such as Schering-Plough antagonists SC-351125, SCH-55700 and SCH-D, and Takeda antagonists such as N-[[4-[[[6,7-dihydro-2-(4-methylphenyl)-5H-benzo-cyclohepten-8-yl]carbonyl]amino]phenyl]-methyl] tetrahydro-N,N-dimethyl-2H-pyran-4-aminium chloride (TAK-770).

The structure of the active compounds identified by code numbers, generic or trade names may be taken from the actual edition of the standard compendium "The Merck Index" or from databases, e.g. Patents International (e.g. IMS World Publications).

A compound of the current invention may also be used in combination with known therapeutic processes, for example, the administration of hormones or radiation. In certain embodiments, a provided compound is used as a radiosensitizer, especially for the treatment of tumors which exhibit poor sensitivity to radiotherapy.

A compound of the current invention can be administered alone or in combination with one or more other therapeutic compounds, possible combination therapy taking the form of fixed combinations or the administration of a compound of the invention and one or more other therapeutic compounds being staggered or given independently of one another, or the combined administration of fixed combinations and one or more other therapeutic compounds. A compound of the current invention can besides or in addition be administered especially for tumor therapy in combination with chemotherapy, radiotherapy, immunotherapy, phototherapy, surgical intervention, or a combination of these. Long-term therapy is equally possible as is adjuvant therapy in the context of other treatment strategies, as described above. Other possible treatments are therapy to maintain the patient's status after tumor regression, or even chemopreventive therapy, for example in patients at risk.

Those additional agents may be administered separately from an inventive compound-containing composition, as part of a multiple dosage regimen. Alternatively, those agents may be part of a single dosage form, mixed together with a compound of this invention in a single composition. If administered as part of a multiple dosage regime, the two active agents may be submitted simultaneously, sequentially or within a period of time from one another normally within five hours from one another.

As used herein, the term "combination," "combined," and related terms refers to the simultaneous or sequential administration of therapeutic agents in accordance with this invention. For example, a compound of the present invention may be administered with another therapeutic agent simultaneously or sequentially in separate unit dosage forms or together in a single unit dosage form. Accordingly, the present invention provides a single unit dosage form comprising a compound of the current invention, an additional therapeutic agent, and a pharmaceutically acceptable carrier, adjuvant, or vehicle.

The amount of both an inventive compound and additional therapeutic agent (in those compositions which comprise an additional therapeutic agent as described above) that may be combined with the carrier materials to produce a single dosage form will vary depending upon the host treated and the particular mode of administration. Preferably, compositions of this invention should be formulated so that a dosage of between 0.01-100 mg/kg body weight/day of an inventive compound can be administered.

In those compositions which comprise an additional therapeutic agent, that additional therapeutic agent and the compound of this invention may act synergistically. Therefore, the amount of additional therapeutic agent in such compositions will be less than that required in a monotherapy utilizing only that therapeutic agent. In such compositions a dosage of between 0.01-1,000 μg/kg body weight/day of the additional therapeutic agent can be administered.

The amount of one or more other therapeutic agent present in the compositions of this invention may be no more than the amount that would normally be administered in a composition comprising that therapeutic agent as the only active agent. Preferably the amount of one or more other therapeutic agent in the presently disclosed compositions will range from about 50% to 100% of the amount normally present in a composition comprising that agent as the only therapeutically active agent. In some embodiments, one or more other therapeutic agent is administered at a dosage of about 50%, about 55%, about 60%, about 65%, about 70%, about 75%, about 80%, about 85%, about 90%, or about 95% of the amount normally administered for that agent. As used herein, the phrase "normally administered" means the amount an FDA approved therapeutic agent is provided for dosing per the FDA label insert.

The compounds of this invention, or pharmaceutical compositions thereof, may also be incorporated into compositions for coating an implantable medical device, such as prostheses, artificial valves, vascular grafts, stents and catheters. Vascular stents, for example, have been used to overcome restenosis (re-narrowing of the vessel wall after injury). However, patients using stents or other implantable devices risk clot formation or platelet activation. These unwanted effects may be prevented or mitigated by precoating the device with a pharmaceutically acceptable composition comprising a kinase inhibitor. Implantable devices coated with a compound of this invention are another embodiment of the present invention.

Exemplary Immuno-Oncology Agents

In some embodiments, one or more other therapeutic agent is an immuno-oncology agent. As used herein, the term "an immuno-oncology agent" refers to an agent which is effective to enhance, stimulate, and/or up-regulate immune responses in a subject. In some embodiments, the administration of an immuno-oncology agent with a compound of the invention has a synergic effect in treating a cancer.

An immuno-oncology agent can be, for example, a small molecule drug, an antibody, or a biologic or small molecule. Examples of biologic immuno-oncology agents include, but are not limited to, cancer vaccines, antibodies, and cytokines. In some embodiments, an antibody is a monoclonal antibody. In some embodiments, a monoclonal antibody is humanized or human.

In some embodiments, an immuno-oncology agent is (i) an agonist of a stimulatory (including a co-stimulatory) receptor or (ii) an antagonist of an inhibitory (including a co-inhibitory) signal on T cells, both of which result in amplifying antigen-specific T cell responses.

Certain of the stimulatory and inhibitory molecules are members of the immunoglobulin super family (IgSF). One important family of membrane-bound ligands that bind to co-stimulatory or co-inhibitory receptors is the B7 family, which includes B7-1, B7-2, B7-H1 (PD-L1), B7-DC (PD-L2), B7-H2 (ICOS-L), B7-H3, B7-H4, B7-H5 (VISTA), and B7-H6. Another family of membrane bound ligands that bind to co-stimulatory or co-inhibitory receptors is the TNF family of molecules that bind to cognate TNF receptor family members, which includes CD40 and CD40L, OX-40, OX-40L, CD70, CD27L, CD30, CD30L, 4-1BBL, CD137 (4-1BB), TRAIL/Apo2-L, TRAILR1/DR4, TRAILR2/DR5, TRAILR3, TRAILR4, OPG, RANK, RANKL, TWEAKR/Fn14, TWEAK, BAFFR, EDAR, XEDAR, TACI, APRIL, BCMA, LTβR, LIGHT, DcR3, HVEM, VEGI/TL1A, TRAMP/DR3, EDAR, EDA1, XEDAR, EDA2, TNFR1, Lymphotoxin α/TNFβ, TNFR2, TNFα, LTβR, Lymphotoxin α1 β2, FAS, FASL, RELT, DR6, TROY, NGFR.

In some embodiments, an immuno-oncology agent is a cytokine that inhibits T cell activation (e.g., IL-6, IL-10, TGF-β, VEGF, and other immunosuppressive cytokines) or a cytokine that stimulates T cell activation, for stimulating an immune response.

In some embodiments, a combination of a compound of the invention and an immuno-oncology agent can stimulate T cell responses. In some embodiments, an immuno-oncology agent is: (i) an antagonist of a protein that inhibits T cell activation (e.g., immune checkpoint inhibitors) such as CTLA-4, PD-1, PD-L1, PD-L2, LAG-3, TIM-3, Galectin 9, CEACAM-1, BTLA, CD69, Galectin-1, TIGIT, CD113, GPR56, VISTA, 2B4, CD48, GARP, PD1H, LAIR1, TIM-1, and TIM-4; or (ii) an agonist of a protein that stimulates T cell activation such as B7-1, B7-2, CD28, 4-1BB (CD137), 4-1BBL, ICOS, ICOS-L, OX40, OX40L, GITR, GITRL, CD70, CD27, CD40, DR3 and CD28H.

In some embodiments, an immuno-oncology agent is an antagonist of inhibitory receptors on NK cells or an agonists of activating receptors on NK cells. In some embodiments, an immuno-oncology agent is an antagonists of KIR, such as lirilumab.

In some embodiments, an immuno-oncology agent is an agent that inhibits or depletes macrophages or monocytes, including but not limited to CSF-1R antagonists such as CSF-1R antagonist antibodies including RG7155 (WO 2011/070024, US 2011/0165156, WO 2011/0107553, US 2012/0329997, WO 2011/131407, US 2013/0005949, WO 2013/087699, US 2014/0336363, WO 2013/119716, WO 2013/132044, US 2014/0079706) or FPA-008 (WO 2011/140249, US 2011/0274683; WO 2013/169264; WO 2014/036357, US 2014/0079699).

In some embodiments, an immuno-oncology agent is selected from agonistic agents that ligate positive costimulatory receptors, blocking agents that attenuate signaling through inhibitory receptors, antagonists, and one or more agents that increase systemically the frequency of anti-tumor T cells, agents that overcome distinct immune suppressive pathways within the tumor microenvironment (e.g., block inhibitory receptor engagement (e.g., PD-L1/PD-1 interactions), deplete or inhibit Tregs (e.g., using an anti-CD25 monoclonal antibody (e.g., daclizumab) or by ex vivo anti-CD25 bead depletion), inhibit metabolic enzymes such as IDO, or reverse/prevent T cell energy or exhaustion) and agents that trigger innate immune activation and/or inflammation at tumor sites.

In some embodiments, an immuno-oncology agent is a CTLA-4 antagonist. In some embodiments, a CTLA-4 antagonist is an antagonistic CTLA-4 antibody. In some embodiments, an antagonistic CTLA-4 antibody is YERVOY (ipilimumab) or tremelimumab.

In some embodiments, an immuno-oncology agent is a PD-1 antagonist. In some embodiments, a PD-1 antagonist is administered by infusion. In some embodiments, an immuno-oncology agent is an antibody or an antigen-binding portion thereof that binds specifically to a Programmed Death-1 (PD-1) receptor and inhibits PD-1 activity. In some embodiments, a PD-1 antagonist is an antagonistic PD-1 antibody. In some embodiments, an antagonistic PD-1 antibody is OPDIVO (nivolumab), KEYTRUDA (pembrolizumab), or MEDI-0680 (AMP-514; WO2012/145493). In some embodiments, an immuno-oncology agent may be pidilizumab (CT-011). In some embodiments, an immuno-oncology agent is a recombinant protein composed of the extracellular domain of PD-L2 (B7-DC) fused to the Fc portion of IgG1, called AMP-224.

In some embodiments, an immuno-oncology agent is a PD-L1 antagonist. In some embodiments, a PD-L1 antagonist is an antagonistic PD-L1 antibody. In some embodiments, a PD-L1 antibody is MPDL3280A (RG7446; WO 2010/077634, US 2010/0203056), durvalumab (MEDI4736), BMS-936559 (WO 2007/005874, US 2009/0055944), and MSB0010718C (WO 2013/079174, US 2014/0341917).

In some embodiments, an immuno-oncology agent is a LAG-3 antagonist. In some embodiments, a LAG-3 antagonist is an antagonistic LAG-3 antibody. In some embodiments, a LAG3 antibody is BMS-986016 (WO 2010/019570, US 2010/0150892, WO 2014/008218, US 2014/0093511), or IMP-731 or IMP-321 (WO 2008/132601, US 2010/0233183, WO 2009/044273, US 2011/0008331).

In some embodiments, an immuno-oncology agent is a CD137 (4-1BB) agonist. In some embodiments, a CD137 (4-1BB) agonist is an agonistic CD137 antibody. In some embodiments, a CD137 antibody is urelumab or PF-05082566 (WO12/32433).

In some embodiments, an immuno-oncology agent is a GITR agonist. In some embodiments, a GITR agonist is an agonistic GITR antibody. In some embodiments, a GITR antibody is BMS-986153, BMS-986156, TRX-518 (WO 2006/105021, US 2007/0098719, WO 2009/009116, US 2009/0136494), or MK-4166 (WO 2011/028683, US 2012/0189639).

In some embodiments, an immuno-oncology agent is an indoleamine (2,3)-dioxygenase (IDO) antagonist. In some embodiments, an IDO antagonist is selected from epacadostat (INCB024360, Incyte); indoximod (NLG-8189, NewLink Genetics Corporation); capmanitib (INC280, Novartis); GDC-0919 (Genentech/Roche); PF-06840003 (Pfizer); BMS.F001287 (Bristol-Myers Squibb); Phy906/KD108 (Phytoceutica); an enzyme that breaks down kynurenine (Kynase, Kyn Therapeutics); and NLG-919 (WO 2009/073620, US 2011/0053941, WO 2009/132238, US 2011/0136796, WO 2011/056652, US 2012/0277217, WO 2012/142237, US 2014/0066625).

In some embodiments, an immuno-oncology agent is an OX40 agonist. In some embodiments, an OX40 agonist is an agonistic OX40 antibody. In some embodiments, an OX40 antibody is MEDI-6383 or MEDI-6469.

In some embodiments, an immuno-oncology agent is an OX40L antagonist. In some embodiments, an OX40L antagonist is an antagonistic OX40 antibody. In some embodiments, an OX40L antagonist is RG-7888 (WO 2006/029879, U.S. Pat. No. 7,501,496).

In some embodiments, an immuno-oncology agent is a CD40 agonist. In some embodiments, a CD40 agonist is an agonistic CD40 antibody. In some embodiments, an immuno-oncology agent is a CD40 antagonist. In some embodiments, a CD40 antagonist is an antagonistic CD40 antibody. In some embodiments, a CD40 antibody is lucatumumab or dacetuzumab.

In some embodiments, an immuno-oncology agent is a CD27 agonist. In some embodiments, a CD27 agonist is an agonistic CD27 antibody. In some embodiments, a CD27 antibody is varlilumab.

In some embodiments, an immuno-oncology agent is MGA271 (to B7H3) (WO 2011/109400, US 2013/0149236).

In some embodiments, an immuno-oncology agent is abagovomab, adecatumumab, afutuzumab, alemtuzumab, anatumomab mafenatox, apolizumab, atezolimab, avelumab, blinatumomab, BMS-936559, catumaxomab, durvalumab, epacadostat, epratuzumab, indoximod, inotuzumab ozogamicin, intelumumab, ipilimumab, isatuximab, lambrolizumab, MEDI4736, MPDL3280A, nivolumab, obinutuzumab, ocaratuzumab, ofatumumab, olatatumab, pembrolizumab, pidilizumab, rituximab, ticilimumab, samalizumab, or tremelimumab.

In some embodiments, an immuno-oncology agent is an immunostimulatory agent. For example, antibodies blocking the PD-1 and PD-L1 inhibitory axis can unleash activated tumor-reactive T cells and have been shown in clinical trials to induce durable anti-tumor responses in increasing numbers of tumor histologies, including some tumor types that conventionally have not been considered immunotherapy sensitive. See, e.g., Okazaki, T. et al. (2013) Nat. Immunol. 14, 1212-1218; Zou et al. (2016) Sci. Transl. Med. 8. The anti-PD-1 antibody nivolumab (Opdivo®, Bristol-Myers Squibb, also known as ONO-4538, MDX1106 and BMS-936558), has shown potential to improve the overall survival inpatients with RCC who had experienced disease progression during or after prior anti-angiogenic therapy.

In some embodiments, the immunomodulatory therapeutic specifically induces apoptosis of tumor cells. Approved immunomodulatory therapeutics which may be used in the present invention include pomalidomide (Pomalyst®, Celgene); lenalidomide (Revlimid®, Celgene); ingenol mebutate (Picato®, LEO Pharma).

In some embodiments, an immuno-oncology agent is a cancer vaccine. In some embodiments, the cancer vaccine is selected from sipuleucel-T (Provenge®, Dendreon/Valeant Pharmaceuticals), which has been approved for treatment of asymptomatic, or minimally symptomatic metastatic castrate-resistant (hormone-refractory) prostate cancer; and talimogene laherparepvec (Imlygic®, BioVex/Amgen, previously known as T-VEC), a genetically modified oncolytic viral therapy approved for treatment of unresectable cutaneous, subcutaneous and nodal lesions in melanoma. In some embodiments, an immuno-oncology agent is selected from an oncolytic viral therapy such as pexastimogene devacirepvec (PexaVec/JX-594, SillaJen/formerly Jennerex Biotherapeutics), a thymidine kinase- (TK-) deficient vaccinia virus engineered to express GM-CSF, for hepatocellular carcinoma (NCT02562755) and melanoma (NCT00429312); pelareorep (Reolysin®, Oncolytics Biotech), a variant of respiratory enteric orphan virus (reovirus) which does not replicate in cells that are not RAS-activated, in numerous cancers, including colorectal cancer (NCT01622543); prostate cancer (NCT01619813); head and neck squamous cell cancer (NCT01166542); pancreatic adenocarcinoma (NCT00998322); and non-small cell lung cancer (NSCLC) (NCT 00861627); enadenotucirev (NG-348, PsiOxus, formerly known as ColoAdl), an adenovirus engineered to express a full length CD80 and an antibody fragment specific for the T-cell receptor CD3 protein, in ovarian cancer (NCT02028117); metastatic or advanced epithelial tumors such as in colorectal cancer, bladder cancer, head and neck squamous cell carcinoma and salivary gland cancer (NCT02636036); ONCOS-102 (Targovax/formerly Oncos), an adenovirus engineered to express GM-CSF, in melanoma (NCT03003676); and peritoneal disease, colorectal cancer or ovarian cancer (NCT02963831); GL-ONC1 (GLV-lh68/GLV-1h153, Genelux GmbH), vaccinia viruses engineered to express beta-galactosidase (beta-gal)/beta-glucoronidase or beta-gal/human sodium iodide symporter (hNIS), respectively, were studied in peritoneal carcinomatosis (NCT01443260); fallopian tube cancer, ovarian cancer (NCT 02759588); or CG0070 (Cold Genesys), an adenovirus engineered to express GM-CSF, in bladder cancer (NCT02365818).

In some embodiments, an immuno-oncology agent is selected from JX-929 (SillaJen/formerly Jennerex Biotherapeutics), a TK- and vaccinia growth factor-deficient vaccinia virus engineered to express cytosine deaminase, which is able to convert the prodrug 5-fluorocytosine to the cytotoxic drug 5-fluorouracil; TG01 and TG02 (Targovax/formerly Oncos), peptide-based immunotherapy agents targeted for difficult-to-treat RAS mutations; and TILT-123 (TILT Biotherapeutics), an engineered adenovirus designated: Ad5/3-E2F-delta24-hTNFα-IRES-hIL20; and VSV-GP (ViraTherapeutics) a vesicular stomatitis virus (VSV) engineered to express the glycoprotein (GP) of lymphocytic choriomeningitis virus (LCMV), which can be further engineered to express antigens designed to raise an antigen-specific $CD8^+$ T cell response.

In some embodiments, an immuno-oncology agent is a T-cell engineered to express a chimeric antigen receptor, or CAR. The T-cells engineered to express such chimeric antigen receptor are referred to as a CAR-T cells.

CARs have been constructed that consist of binding domains, which may be derived from natural ligands, single chain variable fragments (scFv) derived from monoclonal antibodies specific for cell-surface antigens, fused to endodomains that are the functional end of the T-cell receptor (TCR), such as the CD3-zeta signaling domain from TCRs, which is capable of generating an activation signal in T lymphocytes. Upon antigen binding, such CARs link to endogenous signaling pathways in the effector cell and generate activating signals similar to those initiated by the TCR complex.

For example, in some embodiments the CAR-T cell is one of those described in U.S. Pat. No. 8,906,682, the entirety of each of which is herein incorporated by reference, which discloses CAR-T cells engineered to comprise an extracellular domain having an antigen binding domain (such as a domain that binds to CD19), fused to an intracellular signaling domain of the T cell antigen receptor complex zeta chain (such as CD3 zeta). When expressed in the T cell, the CAR is able to redirect antigen recognition based on the antigen binding specificity. In the case of CD19, the antigen is expressed on malignant B cells. Over 200 clinical trials are currently in progress employing CAR-T in a wide range of indications. [https://clinicaltrials.gov/ct2/results?term=chimeric+antigen+receptors&pg=1].

In some embodiments, an immunostimulatory agent is an activator of retinoic acid receptor-related orphan receptor γ (RORγt). RORγt is a transcription factor with key roles in the differentiation and maintenance of Type 17 effector subsets of CD4+ (Th17) and CD8+ (Tc17) T cells, as well as the differentiation of IL-17 expressing innate immune cell subpopulations such as NK cells. In some embodiments, an activator of RORγt is LYC-55716 (Lycera), which is currently being evaluated in clinical trials for the treatment of solid tumors (NCT02929862).

In some embodiments, an immunostimulatory agent is an agonist or activator of a toll-like receptor (TLR). Suitable activators of TLRs include an agonist or activator of TLR9 such as SD-101 (Dynavax). SD-101 is an immunostimulatory CpG which is being studied for B-cell, follicular and other lymphomas (NCT02254772). Agonists or activators of TLR8 which may be used in the present invention include motolimod (VTX-2337, VentiRx Pharmaceuticals) which is being studied for squamous cell cancer of the head and neck (NCT02124850) and ovarian cancer (NCT02431559).

Other immuno-oncology agents that may be used in the present invention include urelumab (BMS-663513, Bristol-Myers Squibb), an anti-CD137 monoclonal antibody; varlilumab (CDX-1127, Celldex Therapeutics), an anti-CD27 monoclonal antibody; BMS-986178 (Bristol-Myers Squibb), an anti-OX40 monoclonal antibody; lirilumab (IPH2102/BMS-986015, Innate Pharma, Bristol-Myers Squibb), an anti-KIR monoclonal antibody; monalizumab (IPH2201, Innate Pharma, AstraZeneca) an anti-NKG2A monoclonal antibody; andecaliximab (GS-5745, Gilead Sciences), an anti-MMP9 antibody; MK-4166 (Merck & Co.), an anti-GITR monoclonal antibody.

In some embodiments, an immunostimulatory agent is selected from elotuzumab, mifamurtide, an agonist or activator of a toll-like receptor, and an activator of RORγt.

In some embodiments, an immunostimulatory therapeutic is recombinant human interleukin 15 (rhIL-15). rhIL-15 has been tested in the clinic as a therapy for melanoma and renal cell carcinoma (NCT01021059 and NCT01369888) and leukemias (NCT02689453). In some embodiments, an immunostimulatory agent is recombinant human interleukin 12 (rhIL-12). In some embodiments, an IL-15 based immunotherapeutic is heterodimeric IL-15 (hetIL-15, Novartis/Admune), a fusion complex composed of a synthetic form of endogenous IL-15 complexed to the soluble IL-15 binding protein IL-15 receptor alpha chain (IL15:sIL-15RA), which has been tested in Phase 1 clinical trials for melanoma, renal cell carcinoma, non-small cell lung cancer and head and neck squamous cell carcinoma (NCT02452268). In some embodiments, a recombinant human interleukin 12 (rhIL-12) is NM-IL-12 (Neumedicines, Inc.), NCT02544724, or NCT02542124.

In some embodiments, an immuno-oncology agent is selected from those descripted in Jerry L. Adams ET. AL., "Big opportunities for small molecules in immuno-oncology," Cancer Therapy 2015, Vol. 14, pages 603-622, the content of which is incorporated herein by reference in its entirety. In some embodiments, an immuno-oncology agent is selected from the examples described in Table 1 of Jerry L. Adams ET. AL. In some embodiments, an immuno-oncology agent is a small molecule targeting an immuno-oncology target selected from those listed in Table 2 of Jerry L. Adams ET. AL. In some embodiments, an immuno-oncology agent is a small molecule agent selected from those listed in Table 2 of Jerry L. Adams ET. AL.

In some embodiments, an immuno-oncology agent is selected from the small molecule immuno-oncology agents described in Peter L. Toogood, "Small molecule immuno-oncology therapeutic agents," Bioorganic & Medicinal Chemistry Letters 2018, Vol. 28, pages 319-329, the content of which is incorporated herein by reference in its entirety. In some embodiments, an immuno-oncology agent is an agent targeting the pathways as described in Peter L. Toogood.

In some embodiments, an immuno-oncology agent is selected from those described in Sandra L. Ross et al., "Bispecific T cell engager (BiTE®) antibody constructs can mediate bystander tumor cell killing", PLoS ONE 12(8): e0183390, the content of which is incorporated herein by reference in its entirety. In some embodiments, an immuno-oncology agent is a bispecific T cell engager (BiTE®) antibody construct. In some embodiments, a bispecific T cell engager (BiTE®) antibody construct is a CD19/CD3 bispecific antibody construct. In some embodiments, a bispecific T cell engager (BiTE®) antibody construct is an EGFR/CD3 bispecific antibody construct. In some embodiments, a bispecific T cell engager (BiTE®) antibody construct activates T cells. In some embodiments, a bispecific T cell engager (BiTE®) antibody construct activates T cells, which release cytokines inducing upregulation of intercellular adhesion molecule 1 (ICAM-1) and FAS on bystander cells. In some embodiments, a bispecific T cell engager (BiTE®) antibody construct activates T cells which result in induced bystander cell lysis. In some embodiments, the bystander cells are in solid tumors. In some embodiments, the bystander cells being lysed are in proximity to the BiTE®-activated T cells. In some embodiment, the bystander cells comprises tumor-associated antigen (TAA) negative cancer cells. In some embodiment, the bystander cells comprise EGFR-negative cancer cells. In some embodiments, an immuno-oncology agent is an antibody which blocks the PD-L1/PD1 axis and/or CTLA4. In some embodiments, an immuno-oncology agent is an ex-vivo expanded tumor-infiltrating T cell. In some embodiments, an immuno-oncology agent is a bispecific antibody construct or chimeric antigen receptors (CARs) that directly connect T cells with tumor-associated surface antigens (TAAs).

Exemplary Immune Checkpoint Inhibitors

In some embodiments, an immuno-oncology agent is an immune checkpoint inhibitor as described herein.

The term "checkpoint inhibitor" as used herein relates to agents useful in preventing cancer cells from avoiding the immune system of the patient. One of the major mechanisms of anti-tumor immunity subversion is known as "T-cell exhaustion," which results from chronic exposure to antigens that has led to up-regulation of inhibitory receptors. These inhibitory receptors serve as immune checkpoints in order to prevent uncontrolled immune reactions.

PD-1 and co-inhibitory receptors such as cytotoxic T-lymphocyte antigen 4 (CTLA-4, B and T Lymphocyte Attenuator (BTLA; CD272), T cell Immunoglobulin and Mucin domain-3 (Tim-3), Lymphocyte Activation Gene-3 (Lag-3; CD223), and others are often referred to as a checkpoint regulators. They act as molecular "gatekeepers" that allow extracellular information to dictate whether cell cycle progression and other intracellular signaling processes should proceed.

In some embodiments, an immune checkpoint inhibitor is an antibody to PD-1. PD-1 binds to the programmed cell death 1 receptor (PD-1) to prevent the receptor from binding to the inhibitory ligand PDL-1, thus overriding the ability of tumors to suppress the host anti-tumor immune response.

In one aspect, the checkpoint inhibitor is a biologic therapeutic or a small molecule. In another aspect, the checkpoint inhibitor is a monoclonal antibody, a humanized antibody, a fully human antibody, a fusion protein or a combination thereof. In a further aspect, the checkpoint inhibitor inhibits a checkpoint protein selected from CTLA-4, PDL1, PDL2, PD1, B7-H3, B7-H4, BTLA, HVEM, TIM3, GAL9, LAG3, VISTA, KIR, 2B4, CD160, CGEN-15049, CHK 1, CHK2, A2aR, B-7 family ligands or a combination thereof. In an additional aspect, the checkpoint inhibitor interacts with a ligand of a checkpoint protein selected from CTLA-4, PDL1, PDL2, PD1, B7-H3, B7-H4, BTLA, HVEM, TIM3, GAL9, LAG3, VISTA, KIR, 2B4, CD160, CGEN-15049, CHK 1, CHK2, A2aR, B-7 family ligands or a combination thereof. In an aspect, the checkpoint inhibitor is an immunostimulatory agent, a T cell growth factor, an interleukin, an antibody, a vaccine or a combination thereof. In a further aspect, the interleukin is IL-7 or IL-15. In a specific aspect, the interleukin is glycosylated IL-7. In an additional aspect, the vaccine is a dendritic cell (DC) vaccine.

Checkpoint inhibitors include any agent that blocks or inhibits in a statistically significant manner, the inhibitory pathways of the immune system. Such inhibitors may include small molecule inhibitors or may include antibodies, or antigen binding fragments thereof, that bind to and block or inhibit immune checkpoint receptors or antibodies that bind to and block or inhibit immune checkpoint receptor ligands. Illustrative checkpoint molecules that may be targeted for blocking or inhibition include, but are not limited to, CTLA-4, PDL1, PDL2, PD1, B7-H3, B7-H4, BTLA, HVEM, GAL9, LAG3, TIM3, VISTA, KIR, 2B4 (belongs to the CD2 family of molecules and is expressed on all NK, γδ, and memory $CD8^+$ (αβ) T cells), CD160 (also referred to as BY55), CGEN-15049, CHK 1 and CHK2 kinases, A2aR, and various B-7 family ligands. B7 family ligands include, but are not limited to, B7-1, B7-2, B7-DC, B7-H1, B7-H2, B7-H3, B7-H4, B7-H5, B7-H6 and B7-H7. Checkpoint inhibitors include antibodies, or antigen binding fragments thereof, other binding proteins, biologic therapeutics, or small molecules, that bind to and block or inhibit the activity of one or more of CTLA-4, PDL1, PDL2, PD1, BTLA, HVEM, TIM3, GAL9, LAG3, VISTA, KIR, 2B4, CD 160 and CGEN-15049. Illustrative immune checkpoint inhibitors include Tremelimumab (CTLA-4 blocking antibody), anti-OX40, PD-L1 monoclonal Antibody (Anti-B7-H1; MEDI4736), MK-3475 (PD-1 blocker), Nivolumab (anti-PD1 antibody), CT-011 (anti-PD1 antibody), BY55 monoclonal antibody, AMP224 (anti-PDL1 antibody), BMS-936559 (anti-PDL1 antibody), MPLDL3280A (anti-PDL1 antibody), MSB0010718C (anti-PDL1 antibody), and ipilimumab (anti-CTLA-4 checkpoint inhibitor). Checkpoint protein ligands include, but are not limited to PD-L1, PD-L2, B7-H3, B7-H4, CD28, CD86 and TIM-3.

In certain embodiments, the immune checkpoint inhibitor is selected from a PD-1 antagonist, a PD-L1 antagonist, and a CTLA-4 antagonist. In some embodiments, the checkpoint inhibitor is selected from the group consisting of nivolumab (Opdivo®), ipilimumab (Yervoy®), and pembrolizumab (Keytruda®). In some embodiments, the checkpoint inhibitor is selected from nivolumab (anti-PD-1 antibody, Opdivo®, Bristol-Myers Squibb); pembrolizumab (anti-PD-1 antibody, Keytruda®, Merck); ipilimumab (anti-CTLA-4 antibody, Yervoy®, Bristol-Myers Squibb); durvalumab (anti-PD-L1 antibody, Imfinzi®, AstraZeneca); and atezolizumab (anti-PD-L1 antibody, Tecentriq®, Genentech).

In some embodiments, the checkpoint inhibitor is selected from the group consisting of lambrolizumab (MK-3475), nivolumab (BMS-936558), pidilizumab (CT-011), AMP-224, MDX-1105, MEDI4736, MPDL3280A, BMS-936559, ipilimumab, lirlumab, IPH2101, pembrolizumab (Keytruda®), and tremelimumab.

In some embodiments, an immune checkpoint inhibitor is REGN2810 (Regeneron), an anti-PD-1 antibody tested in patients with basal cell carcinoma (NCT03132636); NSCLC (NCT03088540); cutaneous squamous cell carcinoma (NCT02760498); lymphoma (NCT02651662); and melanoma (NCT03002376); pidilizumab (CureTech), also known as CT-011, an antibody that binds to PD-1, in clinical trials for diffuse large B-cell lymphoma and multiple myeloma; avelumab (Bavencio®, Pfizer/Merck KGaA), also known as MSB0010718C), a fully human IgG1 anti-PD-L1 antibody, in clinical trials for non-small cell lung cancer, Merkel cell carcinoma, mesothelioma, solid tumors, renal cancer, ovarian cancer, bladder cancer, head and neck cancer, and gastric cancer; or PDR001 (Novartis), an inhibitory antibody that binds to PD-1, in clinical trials for non-small cell lung cancer, melanoma, triple negative breast cancer and advanced or metastatic solid tumors. Tremelimumab (CP-675,206; Astrazeneca) is a fully human monoclonal antibody against CTLA-4 that has been in studied in clinical trials for a number of indications, including: mesothelioma, colorectal cancer, kidney cancer, breast cancer, lung cancer and non-small cell lung cancer, pancreatic ductal adenocarcinoma, pancreatic cancer, germ cell cancer, squamous cell cancer of the head and neck, hepatocellular carcinoma, prostate cancer, endometrial cancer, metastatic cancer in the liver, liver cancer, large B-cell lymphoma, ovarian cancer, cervical cancer, metastatic anaplastic thyroid cancer, urothelial cancer, fallopian tube cancer, multiple myeloma, bladder cancer, soft tissue sarcoma, and melanoma. AGEN-1884 (Agenus) is an anti-CTLA4 antibody that is being studied in Phase 1 clinical trials for advanced solid tumors (NCT02694822).

In some embodiments, a checkpoint inhibitor is an inhibitor of T-cell immunoglobulin mucin containing protein-3 (TIM-3). TIM-3 inhibitors that may be used in the present invention include TSR-022, LY3321367 and MBG453. TSR-022 (Tesaro) is an anti-TIM-3 antibody which is being studied in solid tumors (NCT02817633). LY3321367 (Eli Lilly) is an anti-TIM-3 antibody which is being studied in solid tumors (NCT03099109). MBG453 (Novartis) is an anti-TIM-3 antibody which is being studied in advanced malignancies (NCT02608268).

In some embodiments, a checkpoint inhibitor is an inhibitor of T cell immunoreceptor with Ig and ITIM domains, or TIGIT, an immune receptor on certain T cells and NK cells. TIGIT inhibitors that may be used in the present invention include BMS-986207 (Bristol-Myers Squibb), an anti-TIGIT monoclonal antibody (NCT02913313); OMP-313M32 (Oncomed); and anti-TIGIT monoclonal antibody (NCT03119428).

In some embodiments, a checkpoint inhibitor is an inhibitor of Lymphocyte Activation Gene-3 (LAG-3). LAG-3 inhibitors that may be used in the present invention include BMS-986016 and REGN3767 and IMP321. BMS-986016 (Bristol-Myers Squibb), an anti-LAG-3 antibody, is being studied in glioblastoma and gliosarcoma (NCT02658981). REGN3767 (Regeneron), is also an anti-LAG-3 antibody, and is being studied in malignancies (NCT03005782). IMP321 (Immutep S.A.) is an LAG-3-Ig fusion protein, being studied in melanoma (NCT02676869); adenocarcinoma (NCT02614833); and metastatic breast cancer (NCT00349934).

Checkpoint inhibitors that may be used in the present invention include OX40 agonists. OX40 agonists that are being studied in clinical trials include PF-04518600/PF-8600 (Pfizer), an agonistic anti-OX40 antibody, in metastatic kidney cancer (NCT03092856) and advanced cancers and neoplasms (NCT02554812; NCT05082566); GSK3174998 (Merck), an agonistic anti-OX40 antibody, in Phase 1 cancer trials (NCT02528357); MEDI0562 (Medimmune/AstraZeneca), an agonistic anti-OX40 antibody, in advanced solid tumors (NCT02318394 and NCT02705482); MEDI6469, an agonistic anti-OX40 antibody (Medimmune/AstraZeneca), in patients with colorectal cancer (NCT02559024), breast cancer (NCT01862900), head and neck cancer (NCT02274155) and metastatic prostate cancer (NCT01303705); and BMS-986178 (Bristol-Myers Squibb) an agonistic anti-OX40 antibody, in advanced cancers (NCT02737475).

Checkpoint inhibitors that may be used in the present invention include CD137 (also called 4-1BB) agonists. CD137 agonists that are being studied in clinical trials include utomilumab (PF-05082566, Pfizer) an agonistic anti-CD137 antibody, in diffuse large B-cell lymphoma (NCT02951156) and in advanced cancers and neoplasms (NCT02554812 and NCT05082566); urelumab (BMS-663513, Bristol-Myers Squibb), an agonistic anti-CD137 antibody, in melanoma and skin cancer (NCT02652455) and glioblastoma and gliosarcoma (NCT02658981).

Checkpoint inhibitors that may be used in the present invention include CD27 agonists. CD27 agonists that are being studied in clinical trials include varlilumab (CDX-1127, Celldex Therapeutics) an agonistic anti-CD27 antibody, in squamous cell head and neck cancer, ovarian carcinoma, colorectal cancer, renal cell cancer, and glioblastoma (NCT02335918); lymphomas (NCT01460134); and glioma and astrocytoma (NCT02924038).

Checkpoint inhibitors that may be used in the present invention include glucocorticoid-induced tumor necrosis factor receptor (GITR) agonists. GITR agonists that are being studied in clinical trials include TRX518 (Leap Therapeutics), an agonistic anti-GITR antibody, in malignant melanoma and other malignant solid tumors (NCT01239134 and NCT02628574); GWN323 (Novartis), an agonistic anti-GITR antibody, in solid tumors and lymphoma (NCT 02740270); INCAGN01876 (Incyte/Agenus), an agonistic anti-GITR antibody, in advanced cancers (NCT02697591 and NCT03126110); MK-4166 (Merck), an agonistic anti-GITR antibody, in solid tumors (NCT02132754) and MEDI1873 (Medimmune/AstraZeneca), an agonistic hexameric GITR-ligand molecule with a human IgG1 Fc domain, in advanced solid tumors (NCT02583165).

Checkpoint inhibitors that may be used in the present invention include inducible T-cell co-stimulator (ICOS, also known as CD278) agonists. ICOS agonists that are being studied in clinical trials include MEDI-570 (Medimmune), an agonistic anti-ICOS antibody, in lymphomas (NCT02520791); GSK3359609 (Merck), an agonistic anti-ICOS antibody, in Phase 1 (NCT02723955); JTX-2011 (Jounce Therapeutics), an agonistic anti-ICOS antibody, in Phase 1 (NCT02904226).

Checkpoint inhibitors that may be used in the present invention include killer IgG-like receptor (KIR) inhibitors. KIR inhibitors that are being studied in clinical trials include lirilumab (IPH2102/BMS-986015, Innate Pharma/Bristol-Myers Squibb), an anti-KIR antibody, in leukemias (NCT01687387, NCT02399917, NCT02481297, NCT02599649), multiple myeloma (NCT02252263), and lymphoma (NCT01592370); IPH2101 (1-7F9, Innate Pharma) in myeloma (NCT01222286 and NCT01217203); and IPH4102 (Innate Pharma), an anti-KIR antibody that binds to three domains of the long cytoplasmic tail (KIR3DL2), in lymphoma (NCT02593045).

Checkpoint inhibitors that may be used in the present invention include CD47 inhibitors of interaction between CD47 and signal regulatory protein alpha (SIRPa). CD47/SIRPa inhibitors that are being studied in clinical trials include ALX-148 (Alexo Therapeutics), an antagonistic variant of (SIRPa) that binds to CD47 and prevents CD47/SIRPa-mediated signaling, in phase 1 (NCT03013218); TTI-621 (SIRPa-Fc, Trillium Therapeutics), a soluble recombinant fusion protein created by linking the N-terminal CD47-binding domain of SIRPa with the Fc domain of human IgG1, acts by binding human CD47, and preventing it from delivering its "do not eat" signal to macrophages, is in clinical trials in Phase 1 (NCT02890368 and NCT02663518); CC-90002 (Celgene), an anti-CD47 antibody, in leukemias (NCT02641002); and Hu5F9-G4 (Forty Seven, Inc.), in colorectal neoplasms and solid tumors (NCT02953782), acute myeloid leukemia (NCT02678338) and lymphoma (NCT02953509).

Checkpoint inhibitors that may be used in the present invention include CD73 inhibitors. CD73 inhibitors that are being studied in clinical trials include MEDI9447 (Medimmune), an anti-CD73 antibody, in solid tumors (NCT02503774); and BMS-986179 (Bristol-Myers Squibb), an anti-CD73 antibody, in solid tumors (NCT02754141).

Checkpoint inhibitors that may be used in the present invention include agonists of stimulator of interferon genes protein (STING, also known as transmembrane protein 173, or TMEM173). Agonists of STING that are being studied in clinical trials include MK-1454 (Merck), an agonistic synthetic cyclic dinucleotide, in lymphoma (NCT03010176); and ADU-S100 (MIW815, Aduro Biotech/Novartis), an agonistic synthetic cyclic dinucleotide, in Phase 1 (NCT02675439 and NCT03172936).

Checkpoint inhibitors that may be used in the present invention include CSF1R inhibitors. CSF1R inhibitors that are being studied in clinical trials include pexidartinib (PLX3397, Plexxikon), a CSF1R small molecule inhibitor, in colorectal cancer, pancreatic cancer, metastatic and advanced cancers (NCT02777710) and melanoma, non-small cell lung cancer, squamous cell head and neck cancer, gastrointestinal stromal tumor (GIST) and ovarian cancer (NCT02452424); and IMC-CS4 (LY3022855, Lilly), an anti-CSF-1R antibody, in pancreatic cancer (NCT03153410), melanoma (NCT03101254), and solid tumors (NCT02718911); and BLZ945 (4-[2((1R,2R)-2-hydroxycyclohexylamino)-benzothiazol-6-yloxyl]-pyridine-2-carboxylic acid methylamide, Novartis), an orally available inhibitor of CSF1R, in advanced solid tumors (NCT02829723).

Checkpoint inhibitors that may be used in the present invention include NKG2A receptor inhibitors. NKG2A receptor inhibitors that are being studied in clinical trials include monalizumab (IPH2201, Innate Pharma), an anti-NKG2A antibody, in head and neck neoplasms (NCT02643550) and chronic lymphocytic leukemia (NCT02557516).

In some embodiments, the immune checkpoint inhibitor is selected from nivolumab, pembrolizumab, ipilimumab, avelumab, durvalumab, atezolizumab, or pidilizumab.

EXEMPLIFICATION

General Synthetic Methods

The following examples are intended to illustrate the invention and are not to be construed as being limitations thereon. Temperatures are given in degrees centigrade. If not mentioned otherwise, all evaporations are performed under reduced pressure, preferably between about 15 mm Hg and 100 mm Hg (=20-133 mbar). The structure of final products, intermediates and starting materials is confirmed by standard analytical methods, e.g., microanalysis and spectroscopic characteristics, e.g., MS, IR, NMR. Abbreviations used are those conventional in the art.

All starting materials, building blocks, reagents, acids, bases, dehydrating agents, solvents, and catalysts utilized to synthesis the compounds of the present invention are either commercially available or can be produced by organic synthesis methods known to one of ordinary skill in the art (Houben-Weyl 4th Ed. 1952, Methods of Organic Synthesis, Thieme, Volume 21). Further, the compounds of the present invention can be produced by organic synthesis methods known to one of ordinary skill in the art as shown in the following examples.

All reactions are carried out under nitrogen or argon unless otherwise stated.

Proton NMR ($^1H$ NMR) is conducted in deuterated solvent. In certain compounds disclosed herein, one or more $^1H$ shifts overlap with residual proteo solvent signals; these signals have not been reported in the experimental provided hereinafter.

TABLE 5

| Analytical instruments | |
|---|---|
| LCMS | Shimadzu UFLC MS: LCMS-2020<br>Agilent Technologies 1200 series MS: Agilent Technologies 6110<br>Agilent Technologies 1200 series MS: LC/MSD VL |
| NMR | BRUKER AVANCE III/400; Frequency (MHz) 400.13; Nucleus: 1H;<br>Number of Transients: 8 |
| Prep-HPLC | Gilson GX-281 systems: instruments GX-A, GX-B, GX-C, GX-D, GX-E, GX-F, GX-G and GX-H |
| GCMS | SHIMADZU GCMS-QP2010 Ultra |
| Analytical cSFC | Agilent Technologies 1290 Infinity |
| Prep-cSFC | Waters SFC Prep 80 |

For acidic LCMS data: LCMS was recorded on an Agilent 1200 Series LC/MSD or Shimadzu LCMS2020 equipped with electro-spray ionization and quadruple MS detector [ES+ve to give $MH^+$] and equipped with Chromolith Flash RP-18e 25*2.0 mm, eluting with 0.0375 vol % TFA in water (solvent A) and 0.01875 vol % TFA in acetonitrile (solvent B). Other LCMS was recorded on an Agilent 1290 Infinity RRLC attached with Agilent 6120 Mass detector. The column used was BEH C18 50*2.1 mm, 1.7 micron. Column flow was 0.55 ml/min and mobile phase were used (A) 2 mM Ammonium Acetate in 0.1% Formic Acid in Water and (B) 0.1% Formic Acid in Acetonitrile.

For basic LCMS data: LCMS was recorded on an Agilent 1200 Series LC/MSD or Shimadzu LCMS 2020 equipped with electro-spray ionization and quadruple MS detector [ES+ve to give $MH^+$] and equipped with Xbridge C18, 2.1×50 mm columns packed with 5 mm C18-coated silica or Kinetex EVO C18 2.1×30 mm columns packed with 5 mm C18-coated silica, eluting with 0.05 vol % $NH_3 \cdot H_2O$ in water (solvent A) and acetonitrile (solvent B).

HPLC Analytical Method: HPLC was carried out on X Bridge C18 150*4.6 mm, 5 micron. Column flow was 1.0 ml/min and mobile phase were used (A) 0.1% Ammonia in water and (B) 0.1% Ammonia in Acetonitrile.

Prep HPLC Analytical Method: The compound was purified on Shimadzu LC-20AP and UV detector. The column used was X-BRIDGE C18 (250*19) mm, 5. Column flow was 16.0 ml/min. Mobile phase were used (A) 0.1% Formic Acid in Water and (B) Acetonitrile Basic method used (A) 5 mM ammonium bicarbonate and 0.10% NH3 in Water and (B) Acetonitrile or (A) 0.10% Ammonium Hydroxide in Water and (B) Acetonitrile. The UV spectra were recorded at 202 nm & 254 nm.

NMR Method: The 1H NMR spectra were recorded on a Bruker Ultra Shield Advance 400 MHz/5 mm Probe (BBFO). The chemical shifts are reported in part-per-million.

As depicted in the Examples below, in certain exemplary embodiments, compounds are prepared according to the following general procedures. It will be appreciated that, although the general methods depict the synthesis of certain compounds of the present invention, the following general methods, and other methods known to one of ordinary skill in the art, can be applied to all compounds and subclasses and species of each of these compounds, as described herein.

INTERMEDIATES

[1-[(4-Methoxyphenyl) methyl]-2,6-dioxo-3-piperidyl] trifluoromethanesulfonate (Intermediate IQ)

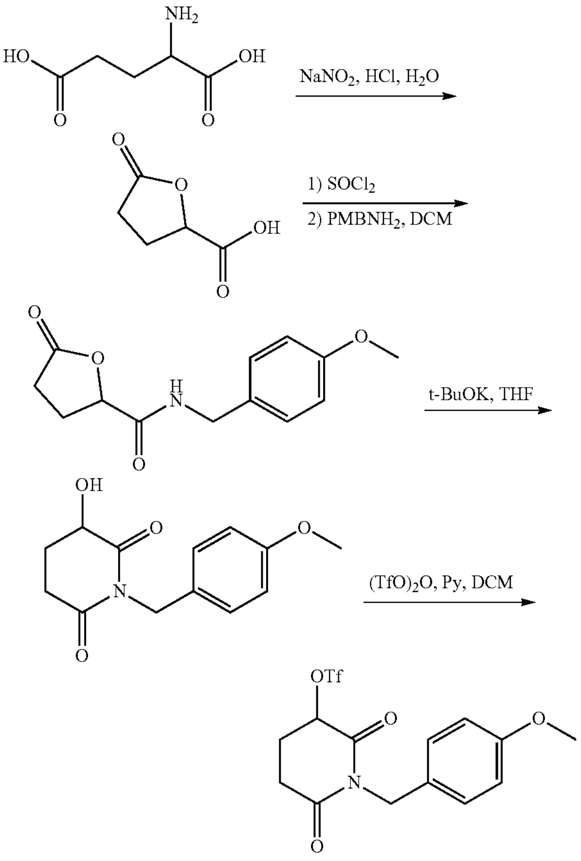

IQ

Step 1—5-Oxotetrahydrofuran-2-carboxylic acid

To a solution of 2-aminopentanedioic acid (210 g, 1.43 mol, CAS #617-65-2) in $H_2O$ (800 mL) and HCl (12 M, 210 mL) was added a solution of $NaNO_2$ (147 g, 2.13 mol) in $H_2O$ (400 mL) at −5° C. The mixture was stirred at 15° C. for 12 hrs. On completion, the mixture was concentrated and then dissolved in EA (500 mL) and filtered and washed with EA (3×100 mL). The filtrate and washed solution were dried over $Na_2SO_4$, filtered and concentrated in vacuo to give the title compound (200 g, crude) as yellow oil. $^1H$ NMR (400 MHz, $CDCl_3$) δ 6.43 (s, 1H), 5.02-4.95 (m, 1H), 2.67-2.38 (m, 4H)

Step 2—N-[(4-methoxyphenyl)methyl]-5-oxo-tetrahydrofuran-2-carboxamide

To 5-oxotetrahydrofuran-2-carboxylic acid (120 g, 922 mmol) was added $SOCl_2$ (246 g, 2.07 mol) at 0° C. slowly. The mixture was stirred at 85° C. for 3 hrs, and then the mixture was stirred at 15° C. for 6 hrs. The mixture was concentrated in vacuo. The residue was dissolved in dry DCM (1 L) at 0° C. under $N_2$. After that a solution of $Et_3N$ (187 g, 1.84 mol) and 4-methoxybenzylamine (101 g, 738 mmol) in DCM (400 mL) was added, then the mixture was stirred at 15° C. for 3 hrs. On completion, water (600 mL) was added and the mixture was extracted with DCM (3×300 mL). The combined organic phase was washed with 0.5 M HCl (500 mL), brine (500 mL), dried over with anhydrous sodium sulfate and filtered. The filtrate was concentrated in vacuo and the residue was purified by flash silica gel chromatography (PE:EA=1:1) to give the title compound (138 g, 60% yield) as a yellow solid. $^1$H NMR (400 MHz, $CDCl_3$) δ 7.22-7.20 (d, J=8.0, 1H), 6.89-6.87 (d, J=8.0, 1H), 4.90-4.86 (m, 1H), 4.47-4.4.36 (m, 2H) 3.81 (s, 3H), 2.67-2.64 (m, 1H), 2.59-2.54 (m, 2H), 2.40-2.38 (m, 1H); LC-MS ($ESI^+$) m/z 272.0 $(M+Na)^+$.

Step 3—3-Hydroxy-1-[(4-methoxyphenyl)methyl]piperidine-2,6-dione

A solution of N-[(4-methoxyphenyl)methyl]-5-oxo-tetrahydrofuran-2-carboxamide (138 g, 553 mmol) in anhydrous THF (1500 mL) was cooled to −78° C. Then, t-BuOK (62.7 g, 559 mmol) in a solution of anhydrous THF (1000 mL) was added dropwise slowly at −78° C. under nitrogen atmosphere. The resulting reaction mixture was stirred at −40° C. for 1 hr. On completion, the reaction mixture was quenched with saturated $NH_4Cl$ solution (100 mL). The mixture was extracted with ethyl acetate (3×1500 mL). The combined organic layer was washed with brine (300 mL), dried over anhydrous sodium sulfate, filtered and the filtrate was concentrated in vacuo. The residue was purified by silica gel chromatography (PE:EA=1:1) to give the title compound (128 g, 92% yield) as a white solid. $^1$H NMR (400 MHz, $CDCl_3$) δ 7.39-7.32 (m, 2H), 6.89-6.81 (m, 2H), 4.91 (s, 2H), 4.17-4.11 (m, 1H), 3.80 (s, 3H), 3.54 (s, 1H), 2.98-2.87 (m, 1H), 2.73-2.60 (m, 1H), 2.26-2.20 (m, 1H), 1.80 (dq, J=4.8, 13.1 Hz, 1H).

Step 4—[1-[(4-Methoxyphenyl) methyl]-2,6-dioxo-3-piperidyl] trifluoromethanesulfonate To a solution of 3-hydroxy-1-[(4-methoxyphenyl) methyl] piperidine-2, 6-dione (43.0 g, 173 mmol) and pyridine (27.3 g, 345 mmol) in DCM (500 mL) was added trifluoromethylsulfonyl trifluoromethanesulfonate (73.0 g, 258 mmol) dropwise at 0° C. The mixture was stirred at −10° C. for 1.5 hours under $N_2$. On completion, the mixture was concentrated in vacuo. The residue was purified by column chromatography on silica gel (PE:EA=20:1/8:1) to give the title compound (45.0 g, 68% yield) as light yellow gum. $^1$H NMR (400 MHz, $CDCl_3$) δ 7.36 (d, J=8.4 Hz, 2H), 6.85-6.82 (m, 2H), 5.32-5.28 (m, 1H), 4.91 (s, 2H), 3.79 (s, 3H), 3.02-2.97 (m, 1H), 2.79-2.74 (m, 1H), 2.41-2.35 (m, 2H).

3-(4-Bromo-3-methyl-2-oxo-2,3-dihydro-1H-benzo[d]imidazol-1-yl)piperidine-2,6-dione (Intermediate HP)

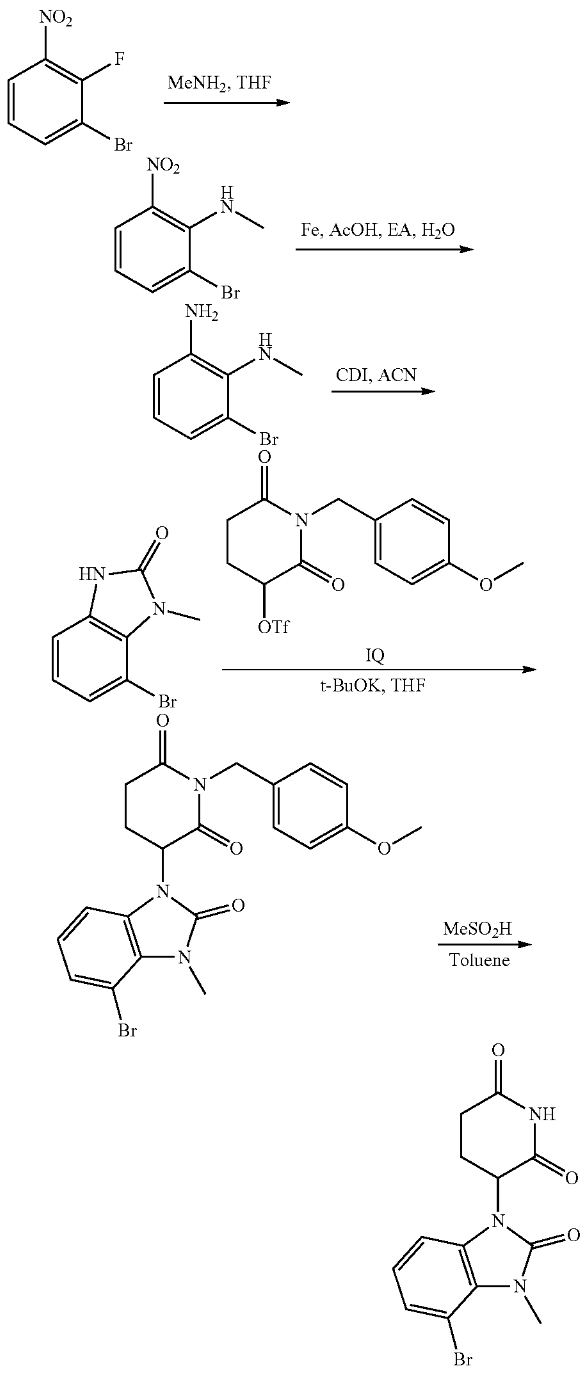

HP

Step 1—2-Bromo-N-methyl-6-nitro-aniline

To a solution of 1-bromo-2-fluoro-3-nitro-benzene (40.0 g, 181 mmol, CAS #58534-94-4) in THF (40 mL) was added $MeNH_2$ (2 M, 400 mL). The reaction mixture was stirred at 60° C. for 12 hours. On completion, the reaction mixture was poured into sat. $NaHCO_3$ (30 mL) and extracted with EA (3×200 mL). The combined organic layers were washed with brine (2×200 mL), dried with anhydrous $Na_2SO_4$, filtered and concentrated in vacuo to give the title compound (40.0 g, 95% yield) as red oil. LC-MS ($ESI^+$) m/z 230.9 $(M+H)^+$.

Step 2—3-Bromo-N2-methyl-benzene-1,2-diamine

To a mixture of 2-bromo-N-methyl-6-nitro-aniline (23.0 g, 99.5 mmol) in EA (300 mL) and $H_2O$ (10 mL) was added AcOH (100 mL). The mixture was warmed to 50° C. Then Fe (22.2 g, 398 mmol) was added to the reaction mixture and the mixture was heated to 80° C. about 4 hours. On completion, the reaction mixture was filtered and concentrated in vacuo. The residue was diluted with water (100 mL) and extracted with EA (3×200 mL). The combined organic layers was dried over $Na_2SO_4$, filtered and concentrated in vacuo to give the title compound (20.0 g, 99% yield) as red oil. $^1H$ NMR (400 MHz, DMSO-$d_6$) δ 6.73-6.70 (m, 1H), 6.68-6.60 (m, 2H), 5.02 (s, 2H), 3.67 (s, 1H), 2.58 (s, 3H).

Step 3—4-Bromo-3-methyl-1H-benzimidazol-2-one

To a mixture of 3-bromo-N2-methyl-benzene-1,2-diamine (20.0 g, 99.4 mmol) in ACN (300 mL) was added CDI (32.2 g, 198 mmol). The reaction mixture was stirred at 85° C. for 12 hours under $N_2$ atmosphere. On completion, the reaction mixture was concentrated in vacuo. The reaction mixture was diluted with water (200 mL), where a solid precipitate was formed, which was filtered off. The solid was washed with water (1 L) and dried in vacuo to give the title compound (20.0 g, 88% yield) as white solid. H NMR (400 MHz, DMSO-$d_6$) δ 11.17 (s, 1H), 7.14 (dd, J=1.2, 8.0 Hz, 1H), 7.00-6.95 (m, 1H), 6.93-6.87 (m, 1H), 3.55 (s, 3H).

Step 4—3-(4-Bromo-3-methyl-2-oxo-benzimidazol-1-yl)-1-[(4-methoxyphenyl)methyl]piperidine-2,6-dione To a solution of 4-bromo-3-methyl-1H-benzimidazol-2-one (12.0 g, 52.8 mmol) in THF (300 mL) was added t-BuOK (7.12 g, 63.4 mmol). The reaction mixture was stirred at 0° C. for 0.5 hr. Subsequently, [1-[(4-methoxyphenyl)methyl]-2,6-dioxo-3-piperidyl] trifluoromethanesulfonate (20.1 g, 52.8 mmol, Intermediate IQ) in a solution of THF (100 mL) was added dropwise. The resulting reaction mixture was stirred at 20° C. for 0.5 hr under $N_2$. On completion, the reaction mixture was quenched with saturated $NH_4Cl$ (100 mL), and extracted with ethyl acetate (200 mL). The combined organic layers were washed with brine (2×100 mL), dried over anhydrous sodium sulfate, filtered, the filtrate was concentrated in vacuo. The crude product was purified by reversed-phase HPLC (0.1% FA condition) to give the title compound (13.3 g, 55% yield) as a yellow solid. $^1H$ NMR (400 MHz, $CDCl_3$) δ 7.38 (d, J=8.8 Hz, 2H), 7.22 (d, J=8.0 Hz, 1H), 6.84 (d, J=8.8 Hz, 2H), 6.80 (t, J=8.0 Hz, 1H), 6.48-6.40 (d, J=8.0 Hz, 1H), 5.22 (dd, J=5.2, 12.8 Hz, 1H), 5.04-4.93 (m, 2H), 3.81 (s, 3H), 3.80 (s, 3H), 3.12-2.98 (m, 1H), 2.93-2.77 (m, 1H), 2.62 (dq, J=4.4, 13.2 Hz, 1H), 2.20-2.17 (m, 1H).

Step 5—3-(4-bromo-3-methyl-2-oxo-2,3-dihydro-1H-benzo[d]imidazol-1-yl)piperidine-2,6-dione A mixture of 3-(4-bromo-3-methyl-2-oxo-benzimidazol-1-yl)-1-[(4-methoxyphenyl)methyl]piperidine-2,6-dione (13.3 g, 29.0 mmol) in a mixed solvent of Tol. (80 mL) and methane sulfonic acid (40 mL) was degassed and purged with $N_2$ for 3 times, and then the mixture was stirred at 120° C. for 2 hrs under $N_2$ atmosphere. On completion, the reaction mixture was concentrated in vacuo to remove toluene. The residue was added 200 mL of ice water, and then white solid precipitate formed. The mixture was filtered and the filtered cake was collected and dried over in vacuo to give the title compound (7.30 g, 74% yield) as white solid. $^1H$ NMR (400 MHz, DMSO-$d_6$) δ 11.13 (s, 1H), 7.25 (d, J=8.0 Hz, 1H), 7.17 (d, J=8.0 Hz, 1H), 7.05-6.93 (m, 1H), 5.41 (dd, J=5.2, 12.8 Hz, 1H), 3.64 (s, 3H), 2.96-2.83 (m, 1H), 2.78-2.59 (m, 2H), 2.08-2.00 (m, 1H).

3-(Difluoromethyl)-4-nitro-1H-pyrazole (Intermediate HS)

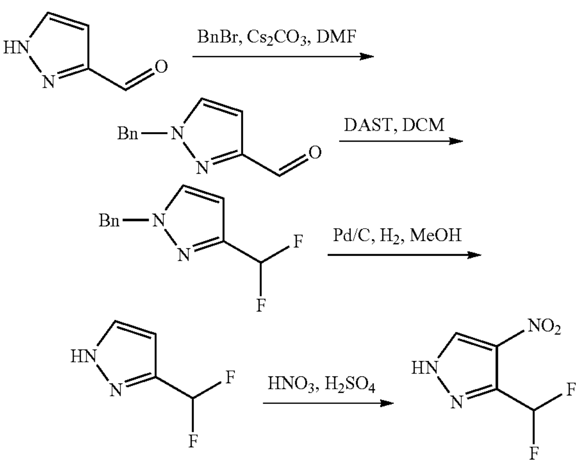

HS

Step 1—1-Benzyl-1H-pyrazole-3-carbaldehyde

To a solution of 1H-pyrazole-3-carbaldehyde (5.00 g, 52.0 mmol, CAS #: 3920-50-1) and BnBr (9.34 g, 54.6 mmol) in DMF (50 mL) was added $Cs_2CO_3$ (42.4 g, 130 mmol). The reaction mixture was stirred at 25° C. for 1 hour. On completion, the reaction mixture was diluted with water, extracted with ethyl acetate (3×100 mL). The combined organic layers was washed with brine (50 mL), dried over anhydrous sodium sulfate, filtered and concentrated in vacuo. The crude product was purified by silica gel chromatography (Petroleum ether:Ethyl acetate=20:1) to give the title compound (8.00 g, 83% yield) as a colorless oil. $^1H$ NMR (400 MHz, $CDCl_3$) δ 10.02 (s, 1H), 7.44 (d, J=2.4 Hz, 1H), 7.43-7.33 (m, 3H), 7.29-7.24 (m, 2H), 6.85 (d, J=2.4 Hz, 1H), 5.42 (s, 2H).

Step 2—1-Benzyl-3-(difluoromethyl)-1H-pyrazole

To a solution of 1-benzylpyrazole-3-carbaldehyde (5.00 g, 26.9 mmol) in DCM (30 mL) was added DAST (17.3 g, 107 mmol) at 0° C. The reaction mixture was stirred at 25° C. for 5 hours. On completion, the reaction mixture was quenched with methanol (30 mL) at 0° C. After, the mixture was concentrated in vacuo. The crude product was purified by silica gel chromatography (petroleum ether:ethyl acetate=20:1) to give the title compound (3.30 g, 59% yield)

as a white solid. $^1$H NMR (400 MHz, $CDCl_3$) δ 7.43-7.36 (m, 3H), 7.27-7.21 (m, 2H), 6.91-6.57 (m, 1H), 6.55-6.51 (m, 1H), 5.35 (s, 2H); LC-MS (ESI$^+$) m/z 209.1 (M+H)$^+$.

Step 3—3-(Difluoromethyl)-1H-pyrazole

To a solution of 1-benzyl-3-(difluoromethyl)pyrazole (1.00 g, 4.80 mmol) in methanol (20 mL) was added $Pd(OH)_2/C$ (0.1 g, 10% purity) under $N_2$ atmosphere. The suspension was degassed and purged with $H_2$ for 3 times. The mixture was stirred at 40° C. for 12 hrs under $H_2$ (50 Psi). On completion, the reaction mixture was filtered and concentrated in vacuo to give the title compound (470 mg, 83% yield) as colorless oil. $^1$H NMR (400 MHz, DMSO-$d_6$) δ 13.16 (s, 1H), 7.85 (s, 1H), 7.14-6.82 (m, 1H), 6.52 (s, 1H).

Step 4—3-(Difluoromethyl)-4-nitro-1H-pyrazole

To a solution of 3-(difluoromethyl)-1H-pyrazole (470 mg, 3.98 mmol) in $H_2SO_4$ (5 mL) was carefully added a 65% solution of $HNO_3$ (965 mg, 9.95 mmol) dropwise at 0° C. After stirring for 10 minutes, the reaction mixture was heated to 115° C., and stirred for 12 hrs. On completion, the reaction mixture was cooled to 25° C. Then, the reaction mixture was poured onto the (100 mL) ice, extracted with ethyl acetate (3x50 mL). The combined organic layers was washed with brine (2x50 mL), dried over with anhydrous sodium sulfate, filtered and concentrated in vacuo to give the title compound (530 mg, 82% yield). $^1$H NMR (400 MHz, DMSO-$d_6$) δ 14.41 (s, 1H), 9.04 (s, 1H), 7.50-7.17 (m, 1H), 7.50-7.17 (m, 1H).

Methyl 4-[4-amino-3-(difluoromethyl)pyrazol-1-yl] cyclohexanecarboxylate (Intermediate QS)

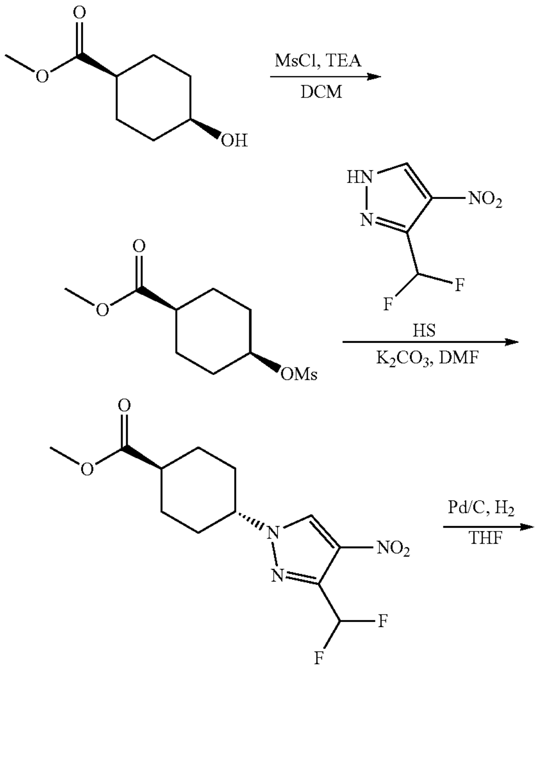

-continued

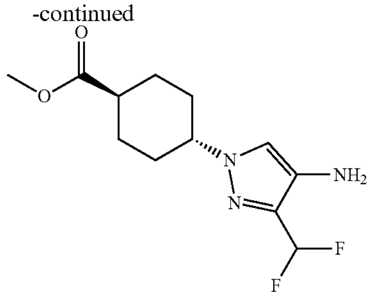

QS

Step 1—Methyl 4-methylsulfonyloxycyclohexanecarboxylate

To a mixture of methyl 4-hydroxycyclohexanecarboxylate (1.00 g, 6.32 mmol, CAS #3618-03-9) in DCM (10 mL) was added TEA (831 mg, 8.22 mmol) and MsCl (1.09 g, 9.48 mmol) at 0° C., the reaction mixture was stirred 0° C. for 2 hours. On completion, the mixture was poured into the ice-water (50 mL) and extracted with DCM (2x30 mL). The combined organic phase was washed with brine (2x50 mL), dried with anhydrous $Na_2SO_4$, filtered and concentrated in vacuo to give the title compound (1.20 g, 80% yield) as colorless oil. $^1$H NMR (400 MHz, $CDCl_3$) δ 4.91 (t, J=2.8, 5.2 Hz, 1H), 3.69 (s, 3H), 3.02 (s, 3H), 2.41-2.39 (m, 1H), 2.09-1.99 (m, 2H), 1.97-1.86 (m, 2H), 1.80 (t, J=4.4, 9.2 Hz, 2H), 1.75-1.66 (m, 2H).

Step 2—Methyl 4-[3-(difluoromethyl)-4-nitro-pyrazol-1-yl]cyclohexanecarboxylate

To a mixture of 3-(difluoromethyl)-4-nitro-1H-pyrazole (555 mg, 3.40 mmol, Intermediate HS) and methyl 4-methyl sulfonyloxycyclohexanecarboxylate (1.20 g, 5.08 mmol) in DMF (30 mL) was added $K_2CO_3$ (2.11 g, 15.2 mmol). The reaction mixture was stirred at 80° C. for 12 hours. On completion, the mixture was poured into water (50 mL). The aqueous phase was extracted with ethyl acetate (2x30 mL). The combined organic phase was washed with brine (2x40 mL), dried with anhydrous $Na_2SO_4$, filtered and concentrated in vacuo. The residue was purified by column chromatography to give the title compound (480 mg, 25% yield) as brown oil. $^1$H NMR (400 MHz, $CDCl_3$) δ 8.23 (s, 1H), 7.25-6.96 (m, 1H), 4.26-4.14 (m, 1H), 3.76-3.65 (m, 3H), 2.40 (t, J=3.6, 12.4 Hz, 1H), 2.36-2.17 (m, 4H), 1.83 (d, J=3.6, 12.8 Hz, 2H), 1.69-1.59 (m, 2H).

Step 3—Methyl 4-[4-amino-3-(difluoromethyl)pyrazol-1-yl]cyclohexanecarboxylate

To a mixture of methyl 4-[3-(difluoromethyl)-4-nitro-pyrazol-1-yl]cyclohexanecarboxylate (430 mg, 1.42 mmol) in THF (20 mL) was added Pd/C (100 mg, 10 wt %) under $N_2$. The suspension was degassed under vacuum and purged with $H_2$ gas three times. The mixture was stirred under $H_2$ (15 psi) at 25° C. for 12 hours. On completion, the mixture was filtered and the filtrate was concentrated in vacuo to give the title compound (350 mg, 90% yield) a brown solid. LC-MS (ESI$^+$) m/z 274.1 (M+H)$^+$.

[4-[4-Amino-3-(difluoromethyl)pyrazol-1-yl]cyclohexyl]methanol (Intermediate TD)

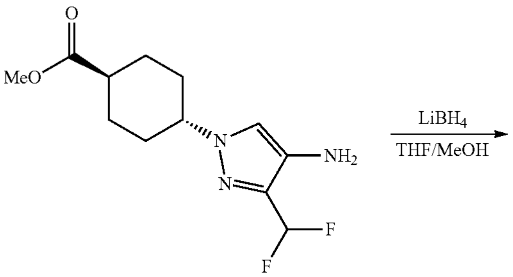

QS

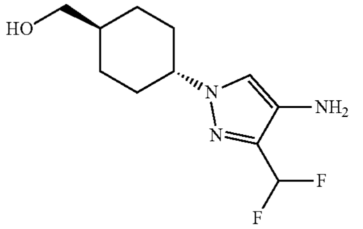

TD

To a mixture of methyl 4-[4-amino-3-(difluoromethyl) pyrazol-1-yl]cyclohexanecarboxylate (1.20 g, 4.39 mmol, Intermediate QS) in THF (80 mL) and MeOH (10 mL) was added $LiBH_4$ (191 mg, 8.78 mmol) at 0° C., then the mixture was stirred at 60° C. for 1 hour. On completion, the reaction mixture was poured into water (120 mL), and the aqueous phase was extracted with ethyl acetate (2×50 mL). The combined organic phase was washed with brine (2×40 mL), dried with anhydrous $Na_2SO_4$, filtered and concentrated in vacuo to give title compound (860 mg, 79% yield) as a brown solid. $^1H$ NMR (400 MHz, $CDCl_3$-d) δ 7.02 (s, 1H), 6.82-6.53 (m, 1H), 3.94 (tt, J=4.0, 12.0 Hz, 1H), 3.50 (d, J=6.4 Hz, 2H), 2.21-2.12 (m, 3H), 2.01-1.92 (m, 3H), 1.69 (d, J=3.6, 12.4 Hz, 2H), 1.56 (tt, J=3.0, 6.4, 12.0 Hz, 2H), 1.20-1.08 (m, 2H). Absolute stereochemistry randomly assigned, compound is the trans isomer.

5-[(1R,4R)-2-oxa-5-azabicyclo[2.2.1]heptan-5-yl] pyrazolo[1,5-a]pyrimidine-3-carboxylic acid (Intermediate AEH)

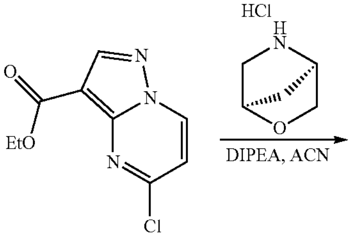

-continued

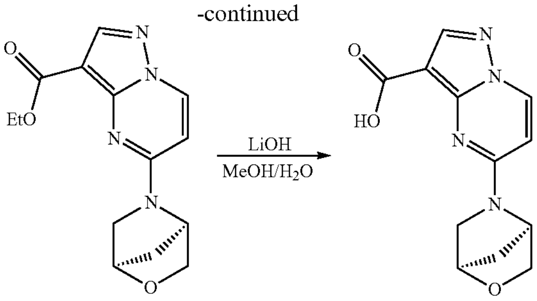

AEH

Step 1—Ethyl 5-[(1R,4R)-2-oxa-5-azabicyclo[2.2.1] heptan-5-yl]pyrazolo[1,5-a]pyrimidine-3-carboxylate To a solution of ethyl 5-chloropyrazolo[1,5-a]pyrimidine-3-carboxylate (200 mg, 886 umol, CAS #1224944-77-7) and (1R,4R)-2-oxa-5-azabicyclo[2.2.1]heptane (144 mg, 1.06 mmol, HCl salt, CAS #661470-56-0) in ACN (5.00 mL) was added DIPEA (343 mg, 2.66 mmol). The mixture was stirred at 60° C. for 3 hours. On completion, the reaction mixture was concentrated in vacuo, then diluted with water (5 mL) and extracted with EA (2×10 mL). The combined organic layers were washed with brine (2×30 mL), dried over $Na_2SO_4$, concentrated in vacuo to give the title compound (180 mg, 70% yield) as a white solid. $^1H$ NMR (400 MHz, $CDCl_3$) δ 8.38-8.18 (m, 2H), 6.12 (s, 1H), 5.46 (s, 1H), 4.77 (s, 1H), 4.34 (q, J=7.2 Hz, 2H), 4.06-3.87 (m, 2H), 3.75-3.38 (m, 2H), 2.09-1.90 (m, 2H), 1.38 (t, J=7.2 Hz, 3H).

Step 2—5-[(1R,4R)-2-oxa-5-azabicyclo[2.2.1]heptan-5-yl]pyrazolo[1,5-a]pyrimidine-3-carboxylic acid To a solution of ethyl 5-[(1R, 4R)-2-oxa-5-azabicyclo [2.2.1]heptan-5-yl]pyrazolo[1,5-a]pyrimidine-3-carboxylate (150 mg, 520 umol) in MeOH (10.0 mL) and $H_2O$ (2.00 mL) was added $LiOH·H_2O$ (43.6 mg, 1.04 mmol). The mixture was stirred at 60° C. for 16 hours. On completion, the reaction mixture was quenched with water (1 mL), and concentrated in vacuo to remove MeOH. Then the mixture was acidified with HCl (1 N) until the pH=5. The aqueous phase was extracted with EA (3×5 mL). The combined organic layer was washed with brine (2×10 mL), dried with anhydrous $Na_2SO_4$, filtered and concentrated in vacuo to give the title compound (135 mg, 99% yield) as a white solid. $^1H$ NMR (400 MHz, $CDCl_3$) δ 11.31-9.30 (m, 1H), 8.32 (d, J=7.6 Hz, 1H), 8.28 (s, 1H), 6.44-6.12 (m, 1H), 5.29-4.58 (m, 2H), 4.00-3.85 (m, 2H), 3.77-3.49 (m, 2H), 2.20-1.97 (m, 2H).

N-[3-(difluoromethyl)-1-(4-formylcyclohexyl)pyrazol-4-yl]-5-[(1R,4R)-2-oxa-5-azabicyclo [2.2.1]heptan-5-yl]pyrazolo[1,5-a]pyrimidine-3-carboxamide (Intermediate AJB)

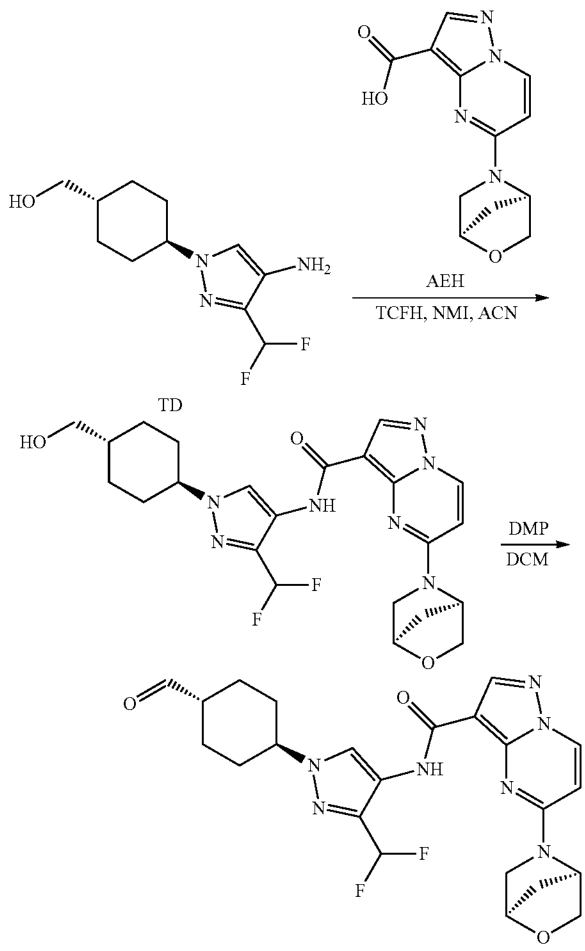

AJB

Step 1—N-[3-(difluoromethyl)-1-[4-(hydroxymethyl)cyclohexyl]pyrazol-4-yl]-5-[(1R,4R)-2-oxa-5-azabicyclo[2.2.1]heptan-5-yl]pyrazolo[1,5-a]pyrimidine-3-carboxamide To a solution of 5-[(1R,4R)-2-oxa-5-azabicyclo[2.2.1]heptan-5-yl]pyrazolo[1,5-a]pyrimidine-3-carboxylic acid (3.71 g, 14.2 mmol, Intermediate AEH) in MeCN (75 mL) was added 1-methylimidazole (4.10 g, 49.9 mmol, 3.98 mL), [chloro(dimethylamino)methylene]-dimethyl-ammonium; hexafluorophosphate (4.80 g, 17.1 mmol). The mixture was stirred at 20° C. for 30 min. Then [4-[4-amino-3-(difluoromethyl)pyrazol-1-yl]cyclohexyl]methanol (3.5 g, 14.2 mmol, Intermediate TD) was added to the mixture, the reaction mixture was stirred at 20° C. for 2 hrs. On completion, the reaction mixture was filtered and the filter cake was concentrated in vacuo to give the title compound (3.80 g, 55% yield) as white solid. $^1$H NMR (400 MHz, DMSO-$d_6$) δ 9.49 (d, J=5.2 Hz, 1H), 8.77 (dd, J=2.4, 8.0 Hz, 1H), 8.39 (d, J=4.0 Hz, 1H), 8.25 (d, J=5.2 Hz, 1H), 7.27-6.95 (m, 1H), 6.88-6.40 (m, 1H), 5.32-5.01 (m, 1H), 4.76 (d, J=14.8 Hz, 1H), 4.47 (t, J=5.2 Hz, 1H), 4.23-4.10 (m, 1H), 3.84-3.72 (m, 2H), 3.65-3.42 (m, 2H), 3.25 (t, J=5.6 Hz, 2H), 2.07-1.90 (m, 4H), 1.89-1.81 (m, 2H), 1.78-1.66 (m, 2H), 1.50-1.36 (m, 1H), 1.17-1.00 (m, 2H); LC-MS (ESI$^+$) m/z 488.3 (M+H)$^+$.

Step 2—N-[3-(difluoromethyl)-1-(4-formylcyclohexyl)pyrazol-4-yl]-5-[(1R,4R)-2-oxa-5-azabicyclo[2.2.1]heptan-5-yl]pyrazolo[1,5-a]pyrimidine-3-carboxamide To a solution of N-[3-(difluoromethyl)-1-[4-(hydroxymethyl)cyclohexyl]pyrazol-4-yl]-5-[(1R,4R)-2-oxa-5-azabicyclo[2.2.1]heptan-5-yl]pyrazolo[1,5-a]pyrimidine-3-carboxamide (3.80 g, 7.79 mmol) in DCM (78 mL) was added DMP (3.64 g, 8.57 mmol), the reaction mixture was stirred at 20° C. for 3 hr. On completion, the reaction mixture was quenched with $Na_2S_2O_3$ (50 mL) and extracted with DCM (2×60 mL). The combined organic phase was washed with $NaHCO_3$ and brine (2×20 mL), dried with anhydrous $Na_2SO_4$, filtered and concentrated in vacuo to give the title compound (3.30 g, 87% yield) as yellow solid. $^1$H NMR (400 MHz, DMSO-$d_6$) δ 9.60 (s, 1H), 9.49 (d, J=5.2 Hz, 1H), 8.76 (dd, J=4.0, 8.0 Hz, 1H), 8.40 (d, J=4.0 Hz, 1H), 8.25 (d, J=4.8 Hz, 1H), 7.27-6.94 (m, 1H), 6.88-6.40 (m, 1H), 5.30-5.02 (m, 1H), 4.76 (d, J=14.0 Hz, 1H), 4.29-4.14 (m, 1H), 3.85-3.72 (m, 2H), 3.64-3.41 (m, 2H), 2.43-2.31 (m, 1H), 2.14-1.90 (m, 6H), 1.88-1.73 (m, 2H), 1.48-1.24 (m, 2H).

Tert-butyl 4-methyl-4-prop-2-ynoxy-piperidine-1-carboxylate (Intermediate BKF)

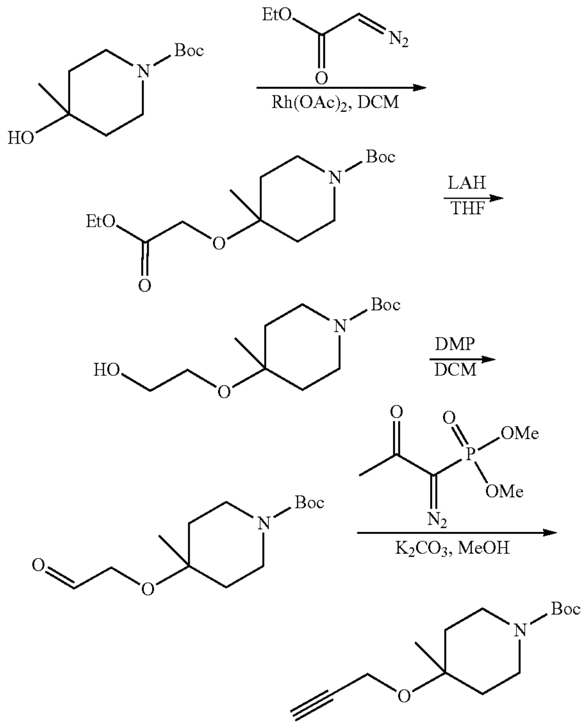

BKF

Step 1—Tert-butyl 4-(2-ethoxy-2-oxo-ethoxy)-4-methyl-piperidine-1-carboxylate

To a solution of tert-butyl 4-hydroxy-4-methyl-piperidine-1-carboxylate (5 g, 23.2 mmol, CAS #406235-30-1) and $Rh(OAc)_2$ (102 mg, 464 umol) in DCM (100 mL) was added ethyl 2-diazoacetate (5.30 g, 46.4 mmol) in DCM (100 mL) at 25° C. and the mixture reaction was stirred 25° C. for 12 hr. On completion, the reaction mixture was partitioned between $H_2O$ (100 mL) and DCM (200 mL). The organic phase was separated, washed with brine 60 mL (30 mL×2), dried over $Na_2SO_4$, filtered and concentrated under reduced pressure to give a residue. The residue was purified by column chromatography ($SiO_2$, petroleum ether/ethyl acetate=40/1 to 1/1) to give the title compound (5 g, 71% yield) as yellow oil. $^1H$ NMR (400 MHz, $CDCl_3$) δ 4.20-4.10 (m, 2H), 3.92 (s, 2H), 3.55-3.50 (m, 2H), 1.75-1.65 (m, 2H), 1.38 (s, 9H), 1.25-1.15 (m, 3H), 1.11 (s, 3H).

Step 2—Tert-butyl 4-(2-hydroxyethoxy)-4-methyl-piperidine-1-carboxylate

To a solution of tert-butyl 4-(2-ethoxy-2-oxo-ethoxy)-4-methyl-piperidine-1-carboxylate (5 g, 16.5 mmol) in THF (30 mL) was added $LiAlH_4$ (755 mg, 19.9 mmol). The mixture was stirred at 0° C. for 1 hr. On completion, the mixture was quenched with sat. NaOH (15% wt, 3.7 mL), stirred and dried in $Na_2SO_4$, filtered and the filtrate was concentrated in vacuo. The residue was purified by column chromatography ($SiO_2$, petroleum ether/ethyl acetate=20/1 to 1/1) to give the title compound (2 g, 46% yield) as yellow oil. $^1H$ NMR (400 MHz, $CDCl_3$) δ 3.65 (t, J=4.4 Hz 1H), 3.37 (t, J=4.4 Hz 2H), 3.07 (t, J=7.2 Hz 1H), 2.05-1.90 (m, 1H), 1.70-1.60 (m, 2H), 1.41-1.39 (m, 2H), 1.38 (s, 9H); 1.11 (s, 3H).

Step 3—Tert-butyl 4-methyl-4-(2-oxoethoxy)piperidine-1-carboxylate

To a solution of tert-butyl 4-(2-hydroxyethoxy)-4-methyl-piperidine-1-carboxylate (2 g, 7.71 mmol) in DCM (15 mL) was added DMP (4.25 g, 10.0 mmol). The mixture was stirred at 0-25° C. for 1 hr. On completion, the reaction mixture was quenched by addition saturated $NaHCO_3$ (5 mL) and $Na_2S_2O_3$ (5 mL), and then diluted with $H_2O$ (10 mL), and extracted with DCM (2×25 mL). The combined organic layers were washed with brine (10 mL), dried over $Na_2SO_4$, filtered and concentrated in vacuo to give the title compound (1.5 g, 75% yield) as yellow oil.

Step 4—Tert-butyl 4-methyl-4-prop-2-ynoxy-piperidine-1-carboxylate

To a solution of tert-butyl 4-methyl-4-(2-oxoethoxy)piperidine-1-carboxylate (1.5 g, 5.83 mmol) and $K_2CO_3$ (1.61 g, 11.6 mmol) in MeOH (150 mL) was added 1-diazo-1-dimethoxyphosphoryl-propan-2-one (1.68 g, 8.74 mmol) at 0° C. Then the mixture was stirred at 25° C. for 12 hrs. On completion, the reaction mixture was concentrated under reduced pressure to remove MeOH. The residue was diluted with $H_2O$ (20 mL) and extracted with EA (2×40 mL). The combined organic layers were washed with brine (50 mL), dried over $Na_2SO_4$, filtered and concentrated in vacuo to give a residue. The residue was purified by column chromatography ($SiO_2$, petroleum ether/ethyl acetate=20/1 to 1/1) to give the title compound (400 mg, 27% yield) as yellow oil. $^1H$ NMR (400 MHz, $CDCl_3$) δ 4.00 (d, J=2.4, 2H), 3.75-3.45 (m, 2H), 3.20-3.05 (m, 2H), 2.32 (t, J=2.4 Hz, 1H), 1.80-1.65 (m, 2H), 1.55-1.45 (m, 2H), 1.41 (s, 9H), 1.15 (s, 3H).

3-[3-Methyl-4-[3-[(4-methyl-4-piperidyl)oxy]prop-1-ynyl]-2-oxo-benzimidazol-1-yl]piperidine-2,6-dione (Intermediate BKG)

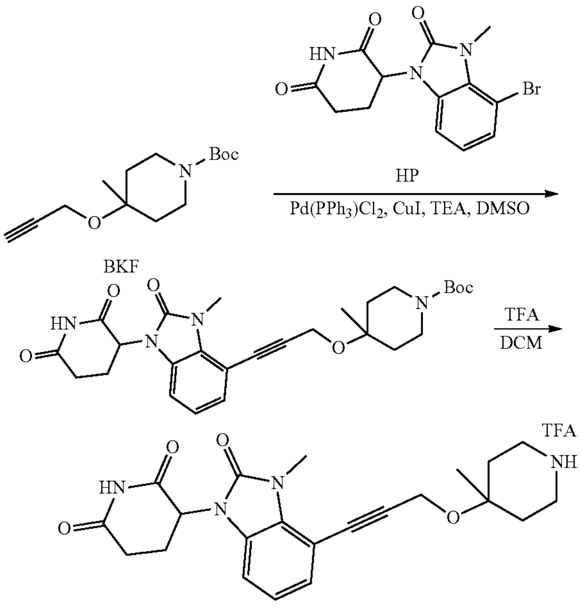

BKG

Step 1—Tert-butyl 4-[3-[1-(2,6-dioxo-3-piperidyl)-3-methyl-2-oxo-benzimidazol-4-yl]prop-2-ynoxy]-4-methyl-piperidine-1-carboxylate A mixture of tert-butyl 4-methyl-4-prop-2-ynoxy-piperidine-1-carboxylate (100 mg, 394 umol, Intermediate BKF), 3-(4-bromo-3-methyl-2-oxo-benzimidazol-1-yl)piperidine-2,6-dione (133 mg, 394 umol, Intermediate HP), $Pd(PPh_3)_4$ (45.6 mg, 39.4 umol), CuI (15.0 mg, 78.9 umol), 4 Å molecular sieves (50 mg) and TEA (199 mg, 1.97 mmol, 274 uL) in DMSO (3 mL) was degassed and purged with $N_2$ for 3 times. Then the mixture was stirred at 80° C. for 12 hr under $N_2$ atmosphere. On completion, the reaction mixture was partitioned between EA (40 mL) and $H_2O$ (20 mL). The organic phase was separated, washed with brine (2×10 mL), dried over $Na_2SO$, filtered and concentrated in vacuo to give a residue. The residue was purified by reverse phase (0.1% FA condition) to give the title compound (100 mg, 50% yield) as a yellow solid. LC-MS ($ESI^+$) m/z 411.2 $(M+H-100)^+$.

Step 2—3-[3-Methyl-4-[3-[(4-methyl-4-piperidyl)oxy]prop-1-ynyl]-2-oxo-benzimidazol-1-yl piperidine-2,6-dione To a solution of tert-butyl 4-[3-[1-(2,6-dioxo-3-piperidyl)-3-methyl-2-oxo-benzimidazol-4-yl]prop-2-ynoxy]-4-methyl-piperidine-1-carboxylate (25 mg, 48.9 umol) in DCM (2 mL) was added TFA (385 mg, 3.38 mmol), the reaction mixture was stirred at 15° C. for 30 min. On completion, the reaction mixture was concentrated in vacuo to give the title compound (20 mg, 77% yield, TFA) as yellow oil. LC-MS (ESI+) m/z 411.1 $(M+H)^+$.

Tert-butyl 4-prop-2-ynoxypiperidine-1-carboxylate (Intermediate TM)

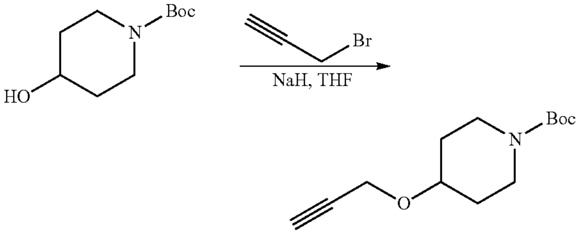

TM

To a solution of tert-butyl 4-hydroxypiperidine-1-carboxylate (2.00 g, 9.94 mmol, CAS #109384-19-2) in anhydrous THF (10 mL) was cooled to 0° C., and subsequently NaH (477 mg, 11.9 mmol, 60% oil dispersion) was added. The reaction mixture was stirred at 0° C. for 0.5 hr. Then, 3-bromoprop-1-yne (1.18 g, 9.94 mmol, 856 uL) was added. The resulting reaction mixture was stirred at 25° C. for 12 hrs. On completed, the reaction mixture was quenched with water (1 mL), then diluted with ethyl acetate (100 mL). The organic layers were washed with brine (20 mL), dried over anhydrous sodium sulfate, filtered and the filtrate was concentrated in vacuo. The residue was purified by column chromatography to give the title compound (2.38 g, 100% yield) as yellow oil. $^1$H NMR (400 MHz, $CDCl_3$) δ 4.22 (d, J=2.4 Hz, 2H), 3.84-3.75 (m, 2H), 3.73-3.70 (m, 1H), 3.15-3.09 (m, 2H), 2.43 (t, J=2.4 Hz, 1H), 1.93-1.82 (m, 2H), 1.61-1.50 (m, 2H), 1.47 (s, 9H).

3-[3-Methyl-2-oxo-4-[3-(4-piperidyloxy)propyl]benzimidazol-1-yl]piperidine-2,6-dione (Intermediate TN)

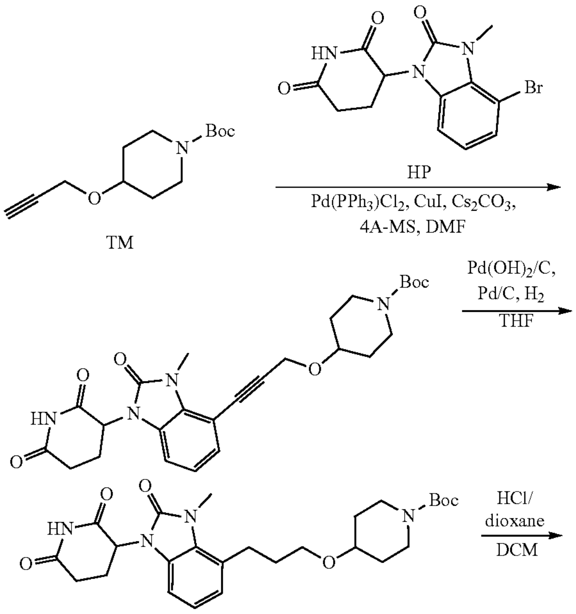

-continued

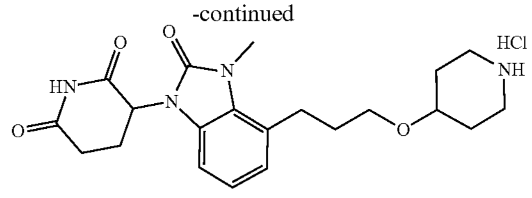

TN

Step 1—Tert-butyl 4-[3-[1-(2,6-dioxo-3-piperidyl)-3-methyl-2-oxo-benzimidazol-4-yl]prop-2-ynoxy]piperidine-1-carboxylate A suspension of 3-(4-bromo-3-methyl-2-oxo-benzimidazol-1-yl)piperidine-2,6-dione (300 mg, 887 umol, Intermediate HP), tert-butyl 4-prop-2-ynoxypiperidine-1-carboxylate (318 mg, 1.33 mmol, Intermediate TM), $Pd(PPh_3)_2Cl_2$ (124 mg, 177 umol), CuI (33.8 mg, 177 umol), 4 Å molecular sieves (400 mg) and $Cs_2CO_3$ (1.16 g, 3.55 mmol) in DMF (5 mL) was de-gassed under vacuum and purged with $N_2$ several times and then heated to 80° C. for 2 hours under $N_2$. On completion, the reaction mixture was concentrated in vacuo to remove DMF. The residue was diluted with EA (50 mL) and water (20 mL). After, the organic layer was separated and washed with brine (5 mL×2), dried over anhydrous $Na_2SO_4$, filtered and the filtrate was concentrated in vacuo to give a residue. The residue was purified by reverse phase to give the title compound (222 mg, 48% yield) as a yellow solid. $^1$H NMR (400 MHz, $CDCl_3$) δ 8.09 (s, 1H), 7.10 (d, J=8.0 Hz, 1H), 6.92 (t, J=8.0 Hz, 1H), 6.69 (d, J=8.0 Hz, 1H), 5.13 (dd, J=5.2, 12.8 Hz, 1H), 4.39 (s, 2H), 3.76-3.66 (m, 6H), 3.09-3.03 (m, 2H), 2.94-2.84 (m, 1H), 2.82-2.71 (m, 1H), 2.71-2.59 (m, 1H), 2.22-2.11 (m, 1H), 1.83-1.78 (m, 2H), 1.57-1.49 (m, 2H), 1.39 (s, 9H), LC-MS (ESI+) m/z 441.2 $(M+H-56)^+$.

Step 2—Tert-butyl4-[3-[1-(6-dioxo-3-piperidyl)-3-methyl-2-oxo-benzimidazol-4-yl]propoxy] piperidine-1-carboxylate To a solution of tert-butyl 4-[3-[1-(2,6-dioxo-3-piperidyl)-3-methyl-2-oxo-benzimidazol-4-yl]prop-2-ynoxy] piperidine-1-carboxylate (370 mg, 745 umol) in THF (10 mL) was added Pd/C (0.1 g, 10% wt) and $Pd(OH)_2/C$ (0.1 g, 10% wt). The suspension was degassed under vacuum and purged with $H_2$ several times. The mixture was stirred under $H_2$ (15 psi) at 25° C. for 12 hours. On completion, the reaction mixture was filtered and the filtrate was concentrated in vacuo to give the title compound (330 mg, 88% yield) as a white solid. $^1$H NMR (400 MHz, $CDCl_3$) δ 8.03 (s, 1H), 6.91 (d, J=8.0 Hz, 1H), 6.83 (d, J=8.0 Hz, 1H), 6.59 (t, J=8.0 Hz, 1H), 5.20-5.09 (m, 1H), 3.70-3.64 (m, 2H), 3.62 (s, 3H), 3.44 (t, J=5.6 Hz, 2H), 3.41-3.34 (m, 1H), 3.06-3.04 (m, 2H), 2.98-2.93 (m, 2H), 2.91-2.80 (m, 1H), 2.79-2.63 (m, 2H), 2.19-2.10 (m, 1H), 1.89-1.81 (m, 2H), 1.80-1.73 (m, 2H), 1.47-1.39 (m, 2H), 1.39 (s, 9H); LC-MS (ESI+) m/z 523.1 $(M+Na)^+$.

Step 3—3-[3-Methyl-2-oxo-4-[3-(4-piperidyloxy)propyl]benzimidazol-1-yl]piperidine-2,6-dione To a solution of tert-butyl 4-[3-[1-(2,6-dioxo-3-piperidyl)-3-methyl-2-oxo-benzimidazol-4-yl]propoxy] piperidine-1-carboxylate (100 mg, 199 umol) in DCM (4 mL) was added HCl/dioxane (4 M, 2 mL). The reaction mixture was stirred at 25° C. for 0.5 hr. On completion, the reaction mixture was concentrated in vacuo to give the title compound (87.0 mg, 100% yield, HCl salt) as a white solid. LC-MS ($ESI^+$) m/z 401.1 $(M+H)^+$.

3-[3-Methyl-2-oxo-4-[3-(4-piperidyloxy)prop-1-ynyl]benzimidazol-1-yl]piperidine-2,6-dione (Intermediate APT)

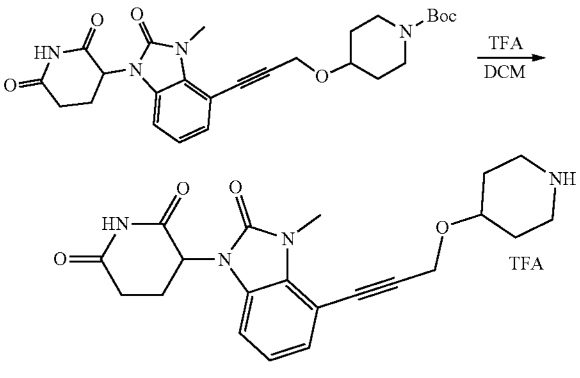

APT

To a mixture of tert-butyl 4-[3-[1-(2,6-dioxo-3-piperidyl)-3-methyl-2-oxo-benzimidazol-4-yl]prop-2-ynoxy]piperidine-1-carboxylate (1.50 g, 3.02 mmol, synthesized via Step 1 of Intermediate TN) in DCM (30 mL) was added TFA (23.1 g, 202 mmol, 15 mL). The reaction mixture was stirred at 20° C. for 1 hr. On completion, the reaction mixture was concentrated in vacuo to give the title compound (1.50 g, 97% yield, TFA salt) as yellow oil. LC-MS ($ESI^+$) m/z 397.2 $(M+H)^+$.

((1S,4s)-4-(4-amino-3-(difluoromethyl)-1H-pyrazol-1-yl)cyclohexyl)methanol (Intermediate BKH)

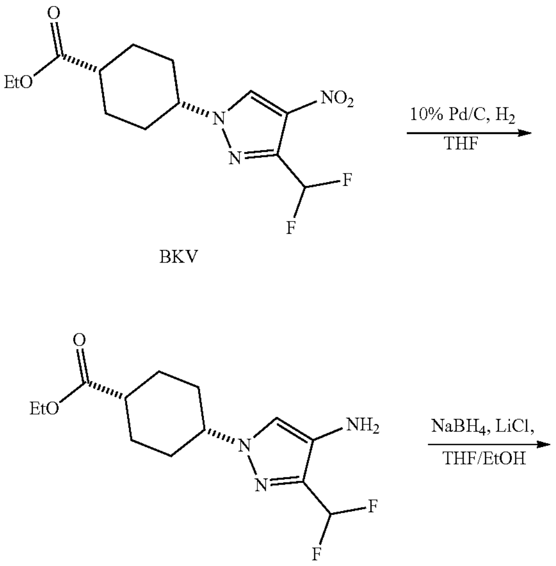

-continued

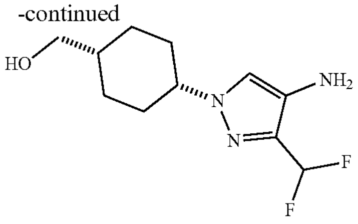

BKH

Step 1—(1S,4s)-ethyl 4-(4-amino-3-(difluoromethyl)-1H-pyrazol-1-yl)cyclohexanecarboxylate To a solution of (1s,4s)-ethyl 4-(3-(difluoromethyl)-4-nitro-1H-pyrazol-1-yl)cyclohexanecarboxylate (15.0 g, 47.2 mmol, Intermediate BKV) in THF (150 mL) was added Pd/C (1.50 g, 47.2 mmol, 10 wt %) and $H_2$ (50 PSI). The mixture was stirred at 40° C. for 18 hrs. On completion, the reaction mixture was concentrated in vacuo to give the title compound (13.5 g, 45.0 mmol, 95% yield) as black brown oil. LC-MS ($ESI^+$) m/z 288.2 $(M+H)^+$.

Step 2—((1S,4s)-4-(4-amino-3-(difluoromethyl)-1H-pyrazol-1-yl)cyclohexyl)methanol To a solution of (1s,4s)-ethyl 4-(4-amino-3-(difluoromethyl)-1H-pyrazol-1-yl)cyclohexanecarboxylate (13.0 g, 45.2 mmol) in THF (65.0 mL), EtOH (65.0 mL) were added LiCl (4.80 g, 113 mmol, 2.32 mL), $NaBH_4$ (3.42 g, 90.5 mmol). The mixture was stirred at 30° C. for 9 hrs. Then $NaBH_4$ (1.71 g, 45.2 mmol) was added into the mixture, which was stirred at 30° C. for 1 hr. On completion, the reaction mixture was cooled to 20° C., then the reaction mixture was dropped in MeOH (100 mL) at 25° C. for 0.5 hr. The mixture was concentrated under reduce pressure at 45° C. The residue was dissolved with EA (200 mL) and 6% citric acid solution (90.0 mL), then the organic layer was separated and washed with 100 mL brine. The organic layer was dried over $Na_2SO_4$, filtered and filtrate was concentrated under reduced pressure to give the title compound (10.0 g, 34.6 mmol, 77% yield, 85% purity) as brown oil. LC-MS ($ESI^+$) m/z 246.0 $(M+H)^+$.

5-((1R,4R)-2-oxa-5-azabicyclo[2.2.1]heptan-5-yl)-N-(3-(difluoromethyl)-1-((1s,4S)-4-formyl cyclohexyl)-1H-pyrazol-4-yl)pyrazolo[1,5-a]pyrimidine-3-carboxamide (Intermediate BKI)

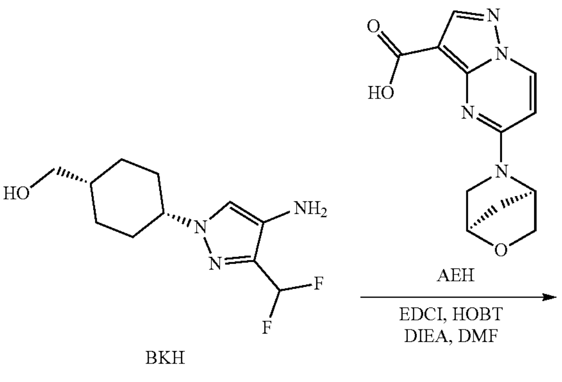

-continued

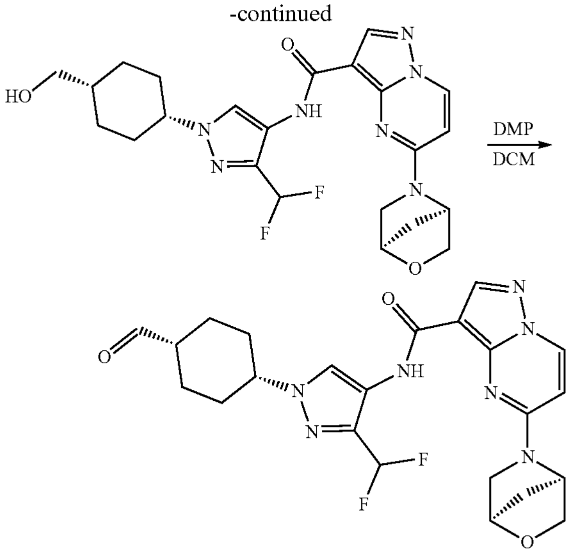

BKI

Step 1—5-((1R,4R)-2-oxa-5-azabicyclo[2.2.1]heptan-5-yl)-N-(3-(difluoromethyl)-1-((1s,4S)-4-(hydroxymethyl)cyclohexyl)-1H-pyrazol-4-yl)pyrazolo[1,5-a]pyrimidine-3-carboxamide To a solution of ((1s,4s)-4-(4-amino-3-(difluoromethyl)-1H-pyrazol-1-yl)cyclohexyl)methanol (6.00 g, 20.7 mmol, Intermediate BKH), 5-((1R,4R)-2-oxa-5-azabicyclo[2.2.1]heptan-5-yl)pyrazolo[1,5-a]pyrimidine-3-carboxylic acid (6.09 g, 22.8 mmol, Intermediate AEH) in DMF (30.0 mL) was added EDCI (5.98 g, 31.1 mmol), DIEA (8.06 g, 62.3 mmol, 10.8 mL) and HOBT (4.21 g, 31.1 mmol). The mixture was stirred at 30° C. for 10 hrs. On completion, the reaction mixture was diluted with 60 mL water and extracted with DCM (2×20 mL). The combined organic layers were washed with 60 mL brine, dried over $Na_2SO_4$, filtered and concentrated in vacuo to give a residue. The residue was purified by prep-HPLC (FA, MeOH) to give the title compound (4.00 g, 8.12 mmol, 39% yield) as a light yellow solid. $^1H$ NMR (400 MHz, $CDCl_3$) δ 9.58 (s, 1H), 8.52-8.22 (m, 3H), 6.98-6.57 (m, 1H), 6.35-5.98 (m, 1H), 5.42 (s, 1H), 4.90-4.53 (m, 1H), 4.20 (td, J=4.2, 7.6 Hz, 1H), 4.01-3.90 (m, 2H), 3.88-3.67 (m, 1H), 3.65-3.51 (m, 3H), 3.48-3.41 (m, 1H), 3.42-3.40 (m, 1H), 2.17-2.15 (m, 1H), 2.17-2.09 (m, 2H), 2.01-1.85 (m, 3H), 1.84-1.57 (m, 5H); LC-MS ($ESI^+$) m/z 488.2 $(M+H)^+$.

Step 2—5-((1R,4R)-2-oxa-5-azabicyclo[2.2.1]heptan-5-yl)-N-(3-(difluoromethyl)-1-((1s,4S)-4-formyl cyclohexyl)-1H-pyrazol-4-yl)pyrazolo[1,5-a]pyrimidine-3-carboxamide A mixture of 5-((1R,4R)-2-oxa-5-azabicyclo[2.2.1]heptan-5-yl)-N-(3-(difluoromethyl)-1-((1s,4S)-4-(hydroxymethyl)cyclohexyl)-1H-pyrazol-4-yl)pyrazolo[1,5-a]pyrimidine-3-carboxamide (3.00 g, 6.15 mmol), DMP (2.87 g, 6.77 mmol, 2.10 mL) in DCM (60.0 mL) was degassed and purged with $N_2$ for 3 times, and then the mixture was stirred at 30° C. for 2 hrs under $N_2$ atmosphere. On completion, the mixture was poured into saturated $Na_2S_2O_3$ (6.00 g) and $NaHCO_3$ (6.00 g) aqueous solution (100 mL), The organic phase was separated and the aqueous solution and was extracted with DCM (100 mL). The combined organic phase was washed with 100 mL brine, then separated and dried with $Na_2SO_4$; the filtrate was concentrated under reduced pressure to give a crude. The crude product was triturated with MTBE (20.0 mL) at 25° C. for 30 min, and then filtered to give filter cake as the title compound (2.50 g, 5.15 mmol, 84% yield) as a red solid. $^1H$ NMR (400 MHz, DMSO-$d_6$) δ 9.67 (s, 1H), 9.48 (d, J=5.4 Hz, 1H), 8.77 (dd, J=1.6, 7.6 Hz, 1H), 8.36 (d, J=3.6 Hz, 1H), 8.24 (d, J=5.2 Hz, 1H), 7.32-6.94 (m, 1H), 6.90-6.35 (m, 1H), 5.36-5.02 (m, 1H), 4.76 (d, J=14.8 Hz, 1H), 4.27 (s, 1H), 3.89-3.69 (m, 2H), 3.66-3.40 (m, 2H), 2.63-2.53 (m, 1H), 2.25-2.10 (m, 2H), 2.09-1.84 (m, 4H), 1.78-1.62 (m, 4H).

5-[(1S,4S)-2-oxa-5-azabicyclo[2.2.1]heptan-5-yl]pyrazolo[1,5-a]pyrimidine-3-carboxylic acid (Intermediate AEG)

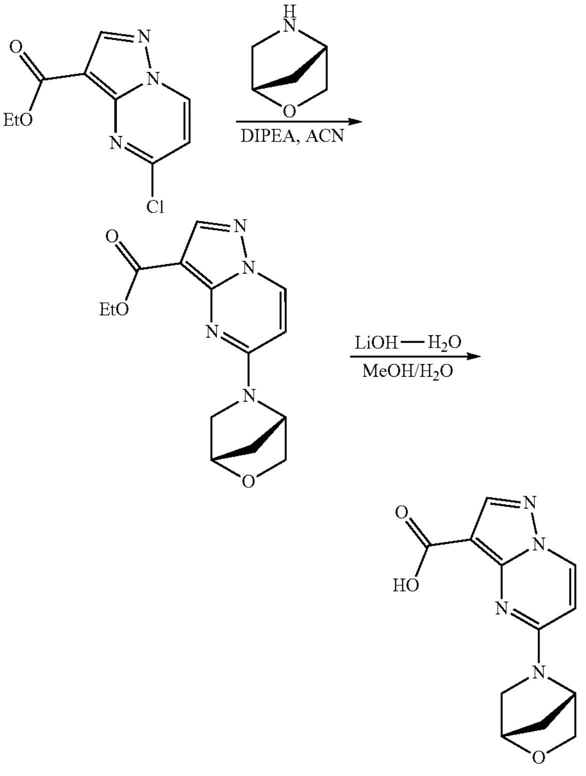

AEG

Step 1—Ethyl 5-[(1S,4S)-2-oxa-5-azabicyclo[2.2.1]heptan-5-yl]pyrazolo[1,5-a]pyrimidine-3-carboxylate To a solution of ethyl 5-chloropyrazolo[1,5-a]pyrimidine-3-carboxylate (200 mg, 886 umol, CAS #1224944-77-7) and (1S,4S)-2-oxa-5-azabicyclo[2.2.1]heptane (131 mg, 1.33 mmol, CAS #279-33-4) in ACN (6 mL) was added DIPEA (458 mg, 3.55 mmol). The mixture was stirred at 60° C. for 2 hours. On completion, the mixture was concentrated in vacuo. The residue was purified by reverse phase (0.1% FA) to give the title compound (210 mg, 82% yield) as yellow oil. $^1H$ NMR (400 MHz, DMSO-$d_6$) δ 8.71 (d, J=8.0 Hz, 1H), 8.19 (s, 1H), 6.87-6.31 (m, 1H), 5.25-4.92 (m, 1H), 4.24-4.14 (m, 3H), 3.90-3.78 (m, 1H), 3.78-3.62 (m, 1H), 3.61-3.35 (m, 2H), 2.01-1.89 (m, 2H), 1.29 (t, J=7.2 Hz, 3H), LC-MS ($ESI^+$) m/z 289.1 $(M+H)^+$.

Step 2—5-[(1S,4S)-2-oxa-5-azabicyclo[2.2.1]heptan-5-yl]pyrazolo[1,5-a]pyrimidine-3-carboxylic acid To a solution of ethyl 5-[(1S,4S)-2-oxa-5-azabicyclo[2.2.1]heptan-5-yl]pyrazolo[1,5-a]pyrimidine-3-carboxylate (210 mg, 728 umol) in a mixed solvent of MeOH (5 mL) and $H_2O$ (1 mL) was added $LiOH{\cdot}H_2O$ (152 mg, 3.64 mmol). The mixture was stirred at 60° C. for 16 hours. On completion, the mixture was concentrated in vacuo. The residue was diluted with $H_2O$ (10 mL) and acidified with 1N HCl solution until the pH=3. Then, the mixture was extracted with EA (5×20 mL), the combined organic layers dried over anhydrous $Na_2SO_4$, filtered and concentrated in vacuo to give the title compound (170 mg, 89% yield) as white solid. $^1H$ NMR (400 MHz, DMSO-$d_6$) δ 8.71 (d, J=8.0 Hz, 1H), 8.17 (s, 1H), 7.00-6.23 (m, 1H), 5.23-4.94 (m, 1H), 4.80-4.68 (m, 1H), 3.90-3.77 (m, 1H), 3.77-3.67 (m, 1H), 3.58-3.39 (m, 2H), 2.01-1.85 (m, 2H).

5-((1S,4S)-2-oxa-5-azabicyclo[2.2.1]heptan-5-yl)-N-(3-(difluoromethyl)-1-((1s,4R)-4-formyl cyclohexyl)-1H-pyrazol-4-yl)pyrazolo[1,5-a]pyrimidine-3-carboxamide (Intermediate BKJ)

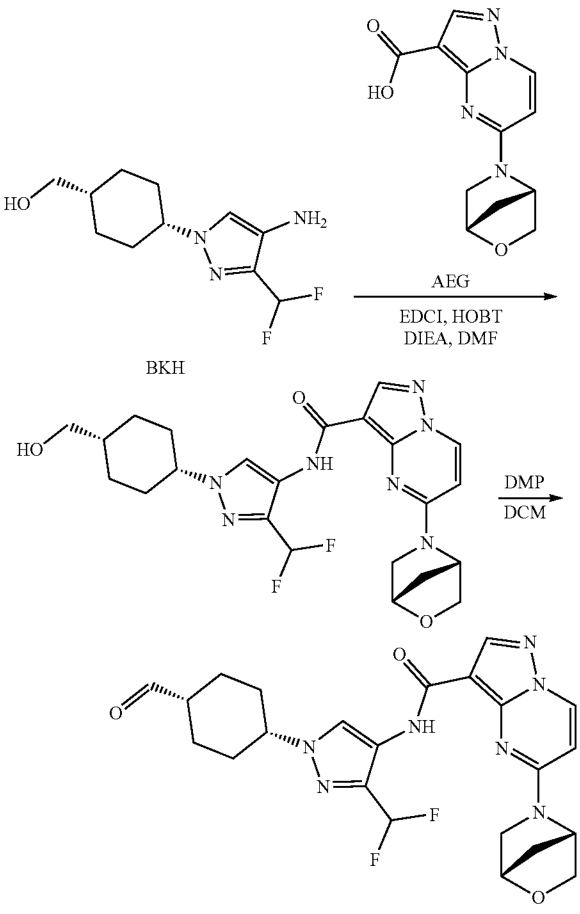

BKH

BKJ

Step 1—5-((1S,4S)-2-oxa-5-azabicyclo[2.2.1]heptan-5-yl)-N-(3-(difluoromethyl)-1-((1s,4R)-4-(hydroxymethyl)cyclohexyl)-1H-pyrazol-4-yl)pyrazolo[1,5-a]pyrimidine-3-carboxamide To a solution of ((1s,4s)-4-(4-amino-3-(difluoromethyl)-1H-pyrazol-1-yl)cyclohexyl)methanol (4.00 g, 13.8 mmol, Intermediate BKH), 5-((1S,4S)-2-oxa-5-azabicyclo[2.2.1]heptan-5-yl)pyrazolo[1,5-a]pyrimidine-3-carboxylic acid (4.06 g, 15.2 mmol, Intermediate AEG) in DMF (20.0 mL) was added EDCI (3.99 g, 20.7 mmol), DIEA (5.37 g, 41.5 mmol, 7.24 mL) and HOBt (2.81 g, 20.7 mmol). The mixture was stirred at 30° C. for 10 hrs. On completion, the reaction mixture was diluted with 60.0 mL $H_2O$ and extracted with DCM (20 mL×2). The combined organic layers were washed with 60.0 mL brine, dried over $Na_2SO_4$, filtered and concentrated in vacuo to give a residue. The residue was purified by prep-HPLC (FA condition) to give the title compound (3.00 g, 5.91 mmol, 43% yield) as a light yellow solid. $^1H$ NMR (400 MHz, $CDCl_3$) δ 9.58 (s, 1H), 8.44 (s, 1H), 8.37 (s, 1H), 8.28 (d, J=7.6 Hz, 1H), 6.95-6.58 (m, 1H), 6.31-5.98 (m, 1H), 5.41 (s, 1H), 4.90-4.50 (m, 1H), 4.20 (td, J=3.6, 7.6 Hz, 1H), 4.01-3.90 (m, 2H), 3.88-3.66 (m, 1H), 3.65-3.51 (m, 3H), 3.50-3.41 (m, 1H), 2.17-2.12 (m, 3H), 2.02-1.84 (m, 3H), 1.84-1.73 (m, 1H), 1.72-1.55 (m, 4H); LC-MS ($ESI^+$) m/z 488.2 $(M+H)^+$.

Step 2—5-((1S,4S)-2-oxa-5-azabicyclo[2.2.1]heptan-5-yl)-N-(3-(difluoromethyl)-1-((1s,4R)-4-formyl cyclohexyl)-1H-pyrazol-4-yl)pyrazolo[1,5-a]pyrimidine-3-carboxamide A mixture of 5-((1S,4S)-2-oxa-5-azabicyclo[2.2.1]heptan-5-yl)-N-(3-(difluoromethyl)-1-((1s,4R)-4-(hydroxymethyl)cyclohexyl)-1H-pyrazol-4-yl)pyrazolo[1,5-a]pyrimidine-3-carboxamide (2.00 g, 4.10 mmol), DMP (1.91 g, 4.51 mmol, 1.40 mL) in DCM (40.0 mL) was degassed and purged with $N_2$ for 3 times, and then the mixture was stirred at 30° C. for 2 hrs under $N_2$ atmosphere. On completion, the mixture was poured into saturated $Na_2S_2O_3$ (6.00 g) and $NaHCO_3$ (6.00 g) aqueous solution (100 mL). Then the organic phase was separated and the aqueous solution was extracted with DCM (100 mL). The combined organic phase was washed with 100 mL brine, then separated and dried over $Na_2SO_4$. The filtrate was concentrated in vacuo to give a crude product. The crude product was triturated with MTBE (20.0 mL) at 25° C. for 30 min to give the title compound (1.60 g, 80.3% yield) as a red solid. $^1H$ NMR (400 MHz, DMSO-$d_6$) δ 9.67 (s, 1H), 9.48 (d, J=5.2 Hz, 1H), 8.77 (dd, J=1.6, 7.8 Hz, 1H), 8.36 (d, J=3.6 Hz, 1H), 8.25 (d, J=5.2 Hz, 1H), 7.35-6.94 (m, 1H), 6.90-6.36 (m, 1H), 5.35-5.01 (m, 1H), 4.76 (d, J=15.2 Hz, 1H), 4.27 (s, 1H), 3.89-3.70 (m, 2H), 3.66-3.40 (m, 2H), 2.57 (s, 1H), 2.23-2.09 (m, 2H), 2.08-1.85 (m, 4H), 1.80-1.63 (m, 4H).

5-((1S,4S)-2-oxa-5-azabicyclo[2.2.1]heptan-5-yl)-N-(3-(difluoromethyl)-1-((1r,4S)-4-formyl cyclohexyl)-1H-pyrazol-4-yl)pyrazolo[1,5-a]pyrimidine-3-carboxamide (Intermediate BKK)

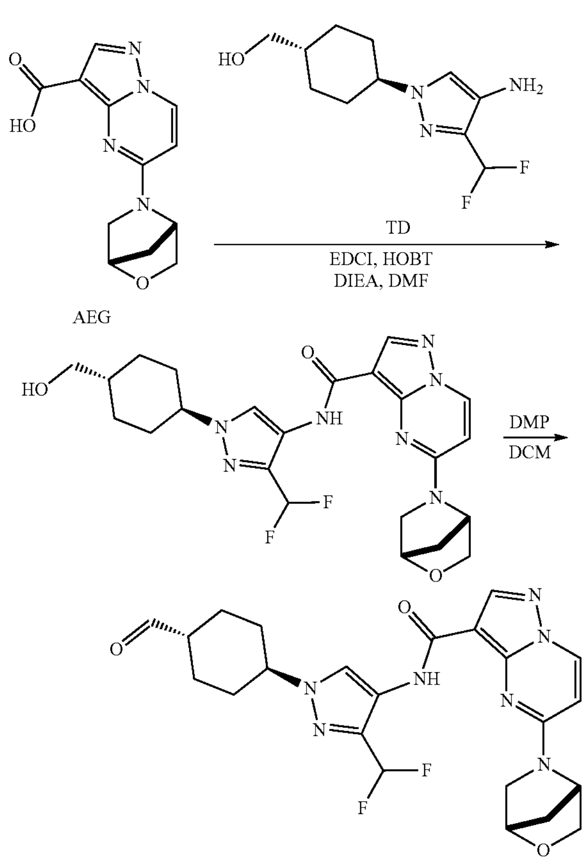

AEG

BKK

Step 1—5-((1S,4S)-2-oxa-5-azabicyclo[2.2.1]heptan-5-yl)-N-(3-(difluoromethyl)-1-((1r,4S)-4-(hydroxymethyl)cyclohexyl)-1H-pyrazol-4-yl)pyrazolo[1,5-a]pyrimidine-3-carboxamide To a solution of ((1r,4r)-4-(4-amino-3-(difluoromethyl)-1H-pyrazol-1-yl)cyclohexyl)methanol (5.20 g, 20.5 mmol, Intermediate TD), 5-((1S,4S)-2-oxa-5-azabicyclo[2.2.1]heptan-5-yl)pyrazolo[1,5-a]pyrimidine-3-carboxylic acid (6.02 g, 22.6 mmol, Intermediate AEG) in DMF (30.0 mL) were added EDCI (5.91 g, 30.8 mmol), DIEA (7.97 g, 61.7 mmol, 10.7 mL) and HOBt (4.17 g, 30.8 mmol). The mixture was stirred at 30° C. for 10 hrs. On completion, the reaction mixture was diluted with 40 mL $H_2O$. The crude product was triturated with $H_2O$ at 0° C. for 20 min, then filtered to give a cake which was washed with $H_2O$ (10 mL). Then the filter cake was dried in vacuo to give the title compound (7.00 g, 69% yield) as a white solid. $^1H$ NMR (400 MHz, DMSO-$d_6$) δ 9.58 (s, 1H), 8.40 (d, J=7.2 Hz, 2H), 8.29 (d, J=7.6 Hz, 1H), 6.92-6.58 (m, 1H), 6.33-6.04 (m, 1H), 5.43 (s, 1H), 4.88-4.53 (m, 1H), 4.06 (tt, J=3.6, 12.0 Hz, 1H), 3.99-3.92 (m, 2H), 3.89-3.68 (m, 1H), 3.59-3.43 (m, 4H), 2.29-2.16 (m, 2H), 2.14-2.05 (m, 1H), 1.99-1.89 (m, 3H), 1.79-1.70 (m, 2H), 1.59-1.52 (m, 1H), 1.17-1.10 (m, 2H); LC-MS ($ESI^+$) m/z 488.2 $(M+H)^+$.

Step 2—5-((1S,4S)-2-oxa-5-azabicyclo[2.2.1]heptan-5-yl)-N-(3-(difluoromethyl)-1-((1r,4S)-4-formyl cyclohexyl)-1H-pyrazol-4-yl)pyrazolo[1,5-a]pyrimidine-3-carboxamide To a solution of 5-((1S,4S)-2-oxa-5-azabicyclo[2.2.1]heptan-5-yl)-N-(3-(difluoromethyl)-1-((1r,4S)-4-(hydroxymethyl)cyclohexyl)-1H-pyrazol-4-yl)pyrazolo[1,5-a]pyrimidine-3-carboxamide (4.00 g, 8.09 mmol) in DCM (80.0 mL) was added DMP (3.77 g, 8.90 mmol, 2.76 mL). The mixture was stirred at 30° C. for 2 hrs under $N_2$. On completion, the crude product was triturated with MTBE at 25° C. for 30 min to give compound the title compound (3.50 g, 6.78 mmol, 84% yield) as a white solid. $^1H$ NMR (400 MHz, DMSO-$d_6$) δ 9.61 (s, 1H), 9.50 (d, J=5.6 Hz, 1H), 8.77 (dd, J=2.4, 7.6 Hz, 1H), 8.40 (d, J=4.2 Hz, 1H), 8.25 (d, J=5.2 Hz, 1H), 7.28-6.94 (m, 1H), 6.89-6.39 (m, 1H), 5.34-5.02 (m, 1H), 4.76 (d, J=15.6 Hz, 1H), 4.21 (t, J=10.8 Hz, 1H), 3.86-3.67 (m, 2H), 3.65-3.40 (m, 2H), 3.07 (s, 1H), 2.38 (t, J=12.4 Hz, 1H), 2.13-1.75 (m, 8H), 1.48-1.29 (m, 2H).

Tert-butyl 2,2,6,6-tetradeuterio-4-prop-2-ynoxy-piperidine-1-carboxylate (Intermediate BKL)

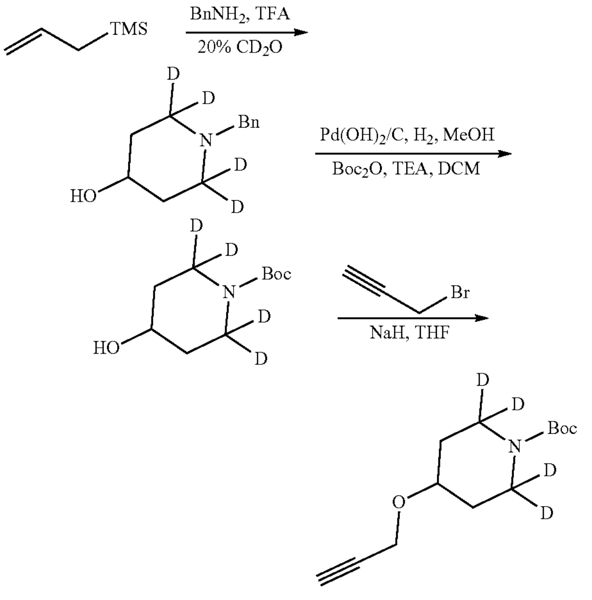

BKL

Step 1—1-Benzyl-2,2,6,6-tetradeuterio-piperidin-4-ol

A solution of dideuteriomethanone (8.33 g, 260 mmol, 36.1 mL) (A 20% solution of [2H2]-formaldehyde in $D_2O$, 36.1 mL, CAS #1664-98-8) was added to phenylmethanamine (25.0 g, 113 mmol, 25.4 mL, TFA salt) and the resulting mixture sonicated for 10 mins and then stirred for 1 h at 20° C. To the resulting clear solution was added allyl(trimethyl)silane (14.2 g, 124 mmol, 19.8 mL, CAS #762-72-1) and the reaction was heated at 40° C. 16 hrs. On completion, the resulting two phase mixture was diluted with water (50 ml) and solid potassium carbonate was added until the pH was greater than pH=9. The product was extracted with ether (3×45 mL), the layers were combined, dried over anhydrous sodium sulfate, filtered and evaporated to an oil. The product was purified by silica gel chromatography ($DCM:MeOH:NH_3 \cdot H_2O$=10:1:0.1) to give the title compound (22.0 g, 99% yield) as a colorless oil. $^1H$ NMR (400 MHz, $CDCl_3$) δ 7.40 (s, 5H), 4.03 (s, 2H), 3.95 (s, 1H), 2.05 (dd, J=2.8, 14.4 Hz, 2H), 1.81 (dd, J=6.0, 14.4 Hz, 2H).

Step 2—Tert-butyl 2,2,6,6-tetradeuterio-4-hydroxy-piperidine-1-carboxylate

To a solution of 1-benzyl-2,2,6,6-tetradeuterio-piperidin-4-ol (22.0 g, 112 mmol), $(Boc)_2O$ (24.6 g, 112 mmol, 25.8 mL) in MeOH (250 mL) was added $Pd(OH)_2/C$ (5 g, 10% wt) under $N_2$. The suspension was degassed under vacuum and purged with $H_2$ several times. The mixture was stirred under $H_2$ (50 Psi) at 40° C. for 20 hours. On completion, the reaction mixture was filtered and the filter was concentrated. The crude product was purified by silica gel chromatography eluted with petroleum ether/ethyl acetate=2:1 to give the title compound (4.70 g, 20% yield) as a white solid. $^1H$ NMR (400 MHz, $CDCl_3$) δ 3.93-3.80 (m, 1H), 1.86 (dd, J=3.6, 12.8 Hz, 2H), 1.48 (s, 9H), 1.47-1.44 (m, 2H).

Step 3—Tert-butyl 2,2,6,6-tetradeuterio-4-prop-2-ynoxy-piperidine-1-carboxylate To a solution of tert-butyl 2,2,6,6-tetradeuterio-4-hydroxy-piperidine-1-carboxylate (760 mg, 3.70 mmol) in THF (10 mL) was added NaH (222 mg, 5.55 mmol, 60% dispersion in mineral oil) at 0° C. Thirty minutes later, 3-bromoprop-1-yne (550 mg, 3.70 mmol, 80% toluene solution) was added. The reaction mixture was stirred at 20° C. for 12 hrs. On completion, the reaction mixture was quenched with saturated $NH_4Cl$ (5 mL), and extracted with ethyl acetate (3×50 mL). The combined organic layers were washed with brine (30 mL), dried over anhydrous sodium sulfate, filtered and the filtrate was concentrated in vacuo. The residue was purified by silica gel chromatography (PE:EA=20:1) to give the title compound (810 mg, 90% yield) as a yellow oil. $^1H$ NMR (400 MHz, $CDCl_3$) δ 4.20 (d, J=2.4 Hz, 2H), 3.79-3.63 (m, 1H), 2.42 (t, J=2.4 Hz, 1H), 1.84 (dd, J=3.2, 13.2 Hz, 2H), 1.58-1.49 (m, 2H), 1.46 (s, 9H).

3-[3-Methyl-2-oxo-4-[3-[(2,2,6,6-tetradeuterio-4-piperidyl)oxy]prop-1-ynyl]benzimidazol-1-yl]piperidine-2,6-dione (Intermediate BKM)

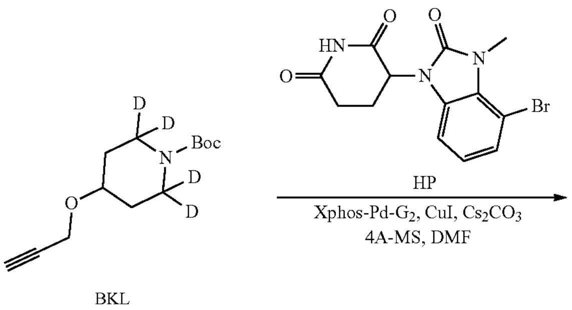

-continued

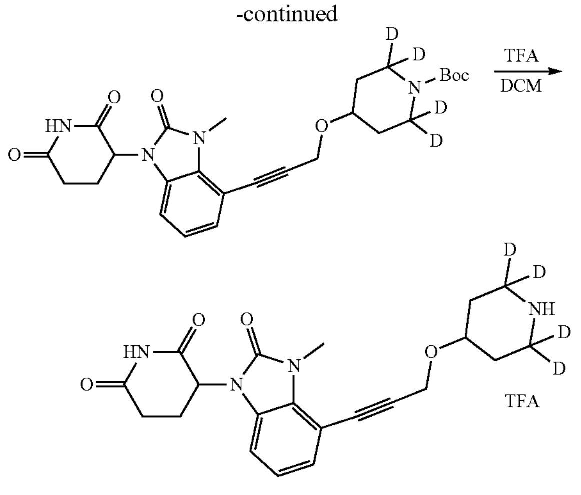

BKM

Step 1—Tert-butyl 2,2,6,6-tetradeuterio-4-[3-[1-(2,6-dioxo-3-piperidyl)-3-methyl-2-oxo-benzimidazol-4-yl]prop-2-ynoxy]piperidine-1-carboxylate A mixture of 3-(4-bromo-3-methyl-2-oxo-benzimidazol-1-yl)piperidine-2,6-dione (700 mg, 2.07 mmol, Intermediate HP), tert-butyl 2,2,6,6-tetradeuterio-4-prop-2-ynoxy-piperidine-1-carboxylate (610 mg, 2.51 mmol, Intermediate BKL), $Cs_2CO_3$ (1.39 g, 4.26 mmol), 4 Å molecular sieves (1.00 g), CuI (19.7 mg, 103 umol) and [2-(2-aminophenyl)phenyl]-chloro-palladium;dicyclohexyl-[3-(2,4,6-triisopropylphenyl)phenyl]phosphane (163 mg, 207 umol) in DMF (30 mL) was stirred at 80° C. for 3 hrs under nitrogen atmosphere. On completion, the reaction mixture was filtered and the filtrate was concentrated in vacuo. The crude product was purified by reversed-phase flash (0.1% FA condition) to give the title compound (400 mg, 38% yield) as a white solid. $^1H$ NMR (400 MHz, $CDCl_3$) δ 8.23 (s, 1H), 7.17 (d, J=8.0 Hz, 1H), 7.05-6.94 (m, 1H), 6.77 (d, J=8.0 Hz, 1H), 5.21 (dd, J=5.2, 12.4 Hz, 1H), 4.46 (s, 2H), 3.78 (s, 3H), 3.77-3.73 (m, 1H), 3.01-2.92 (m, 1H), 2.89-2.79 (m, 1H), 2.78-2.66 (m, 1H), 2.31-2.19 (m, 1H), 1.88 (dd, J=2.8, 13.2 Hz, 2H), 1.60-1.55 (m, 2H), 1.47 (s, 9H); LC-MS ($ESI^+$) m/z 523.2 $(M+23)^+$.

Step 2—3-[3-Methyl-2-oxo-4-[3-[(2,2,6,6-tetradeuterio-4-piperidyl)oxy]prop-1-ynyl]benzimidazol-1-yl]piperidine-2,6-dione To a solution of tert-butyl 2,2,6,6-tetradeuterio-4-[3-[1-(2,6-dioxo-3-piperidyl)-3-methyl-2-oxo-benzimidazol-4-yl]prop-2-ynoxy]piperidine-1-carboxylate (470 mg, 939 umol) in DCM (5 mL) was TFA (3.85 g, 33.7 mmol, 2.5 mL). The reaction mixture was stirred at 20° C. for 0.5 hr. On completion, the reaction mixture was the reaction mixture was concentrated in vacuo to give the title compound (483 mg, 100% yield) as a yellow solid. LC-MS ($ESI^+$) m/z 401.2 $(M+H)^+$.

(E)-4-ethoxy-1,1-difluoro-but-3-en-2-one (Intermediate BKN)

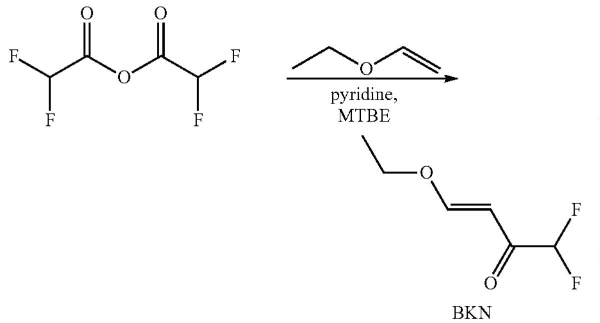

BKN

The reaction was performed in parallel for four batches: to a solution of vinyloxyethane (149 g, 2.07 mol, CAS #109-92-2) and pyridine (143 g, 1.81 mol) in MTBE (600 mL) was added (2,2-difluoroacetyl) 2,2-difluoroacetate (300 g, 1.72 mol, CAS #401-67-2) slowly at 0-5° C. during 1 hour. The mixture was stirred at 15° C. for 16 hours. On completion, the mixture of four batches were combined, diluted with water (1.0 L), and partitioned. The aqueous phase was extracted with a mixed solution (PE:EA=5:1, 2×500 mL). The combined organic layer was washed with saturated $NaHCO_3$ (800 mL) and brine (800 mL), dried over $Na_2SO_4$, filtered and concentrated in vacuo to give the title compound (860 g, 83% yield) as yellow oil. $^1H$ NMR (400 MHz, DMSO-$d_6$) δ 7.93 (d, J=12.8 Hz, 1H), 6.49-6.19 (m, 1H), 5.87 (td, J=1.2, 12.8 Hz, 1H), 4.14 (q, J=7.2 Hz, 2H), 1.28 (t, J=7.2 Hz, 3H).

Ethyl 4-[3-(difluoromethyl)-4-nitro-pyrazol-1-yl]cyclohexanecarboxylate (Intermediate BKU) and (1s,4s)-ethyl 4-(3-(difluoromethyl)-4-nitro-1H-pyrazol-1-yl)cyclohexanecarboxylate (Intermediate BKV

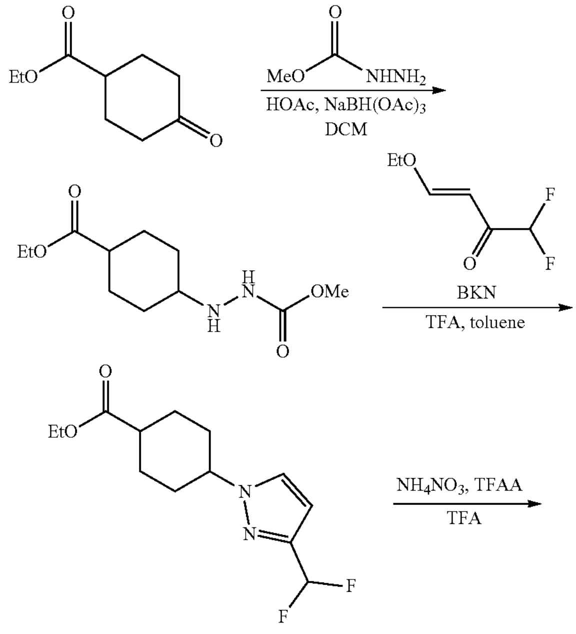

-continued

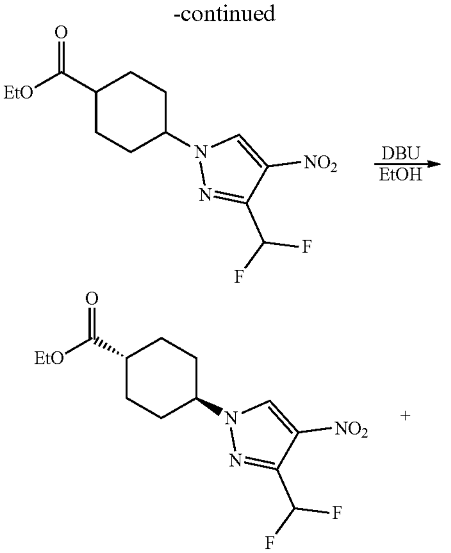

BKU

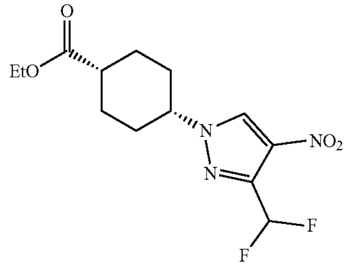

BKV

Step 1—Ethyl 4-(2-methoxycarbonylhydrazino)cyclohexanecarboxylate

The reaction was performed in parallel for two batches: to a solution of ethyl 4-oxocyclohexanecarboxylate (250 g, 1.47 mol, CAS #17159-79-4) and methyl N-aminocarbamate (132 g, 1.47 mol, CAS #6294-89-9) in DCM (1500 mL) was added AcOH (176 g, 2.94 mol) at 0° C. The reaction mixture was stirred at 15° C. for 2 hrs. Then $NaBH(OAc)_3$ (622 g, 2.94 mol) was added in portions and the reaction mixture was stirred at 15° C. for 14 hrs. On completion, the reaction mixture was diluted with DCM (500 mL), then quenched by saturated $NH_4Cl$ (500 mL). The organic layer was washed with brine (3×1 L), dried over $Na_2SO_4$, filtered and concentrated in vacuo to give the title compound (725 g, 95% yield) as yellow oil. $^1H$ NMR (400 MHz, $CDCl_3$) δ 6.91-6.20 (m, 1H), 5.96-5.34 (m, 1H), 4.17-4.06 (m, 2H), 3.70 (s, 3H), 3.08-2.74 (m, 1H), 2.50-2.17 (m, 1H), 2.03-1.89 (m, 3H), 1.67-1.38 (m, 4H), 1.27-1.20 (m, 3H), 1.19-1.05 (m, 1H).

Step 2—Ethyl 4-[3-(difluoromethyl)pyrazol-1-yl]cyclohexanecarboxylate

The reaction was performed in four batches for four batches: to a solution of ethyl 4-(2-methoxycarbonylhydrazino)cyclohexanecarboxylate (280 g, 1.15 mol) in toluene (2.0 L) was added (E)-4-ethoxy-1,1-difluoro-but-3-en-2-one (203 g, 1.35 mol, Intermediate BKN) slowly at 0° C. Then TFA (156 g, 1.38 mol) was added to the mixture at 0° C. The mixture was stirred at 15° C. for 2 hours, then the mixture was stirred at 30° C. for 30 hours. On completion, the mixture of four batches was combined, and washed with water (1.5 L). The organic layer was washed with saturated $NaHCO_3$ (2.0 L) and brine (1.0 L), dried over $Na_2SO_4$, filtered and concentrated in vacuo. The residue was purified by column chromatography on silica gel (PE:EA=100:1 to 50:1) to give the title compound (940 g, 75% yield) as light yellow oil. $^1H$ NMR (400 MHz, $CDCl_3$) δ 7.44 (dd, J=2.2, 7.1 Hz, 1H), 6.84-6.52 (m, 1H), 6.46 (s, 1H), 4.24-4.08 (m, 3H), 2.69-2.32 (m, 1H), 2.29-2.13 (m, 3H), 2.09-1.96 (m, 2H), 1.88-1.56 (m, 3H), 1.27 (dt, J=2.6, 7.1 Hz, 3H).

Step 3—Ethyl 4-[3-(difluoromethyl)-4-nitro-pyrazol-1-yl]cyclohexanecarboxylate The reaction was performed in parallel for four batches: to a solution of ethyl 4-[3-(difluoromethyl)pyrazol-1-yl] cyclohexanecarboxylate (280 g, 1.03 mol) and TFAA (431 g, 2.06 mol) in TFA (390 mL) was added azane-nitric acid (164 g, 2.06 mol) in portions at 0° C. The reaction mixture was stirred at 0~ 5° C. for 16 hrs. On completion, the reaction mixture of four batches were poured into cold water (1000 mL) and extracted with PE:EA=2:1 (3×800 mL). The combined organic layers were washed with brine (2×800 mL), then saturated $NaHCO_3$ (5×700 mL) until the pH=7. The combined organic layer was dried over $Na_2SO_4$, filtered and concentrated in vacuo to give the title compound (1300 g, 99% yield) as yellow oil. $^1H$ NMR (400 MHz, $CDCl_3$) δ 8.23 (s, 1H), 7.26-6.96 (m, 1H), 4.31-4.05 (m, 3H), 2.76-2.36 (m, 1H), 2.35-2.05 (m, 4H), 2.04-1.57 (m, 4H), 1.34-1.21 (m, 3H).

Step 4—Ethyl 4-[3-(difluoromethyl)-4-nitro-pyrazol-1-yl]cyclohexanecarboxylate and (1s,4s)-ethyl 4-(3-(difluoromethyl)-4-nitro-1H-pyrazol-1-yl)cyclohexanecarboxylate The reaction was performed in parallel for four batches: to a solution of ethyl 4-[3-(difluoromethyl)-4-nitro-pyrazol-1-yl]cyclohexanecarboxylate (325 g, 1.02 mol) in EtOH (1625 mL) was added DBU (467 g, 3.07 mol). The reaction mixture was stirred at 85° C. for 16 hrs. On completion, the reaction mixture of four batches were concentrated in vacuo to remove ethanol, diluted with EA (3000 mL), and washed with HCl (1 N) until the pH=6, then washed with brine (2×1000 mL). The organic phase was dried over $Na_2SO_4$, filtered and concentrated in vacuo. The residue was purified by recrystallization with i-PrOH (1200 mL) at 50° C. to give the impure product (680 g) (cis:trans=8:92). The impure product was purified by recrystallization with i-PrOH (680 mL) at 50° C., and then the mixture was filtered. The filter cake was collected to give the title compound ethyl 4-[3-(difluoromethyl)-4-nitro-pyrazol-1-yl]cyclohexanecarboxylate (610 g, 46% yield) as yellow solid. $^1H$ NMR (400 MHz, $CDCl_3$) δ 8.22 (s, 1H), 7.26-6.90 (m, 1H), 4.26-4.11 (m, 3H), 2.45-2.16 (m, 5H), 1.82 (dq, J=3.6, 12.8 Hz, 2H), 1.71-1.59 (m, 2H), 1.27 (t, J=7.2 Hz, 3H).

The filtrate was concentrated in vacuo at 45° C. to afford an oil. SFC showed the ration of Cis:Trans is 80:20. The oil (30 g) was purified by SFC (2_A RT=0.811 mins, 2_B RT=1.767 mins, Column: Chiralpak AD-3 50×4.6 mm I.D., 3 um; Mobile phase: Phase A for C02, and Phase B for EtOH (0.05% DEA); Gradient elution: EtOH (0.05% DEA) in C02 from 5% to 40% Flow rate: 3 mL/min; Detector: PDA; Column Temp: 35 C; Back Pressure: 100 Bar) to give 17 g of cis isomer 1s,4s)-ethyl 4-(3-(difluoromethyl)-4-nitro-1H-pyrazol-1-yl)cyclohexanecarboxylate (17 g) as obtained as yellow solid. $^1H$ NMR (400 MHz, MeOD) δ 8.69 (s, 1H), 7.12 (J=48.8 Hz, 1H), 4.40-4.28 (m, 1H), 4.17 (q, J=7.2 Hz, 2H), 2.76-2.64 (m, 1H), 2.50-2.40 (m, 2H), 2.10-1.97 (m, 4H), 1.85-1.70 (m, 2H), 1.27 (t, J=7.2 Hz, 3H).

Example 1 (Method 2): Synthesis of 5-((1S,4S)-2-oxa-5-azabicyclo[2.2.1]heptan-5-yl)-N-(3-(difluoromethyl)-1-((1r,4S)-4-((4-((3-(1-(2,6-dioxopiperidin-3-yl)-3-methyl-2-oxo-2,3-dihydro-1H-benzo[d]imidazol-4-yl)prop-2-yn-1-yl)oxy)piperidin-1-yl)methyl)cyclohexyl)-1H-pyrazol-4-yl)pyrazolo[1,5-a]pyrimidine-3-carboxamide (1)

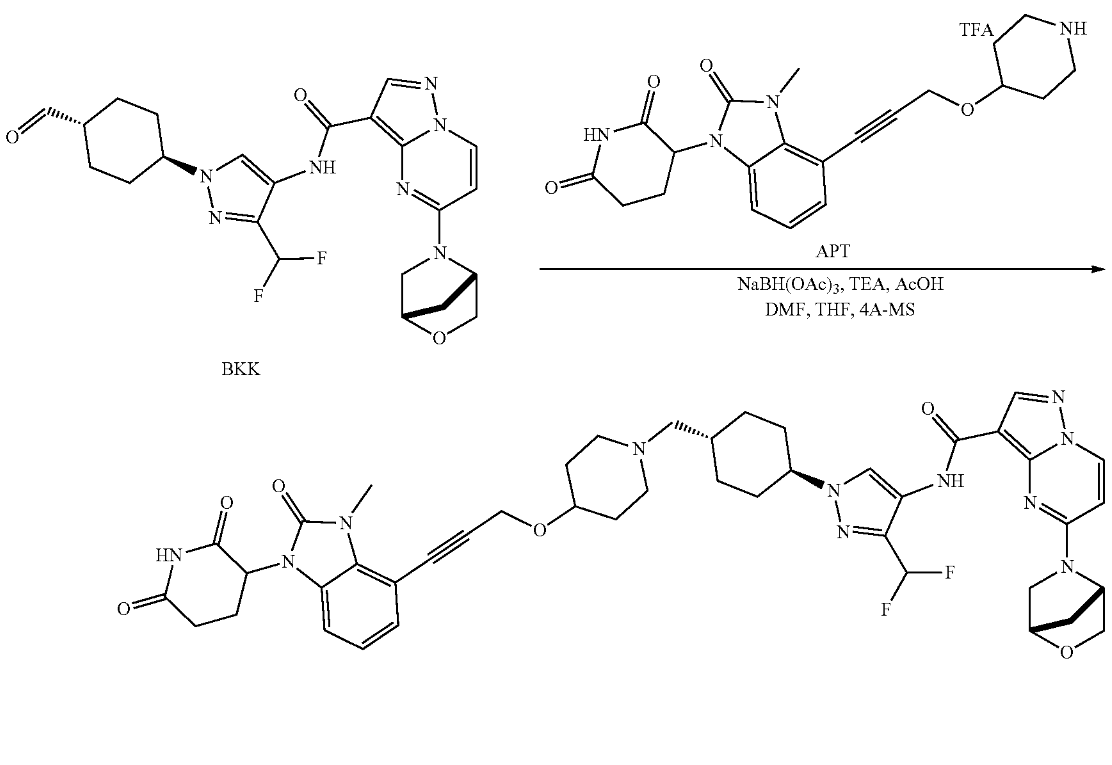

A mixture of 3-(3-methyl-2-oxo-4-(3-(piperidin-4-yloxy)prop-1-yn-1-yl)-2,3-dihydro-1H-benzo[d]imidazol-1-yl)piperidine-2,6-dione (2.00 g, 3.68 mmol, TFA, Intermediate APT), $Et_3N$ (1.12 g, 11.0 mmol, 1.54 mL), 4 Å molecular sieves (3.00 g) in THF (50.0 mL) and DMF (10.0 mL) was stirred at −25° C. for 0.5 hr. Then the reaction mixture pH was adjusted to 7-8 with AcOH (5.25 g, 87.4 mmol, 5.00 mL). Next, 5-((1S,4S)-2-oxa-5-azabicyclo[2.2.1]heptan-5-yl)-N-(3-(difluoromethyl)-1-((1r,4S)-4-formylcyclohexyl)-1H-pyrazol-4-yl)pyrazolo[1,5-a]pyrimidine-3-carboxamide (1.79 g, 3.68 mmol, Intermediate BKK) and $NaBH(OAc)_3$ (1.33 g, 6.26 mmol) were added and the reaction mixture was stirred at −25° C. for 1.5 hrs. On completion, the reaction mixture was diluted with 50.0 mL $H_2O$ and extracted with EA (25 mL×2). The combined organic layers were washed with 50 mL brine, dried over $Na_2SO_4$, filtered and concentrated in vacuo to give a residue. The residue was purified by prep-HPLC (HCl condition) to give the title compound (100 g, 31% yield) as a brown solid. $^1H$ NMR (400 MHz, DMSO-$d_6$) δ 11.5-10.7 (m, 1H), 9.51 (d, J=1.2 Hz, 1H), 8.78 (d, J=7.2 Hz, 1H), 8.48-8.04 (d, 2H), 7.49 (s, 1H), 7.31-6.93 (m, 4H), 6.90-6.36 (m, 1H), 5.83-4.70 (i, 3H), 4.47 (s, 2H), 4.25-4.04 (m, 1H), 3.87-3.43 (m, 9H), 2.75-2.58 (m, 3H), 2.17-1.70 (m, 16H), 1.60-1.37 (m, 3H), 1.02 (d, J=11.2 Hz, 2H); LC-MS (ESI$^+$) m/z 866.1 $(M+H)^+$.

TABLE 3

Compounds synthesized via Method 2 with the reductive amination of various amines and aldehydes.

| I-#[a] | Intermediate Amine | Intermediate Aldehyde | LCMS (ES+) m/z $(M + H)^+$ | $^1$HNMR (400 MHz, DMSO-d6) δ |
|---|---|---|---|---|
| I-1 | BKM | AJB | 870.3 | 11.19 (s, 1H), 9.56 (d, J = 6.0 Hz, 1H), 8.84 (d, J = 7.6 Hz, 1H), 8.44 (d, J = 4.0 Hz, 1H), 8.32 (d, J = 5.6 Hz, 1H), 7.32-7.01 (m, 4H), 6.98-6.45 (m, 1H), 5.46 (dd, J = 5.2, 12.8 Hz, 1H), 5.37-5.10 (m, 1H), 4.83 (d, J = 16.8 Hz, 1H), 4.53 (s, 2H), 4.29-4.16 (m, 1H), 3.91-3.77 (m, 2H), 3.70 (s, 3H), 3.68-3.47 (m, 3H), 3.04-2.86 (m, 1H), 2.84-2.72 (m, 1H), 2.72-2.64 (m, 1H), 2.18-1.88 (m, 11H), 1.85-1.73 (m, 2H), 1.68-1.57 (m, 1H), 1.56-1.46 (m, 2H), 1.12-1.03 (m, 2H) |
| (2)[b] | BKG | AJB | 880.6 | 11.12 (s, 1H), 9.49 (d, J = 6.0 Hz, 1H), 8.78 (d, J = 7.6 Hz, 1H), 8.37 (d, J = 4.4 Hz, 1H), 8.25 (d, J = 5.6 Hz, 1H), 7.25-6.96 (m, 4H), 6.88-6.43 (m, 1H), 5.40 (dd, J = 5.2, 12.8 Hz, 1H), 5.30-5.05 (m, 1H), 4.76 (d, J = 16.4 Hz, 1H), 4.36 (s, 2H), 4.24-4.09 (m, 1H), 3.86-3.68 (m, 3H), 3.65 (s, 3H), 3.62-3.58 (m, 2H), 2.94-2.85 (m, 1H), 2.77-2.58 (m, 2H), 2.42-2.40 (m, 1H), 2.31-2.27 (m, 1H), 2.11 (d, J = 7.2 Hz, 2H), 2.07-1.99 (m, 4H), 1.99-1.84 (m, 4H), 1.79-1.69 (m, 4H), 1.63-1.56 (m, 1H), 1.55-1.48 (m, 2H), 1.19 (s, 3H), 1.07-0.97 (m, 2H) |
| (3) | APT | BKI | 866.2 | 11.1 (s, 1H), 10.4 (d, J = 2.0 Hz, 1H), 9.51 (d, J = 5.6 Hz, 1H), 8.78 (d, J = 7.6 Hz, 1H), 8.46 (d, J = 3.6 Hz, 1H), 8.25 (d, J = 5.2 Hz, 1H), 7.29-6.96 (m, 4H), 6.92-6.43 (m, 1H), 5.52-5.37 (m, 1H), 5.29-5.06 (m, 3H), 4.77 (d, J = 17.6 Hz, 1H), 4.54 (s, 2H), 4.28 (s, 1H), 4.00-3.72 (m, 3H), 3.68-3.33 (m, 7H), 3.16-2.85 (m, 5H), 2.77-2.58 (m, 2H), 2.26-1.80 (m, 13H), 1.70 (d, J = 9.6 Hz, 4H) |
| (4) | APT | BKJ | 866.4 | 11.13 (s, 1H), 10.5-10.0 (m, 1H), 9.51 (d, J = 5.6 Hz, 1H), 8.79 (d, J = 7.6 Hz, 1H), 8.46 (d, J = 3.6 Hz, 1H), 8.26 (d, J = 5.6 Hz, 1H), 7.31-6.96 (m, 4H), 6.93-6.89 (m, 1H), 6.93-6.39 (m, 1H), 5.43 (dd, J = 5.2, 12.8 Hz, 1H), 5.34-5.04 (m, 1H), 4.77 (d, J = 19.2 Hz, 1H), 4.54 (s, 2H), 4.29 (s, 1H), 3.96 (s, 1H), 3.89-3.71 (m, 3H), 3.70-3.42 (m, 6H), 3.21-2.80 (m, 5H), 2.79-2.58 (m, 3H), 2.29-1.78 (m, 14H), 1.36 (s, 2H) |

[a]For Method 2, when the amine is the HCl salt, TEA was added to free base the salt, followed by HOAc to adjust the pH to 3-4 or 5-7. KOAc could also be used in place of the TEA/HOAc combination. The reaction was run anywhere from 0.5-48 hrs The reaction temperature was run anywhere from −25° C. to rt. The final products were isolated under standard purification techniques including reverse HPLC, silica gel chromatography, and prep-TLC with appropriate solvent conditions.

[b]No molecular sieves used in the reaction.

Example 2. IRAK4 MSD Degradation in OCI-LY10

Degradation of IRAK4 in OCI-LY10 was quantitatively measured using Meso Scale Discovery technology. OCI-LY10 cells were seeded in 96-well plates (Corning 3799) with a density of 300,000 cells per well in 100 μL fresh media. Compounds were then added to the assay plates with a final top concentration of 1 to 10 μM in a 1:3 dilution series with total of 8 doses. The assay plates were then incubated for 4 to 24 hours at 37° C. under 5% $CO_2$. The assay plates were then centrifuged for 5 minutes and the cell pellets were treated with 100 μL/well RIPA lysis buffer (Boston Bio-Products BP-115D) with proteinase inhibitors. To prepare MSD assay plates (Meso Scale Discovery Catalog number L15XA-3), the plates were coated with 2 μg/mL capture antibody (mouse Anti-IRAK4 antibody [2H9], ab119942) in PBS, at 40 μL/well. The plates were then incubated overnight at 4° C., washed 3 times with 150 μL/well TBST buffer (Cell Signaling Technology, Catalog number 9997S) and blocked with 150 μL/well blocking buffer (Meso Scale Discovery Catalog number R93BA-4). Cell lysates were then added to MSD assay plates and the plates were incubated at room temperature for 1 hour. The plates were then washed 3 times with 150 μL/well TBST buffer and 25 L/well primary detection antibody (rabbit Anti-IRAK4 antibody [Y279], from Abcam. Catalog number ab32511, 1 μg/mL). The assay plates were then incubated at room temperature for 1 hour, washed 3 times with 150 μL/well TBST buffer and 25 L/well secondary detection antibody, SULFO-TAG anti-rabbit antibody were added (anti rabbit antibody from Meso Scale Discovery, Catalog number R32AB-1, 1 μg/mL). The assay plates were then incubated at room temperature for 1 hour, washed 3 times with 150 μL/well TBST buffer, and 150 μL/well MSD reading buffer (Meso Scale Discovery catalog number R92TC-2) was added. The plates were then analyzed by a MSD reader (Meso Scale Discovery, Model Quick Plex SQ 120). The data was then analyzed by software Prism 7.0 from GraphPad and the dose-depended IRAK4 degradation were fit using a three-parameter logistic equation to calculate DC50.

IRAK4 MSD degradation results in OCI-LY10 cells for compounds of the invention are presented in Table 4. The letter codes for IRAK4 DC50 include: A (<0.05 μM); B (0.05-0.1 μM); C (0.1-0.5 μM); D (0.5-1.0 μM); and E (>1.0 μM).

TABLE 4

IRAK4 MSD Degradation in OCI-LY10 Results

| Compound # | IRAK4 degradation in OCI-LY10 at 24 hrs: DC50 (μM) |
|---|---|
| I-1 | A |

While we have described a number of embodiments of this invention, it is apparent that our basic examples may be altered to provide other embodiments that utilize the compounds and methods of this invention. Therefore, it will be appreciated that the scope of this invention is to be defined by the appended claims rather than by the specific embodiments that have been represented by way of example.

I claim:

1. A compound of formula I:

I

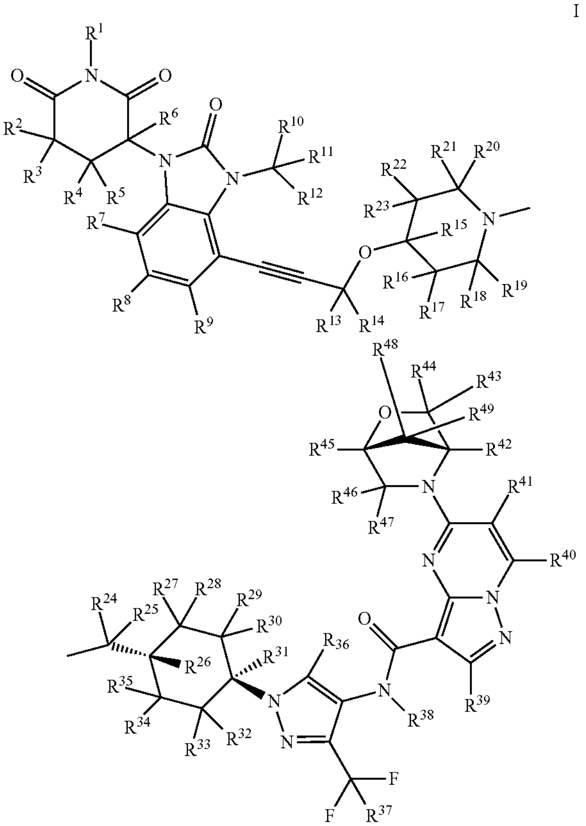

or a pharmaceutically acceptable salt thereof, wherein:

each of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{28}$, $R^{29}$, $R^{30}$, $R^{31}$, $R^{32}$, $R^{33}$, $R^{34}$, $R^{35}$, $R^{36}$, $R^{37}$, $R^{38}$, $R^{39}$, $R^{40}$, $R^{41}$, $R^{42}$, $R^{43}$, $R^{44}$, $R^{45}$, $R^{46}$, $R^{47}$, $R^{48}$, and $R^{49}$ is independently H or D, provided that at least two of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{28}$, $R^{29}$, $R^{30}$, $R^{31}$, $R^{32}$, $R^{33}$, $R^{34}$, $R^{35}$, $R^{36}$, $R^{37}$, $R^{38}$, $R^{39}$, $R^{40}$, $R^{41}$, $R^{42}$, $R^{43}$, $R^{44}$, $R^{45}$, $R^{46}$, $R^{47}$, $R^{48}$, and $R^{49}$ is D.

2. The compound of claim 1, wherein at least one of $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{28}$, $R^{29}$, $R^{30}$, $R^{31}$, $R^{32}$, $R^{33}$, $R^{34}$, and $R^{35}$ is D.

3. The compound of claim 1 or 2, wherein $R^6$ is D.

4. The compound of claim 1 or 2, wherein one or more of $R^7$, $R^8$, and $R^9$ is D.

5. The compound of claim 1 or 2, wherein $R^{10}$, $R^{11}$, and $R^{12}$ is D.

6. The compound of claim 1 or 2, wherein $R^{36}$ is D.

7. The compound of claim 1 or 2, wherein $R^{39}$ is D.

8. The compound of claim 1 or 2, wherein one or more of $R^{40}$ and $R^{41}$ is D.

9. The compound of claim 1 or 2, wherein at least one of $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{28}$, $R^{29}$, $R^{30}$, $R^{31}$, $R^{32}$, $R^{33}$, $R^{34}$, and $R^{35}$ has a % deuterium incorporation of about 50% or greater.

10. The compound of claim 1 or 2, wherein at least one of $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{28}$, $R^{29}$, $R^{30}$, $R^{31}$, $R^{32}$, $R^{33}$, $R^{34}$, and $R^{35}$ has a % deuterium incorporation of about 80% or greater.

11. The compound of claim 1 or 2, wherein at least one of $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{28}$, $R^{29}$, $R^{30}$, $R^{31}$, $R^{32}$, $R^{33}$, $R^{34}$, and $R^{35}$ has a % deuterium incorporation of about 90% or greater.

12. The compound of claim 1 or 2, wherein each of $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{28}$, $R^{29}$, $R^{30}$, $R^{31}$, $R^{32}$, $R^{33}$, $R^{34}$, and $R^{35}$ has a % deuterium incorporation of about 95% or greater.

13. The compound of claim 1 or 2, wherein the compound is represented by Formula I-a, I-b, I-c, I-d, I-e, I-f, I-g, I-h, or I-i:

I-a

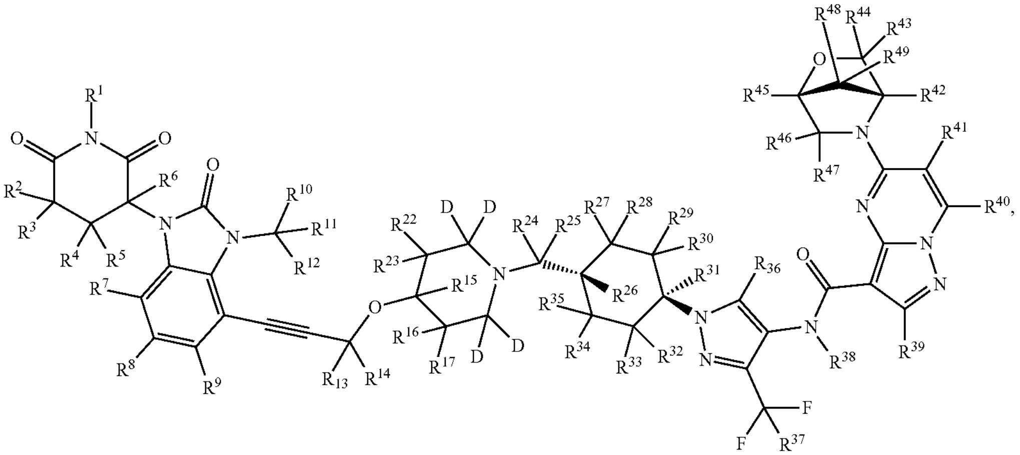

I-b

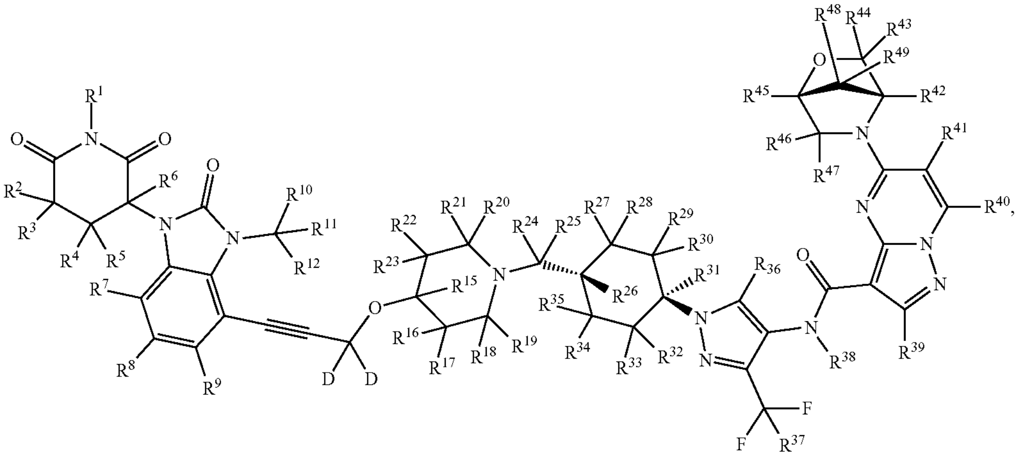

I-c

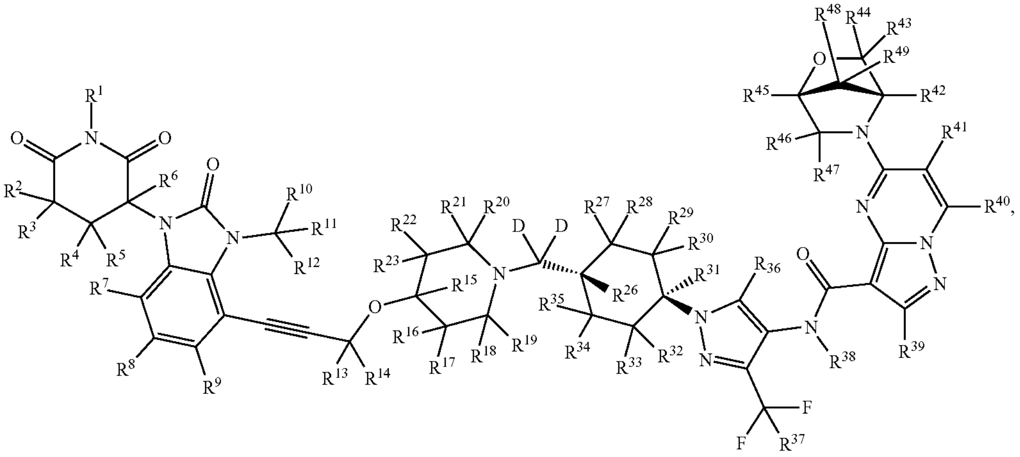

-continued
I-d
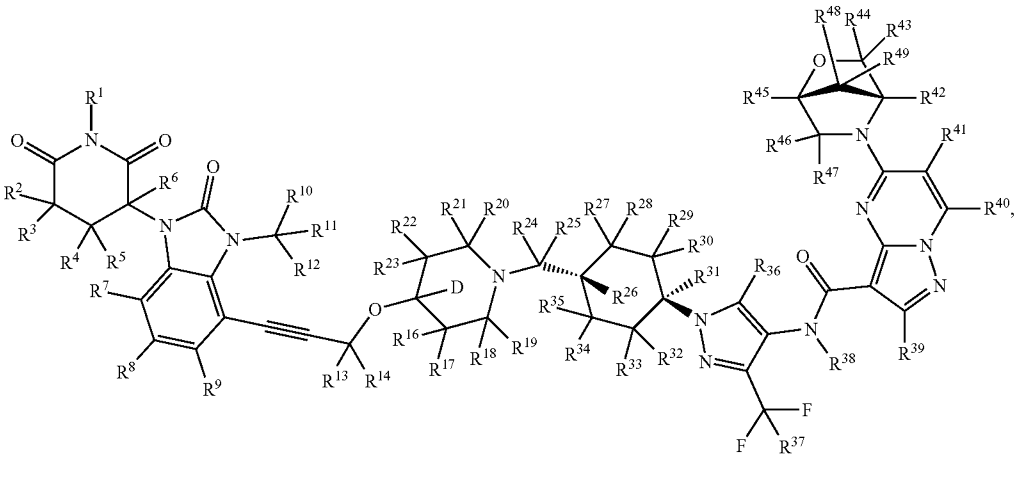
I-e
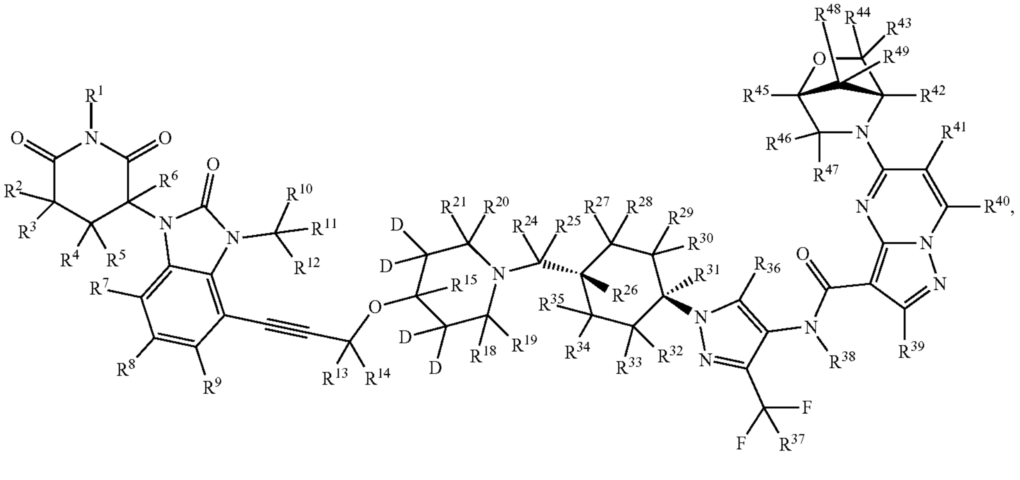
I-f
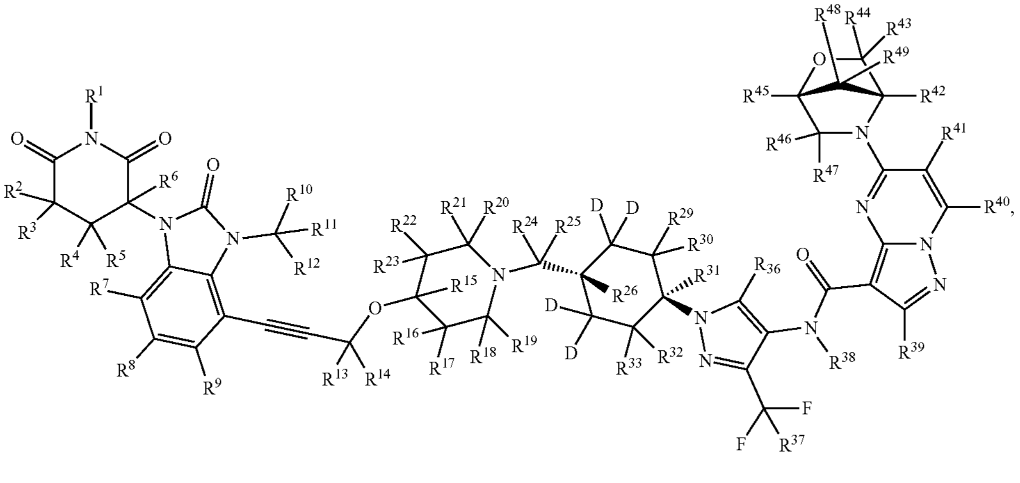

-continued
I-g
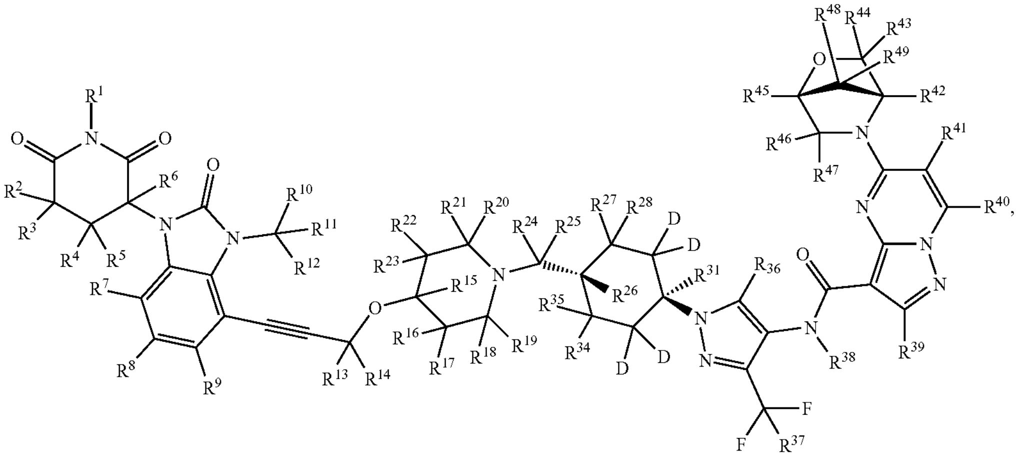
I-h
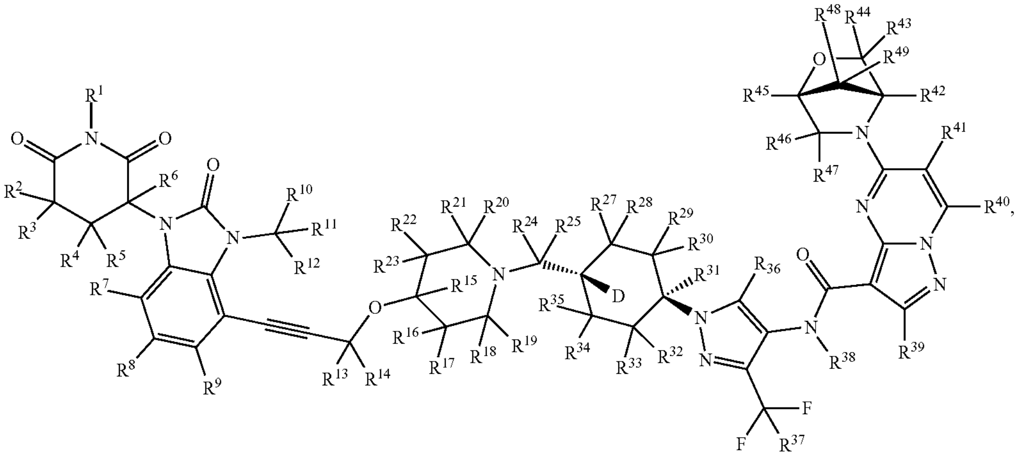
I-i
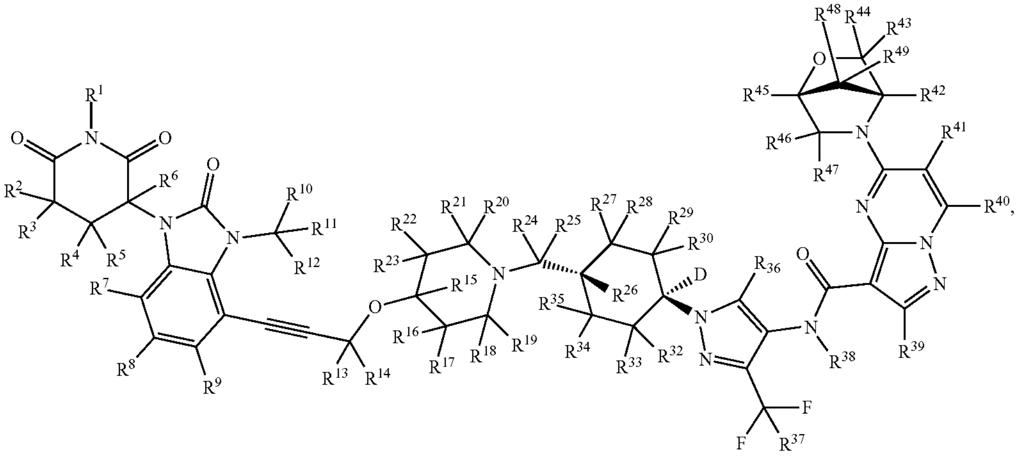

-continued

I-j

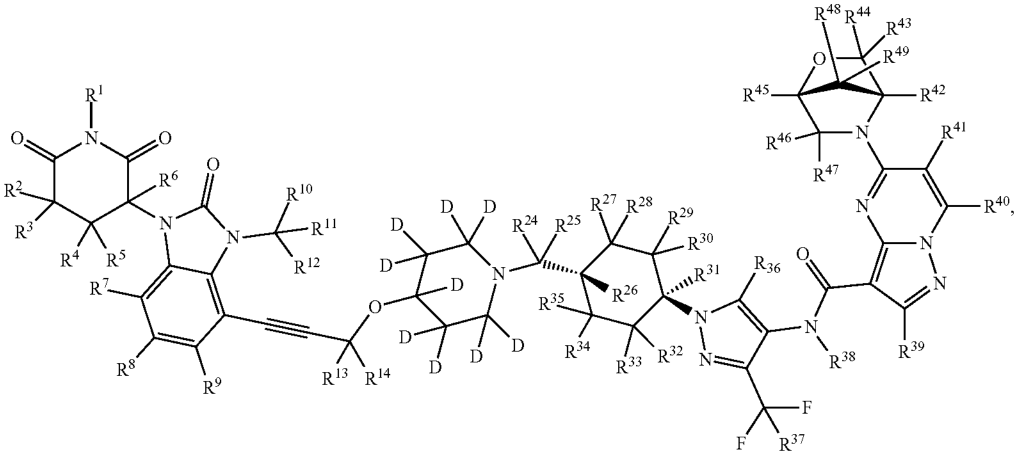

I-k

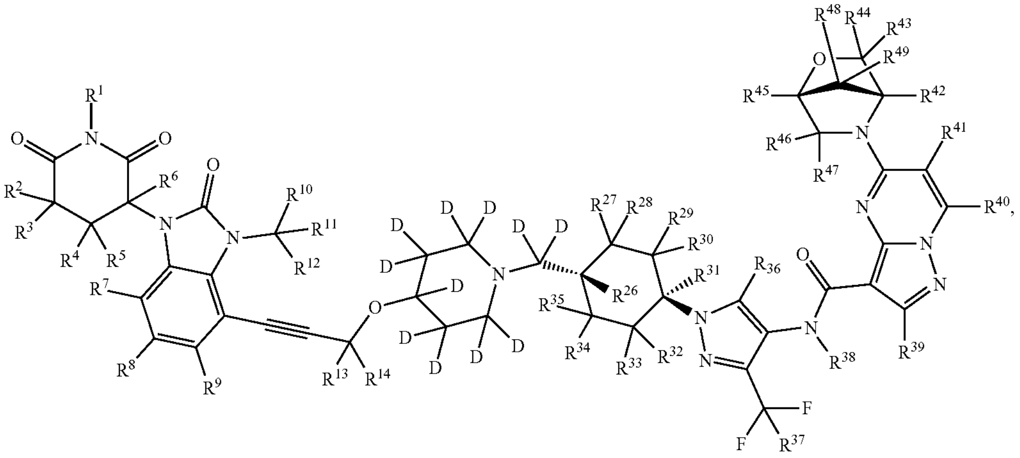

or a pharmaceutically acceptable salt thereof.

14. The compound of claim 1 or 2, wherein each of $R^6$, $R^7$, $R^8$, $R^9$, $R^{10}$, $R^{11}$, $R^{12}$, $R^{36}$, $R^{39}$, $R^{40}$, and $R^{41}$ is as defined in an entry set forth below:

| Entry | $R^6$ | $R^7$ | $R^8$ | $R^9$ | $R^{10}$ | $R^{11}$ | $R^{12}$ | $R^{36}$ | $R^{39}$ | $R^{40}$ | $R^{41}$ |
|---|---|---|---|---|---|---|---|---|---|---|---|
| i | D | D | D | D | H | H | H | H | H | H | H |
| ii | D | H | H | H | D | D | D | H | H | H | H |
| iii | D | H | H | H | H | H | H | D | H | H | H |
| iv | D | H | H | H | H | H | H | H | D | H | H |
| v | D | H | H | H | H | H | H | H | H | D | D |
| vi | H | D | D | D | D | D | D | H | H | H | H |
| vii | H | D | D | D | H | H | H | D | H | H | H |
| viii | H | D | D | D | H | H | H | H | D | H | H |
| ix | H | D | D | D | H | H | H | H | H | D | D |
| x | H | H | H | H | D | D | D | D | H | H | H |
| xi | H | H | H | H | D | D | D | H | D | H | H |
| xii | H | H | H | H | D | D | D | H | H | D | D |
| xiii | H | H | H | H | H | H | H | D | D | H | H |
| xiv | H | H | H | H | H | H | H | D | H | D | D |
| xv | H | H | H | H | H | H | H | H | D | D | D |
| xvi | H | H | H | H | D | D | H | H | H | H | H |
| xvii | H | H | H | H | H | D | D | H | H | H | H |
| xviii | H | H | H | H | D | H | D | H | H | H | H |
| xix | H | H | H | H | D | D | H | D | H | H | H |
| xx | H | H | H | H | H | D | D | D | H | H | H |
| xxi | H | H | H | H | D | H | D | D | H | H | H |
| xxii | H | H | H | H | D | D | H | H | D | H | H |
| xxiii | H | H | H | H | H | D | D | H | D | H | H |
| xxiv | H | H | H | H | D | H | D | H | D | H | H |

-continued

| Entry | $R^6$ | $R^7$ | $R^8$ | $R^9$ | $R^{10}$ | $R^{11}$ | $R^{12}$ | $R^{36}$ | $R^{39}$ | $R^{40}$ | $R^{41}$ |
|---|---|---|---|---|---|---|---|---|---|---|---|
| xxv | H | H | H | H | D | D | H | H | H | D | H |
| xxvi | H | H | H | H | H | D | D | H | H | D | H |
| xxvii | H | H | H | H | D | H | D | H | H | D | H |
| xxviii | H | H | H | H | D | D | H | H | H | H | D |
| xxix | H | H | H | H | H | D | D | H | H | H | D |
| xxx | H | H | H | H | D | H | D | H | H | H | D |
| xxxi | H | H | H | H | D | D | H | H | H | D | D |
| xxxii | H | H | H | H | H | D | D | H | H | D | D |
| xxxiii | H | H | H | H | D | H | D | H | H | D | D |

or a pharmaceutically acceptable salt thereof.

15. The compound of claim 13, wherein each position indicated as "D" has a % deuterium incorporation of about 50% or greater.

16. The compound of claim 13, wherein each position indicated as "D" has a % deuterium incorporation of about 80% or greater.

17. The compound of claim 13, wherein each position indicated as "D" has a % deuterium incorporation of about 90% or greater.

18. A compound selected from any one of the following:

I-1

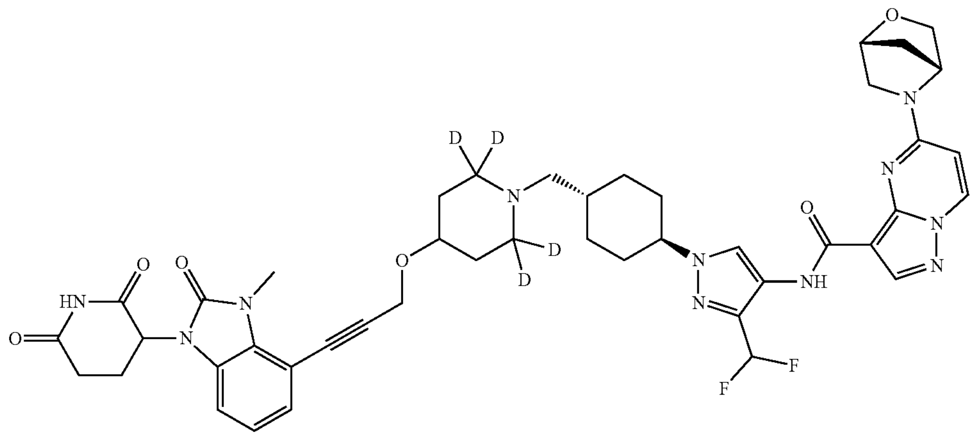

I-2

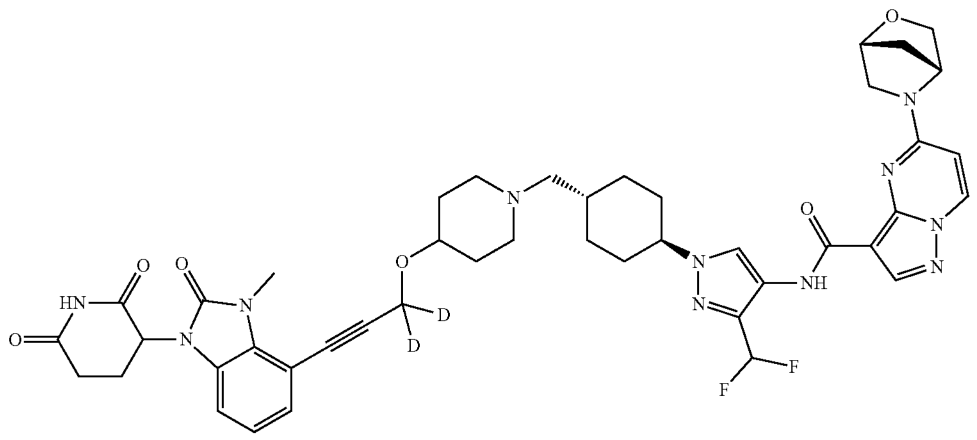

-continued
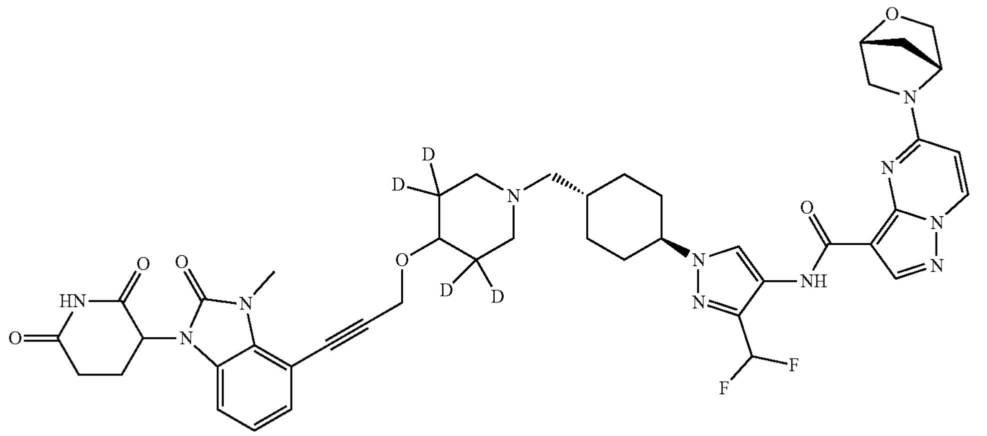
I-4
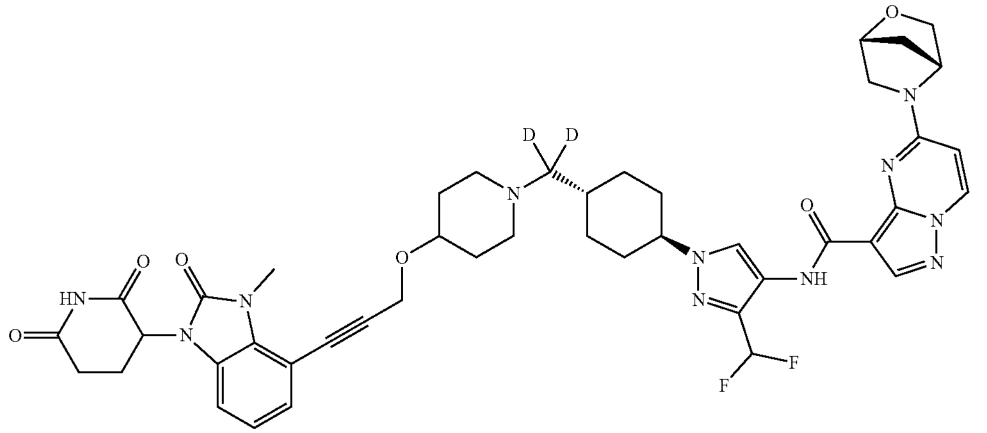
I-5
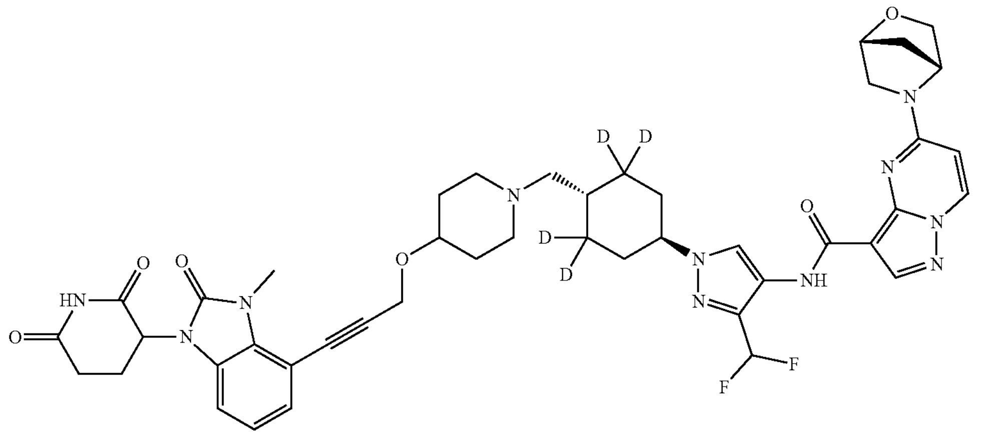
I-7

-continued

I-8

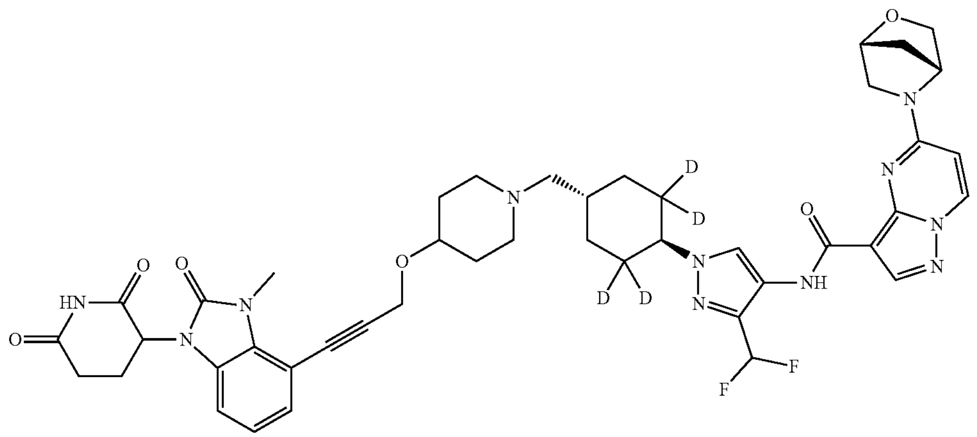

I-10

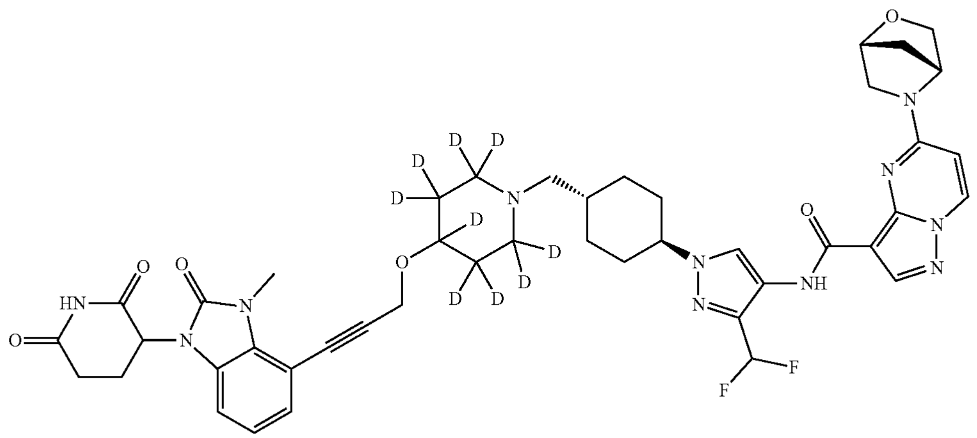

I-11

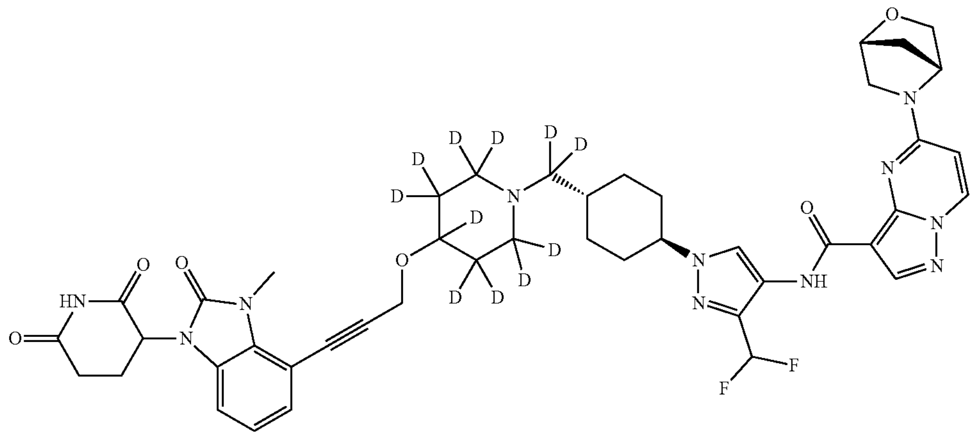

or a pharmaceutically acceptable salt thereof.

19. The compound of claim 18, wherein each position indicated as "D" has a % deuterium incorporation of about 80% or greater.

20. The compound of claim 18, wherein each position indicated as "D" has a % deuterium incorporation of about 90% or greater.

21. The compound of claim 18, wherein each position indicated as "D" has a % deuterium incorporation of about 95% or greater.

22. A composition comprising a compound according to claim 1 or claim 2 and a pharmaceutically acceptable carrier or excipient.

23. The pharmaceutical composition according to claim 22, further comprising an additional therapeutic agent.

24. A method of degrading IRAK1, IRAK2 and/or IRAK4 protein kinase in a patient or biological sample comprising administering to said patient, or contacting said biological sample with a compound according to claim 1 or claim 2, or a pharmaceutical composition thereof.

25. A method of treating an IRAK4-mediated disorder, disease, or condition in a patient comprising administering to said patient a compound according to claim 1 or claim 2, or a pharmaceutical composition thereof, wherein the IRAK4-mediated disorder, disease or condition is an inflammatory disorder, wherein the inflammatory disorder is selected from the group consisting of ocular allergy, conjunctivitis, keratoconjunctivitis sicca, vernal conjunctivitis, allergic rhinitis, systemic lupus erythematosus, rheumatoid arthritis, scleroderma, dermatomyositis, ulcerative colitis, Crohn's disease, multiple sclerosis, Sjögren's syndrome, interstitial lung fibrosis, psoriatic arthritis, systemic juvenile idiopathic arthritis, aging, asthma, anaphylaxis, Type 1 diabetes, Type 2 diabetes, atopic dermatitis, allergy, dermatitis, hidradenitis suppurativa, peritonitis, rhinitis, dermatitis herpetiformis, urticaria, acute gout, chronic gout, chronic gouty arthritis, psoriasis, juvenile rheumatoid arthritis, and Cryopyrin Associated Periodic Syndrome (CAPS).

26. The method according to claim 25, further comprising administration of an additional therapeutic agent.

27. The method according to claim 25, wherein the inflammatory disorder is atopic dermatitis or hidradenitis suppurativa.

* * * * *